(12) United States Patent
Dindot

(10) Patent No.: US 11,685,920 B2
(45) Date of Patent: *Jun. 27, 2023

(54) ANGELMAN SYNDROME ANTISENSE TREATMENT

(71) Applicant: The Texas A&M University System, College Station, TX (US)

(72) Inventor: Scott Victor Dindot, College Station, TX (US)

(73) Assignee: The Texas A&M University System, College Station, TX (US)

(*) Notice: Subject to any disclaimer, the term of this patent is extended or adjusted under 35 U.S.C. 154(b) by 80 days.

This patent is subject to a terminal disclaimer.

(21) Appl. No.: 17/523,456

(22) Filed: Nov. 10, 2021

(65) Prior Publication Data

US 2022/0090075 A1    Mar. 24, 2022

Related U.S. Application Data

(63) Continuation of application No. 16/767,916, filed as application No. PCT/US2018/063416 on Nov. 30, 2018, now Pat. No. 11,198,869.

(60) Provisional application No. 62/676,034, filed on May 24, 2018, provisional application No. 62/593,431, filed on Dec. 1, 2017.

(51) Int. Cl.
*C12N 15/113* (2010.01)
*C07H 21/04* (2006.01)
*C12Q 1/68* (2018.01)

(52) U.S. Cl.
CPC .......... *C12N 15/113* (2013.01); *C07H 21/04* (2013.01); *C12N 2310/113* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 9,617,539 B2 | 4/2017 | Rigo et al. | |
| 2004/0259247 A1 | 12/2004 | Tuschl et al. | |
| 2008/0299659 A1 | 12/2008 | Quay et al. | |
| 2011/0178283 A1 | 7/2011 | Rigoutsos et al. | |
| 2015/0099791 A1 | 4/2015 | Krieg et al. | |
| 2015/0141320 A1 | 5/2015 | Krieg et al. | |
| 2015/0191723 A1 | 7/2015 | Rigo et al. | |
| 2017/0191064 A1 | 7/2017 | Costa et al. | |

FOREIGN PATENT DOCUMENTS

| | | |
|---|---|---|
| JP | 2011256171 A | 12/2011 |
| WO | 2017/081223 A1 | 5/2017 |

OTHER PUBLICATIONS

Japan Office Action, JP Application No. 2020-529238, dated Nov. 15, 2022.
International Search Report issued for PCT/US2018/063416, dated May 10, 2019.
Meng et al. Towards a therapy for Angelman syndrome by reduction of a long non-coding RNA, Nature, vol. 518 (7539), p. 402-12, 2015.
Burel et al., Hepatotoxicity of high affinity gapmer antisense oligonucleotides is mediated by RNase H1 dependent promiscuous reduction of very long pre-mRNA transcripts, Nucleic Acids Res., vol. 44(5), p. 2093-109, 2016.
Elmen et al., Nucleic Acids Research vol. 33(1):439-447, 2005.
Office Action and Prior Art Search, issued by Russia Patent Office, Russian Patent Application No. 2020121752, dated Jun. 8, 2022.
Chan, Wai-Yee, et al., "The complexity of antisense transcription revealed by the study of developing male germ cells," Genomics, vol. 87 (2006), pp. 681-692.
Lapidot, Michal, et al., "Genome-wide natural antisense transcription: coupling it's regulation to its different regulatory mechanisms," EMBO Reports, vol. 7, No. 12 (2006), pp. 1216-1222.

*Primary Examiner* — Sean McGarry
(74) *Attorney, Agent, or Firm* — Thomas | Horstemeyer, LLP

(57) ABSTRACT

Disclosed herein are antisense oligonucleotides that are capable of inducing expression of ubiquitin-protein ligase E3A (UBE3A) from the paternal allele in animal or human neurons. The oligonucleotides target the suppressor of the UBE3A paternal allele by hybridization to SNHG14 long non-coding RNA at the 5'-end of UBE3A-AS, which is downstream of SNORD115-45 snoRNA. Also disclosed are pharmaceutical compositions and methods for treatment of Angelman syndrome.

1 Claim, 30 Drawing Sheets
Specification includes a Sequence Listing.

ASO-C

Topotecan

ASO-B

ASO-1.1

Ube3a$^{YFP}$

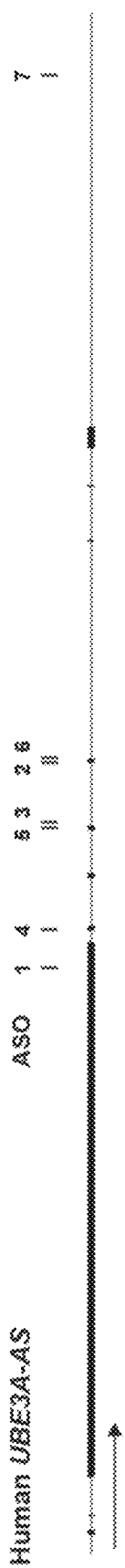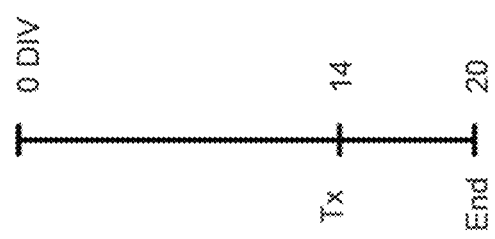
FIG. 3A
FIG. 3B

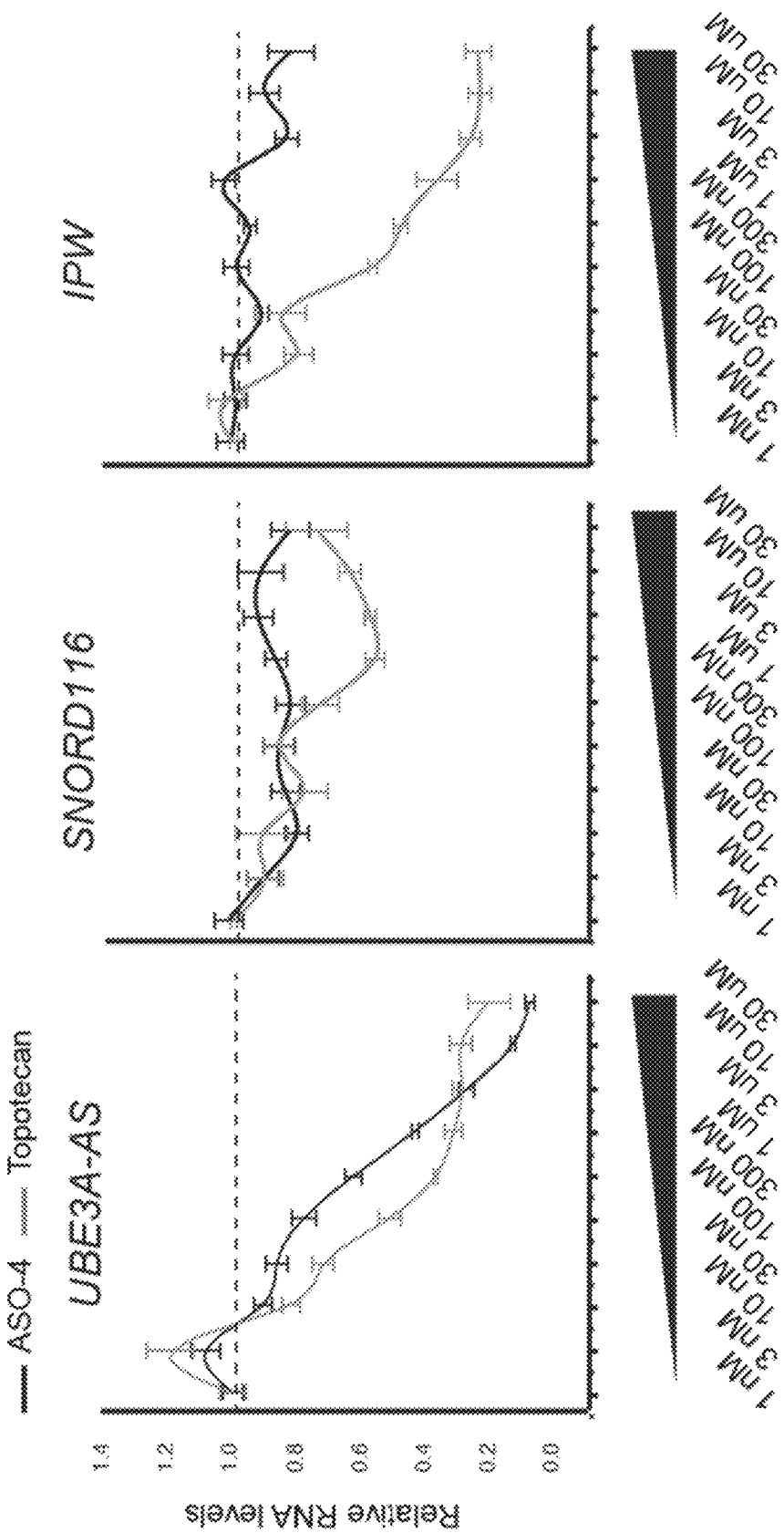

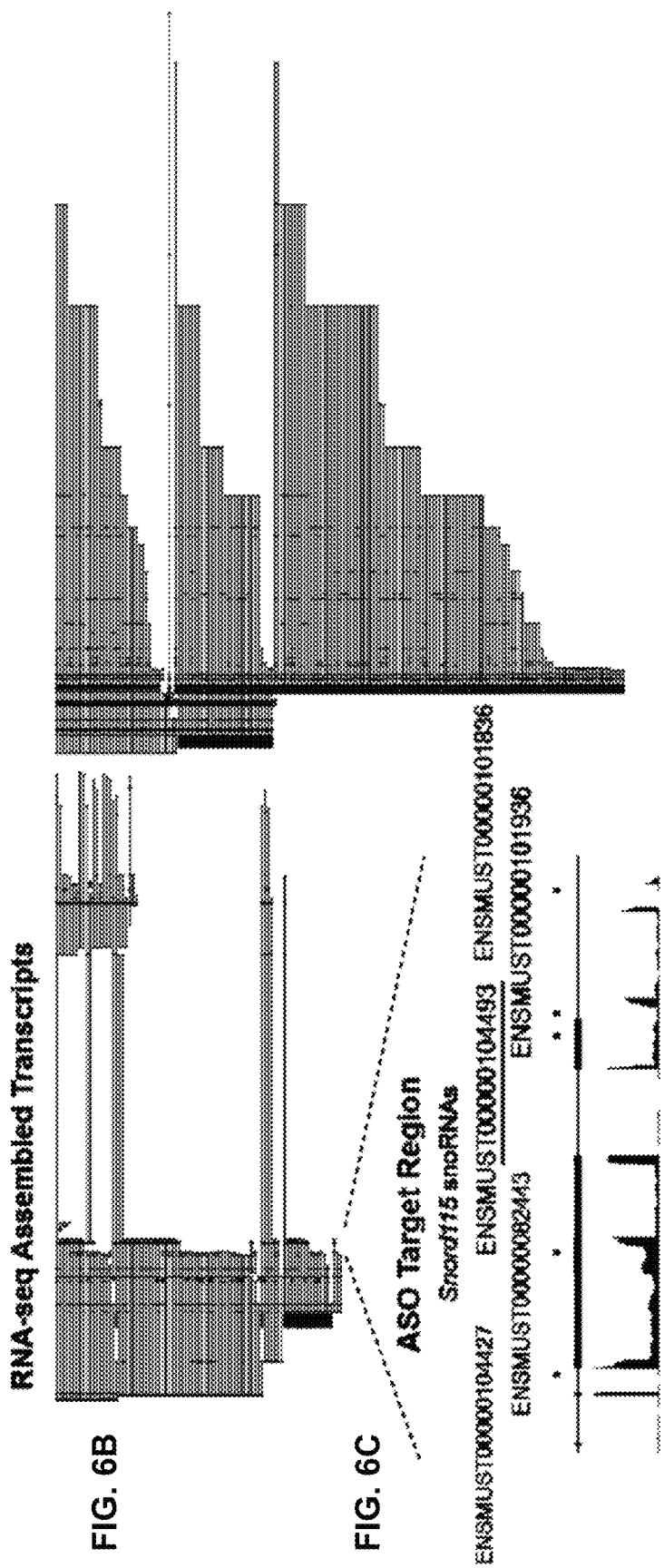

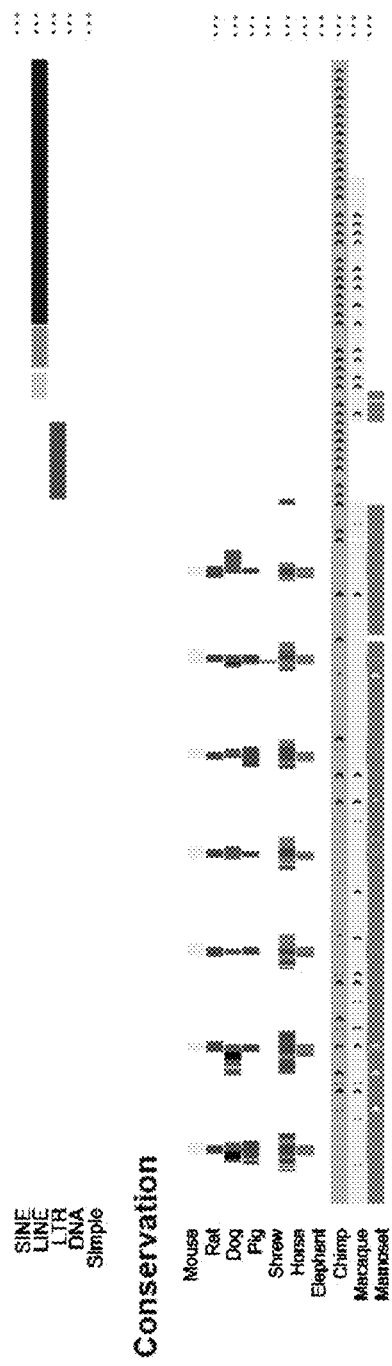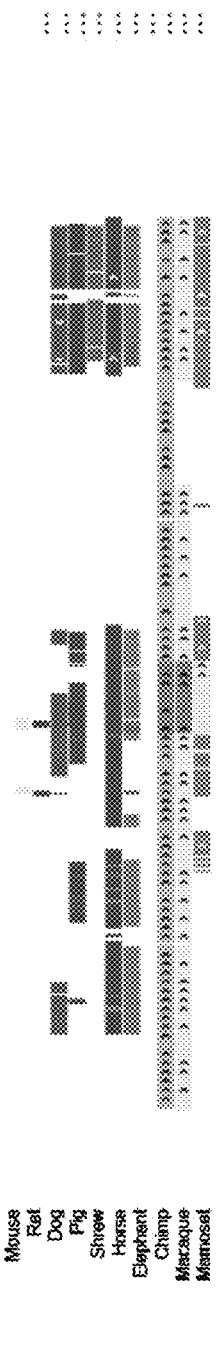

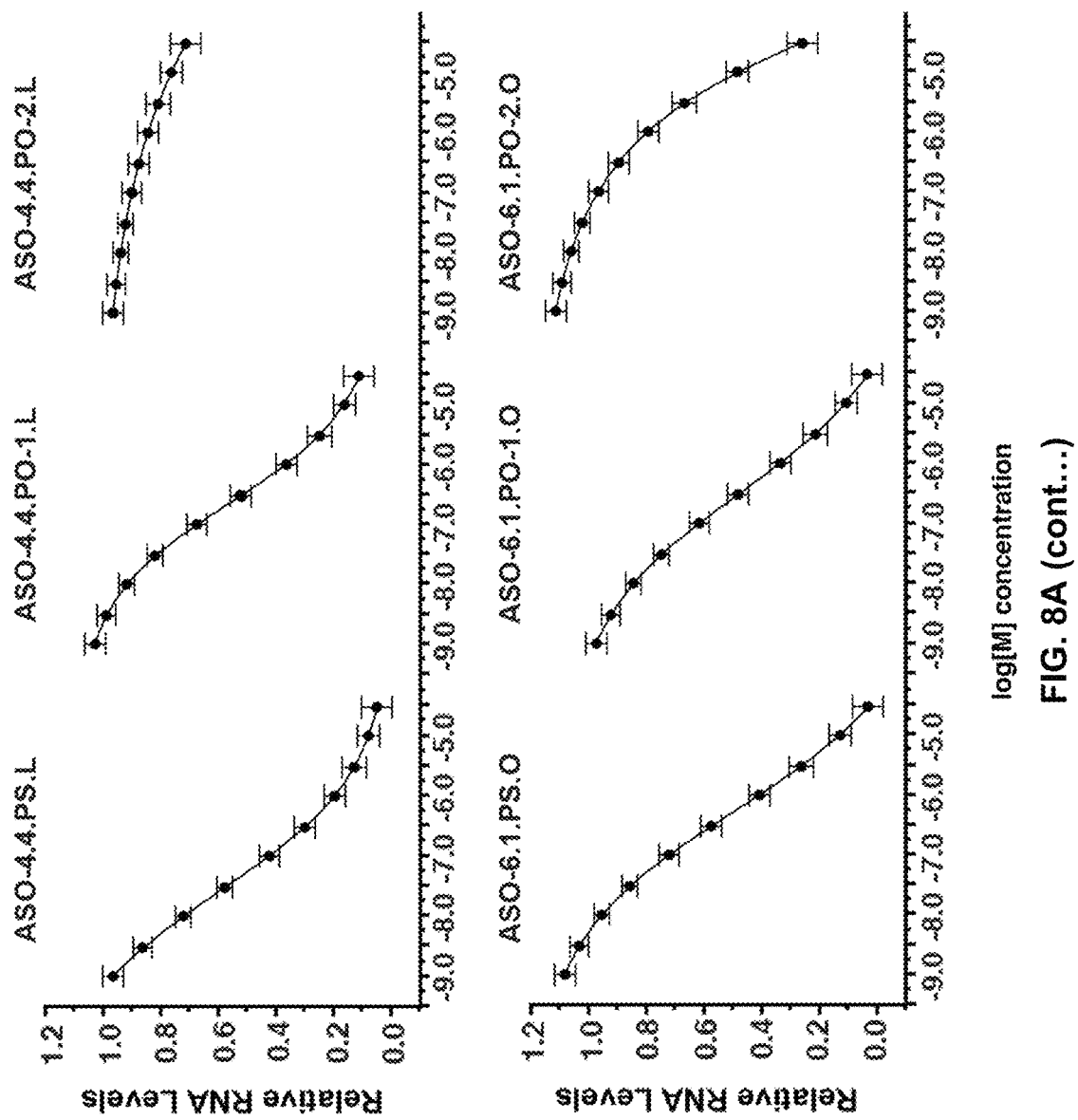
FIG. 8A (cont...)

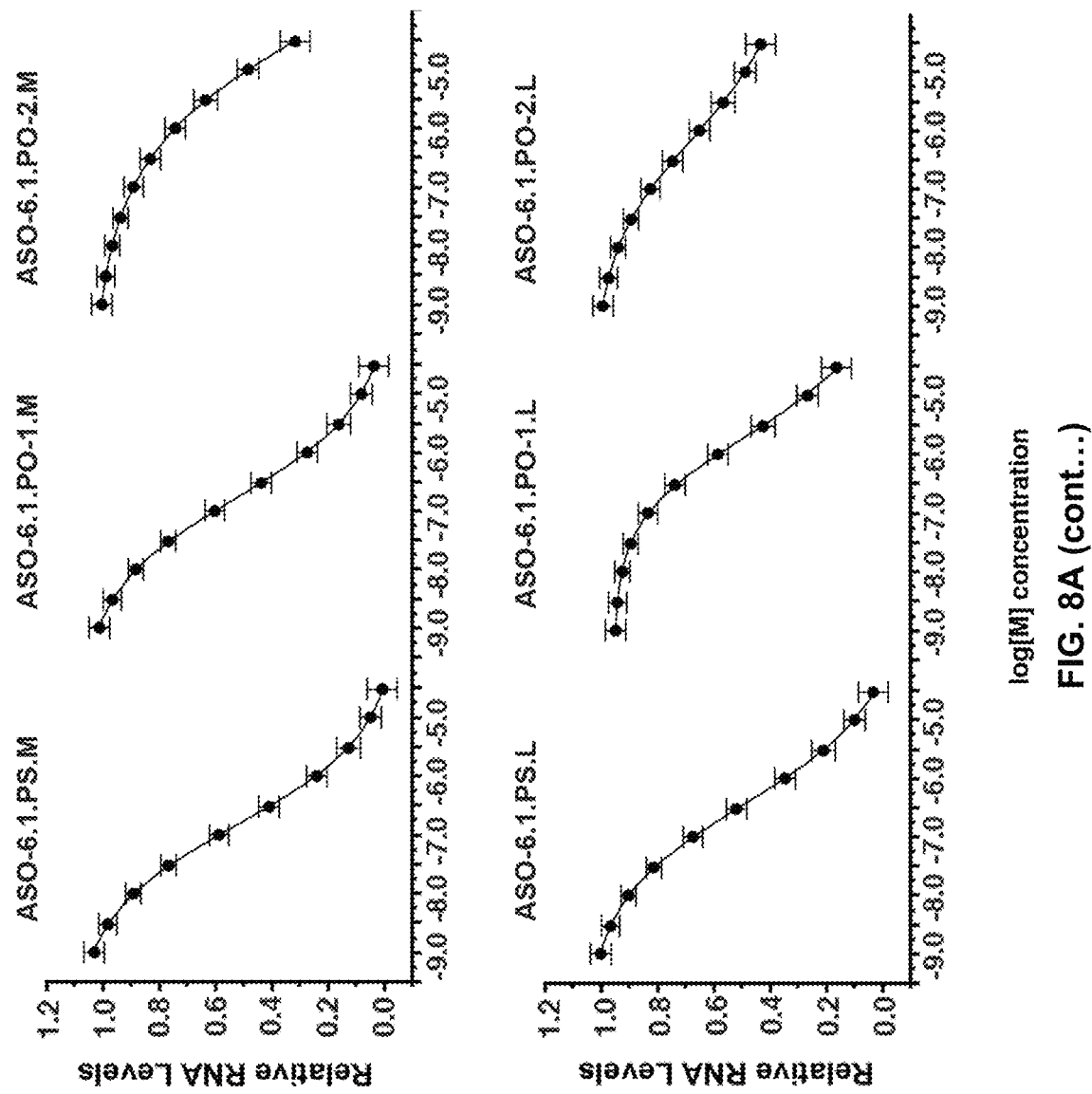
FIG. 8A (cont...)

SEQUENCE LISTING

```
<160> NUMBER OF SEQ ID NOS: 605

<210> SEQ ID NO 1
<211> LENGTH: 184
<212> TYPE: DNA
<213> ORGANISM: Artificial Sequence
<220> FEATURE:
<223> OTHER INFORMATION: Synthetic Construct

<400> SEQUENCE: 1
atgatgatat ggaagaaaag cactctttgg cctgttgtga ctgggacagt tgacagcacc      60
caggtgtcct ttaatgaaaa tgctcttgac accaatgcat cctagcatca cagcttcagg     120
aagccttctc aagtgtgcat ggggagtact atgtctttca tcaataatga aatcttctga     180
tttg                                                                   184

<210> SEQ ID NO 2
<211> LENGTH: 133
<212> TYPE: DNA
<213> ORGANISM: Artificial Sequence
<220> FEATURE:
<223> OTHER INFORMATION: Synthetic Construct

<400> SEQUENCE: 2
taagacatgc tgccaagaga tgtgccattc tattataaaa gatcagtagc ttcctttacc      60
gacgtgtata ttctatctag aacattgagc tatggaagac tcccacctaa gggaattagt     120 tttacaccctt cag                                                        133

<210> SEQ ID NO 3
<211> LENGTH: 125
<212> TYPE: DNA
<213> ORGANISM: Artificial Sequence
<220> FEATURE:
<223> OTHER INFORMATION: Synthetic Construct

<400> SEQUENCE: 3
ataaagactg ctgagaagag caccctctgg tgttgtcaca gaggcaagtg ctaccgcaca      60
```

```
ggcatgctgc agtgaattta actgatcctc tgtccctgca accgttgttt aaggatgcta      120
ttctg                                                                 125

<210> SEQ ID NO 4
<211> LENGTH: 129
<212> TYPE: DNA
<213> ORGANISM: Artificial Sequence
<220> FEATURE:
<223> OTHER INFORMATION: Synthetic Construct

<400> SEQUENCE: 4
aaaagactgt ggaggaagaa aacccttttac cctgttgttc agggagaaac tgacaccact      60
caactgcctg gcactgaaaa tgtggcatcc agtccacttt accatcagtg tttaaggaaa     120
ccatctctg                                                             129

<210> SEQ ID NO 5
<211> LENGTH: 117
<212> TYPE: DNA
<213> ORGANISM: Artificial Sequence
<220> FEATURE:
<223> OTHER INFORMATION: Synthetic Construct

<400> SEQUENCE: 5
ataaggatga ctgaggaaga gtactctttg gcttgttgac accagcacag ctgacacacc      60
cagatatctg tttggtctcc tgtgaacttt caaccaggat ttaaggatgc cactctg        117

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tagaggtgaa ggccaggcac                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gtactcttcc tcagtcatcc                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
tgtcagtttc tccctgaaca                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
```
tagaatggca catctcttgg                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gttttcttcc tccacagtct                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ctggtgtcaa caagccaaag                                          20

<210> SEQ ID NO 12
<211> LENGTH: 18
<212> TYPE: RNA
<213> ORGANISM: Artificial Sequence
<220> FEATURE:
<223> OTHER INFORMATION: Synthetic Construct

<400> SEQUENCE: 12
gaaaaugcuc uugacacc                                            18

<210> SEQ ID NO 13
<211> LENGTH: 19
<212> TYPE: RNA
<213> ORGANISM: Artificial Sequence
<220> FEATURE:
<223> OTHER INFORMATION: Synthetic Construct

<400> SEQUENCE: 13
gaaaaugcuc uugacacca                                           19

<210> SEQ ID NO 14
<211> LENGTH: 20
<212> TYPE: RNA
<213> ORGANISM: Artificial Sequence
<220> FEATURE:
<223> OTHER INFORMATION: Synthetic Construct

<400> SEQUENCE: 14
gaaaaugcuc uugacaccaa                                          20

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
ggtgtcaaga gcattttc                                            18

<210> SEQ ID NO 16
<211> LENGTH: 19
<212> TYPE: DNA

```
<213> ORGANISM: Artificial Sequence
<220> FEATURE:
<223> OTHER INFORMATION: Synthetic Construct

<400> SEQUENCE: 16
tggtgtcaag agcattttc                                                   19

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
ttggtgtcaa gagcattttc                                                  20

<210> SEQ ID NO 18
<211> LENGTH: 18
<212> TYPE: RNA
<213> ORGANISM: Artificial Sequence
<220> FEATURE:
<223> OTHER INFORMATION: Synthetic Construct

<400> SEQUENCE: 18
caugcugcca agagaugu                                                    18

<210> SEQ ID NO 19
<211> LENGTH: 19
<212> TYPE: RNA
<213> ORGANISM: Artificial Sequence
<220> FEATURE:
<223> OTHER INFORMATION: Synthetic Construct

<400> SEQUENCE: 19
caugcugcca agagaugug                                                   19

<210> SEQ ID NO 20
<211> LENGTH: 20
<212> TYPE: RNA
<213> ORGANISM: Artificial Sequence
<220> FEATURE:
<223> OTHER INFORMATION: Synthetic Construct

<400> SEQUENCE: 20
caugcugcca agagaugugc                                                  20

<210> SEQ ID NO 21
<211> LENGTH: 18
<212> TYPE: RNA
<213> ORGANISM: Artificial Sequence
<220> FEATURE:
<223> OTHER INFORMATION: Synthetic Construct

<400> SEQUENCE: 21
augcugccaa gagaugug                                                    18

<210> SEQ ID NO 22
<211> LENGTH: 19
<212> TYPE: RNA
<213> ORGANISM: Artificial Sequence
<220> FEATURE:
<223> OTHER INFORMATION: Synthetic Construct

<400> SEQUENCE: 22
augcugccaa gagaugugc                                                   19
```

<210> SEQ ID NO 23
<211> LENGTH: 20
<212> TYPE: RNA
<213> ORGANISM: Artificial Sequence
<220> FEATURE:
<223> OTHER INFORMATION: Synthetic Construct

<400> SEQUENCE: 23
augcugccaa gagaugugcc                                               20

<210> SEQ ID NO 24
<211> LENGTH: 19
<212> TYPE: RNA
<213> ORGANISM: Artificial Sequence
<220> FEATURE:
<223> OTHER INFORMATION: Synthetic Construct

<400> SEQUENCE: 24
ugcugccaag agaugugcc                                                19

<210> SEQ ID NO 25
<211> LENGTH: 20
<212> TYPE: RNA
<213> ORGANISM: Artificial Sequence
<220> FEATURE:
<223> OTHER INFORMATION: Synthetic Construct

<400> SEQUENCE: 25
ugcugccaag agaugugcca                                               20

<210> SEQ ID NO 26
<211> LENGTH: 19
<212> TYPE: RNA
<213> ORGANISM: Artificial Sequence
<220> FEATURE:
<223> OTHER INFORMATION: Synthetic Construct

<400> SEQUENCE: 26
gcugccaaga gaugugcca                                                19

<210> SEQ ID NO 27
<211> LENGTH: 20
<212> TYPE: RNA
<213> ORGANISM: Artificial Sequence
<220> FEATURE:
<223> OTHER INFORMATION: Synthetic Construct

<400> SEQUENCE: 27
gcugccaaga gaugugccau                                               20

<210> SEQ ID NO 28
<211> LENGTH: 18
<212> TYPE: RNA
<213> ORGANISM: Artificial Sequence
<220> FEATURE:
<223> OTHER INFORMATION: Synthetic Construct

<400> SEQUENCE: 28
cugccaagag augugcca                                                 18

<210> SEQ ID NO 29
<211> LENGTH: 19
<212> TYPE: RNA
<213> ORGANISM: Artificial Sequence
<220> FEATURE:

<223> OTHER INFORMATION: Synthetic Construct

<400> SEQUENCE: 29
cugccaagag augugccau                                                          19

<210> SEQ ID NO 30
<211> LENGTH: 20
<212> TYPE: RNA
<213> ORGANISM: Artificial Sequence
<220> FEATURE:
<223> OTHER INFORMATION: Synthetic Construct

<400> SEQUENCE: 30
cugccaagag augugccauu                                                         20

<210> SEQ ID NO 31
<211> LENGTH: 18
<212> TYPE: RNA
<213> ORGANISM: Artificial Sequence
<220> FEATURE:
<223> OTHER INFORMATION: Synthetic Construct

<400> SEQUENCE: 31
ugccaagaga ugugccau                                                           18

<210> SEQ ID NO 32
<211> LENGTH: 19
<212> TYPE: RNA
<213> ORGANISM: Artificial Sequence
<220> FEATURE:
<223> OTHER INFORMATION: Synthetic Construct

<400> SEQUENCE: 32
ugccaagaga ugugccauu                                                          19

<210> SEQ ID NO 33
<211> LENGTH: 20
<212> TYPE: RNA
<213> ORGANISM: Artificial Sequence
<220> FEATURE:
<223> OTHER INFORMATION: Synthetic Construct

<400> SEQUENCE: 33
ugccaagaga ugugccauuc                                                         20

<210> SEQ ID NO 34
<211> LENGTH: 18
<212> TYPE: RNA
<213> ORGANISM: Artificial Sequence
<220> FEATURE:
<223> OTHER INFORMATION: Synthetic Construct

<400> SEQUENCE: 34
gccaagagau gugccauu                                                           18

<210> SEQ ID NO 35
<211> LENGTH: 19
<212> TYPE: RNA
<213> ORGANISM: Artificial Sequence
<220> FEATURE:
<223> OTHER INFORMATION: Synthetic Construct

<400> SEQUENCE: 35
gccaagagau gugccauuc                                                          19

```
<210> SEQ ID NO 36
<211> LENGTH: 20
<212> TYPE: RNA
<213> ORGANISM: Artificial Sequence
<220> FEATURE:
<223> OTHER INFORMATION: Synthetic Construct

<400> SEQUENCE: 36
gccaagagau gugccauucu                                                20

<210> SEQ ID NO 37
<211> LENGTH: 18
<212> TYPE: RNA
<213> ORGANISM: Artificial Sequence
<220> FEATURE:
<223> OTHER INFORMATION: Synthetic Construct

<400> SEQUENCE: 37
ccaagagaug ugccauuc                                                  18

<210> SEQ ID NO 38
<211> LENGTH: 19
<212> TYPE: RNA
<213> ORGANISM: Artificial Sequence
<220> FEATURE:
<223> OTHER INFORMATION: Synthetic Construct

<400> SEQUENCE: 38
ccaagagaug ugccauucu                                                 19

<210> SEQ ID NO 39
<211> LENGTH: 20
<212> TYPE: RNA
<213> ORGANISM: Artificial Sequence
<220> FEATURE:
<223> OTHER INFORMATION: Synthetic Construct

<400> SEQUENCE: 39
ccaagagaug ugccauucua                                                20

<210> SEQ ID NO 40
<211> LENGTH: 18
<212> TYPE: RNA
<213> ORGANISM: Artificial Sequence
<220> FEATURE:
<223> OTHER INFORMATION: Synthetic Construct

<400> SEQUENCE: 40
caagagaugu gccauucu                                                  18

<210> SEQ ID NO 41
<211> LENGTH: 19
<212> TYPE: RNA
<213> ORGANISM: Artificial Sequence
<220> FEATURE:
<223> OTHER INFORMATION: Synthetic Construct

<400> SEQUENCE: 41
caagagaugu gccauucua                                                 19

<210> SEQ ID NO 42
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 42
caagagaugu gccauucuau                                                   20

<210> SEQ ID NO 43
<211> LENGTH: 18
<212> TYPE: RNA
<213> ORGANISM: Artificial Sequence
<220> FEATURE:
<223> OTHER INFORMATION: Synthetic Construct

<400> SEQUENCE: 43
uccuuuaccg acguguau                                                     18

<210> SEQ ID NO 44
<211> LENGTH: 19
<212> TYPE: RNA
<213> ORGANISM: Artificial Sequence
<220> FEATURE:
<223> OTHER INFORMATION: Synthetic Construct

<400> SEQUENCE: 44
uccuuuaccg acguguaua                                                    19

<210> SEQ ID NO 45
<211> LENGTH: 20
<212> TYPE: RNA
<213> ORGANISM: Artificial Sequence
<220> FEATURE:
<223> OTHER INFORMATION: Synthetic Construct

<400> SEQUENCE: 45
uccuuuaccg acguguauau                                                   20

<210> SEQ ID NO 46
<211> LENGTH: 18
<212> TYPE: RNA
<213> ORGANISM: Artificial Sequence
<220> FEATURE:
<223> OTHER INFORMATION: Synthetic Construct

<400> SEQUENCE: 46
ccuuuaccga cguguaua                                                     18

<210> SEQ ID NO 47
<211> LENGTH: 19
<212> TYPE: RNA
<213> ORGANISM: Artificial Sequence
<220> FEATURE:
<223> OTHER INFORMATION: Synthetic Construct

<400> SEQUENCE: 47
ccuuuaccga cguguauau                                                    19

<210> SEQ ID NO 48
<211> LENGTH: 20
<212> TYPE: RNA
<213> ORGANISM: Artificial Sequence
<220> FEATURE:
<223> OTHER INFORMATION: Synthetic Construct

<400> SEQUENCE: 48
ccuuuaccga cguguauauu                                                   20

<210> SEQ ID NO 49
<211> LENGTH: 20
```

```
<212> TYPE: RNA
<213> ORGANISM: Artificial Sequence
<220> FEATURE:
<223> OTHER INFORMATION: Synthetic Construct

<400> SEQUENCE: 49
accgacgugu auauucuauc                                               20

<210> SEQ ID NO 50
<211> LENGTH: 19
<212> TYPE: RNA
<213> ORGANISM: Artificial Sequence
<220> FEATURE:
<223> OTHER INFORMATION: Synthetic Construct

<400> SEQUENCE: 50
ccgacgugua uauucuauc                                                19

<210> SEQ ID NO 51
<211> LENGTH: 20
<212> TYPE: RNA
<213> ORGANISM: Artificial Sequence
<220> FEATURE:
<223> OTHER INFORMATION: Synthetic Construct

<400> SEQUENCE: 51
ccgacgugua uauucuaucu                                               20

<210> SEQ ID NO 52
<211> LENGTH: 20
<212> TYPE: RNA
<213> ORGANISM: Artificial Sequence
<220> FEATURE:
<223> OTHER INFORMATION: Synthetic Construct

<400> SEQUENCE: 52
ucuagaacau ugagcuaugg                                               20

<210> SEQ ID NO 53
<211> LENGTH: 18
<212> TYPE: RNA
<213> ORGANISM: Artificial Sequence
<220> FEATURE:
<223> OTHER INFORMATION: Synthetic Construct

<400> SEQUENCE: 53
cauugagcua uggaagac                                                 18

<210> SEQ ID NO 54
<211> LENGTH: 20
<212> TYPE: RNA
<213> ORGANISM: Artificial Sequence
<220> FEATURE:
<223> OTHER INFORMATION: Synthetic Construct

<400> SEQUENCE: 54
cuauggaaga cucccaccua                                               20

<210> SEQ ID NO 55
<211> LENGTH: 19
<212> TYPE: RNA
<213> ORGANISM: Artificial Sequence
<220> FEATURE:
<223> OTHER INFORMATION: Synthetic Construct

<400> SEQUENCE: 55
```

```
uauggaagac ucccaccua                                                    19

<210> SEQ ID NO 56
<211> LENGTH: 20
<212> TYPE: RNA
<213> ORGANISM: Artificial Sequence
<220> FEATURE:
<223> OTHER INFORMATION: Synthetic Construct

<400> SEQUENCE: 56
uauggaagac ucccaccuaa                                                   20

<210> SEQ ID NO 57
<211> LENGTH: 18
<212> TYPE: RNA
<213> ORGANISM: Artificial Sequence
<220> FEATURE:
<223> OTHER INFORMATION: Synthetic Construct

<400> SEQUENCE: 57
auggaagacu cccaccua                                                     18

<210> SEQ ID NO 58
<211> LENGTH: 19
<212> TYPE: RNA
<213> ORGANISM: Artificial Sequence
<220> FEATURE:
<223> OTHER INFORMATION: Synthetic Construct

<400> SEQUENCE: 58
auggaagacu cccaccuaa                                                    19

<210> SEQ ID NO 59
<211> LENGTH: 18
<212> TYPE: RNA
<213> ORGANISM: Artificial Sequence
<220> FEATURE:
<223> OTHER INFORMATION: Synthetic Construct

<400> SEQUENCE: 59
uggaagacuc ccaccuaa                                                     18

<210> SEQ ID NO 60
<211> LENGTH: 20
<212> TYPE: RNA
<213> ORGANISM: Artificial Sequence
<220> FEATURE:
<223> OTHER INFORMATION: Synthetic Construct

<400> SEQUENCE: 60
gacucccacc uaagggaauu                                                   20

<210> SEQ ID NO 61
<211> LENGTH: 18
<212> TYPE: RNA
<213> ORGANISM: Artificial Sequence
<220> FEATURE:
<223> OTHER INFORMATION: Synthetic Construct

<400> SEQUENCE: 61
acucccaccu aagggaau                                                     18

<210> SEQ ID NO 62
<211> LENGTH: 19
<212> TYPE: RNA
<213> ORGANISM: Artificial Sequence
```

```
<220> FEATURE:
<223> OTHER INFORMATION: Synthetic Construct

<400> SEQUENCE: 62
acucccaccu aagggaauu                                              19

<210> SEQ ID NO 63
<211> LENGTH: 20
<212> TYPE: RNA
<213> ORGANISM: Artificial Sequence
<220> FEATURE:
<223> OTHER INFORMATION: Synthetic Construct

<400> SEQUENCE: 63
acucccaccu aagggaauua                                             20

<210> SEQ ID NO 64
<211> LENGTH: 18
<212> TYPE: RNA
<213> ORGANISM: Artificial Sequence
<220> FEATURE:
<223> OTHER INFORMATION: Synthetic Construct

<400> SEQUENCE: 64
cucccaccua agggaauu                                               18

<210> SEQ ID NO 65
<211> LENGTH: 19
<212> TYPE: RNA
<213> ORGANISM: Artificial Sequence
<220> FEATURE:
<223> OTHER INFORMATION: Synthetic Construct

<400> SEQUENCE: 65
cucccaccua agggaauua                                              19

<210> SEQ ID NO 66
<211> LENGTH: 18
<212> TYPE: RNA
<213> ORGANISM: Artificial Sequence
<220> FEATURE:
<223> OTHER INFORMATION: Synthetic Construct

<400> SEQUENCE: 66
ucccaccuaa gggaauua                                               18

<210> SEQ ID NO 67
<211> LENGTH: 18
<212> TYPE: DNA
<213> ORGANISM: Artificial Sequence
<220> FEATURE:
<223> OTHER INFORMATION: Synthetic Construct

<400> SEQUENCE: 67
acatctcttg gcagcatg                                               18

<210> SEQ ID NO 68
<211> LENGTH: 19
<212> TYPE: DNA
<213> ORGANISM: Artificial Sequence
<220> FEATURE:
<223> OTHER INFORMATION: Synthetic Construct

<400> SEQUENCE: 68
cacatctctt ggcagcatg                                              19
```

<210> SEQ ID NO 69
<211> LENGTH: 20
<212> TYPE: DNA
<213> ORGANISM: Artificial Sequence
<220> FEATURE:
<223> OTHER INFORMATION: Synthetic Construct

<400> SEQUENCE: 69
gcacatctct tggcagcatg                                              20

<210> SEQ ID NO 70
<211> LENGTH: 18
<212> TYPE: DNA
<213> ORGANISM: Artificial Sequence
<220> FEATURE:
<223> OTHER INFORMATION: Synthetic Construct

<400> SEQUENCE: 70
cacatctctt ggcagcat                                                18

<210> SEQ ID NO 71
<211> LENGTH: 19
<212> TYPE: DNA
<213> ORGANISM: Artificial Sequence
<220> FEATURE:
<223> OTHER INFORMATION: Synthetic Construct

<400> SEQUENCE: 71
gcacatctct tggcagcat                                               19

<210> SEQ ID NO 72
<211> LENGTH: 20
<212> TYPE: DNA
<213> ORGANISM: Artificial Sequence
<220> FEATURE:
<223> OTHER INFORMATION: Synthetic Construct

<400> SEQUENCE: 72
ggcacatctc ttggcagcat                                              20

<210> SEQ ID NO 73
<211> LENGTH: 19
<212> TYPE: DNA
<213> ORGANISM: Artificial Sequence
<220> FEATURE:
<223> OTHER INFORMATION: Synthetic Construct

<400> SEQUENCE: 73
ggcacatctc ttggcagca                                               19

<210> SEQ ID NO 74
<211> LENGTH: 20
<212> TYPE: DNA
<213> ORGANISM: Artificial Sequence
<220> FEATURE:
<223> OTHER INFORMATION: Synthetic Construct

<400> SEQUENCE: 74
tggcacatct cttggcagca                                              20

<210> SEQ ID NO 75
<211> LENGTH: 19
<212> TYPE: DNA
<213> ORGANISM: Artificial Sequence
<220> FEATURE:
<223> OTHER INFORMATION: Synthetic Construct

```
<400> SEQUENCE: 75
tggcacatct cttggcagc                                                19

<210> SEQ ID NO 76
<211> LENGTH: 20
<212> TYPE: DNA
<213> ORGANISM: Artificial Sequence
<220> FEATURE:
<223> OTHER INFORMATION: Synthetic Construct

<400> SEQUENCE: 76
atggcacatc tcttggcagc                                               20

<210> SEQ ID NO 77
<211> LENGTH: 18
<212> TYPE: DNA
<213> ORGANISM: Artificial Sequence
<220> FEATURE:
<223> OTHER INFORMATION: Synthetic Construct

<400> SEQUENCE: 77
tggcacatct cttggcag                                                 18

<210> SEQ ID NO 78
<211> LENGTH: 19
<212> TYPE: DNA
<213> ORGANISM: Artificial Sequence
<220> FEATURE:
<223> OTHER INFORMATION: Synthetic Construct

<400> SEQUENCE: 78
atggcacatc tcttggcag                                                19

<210> SEQ ID NO 79
<211> LENGTH: 20
<212> TYPE: DNA
<213> ORGANISM: Artificial Sequence
<220> FEATURE:
<223> OTHER INFORMATION: Synthetic Construct

<400> SEQUENCE: 79
aatggcacat ctcttggcag                                               20

<210> SEQ ID NO 80
<211> LENGTH: 18
<212> TYPE: DNA
<213> ORGANISM: Artificial Sequence
<220> FEATURE:
<223> OTHER INFORMATION: Synthetic Construct

<400> SEQUENCE: 80
atggcacatc tcttggca                                                 18

<210> SEQ ID NO 81
<211> LENGTH: 19
<212> TYPE: DNA
<213> ORGANISM: Artificial Sequence
<220> FEATURE:
<223> OTHER INFORMATION: Synthetic Construct

<400> SEQUENCE: 81
aatggcacat ctcttggca                                                19

<210> SEQ ID NO 82
```

<210> SEQ ID NO 82
<211> LENGTH: 20
<212> TYPE: DNA
<213> ORGANISM: Artificial Sequence
<220> FEATURE:
<223> OTHER INFORMATION: Synthetic Construct

<400> SEQUENCE: 82
gaatggcaca tctcttggca                                               20

<210> SEQ ID NO 83
<211> LENGTH: 18
<212> TYPE: DNA
<213> ORGANISM: Artificial Sequence
<220> FEATURE:
<223> OTHER INFORMATION: Synthetic Construct

<400> SEQUENCE: 83
aatggcacat ctcttggc                                                 18

<210> SEQ ID NO 84
<211> LENGTH: 19
<212> TYPE: DNA
<213> ORGANISM: Artificial Sequence
<220> FEATURE:
<223> OTHER INFORMATION: Synthetic Construct

<400> SEQUENCE: 84
gaatggcaca tctcttggc                                                19

<210> SEQ ID NO 85
<211> LENGTH: 20
<212> TYPE: DNA
<213> ORGANISM: Artificial Sequence
<220> FEATURE:
<223> OTHER INFORMATION: Synthetic Construct

<400> SEQUENCE: 85
agaatggcac atctcttggc                                               20

<210> SEQ ID NO 86
<211> LENGTH: 18
<212> TYPE: DNA
<213> ORGANISM: Artificial Sequence
<220> FEATURE:
<223> OTHER INFORMATION: Synthetic Construct

<400> SEQUENCE: 86
gaatggcaca tctcttgg                                                 18

<210> SEQ ID NO 87
<211> LENGTH: 19
<212> TYPE: DNA
<213> ORGANISM: Artificial Sequence
<220> FEATURE:
<223> OTHER INFORMATION: Synthetic Construct

<400> SEQUENCE: 87
agaatggcac atctcttgg                                                19

<210> SEQ ID NO 88
<211> LENGTH: 20
<212> TYPE: DNA
<213> ORGANISM: Artificial Sequence
<220> FEATURE:
<223> OTHER INFORMATION: Synthetic Construct

<400> SEQUENCE: 88
tagaatggca catctcttgg                                    20

<210> SEQ ID NO 89
<211> LENGTH: 18
<212> TYPE: DNA
<213> ORGANISM: Artificial Sequence
<220> FEATURE:
<223> OTHER INFORMATION: Synthetic Construct

<400> SEQUENCE: 89
agaatggcac atctcttg                                      18

<210> SEQ ID NO 90
<211> LENGTH: 19
<212> TYPE: DNA
<213> ORGANISM: Artificial Sequence
<220> FEATURE:
<223> OTHER INFORMATION: Synthetic Construct

<400> SEQUENCE: 90
tagaatggca catctcttg                                     19

<210> SEQ ID NO 91
<211> LENGTH: 20
<212> TYPE: DNA
<213> ORGANISM: Artificial Sequence
<220> FEATURE:
<223> OTHER INFORMATION: Synthetic Construct

<400> SEQUENCE: 91
atagaatggc acatctcttg                                    20

<210> SEQ ID NO 92
<211> LENGTH: 18
<212> TYPE: DNA
<213> ORGANISM: Artificial Sequence
<220> FEATURE:
<223> OTHER INFORMATION: Synthetic Construct

<400> SEQUENCE: 92
atacacgtcg gtaaagga                                      18

<210> SEQ ID NO 93
<211> LENGTH: 19
<212> TYPE: DNA
<213> ORGANISM: Artificial Sequence
<220> FEATURE:
<223> OTHER INFORMATION: Synthetic Construct

<400> SEQUENCE: 93
tatacacgtc ggtaaagga                                     19

<210> SEQ ID NO 94
<211> LENGTH: 20
<212> TYPE: DNA
<213> ORGANISM: Artificial Sequence
<220> FEATURE:
<223> OTHER INFORMATION: Synthetic Construct

<400> SEQUENCE: 94
atatacacgt cggtaaagga                                    20

<210> SEQ ID NO 95
<211> LENGTH: 18
<212> TYPE: DNA

```
<213> ORGANISM: Artificial Sequence
<220> FEATURE:
<223> OTHER INFORMATION: Synthetic Construct

<400> SEQUENCE: 95
tatacacgtc ggtaaagg                                                  18

<210> SEQ ID NO 96
<211> LENGTH: 19
<212> TYPE: DNA
<213> ORGANISM: Artificial Sequence
<220> FEATURE:
<223> OTHER INFORMATION: Synthetic Construct

<400> SEQUENCE: 96
atatacacgt cggtaaagg                                                 19

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct

<400> SEQUENCE: 97
aatatacacg tcggtaaagg                                                20

<210> SEQ ID NO 98
<211> LENGTH: 20
<212> TYPE: DNA
<213> ORGANISM: Artificial Sequence
<220> FEATURE:
<223> OTHER INFORMATION: Synthetic Construct

<400> SEQUENCE: 98
gatagaatat acacgtcggt                                                20

<210> SEQ ID NO 99
<211> LENGTH: 19
<212> TYPE: DNA
<213> ORGANISM: Artificial Sequence
<220> FEATURE:
<223> OTHER INFORMATION: Synthetic Construct

<400> SEQUENCE: 99
gatagaatat acacgtcgg                                                 19

<210> SEQ ID NO 100
<211> LENGTH: 20
<212> TYPE: DNA
<213> ORGANISM: Artificial Sequence
<220> FEATURE:
<223> OTHER INFORMATION: Synthetic Construct

<400> SEQUENCE: 100
agatagaata tacacgtcgg                                                20

<210> SEQ ID NO 101
<211> LENGTH: 20
<212> TYPE: DNA
<213> ORGANISM: Artificial Sequence
<220> FEATURE:
<223> OTHER INFORMATION: Synthetic Construct

<400> SEQUENCE: 101
ccatagctca atgttctaga                                                20
```

<210> SEQ ID NO 102
<211> LENGTH: 18
<212> TYPE: DNA
<213> ORGANISM: Artificial Sequence
<220> FEATURE:
<223> OTHER INFORMATION: Synthetic Construct

<400> SEQUENCE: 102
gtcttccata gctcaatg                                                 18

<210> SEQ ID NO 103
<211> LENGTH: 20
<212> TYPE: DNA
<213> ORGANISM: Artificial Sequence
<220> FEATURE:
<223> OTHER INFORMATION: Synthetic Construct

<400> SEQUENCE: 103
taggtgggag tcttccatag                                               20

<210> SEQ ID NO 104
<211> LENGTH: 19
<212> TYPE: DNA
<213> ORGANISM: Artificial Sequence
<220> FEATURE:
<223> OTHER INFORMATION: Synthetic Construct

<400> SEQUENCE: 104
taggtgggag tcttccata                                                19

<210> SEQ ID NO 105
<211> LENGTH: 20
<212> TYPE: DNA
<213> ORGANISM: Artificial Sequence
<220> FEATURE:
<223> OTHER INFORMATION: Synthetic Construct

<400> SEQUENCE: 105
ttaggtggga gtcttccata                                               20

<210> SEQ ID NO 106
<211> LENGTH: 18
<212> TYPE: DNA
<213> ORGANISM: Artificial Sequence
<220> FEATURE:
<223> OTHER INFORMATION: Synthetic Construct

<400> SEQUENCE: 106
taggtgggag tcttccat                                                 18

<210> SEQ ID NO 107
<211> LENGTH: 19
<212> TYPE: DNA
<213> ORGANISM: Artificial Sequence
<220> FEATURE:
<223> OTHER INFORMATION: Synthetic Construct

<400> SEQUENCE: 107
ttaggtggga gtcttccat                                                19

<210> SEQ ID NO 108
<211> LENGTH: 18
<212> TYPE: DNA
<213> ORGANISM: Artificial Sequence
<220> FEATURE:

```
<223> OTHER INFORMATION: Synthetic Construct

<400> SEQUENCE: 108
ttaggtggga gtcttcca                                               18

<210> SEQ ID NO 109
<211> LENGTH: 20
<212> TYPE: DNA
<213> ORGANISM: Artificial Sequence
<220> FEATURE:
<223> OTHER INFORMATION: Synthetic Construct

<400> SEQUENCE: 109 aattcccttα ggtgggagtc                                             20

<210> SEQ ID NO 110
<211> LENGTH: 18
<212> TYPE: DNA
<213> ORGANISM: Artificial Sequence
<220> FEATURE:
<223> OTHER INFORMATION: Synthetic Construct

<400> SEQUENCE: 110
attcccttag gtgggagt                                               18

<210> SEQ ID NO 111
<211> LENGTH: 19
<212> TYPE: DNA
<213> ORGANISM: Artificial Sequence
<220> FEATURE:
<223> OTHER INFORMATION: Synthetic Construct

<400> SEQUENCE: 111 aattcccttα ggtgggagt                                              19

<210> SEQ ID NO 112
<211> LENGTH: 20
<212> TYPE: DNA
<213> ORGANISM: Artificial Sequence
<220> FEATURE:
<223> OTHER INFORMATION: Synthetic Construct

<400> SEQUENCE: 112
taattccctt aggtgggagt                                             20

<210> SEQ ID NO 113
<211> LENGTH: 18
<212> TYPE: DNA
<213> ORGANISM: Artificial Sequence
<220> FEATURE:
<223> OTHER INFORMATION: Synthetic Construct

<400> SEQUENCE: 113 aattcccttα ggtgggag                                               18

<210> SEQ ID NO 114
<211> LENGTH: 19
<212> TYPE: DNA
<213> ORGANISM: Artificial Sequence
<220> FEATURE:
<223> OTHER INFORMATION: Synthetic Construct

<400> SEQUENCE: 114
taattccctt aggtgggag                                              19
```

```
<210> SEQ ID NO 115
<211> LENGTH: 18
<212> TYPE: DNA
<213> ORGANISM: Artificial Sequence
<220> FEATURE:
<223> OTHER INFORMATION: Synthetic Construct

<400> SEQUENCE: 115
taattccctt aggtggga                                                 18

<210> SEQ ID NO 116
<211> LENGTH: 20
<212> TYPE: RNA
<213> ORGANISM: Artificial Sequence
<220> FEATURE:
<223> OTHER INFORMATION: Synthetic Construct

<400> SEQUENCE: 116
gauaaagacu gcugagaaga                                               20

<210> SEQ ID NO 117
<211> LENGTH: 20
<212> TYPE: RNA
<213> ORGANISM: Artificial Sequence
<220> FEATURE:
<223> OTHER INFORMATION: Synthetic Construct

<400> SEQUENCE: 117
auaaagacug cugagaagag                                               20

<210> SEQ ID NO 118
<211> LENGTH: 20
<212> TYPE: RNA
<213> ORGANISM: Artificial Sequence
<220> FEATURE:
<223> OTHER INFORMATION: Synthetic Construct

<400> SEQUENCE: 118
uaaagacugc ugagaagagc                                               20

<210> SEQ ID NO 119
<211> LENGTH: 20
<212> TYPE: RNA
<213> ORGANISM: Artificial Sequence
<220> FEATURE:
<223> OTHER INFORMATION: Synthetic Construct

<400> SEQUENCE: 119
aaagacugcu gagaagagca                                               20

<210> SEQ ID NO 120
<211> LENGTH: 20
<212> TYPE: RNA
<213> ORGANISM: Artificial Sequence
<220> FEATURE:
<223> OTHER INFORMATION: Synthetic Construct

<400> SEQUENCE: 120
aagacugcug agaagagcac                                               20

<210> SEQ ID NO 121
<211> LENGTH: 20
<212> TYPE: RNA
<213> ORGANISM: Artificial Sequence
<220> FEATURE:
<223> OTHER INFORMATION: Synthetic Construct
```

-continued

```
<400> SEQUENCE: 121
agacugcuga gaagagcacc                                              20

<210> SEQ ID NO 122
<211> LENGTH: 20
<212> TYPE: RNA
<213> ORGANISM: Artificial Sequence
<220> FEATURE:
<223> OTHER INFORMATION: Synthetic Construct

<400> SEQUENCE: 122
gacugcugag aagagcaccc                                              20

<210> SEQ ID NO 123
<211> LENGTH: 20
<212> TYPE: RNA
<213> ORGANISM: Artificial Sequence
<220> FEATURE:
<223> OTHER INFORMATION: Synthetic Construct

<400> SEQUENCE: 123
caagugcuac cgcacaggca                                              20

<210> SEQ ID NO 124
<211> LENGTH: 20
<212> TYPE: RNA
<213> ORGANISM: Artificial Sequence
<220> FEATURE:
<223> OTHER INFORMATION: Synthetic Construct

<400> SEQUENCE: 124
aagugcuacc gcacaggcau                                              20

<210> SEQ ID NO 125
<211> LENGTH: 20
<212> TYPE: RNA
<213> ORGANISM: Artificial Sequence
<220> FEATURE:
<223> OTHER INFORMATION: Synthetic Construct

<400> SEQUENCE: 125
agugcuaccg cacaggcaug                                              20

<210> SEQ ID NO 126
<211> LENGTH: 20
<212> TYPE: RNA
<213> ORGANISM: Artificial Sequence
<220> FEATURE:
<223> OTHER INFORMATION: Synthetic Construct

<400> SEQUENCE: 126
ugcuaccgca caggcaugcu                                              20

<210> SEQ ID NO 127
<211> LENGTH: 20
<212> TYPE: RNA
<213> ORGANISM: Artificial Sequence
<220> FEATURE:
<223> OTHER INFORMATION: Synthetic Construct

<400> SEQUENCE: 127
uaccgcacag gcaugcugca                                              20

<210> SEQ ID NO 128
<211> LENGTH: 20
```

```
<212> TYPE: RNA
<213> ORGANISM: Artificial Sequence
<220> FEATURE:
<223> OTHER INFORMATION: Synthetic Construct

<400> SEQUENCE: 128
gcacaggcau gcugcaguga                                              20

<210> SEQ ID NO 129
<211> LENGTH: 20
<212> TYPE: RNA
<213> ORGANISM: Artificial Sequence
<220> FEATURE:
<223> OTHER INFORMATION: Synthetic Construct

<400> SEQUENCE: 129
cacaggcaug cugcagugaa                                              20

<210> SEQ ID NO 130
<211> LENGTH: 20
<212> TYPE: RNA
<213> ORGANISM: Artificial Sequence
<220> FEATURE:
<223> OTHER INFORMATION: Synthetic Construct

<400> SEQUENCE: 130
acaggcaugc ugcagugaau                                              20

<210> SEQ ID NO 131
<211> LENGTH: 20
<212> TYPE: RNA
<213> ORGANISM: Artificial Sequence
<220> FEATURE:
<223> OTHER INFORMATION: Synthetic Construct

<400> SEQUENCE: 131
caggcaugcu gcagugaauu                                              20

<210> SEQ ID NO 132
<211> LENGTH: 20
<212> TYPE: RNA
<213> ORGANISM: Artificial Sequence
<220> FEATURE:
<223> OTHER INFORMATION: Synthetic Construct

<400> SEQUENCE: 132
aggcaugcug cagugaauuu                                              20

<210> SEQ ID NO 133
<211> LENGTH: 20
<212> TYPE: RNA
<213> ORGANISM: Artificial Sequence
<220> FEATURE:
<223> OTHER INFORMATION: Synthetic Construct

<400> SEQUENCE: 133
ggcaugcugc agugaauuua                                              20

<210> SEQ ID NO 134
<211> LENGTH: 20
<212> TYPE: RNA
<213> ORGANISM: Artificial Sequence
<220> FEATURE:
<223> OTHER INFORMATION: Synthetic Construct

<400> SEQUENCE: 134
```
gcaugcugca gugaauuuaa 20

<210> SEQ ID NO 135
<211> LENGTH: 20
<212> TYPE: RNA
<213> ORGANISM: Artificial Sequence
<220> FEATURE:
<223> OTHER INFORMATION: Synthetic Construct

<400> SEQUENCE: 135
caugcugcag ugaauuuaac 20

<210> SEQ ID NO 136
<211> LENGTH: 20
<212> TYPE: RNA
<213> ORGANISM: Artificial Sequence
<220> FEATURE:
<223> OTHER INFORMATION: Synthetic Construct

<400> SEQUENCE: 136
gcagugaauu uaacugaucc 20

<210> SEQ ID NO 137
<211> LENGTH: 20
<212> TYPE: RNA
<213> ORGANISM: Artificial Sequence
<220> FEATURE:
<223> OTHER INFORMATION: Synthetic Construct

<400> SEQUENCE: 137
ucccugcaac cguuguuuaa 20

<210> SEQ ID NO 138
<211> LENGTH: 20
<212> TYPE: RNA
<213> ORGANISM: Artificial Sequence
<220> FEATURE:
<223> OTHER INFORMATION: Synthetic Construct

<400> SEQUENCE: 138
cccugcaacc guuguuuaag 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct

<400> SEQUENCE: 139
tcttctcagc agtctttatc 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct

<400> SEQUENCE: 140
ctcttctcag cagtctttat 20

<210> SEQ ID NO 141
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 141
gctcttctca gcagtcttta                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct

<400> SEQUENCE: 142
tgctcttctc agcagtcttt                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic Construct

<400> SEQUENCE: 143
gtgctcttct cagcagtctt                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct

<400> SEQUENCE: 144
ggtgctcttc tcagcagtct                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Construct

<400> SEQUENCE: 145
gggtgctctt ctcagcagtc                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic Construct

<400> SEQUENCE: 146
tgcctgtgcg gtagcacttg                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct

<400> SEQUENCE: 147
atgcctgtgc ggtagcactt                                              20
```

```
<210> SEQ ID NO 148
<211> LENGTH: 20
<212> TYPE: DNA
<213> ORGANISM: Artificial Sequence
<220> FEATURE:
<223> OTHER INFORMATION: Synthetic Construct

<400> SEQUENCE: 148
catgcctgtg cggtagcact                                         20

<210> SEQ ID NO 149
<211> LENGTH: 20
<212> TYPE: DNA
<213> ORGANISM: Artificial Sequence
<220> FEATURE:
<223> OTHER INFORMATION: Synthetic Construct

<400> SEQUENCE: 149
agcatgcctg tgcggtagca                                         20

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct

<400> SEQUENCE: 150
tgcagcatgc ctgtgcggta                                         20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct

<400> SEQUENCE: 151
tcactgcagc atgcctgtgc                                         20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct

<400> SEQUENCE: 152
ttcactgcag catgcctgtg                                         20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct

<400> SEQUENCE: 153
attcactgca gcatgcctgt                                         20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 154
aattcactgc agcatgcctg                                                        20

<210> SEQ ID NO 155
<211> LENGTH: 20
<212> TYPE: DNA
<213> ORGANISM: Artificial Sequence
<220> FEATURE:
<223> OTHER INFORMATION: Synthetic Construct

<400> SEQUENCE: 155
aaattcactg cagcatgcct                                                        20

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct

<400> SEQUENCE: 156
taaattcact gcagcatgcc                                                        20

<210> SEQ ID NO 157
<211> LENGTH: 20
<212> TYPE: DNA
<213> ORGANISM: Artificial Sequence
<220> FEATURE:
<223> OTHER INFORMATION: Synthetic Construct

<400> SEQUENCE: 157
ttaaattcac tgcagcatgc                                                        20

<210> SEQ ID NO 158
<211> LENGTH: 20
<212> TYPE: DNA
<213> ORGANISM: Artificial Sequence
<220> FEATURE:
<223> OTHER INFORMATION: Synthetic Construct

<400> SEQUENCE: 158
gttaaattca ctgcagcatg                                                        20

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct

<400> SEQUENCE: 159
ggatcagtta aattcactgc                                                        20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct

<400> SEQUENCE: 160
ttaaacaacg gttgcaggga                                                        20

<210> SEQ ID NO 161

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 161
cttaaacaac ggttgcaggg                                          20

<210> SEQ ID NO 162
<211> LENGTH: 19
<212> TYPE: RNA
<213> ORGANISM: Artificial Sequence
<220> FEATURE:
<223> OTHER INFORMATION: Synthetic Construct

<400> SEQUENCE: 162
aaaagacugu ggaggaaga                                           19

<210> SEQ ID NO 163
<211> LENGTH: 20
<212> TYPE: RNA
<213> ORGANISM: Artificial Sequence
<220> FEATURE:
<223> OTHER INFORMATION: Synthetic Construct

<400> SEQUENCE: 163
aaaagacugu ggaggaagaa                                          20

<210> SEQ ID NO 164
<211> LENGTH: 19
<212> TYPE: RNA
<213> ORGANISM: Artificial Sequence
<220> FEATURE:
<223> OTHER INFORMATION: Synthetic Construct

<400> SEQUENCE: 164
aaagacugug gaggaagaa                                           19

<210> SEQ ID NO 165
<211> LENGTH: 20
<212> TYPE: RNA
<213> ORGANISM: Artificial Sequence
<220> FEATURE:
<223> OTHER INFORMATION: Synthetic Construct

<400> SEQUENCE: 165
aaagacugug gaggaagaaa                                          20

<210> SEQ ID NO 166
<211> LENGTH: 20
<212> TYPE: RNA
<213> ORGANISM: Artificial Sequence
<220> FEATURE:
<223> OTHER INFORMATION: Synthetic Construct

<400> SEQUENCE: 166
aagacugugg aggaagaaaa                                          20

<210> SEQ ID NO 167
<211> LENGTH: 20
<212> TYPE: RNA
<213> ORGANISM: Artificial Sequence
<220> FEATURE:
<223> OTHER INFORMATION: Synthetic Construct

<400> SEQUENCE: 167
```

```
agacugugga ggaagaaaac                                              20

<210> SEQ ID NO 168
<211> LENGTH: 18
<212> TYPE: RNA
<213> ORGANISM: Artificial Sequence
<220> FEATURE:
<223> OTHER INFORMATION: Synthetic Construct

<400> SEQUENCE: 168
acuguggagg aagaaaac                                                18

<210> SEQ ID NO 169
<211> LENGTH: 19
<212> TYPE: RNA
<213> ORGANISM: Artificial Sequence
<220> FEATURE:
<223> OTHER INFORMATION: Synthetic Construct

<400> SEQUENCE: 169
acuguggagg aagaaaacc                                               19

<210> SEQ ID NO 170
<211> LENGTH: 20
<212> TYPE: RNA
<213> ORGANISM: Artificial Sequence
<220> FEATURE:
<223> OTHER INFORMATION: Synthetic Construct

<400> SEQUENCE: 170
acuguggagg aagaaaaccc                                              20

<210> SEQ ID NO 171
<211> LENGTH: 18
<212> TYPE: RNA
<213> ORGANISM: Artificial Sequence
<220> FEATURE:
<223> OTHER INFORMATION: Synthetic Construct

<400> SEQUENCE: 171
cuguggagga agaaaacc                                                18

<210> SEQ ID NO 172
<211> LENGTH: 19
<212> TYPE: RNA
<213> ORGANISM: Artificial Sequence
<220> FEATURE:
<223> OTHER INFORMATION: Synthetic Construct

<400> SEQUENCE: 172
cuguggagga agaaaaccc                                               19

<210> SEQ ID NO 173
<211> LENGTH: 19
<212> TYPE: RNA
<213> ORGANISM: Artificial Sequence
<220> FEATURE:
<223> OTHER INFORMATION: Synthetic Construct

<400> SEQUENCE: 173
aaaacccuuu acccuguug                                               19

<210> SEQ ID NO 174
<211> LENGTH: 20
<212> TYPE: RNA
```

```
<213> ORGANISM: Artificial Sequence
<220> FEATURE:
<223> OTHER INFORMATION: Synthetic Construct

<400> SEQUENCE: 174
aaaacccuuu acccuguugu                                          20

<210> SEQ ID NO 175
<211> LENGTH: 20
<212> TYPE: RNA
<213> ORGANISM: Artificial Sequence
<220> FEATURE:
<223> OTHER INFORMATION: Synthetic Construct

<400> SEQUENCE: 175
aaacccuuua cccuguuguu                                          20

<210> SEQ ID NO 176
<211> LENGTH: 18
<212> TYPE: RNA
<213> ORGANISM: Artificial Sequence
<220> FEATURE:
<223> OTHER INFORMATION: Synthetic Construct

<400> SEQUENCE: 176
uuguucaggg agaaacug                                            18

<210> SEQ ID NO 177
<211> LENGTH: 20
<212> TYPE: RNA
<213> ORGANISM: Artificial Sequence
<220> FEATURE:
<223> OTHER INFORMATION: Synthetic Construct

<400> SEQUENCE: 177
uuguucaggg agaaacugac                                          20

<210> SEQ ID NO 178
<211> LENGTH: 18
<212> TYPE: RNA
<213> ORGANISM: Artificial Sequence
<220> FEATURE:
<223> OTHER INFORMATION: Synthetic Construct

<400> SEQUENCE: 178
uguucaggga gaaacuga                                            18

<210> SEQ ID NO 179
<211> LENGTH: 19
<212> TYPE: RNA
<213> ORGANISM: Artificial Sequence
<220> FEATURE:
<223> OTHER INFORMATION: Synthetic Construct

<400> SEQUENCE: 179
uguucaggga gaaacugac                                           19

<210> SEQ ID NO 180
<211> LENGTH: 20
<212> TYPE: RNA
<213> ORGANISM: Artificial Sequence
<220> FEATURE:
<223> OTHER INFORMATION: Synthetic Construct

<400> SEQUENCE: 180
uguucaggga gaaacugaca                                          20
```

<210> SEQ ID NO 181
<211> LENGTH: 19
<212> TYPE: RNA
<213> ORGANISM: Artificial Sequence
<220> FEATURE:
<223> OTHER INFORMATION: Synthetic Construct

<400> SEQUENCE: 181
guucagggag aaacugaca                                                19

<210> SEQ ID NO 182
<211> LENGTH: 20
<212> TYPE: RNA
<213> ORGANISM: Artificial Sequence
<220> FEATURE:
<223> OTHER INFORMATION: Synthetic Construct

<400> SEQUENCE: 182
ucagggagaa acugacacca                                               20

<210> SEQ ID NO 183
<211> LENGTH: 19
<212> TYPE: RNA
<213> ORGANISM: Artificial Sequence
<220> FEATURE:
<223> OTHER INFORMATION: Synthetic Construct

<400> SEQUENCE: 183
cagggagaaa cugacacca                                                19

<210> SEQ ID NO 184
<211> LENGTH: 18
<212> TYPE: RNA
<213> ORGANISM: Artificial Sequence
<220> FEATURE:
<223> OTHER INFORMATION: Synthetic Construct

<400> SEQUENCE: 184
agggagaaac ugacacca                                                 18

<210> SEQ ID NO 185
<211> LENGTH: 19
<212> TYPE: RNA
<213> ORGANISM: Artificial Sequence
<220> FEATURE:
<223> OTHER INFORMATION: Synthetic Construct

<400> SEQUENCE: 185
agggagaaac ugacaccac                                                19

<210> SEQ ID NO 186
<211> LENGTH: 20
<212> TYPE: RNA
<213> ORGANISM: Artificial Sequence
<220> FEATURE:
<223> OTHER INFORMATION: Synthetic Construct

<400> SEQUENCE: 186
agggagaaac ugacaccacu                                               20

<210> SEQ ID NO 187
<211> LENGTH: 18
<212> TYPE: RNA
<213> ORGANISM: Artificial Sequence
<220> FEATURE:

<223> OTHER INFORMATION: Synthetic Construct

<400> SEQUENCE: 187
gggagaaacu gacaccac                                                         18

<210> SEQ ID NO 188
<211> LENGTH: 19
<212> TYPE: RNA
<213> ORGANISM: Artificial Sequence
<220> FEATURE:
<223> OTHER INFORMATION: Synthetic Construct

<400> SEQUENCE: 188
gggagaaacu gacaccacu                                                        19

<210> SEQ ID NO 189
<211> LENGTH: 20
<212> TYPE: RNA
<213> ORGANISM: Artificial Sequence
<220> FEATURE:
<223> OTHER INFORMATION: Synthetic Construct

<400> SEQUENCE: 189
gggagaaacu gacaccacuc                                                       20

<210> SEQ ID NO 190
<211> LENGTH: 18
<212> TYPE: RNA
<213> ORGANISM: Artificial Sequence
<220> FEATURE:
<223> OTHER INFORMATION: Synthetic Construct

<400> SEQUENCE: 190
ggagaaacug acaccacu                                                         18

<210> SEQ ID NO 191
<211> LENGTH: 19
<212> TYPE: RNA
<213> ORGANISM: Artificial Sequence
<220> FEATURE:
<223> OTHER INFORMATION: Synthetic Construct

<400> SEQUENCE: 191
ggagaaacug acaccacuc                                                        19

<210> SEQ ID NO 192
<211> LENGTH: 20
<212> TYPE: RNA
<213> ORGANISM: Artificial Sequence
<220> FEATURE:
<223> OTHER INFORMATION: Synthetic Construct

<400> SEQUENCE: 192
ggagaaacug acaccacuca                                                       20

<210> SEQ ID NO 193
<211> LENGTH: 18
<212> TYPE: RNA
<213> ORGANISM: Artificial Sequence
<220> FEATURE:
<223> OTHER INFORMATION: Synthetic Construct

<400> SEQUENCE: 193
gagaaacuga caccacuc                                                         18

```
<210> SEQ ID NO 194
<211> LENGTH: 19
<212> TYPE: RNA
<213> ORGANISM: Artificial Sequence
<220> FEATURE:
<223> OTHER INFORMATION: Synthetic Construct

<400> SEQUENCE: 194
gagaaacuga caccacuca                                            19

<210> SEQ ID NO 195
<211> LENGTH: 20
<212> TYPE: RNA
<213> ORGANISM: Artificial Sequence
<220> FEATURE:
<223> OTHER INFORMATION: Synthetic Construct

<400> SEQUENCE: 195
gagaaacuga caccacucaa                                           20

<210> SEQ ID NO 196
<211> LENGTH: 18
<212> TYPE: RNA
<213> ORGANISM: Artificial Sequence
<220> FEATURE:
<223> OTHER INFORMATION: Synthetic Construct

<400> SEQUENCE: 196
agaaacugac accacuca                                             18

<210> SEQ ID NO 197
<211> LENGTH: 19
<212> TYPE: RNA
<213> ORGANISM: Artificial Sequence
<220> FEATURE:
<223> OTHER INFORMATION: Synthetic Construct

<400> SEQUENCE: 197
agaaacugac accacucaa                                            19

<210> SEQ ID NO 198
<211> LENGTH: 20
<212> TYPE: RNA
<213> ORGANISM: Artificial Sequence
<220> FEATURE:
<223> OTHER INFORMATION: Synthetic Construct

<400> SEQUENCE: 198
agaaacugac accacucaac                                           20

<210> SEQ ID NO 199
<211> LENGTH: 18
<212> TYPE: RNA
<213> ORGANISM: Artificial Sequence
<220> FEATURE:
<223> OTHER INFORMATION: Synthetic Construct

<400> SEQUENCE: 199
gaaacugaca ccacucaa                                             18

<210> SEQ ID NO 200
<211> LENGTH: 19
<212> TYPE: RNA
<213> ORGANISM: Artificial Sequence
<220> FEATURE:
<223> OTHER INFORMATION: Synthetic Construct
```

<400> SEQUENCE: 200
gaaacugaca ccacucaac                                                    19

<210> SEQ ID NO 201
<211> LENGTH: 20
<212> TYPE: RNA
<213> ORGANISM: Artificial Sequence
<220> FEATURE:
<223> OTHER INFORMATION: Synthetic Construct

<400> SEQUENCE: 201
gaaacugaca ccacucaacu                                                   20

<210> SEQ ID NO 202
<211> LENGTH: 18
<212> TYPE: RNA
<213> ORGANISM: Artificial Sequence
<220> FEATURE:
<223> OTHER INFORMATION: Synthetic Construct

<400> SEQUENCE: 202
aaacugacac cacucaac                                                     18

<210> SEQ ID NO 203
<211> LENGTH: 19
<212> TYPE: RNA
<213> ORGANISM: Artificial Sequence
<220> FEATURE:
<223> OTHER INFORMATION: Synthetic Construct

<400> SEQUENCE: 203
aaacugacac cacucaacu                                                    19

<210> SEQ ID NO 204
<211> LENGTH: 20
<212> TYPE: RNA
<213> ORGANISM: Artificial Sequence
<220> FEATURE:
<223> OTHER INFORMATION: Synthetic Construct

<400> SEQUENCE: 204
aaacugacac cacucaacug                                                   20

<210> SEQ ID NO 205
<211> LENGTH: 18
<212> TYPE: RNA
<213> ORGANISM: Artificial Sequence
<220> FEATURE:
<223> OTHER INFORMATION: Synthetic Construct

<400> SEQUENCE: 205
aacugacacc acucaacu                                                     18

<210> SEQ ID NO 206
<211> LENGTH: 19
<212> TYPE: RNA
<213> ORGANISM: Artificial Sequence
<220> FEATURE:
<223> OTHER INFORMATION: Synthetic Construct

<400> SEQUENCE: 206
aacugacacc acucaacug                                                    19

<210> SEQ ID NO 207
<211> LENGTH: 20

```
<212> TYPE: RNA
<213> ORGANISM: Artificial Sequence
<220> FEATURE:
<223> OTHER INFORMATION: Synthetic Construct

<400> SEQUENCE: 207
aacugacacc acucaacugc                                              20

<210> SEQ ID NO 208
<211> LENGTH: 18
<212> TYPE: RNA
<213> ORGANISM: Artificial Sequence
<220> FEATURE:
<223> OTHER INFORMATION: Synthetic Construct

<400> SEQUENCE: 208
acugacacca cucaacug                                                18

<210> SEQ ID NO 209
<211> LENGTH: 19
<212> TYPE: RNA
<213> ORGANISM: Artificial Sequence
<220> FEATURE:
<223> OTHER INFORMATION: Synthetic Construct

<400> SEQUENCE: 209
acugacacca cucaacugc                                               19

<210> SEQ ID NO 210
<211> LENGTH: 20
<212> TYPE: RNA
<213> ORGANISM: Artificial Sequence
<220> FEATURE:
<223> OTHER INFORMATION: Synthetic Construct

<400> SEQUENCE: 210
acugacacca cucaacugcc                                              20

<210> SEQ ID NO 211
<211> LENGTH: 18
<212> TYPE: RNA
<213> ORGANISM: Artificial Sequence
<220> FEATURE:
<223> OTHER INFORMATION: Synthetic Construct

<400> SEQUENCE: 211
cugacaccac ucaacugc                                                18

<210> SEQ ID NO 212
<211> LENGTH: 19
<212> TYPE: RNA
<213> ORGANISM: Artificial Sequence
<220> FEATURE:
<223> OTHER INFORMATION: Synthetic Construct

<400> SEQUENCE: 212
cugacaccac ucaacugcc                                               19

<210> SEQ ID NO 213
<211> LENGTH: 20
<212> TYPE: RNA
<213> ORGANISM: Artificial Sequence
<220> FEATURE:
<223> OTHER INFORMATION: Synthetic Construct

<400> SEQUENCE: 213
```
cugacaccac ucaacugccu    20

<210> SEQ ID NO 214
<211> LENGTH: 18
<212> TYPE: RNA
<213> ORGANISM: Artificial Sequence
<220> FEATURE:
<223> OTHER INFORMATION: Synthetic Construct

<400> SEQUENCE: 214
ugacaccacu caacugcc    18

<210> SEQ ID NO 215
<211> LENGTH: 19
<212> TYPE: RNA
<213> ORGANISM: Artificial Sequence
<220> FEATURE:
<223> OTHER INFORMATION: Synthetic Construct

<400> SEQUENCE: 215
ugacaccacu caacugccu    19

<210> SEQ ID NO 216
<211> LENGTH: 20
<212> TYPE: RNA
<213> ORGANISM: Artificial Sequence
<220> FEATURE:
<223> OTHER INFORMATION: Synthetic Construct

<400> SEQUENCE: 216
ugacaccacu caacugccug    20

<210> SEQ ID NO 217
<211> LENGTH: 18
<212> TYPE: RNA
<213> ORGANISM: Artificial Sequence
<220> FEATURE:
<223> OTHER INFORMATION: Synthetic Construct

<400> SEQUENCE: 217
gacaccacuc aacugccu    18

<210> SEQ ID NO 218
<211> LENGTH: 19
<212> TYPE: RNA
<213> ORGANISM: Artificial Sequence
<220> FEATURE:
<223> OTHER INFORMATION: Synthetic Construct

<400> SEQUENCE: 218
gacaccacuc aacugccug    19

<210> SEQ ID NO 219
<211> LENGTH: 20
<212> TYPE: RNA
<213> ORGANISM: Artificial Sequence
<220> FEATURE:
<223> OTHER INFORMATION: Synthetic Construct

<400> SEQUENCE: 219
gacaccacuc aacugccugg    20

<210> SEQ ID NO 220
<211> LENGTH: 18
<212> TYPE: RNA
<213> ORGANISM: Artificial Sequence

```
<220> FEATURE:
<223> OTHER INFORMATION: Synthetic Construct

<400> SEQUENCE: 220
acaccacuca acugccug                                               18

<210> SEQ ID NO 221
<211> LENGTH: 19
<212> TYPE: RNA
<213> ORGANISM: Artificial Sequence
<220> FEATURE:
<223> OTHER INFORMATION: Synthetic Construct

<400> SEQUENCE: 221
acaccacuca acugccugg                                              19

<210> SEQ ID NO 222
<211> LENGTH: 20
<212> TYPE: RNA
<213> ORGANISM: Artificial Sequence
<220> FEATURE:
<223> OTHER INFORMATION: Synthetic Construct

<400> SEQUENCE: 222
acaccacuca acugccuggc                                             20

<210> SEQ ID NO 223
<211> LENGTH: 20
<212> TYPE: RNA
<213> ORGANISM: Artificial Sequence
<220> FEATURE:
<223> OTHER INFORMATION: Synthetic Construct

<400> SEQUENCE: 223
caccacucaa cugccuggca                                             20

<210> SEQ ID NO 224
<211> LENGTH: 18
<212> TYPE: RNA
<213> ORGANISM: Artificial Sequence
<220> FEATURE:
<223> OTHER INFORMATION: Synthetic Construct

<400> SEQUENCE: 224
gaaaaugugg cauccagu                                               18

<210> SEQ ID NO 225
<211> LENGTH: 18
<212> TYPE: RNA
<213> ORGANISM: Artificial Sequence
<220> FEATURE:
<223> OTHER INFORMATION: Synthetic Construct

<400> SEQUENCE: 225
aaaauguggc auccaguc                                               18

<210> SEQ ID NO 226
<211> LENGTH: 20
<212> TYPE: RNA
<213> ORGANISM: Artificial Sequence
<220> FEATURE:
<223> OTHER INFORMATION: Synthetic Construct

<400> SEQUENCE: 226
gcauccaguc cacuuuacca                                             20
```

<210> SEQ ID NO 227
<211> LENGTH: 18
<212> TYPE: RNA
<213> ORGANISM: Artificial Sequence
<220> FEATURE:
<223> OTHER INFORMATION: Synthetic Construct

<400> SEQUENCE: 227
cauccagucc acuuuacc                                                 18

<210> SEQ ID NO 228
<211> LENGTH: 19
<212> TYPE: RNA
<213> ORGANISM: Artificial Sequence
<220> FEATURE:
<223> OTHER INFORMATION: Synthetic Construct

<400> SEQUENCE: 228
cauccagucc acuuuacca                                                19

<210> SEQ ID NO 229
<211> LENGTH: 20
<212> TYPE: RNA
<213> ORGANISM: Artificial Sequence
<220> FEATURE:
<223> OTHER INFORMATION: Synthetic Construct

<400> SEQUENCE: 229
cauccagucc acuuuaccau                                               20

<210> SEQ ID NO 230
<211> LENGTH: 18
<212> TYPE: RNA
<213> ORGANISM: Artificial Sequence
<220> FEATURE:
<223> OTHER INFORMATION: Synthetic Construct

<400> SEQUENCE: 230
auccagucca cuuuacca                                                 18

<210> SEQ ID NO 231
<211> LENGTH: 19
<212> TYPE: RNA
<213> ORGANISM: Artificial Sequence
<220> FEATURE:
<223> OTHER INFORMATION: Synthetic Construct

<400> SEQUENCE: 231
auccagucca cuuuaccau                                                19

<210> SEQ ID NO 232
<211> LENGTH: 20
<212> TYPE: RNA
<213> ORGANISM: Artificial Sequence
<220> FEATURE:
<223> OTHER INFORMATION: Synthetic Construct

<400> SEQUENCE: 232
auccagucca cuuuaccauc                                               20

<210> SEQ ID NO 233
<211> LENGTH: 20
<212> TYPE: RNA
<213> ORGANISM: Artificial Sequence
<220> FEATURE:
<223> OTHER INFORMATION: Synthetic Construct

<400> SEQUENCE: 233
guuuaaggaa accaucucug                                         20

<210> SEQ ID NO 234
<211> LENGTH: 20
<212> TYPE: RNA
<213> ORGANISM: Artificial Sequence
<220> FEATURE:
<223> OTHER INFORMATION: Synthetic Construct

<400> SEQUENCE: 234
uuuaaggaaa ccaucucugg                                         20

<210> SEQ ID NO 235
<211> LENGTH: 19
<212> TYPE: RNA
<213> ORGANISM: Artificial Sequence
<220> FEATURE:
<223> OTHER INFORMATION: Synthetic Construct

<400> SEQUENCE: 235
uuaaggaaac caucucugg                                          19

<210> SEQ ID NO 236
<211> LENGTH: 18
<212> TYPE: RNA
<213> ORGANISM: Artificial Sequence
<220> FEATURE:
<223> OTHER INFORMATION: Synthetic Construct

<400> SEQUENCE: 236
uaaggaaacc aucucugg                                           18

<210> SEQ ID NO 237
<211> LENGTH: 19
<212> TYPE: DNA
<213> ORGANISM: Artificial Sequence
<220> FEATURE:
<223> OTHER INFORMATION: Synthetic Construct

<400> SEQUENCE: 237
tcttcctcca cagtctttt                                          19

<210> SEQ ID NO 238
<211> LENGTH: 20
<212> TYPE: DNA
<213> ORGANISM: Artificial Sequence
<220> FEATURE:
<223> OTHER INFORMATION: Synthetic Construct

<400> SEQUENCE: 238
ttcttcctcc acagtctttt                                         20

<210> SEQ ID NO 239
<211> LENGTH: 19
<212> TYPE: DNA
<213> ORGANISM: Artificial Sequence
<220> FEATURE:
<223> OTHER INFORMATION: Synthetic Construct

<400> SEQUENCE: 239
ttcttcctcc acagtcttt                                          19

<210> SEQ ID NO 240

<211> LENGTH: 20
<212> TYPE: DNA
<213> ORGANISM: Artificial Sequence
<220> FEATURE:
<223> OTHER INFORMATION: Synthetic Construct

<400> SEQUENCE: 240
tttcttcctc cacagtcttt            20

<210> SEQ ID NO 241
<211> LENGTH: 20
<212> TYPE: DNA
<213> ORGANISM: Artificial Sequence
<220> FEATURE:
<223> OTHER INFORMATION: Synthetic Construct

<400> SEQUENCE: 241
ttttcttcct ccacagtctt            20

<210> SEQ ID NO 242
<211> LENGTH: 20
<212> TYPE: DNA
<213> ORGANISM: Artificial Sequence
<220> FEATURE:
<223> OTHER INFORMATION: Synthetic Construct

<400> SEQUENCE: 242
gttttcttcc tccacagtct            20

<210> SEQ ID NO 243
<211> LENGTH: 18
<212> TYPE: DNA
<213> ORGANISM: Artificial Sequence
<220> FEATURE:
<223> OTHER INFORMATION: Synthetic Construct

<400> SEQUENCE: 243
gttttcttcc tccacagt              18

<210> SEQ ID NO 244
<211> LENGTH: 19
<212> TYPE: DNA
<213> ORGANISM: Artificial Sequence
<220> FEATURE:
<223> OTHER INFORMATION: Synthetic Construct

<400> SEQUENCE: 244
ggttttcttc ctccacagt             19

<210> SEQ ID NO 245
<211> LENGTH: 20
<212> TYPE: DNA
<213> ORGANISM: Artificial Sequence
<220> FEATURE:
<223> OTHER INFORMATION: Synthetic Construct

<400> SEQUENCE: 245
gggttttctt cctccacagt            20

<210> SEQ ID NO 246
<211> LENGTH: 18
<212> TYPE: DNA
<213> ORGANISM: Artificial Sequence
<220> FEATURE:
<223> OTHER INFORMATION: Synthetic Construct

<400> SEQUENCE: 246

```
ggttttcttc ctccacag                                                    18

<210> SEQ ID NO 247
<211> LENGTH: 19
<212> TYPE: DNA
<213> ORGANISM: Artificial Sequence
<220> FEATURE:
<223> OTHER INFORMATION: Synthetic Construct

<400> SEQUENCE: 247
gggttttctt cctccacag                                                   19

<210> SEQ ID NO 248
<211> LENGTH: 19
<212> TYPE: DNA
<213> ORGANISM: Artificial Sequence
<220> FEATURE:
<223> OTHER INFORMATION: Synthetic Construct

<400> SEQUENCE: 248
caacagggta aagggtttt                                                   19

<210> SEQ ID NO 249
<211> LENGTH: 20
<212> TYPE: DNA
<213> ORGANISM: Artificial Sequence
<220> FEATURE:
<223> OTHER INFORMATION: Synthetic Construct

<400> SEQUENCE: 249
acaacagggt aaagggtttt                                                  20

<210> SEQ ID NO 250
<211> LENGTH: 20
<212> TYPE: DNA
<213> ORGANISM: Artificial Sequence
<220> FEATURE:
<223> OTHER INFORMATION: Synthetic Construct

<400> SEQUENCE: 250
aacaacaggg taaagggttt                                                  20

<210> SEQ ID NO 251
<211> LENGTH: 18
<212> TYPE: DNA
<213> ORGANISM: Artificial Sequence
<220> FEATURE:
<223> OTHER INFORMATION: Synthetic Construct

<400> SEQUENCE: 251
cagtttctcc ctgaacaa                                                    18

<210> SEQ ID NO 252
<211> LENGTH: 20
<212> TYPE: DNA
<213> ORGANISM: Artificial Sequence
<220> FEATURE:
<223> OTHER INFORMATION: Synthetic Construct

<400> SEQUENCE: 252
gtcagtttct ccctgaacaa                                                  20

<210> SEQ ID NO 253
<211> LENGTH: 18
<212> TYPE: DNA
```

<213> ORGANISM: Artificial Sequence
<220> FEATURE:
<223> OTHER INFORMATION: Synthetic Construct

<400> SEQUENCE: 253
tcagtttctc cctgaaca                                            18

<210> SEQ ID NO 254
<211> LENGTH: 19
<212> TYPE: DNA
<213> ORGANISM: Artificial Sequence
<220> FEATURE:
<223> OTHER INFORMATION: Synthetic Construct

<400> SEQUENCE: 254
gtcagtttct ccctgaaca                                           19

<210> SEQ ID NO 255
<211> LENGTH: 20
<212> TYPE: DNA
<213> ORGANISM: Artificial Sequence
<220> FEATURE:
<223> OTHER INFORMATION: Synthetic Construct

<400> SEQUENCE: 255
tgtcagtttc tccctgaaca                                          20

<210> SEQ ID NO 256
<211> LENGTH: 19
<212> TYPE: DNA
<213> ORGANISM: Artificial Sequence
<220> FEATURE:
<223> OTHER INFORMATION: Synthetic Construct

<400> SEQUENCE: 256
tgtcagtttc tccctgaac                                           19

<210> SEQ ID NO 257
<211> LENGTH: 20
<212> TYPE: DNA
<213> ORGANISM: Artificial Sequence
<220> FEATURE:
<223> OTHER INFORMATION: Synthetic Construct

<400> SEQUENCE: 257
tggtgtcagt ttctccctga                                          20

<210> SEQ ID NO 258
<211> LENGTH: 19
<212> TYPE: DNA
<213> ORGANISM: Artificial Sequence
<220> FEATURE:
<223> OTHER INFORMATION: Synthetic Construct

<400> SEQUENCE: 258
tggtgtcagt ttctccctg                                           19

<210> SEQ ID NO 259
<211> LENGTH: 18
<212> TYPE: DNA
<213> ORGANISM: Artificial Sequence
<220> FEATURE:
<223> OTHER INFORMATION: Synthetic Construct

<400> SEQUENCE: 259
tggtgtcagt ttctccct                                            18

<210> SEQ ID NO 260
<211> LENGTH: 19
<212> TYPE: DNA
<213> ORGANISM: Artificial Sequence
<220> FEATURE:
<223> OTHER INFORMATION: Synthetic Construct

<400> SEQUENCE: 260
gtggtgtcag tttctccct                                               19

<210> SEQ ID NO 261
<211> LENGTH: 20
<212> TYPE: DNA
<213> ORGANISM: Artificial Sequence
<220> FEATURE:
<223> OTHER INFORMATION: Synthetic Construct

<400> SEQUENCE: 261
agtggtgtca gtttctccct                                              20

<210> SEQ ID NO 262
<211> LENGTH: 18
<212> TYPE: DNA
<213> ORGANISM: Artificial Sequence
<220> FEATURE:
<223> OTHER INFORMATION: Synthetic Construct

<400> SEQUENCE: 262
gtggtgtcag tttctccc                                                18

<210> SEQ ID NO 263
<211> LENGTH: 19
<212> TYPE: DNA
<213> ORGANISM: Artificial Sequence
<220> FEATURE:
<223> OTHER INFORMATION: Synthetic Construct

<400> SEQUENCE: 263
agtggtgtca gtttctccc                                               19

<210> SEQ ID NO 264
<211> LENGTH: 20
<212> TYPE: DNA
<213> ORGANISM: Artificial Sequence
<220> FEATURE:
<223> OTHER INFORMATION: Synthetic Construct

<400> SEQUENCE: 264
gagtggtgtc agtttctccc                                              20

<210> SEQ ID NO 265
<211> LENGTH: 18
<212> TYPE: DNA
<213> ORGANISM: Artificial Sequence
<220> FEATURE:
<223> OTHER INFORMATION: Synthetic Construct

<400> SEQUENCE: 265
agtggtgtca gtttctcc                                                18

<210> SEQ ID NO 266
<211> LENGTH: 19
<212> TYPE: DNA
<213> ORGANISM: Artificial Sequence
<220> FEATURE:

<223> OTHER INFORMATION: Synthetic Construct

<400> SEQUENCE: 266
gagtggtgtc agtttctcc                                               19

<210> SEQ ID NO 267
<211> LENGTH: 20
<212> TYPE: DNA
<213> ORGANISM: Artificial Sequence
<220> FEATURE:
<223> OTHER INFORMATION: Synthetic Construct

<400> SEQUENCE: 267
tgagtggtgt cagtttctcc                                              20

<210> SEQ ID NO 268
<211> LENGTH: 18
<212> TYPE: DNA
<213> ORGANISM: Artificial Sequence
<220> FEATURE:
<223> OTHER INFORMATION: Synthetic Construct

<400> SEQUENCE: 268
gagtggtgtc agtttctc                                                18

<210> SEQ ID NO 269
<211> LENGTH: 19
<212> TYPE: DNA
<213> ORGANISM: Artificial Sequence
<220> FEATURE:
<223> OTHER INFORMATION: Synthetic Construct

<400> SEQUENCE: 269
tgagtggtgt cagtttctc                                               19

<210> SEQ ID NO 270
<211> LENGTH: 20
<212> TYPE: DNA
<213> ORGANISM: Artificial Sequence
<220> FEATURE:
<223> OTHER INFORMATION: Synthetic Construct

<400> SEQUENCE: 270
ttgagtggtg tcagtttctc                                              20

<210> SEQ ID NO 271
<211> LENGTH: 18
<212> TYPE: DNA
<213> ORGANISM: Artificial Sequence
<220> FEATURE:
<223> OTHER INFORMATION: Synthetic Construct

<400> SEQUENCE: 271
tgagtggtgt cagtttct                                                18

<210> SEQ ID NO 272
<211> LENGTH: 19
<212> TYPE: DNA
<213> ORGANISM: Artificial Sequence
<220> FEATURE:
<223> OTHER INFORMATION: Synthetic Construct

<400> SEQUENCE: 272
ttgagtggtg tcagtttct                                               19

```
<210> SEQ ID NO 273
<211> LENGTH: 20
<212> TYPE: DNA
<213> ORGANISM: Artificial Sequence
<220> FEATURE:
<223> OTHER INFORMATION: Synthetic Construct

<400> SEQUENCE: 273
gttgagtggt gtcagtttct                                                   20

<210> SEQ ID NO 274
<211> LENGTH: 18
<212> TYPE: DNA
<213> ORGANISM: Artificial Sequence
<220> FEATURE:
<223> OTHER INFORMATION: Synthetic Construct

<400> SEQUENCE: 274
ttgagtggtg tcagtttc                                                     18

<210> SEQ ID NO 275
<211> LENGTH: 19
<212> TYPE: DNA
<213> ORGANISM: Artificial Sequence
<220> FEATURE:
<223> OTHER INFORMATION: Synthetic Construct

<400> SEQUENCE: 275
gttgagtggt gtcagtttc                                                    19

<210> SEQ ID NO 276
<211> LENGTH: 20
<212> TYPE: DNA
<213> ORGANISM: Artificial Sequence
<220> FEATURE:
<223> OTHER INFORMATION: Synthetic Construct

<400> SEQUENCE: 276
agttgagtgg tgtcagtttc                                                   20

<210> SEQ ID NO 277
<211> LENGTH: 18
<212> TYPE: DNA
<213> ORGANISM: Artificial Sequence
<220> FEATURE:
<223> OTHER INFORMATION: Synthetic Construct

<400> SEQUENCE: 277
gttgagtggt gtcagttt                                                     18

<210> SEQ ID NO 278
<211> LENGTH: 19
<212> TYPE: DNA
<213> ORGANISM: Artificial Sequence
<220> FEATURE:
<223> OTHER INFORMATION: Synthetic Construct

<400> SEQUENCE: 278
agttgagtgg tgtcagttt                                                    19

<210> SEQ ID NO 279
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 279
cagttgagtg gtgtcagttt                                              20

<210> SEQ ID NO 280
<211> LENGTH: 18
<212> TYPE: DNA
<213> ORGANISM: Artificial Sequence
<220> FEATURE:
<223> OTHER INFORMATION: Synthetic Construct

<400> SEQUENCE: 280
agttgagtgg tgtcagtt                                                18

<210> SEQ ID NO 281
<211> LENGTH: 19
<212> TYPE: DNA
<213> ORGANISM: Artificial Sequence
<220> FEATURE:
<223> OTHER INFORMATION: Synthetic Construct

<400> SEQUENCE: 281
cagttgagtg gtgtcagtt                                               19

<210> SEQ ID NO 282
<211> LENGTH: 20
<212> TYPE: DNA
<213> ORGANISM: Artificial Sequence
<220> FEATURE:
<223> OTHER INFORMATION: Synthetic Construct

<400> SEQUENCE: 282
gcagttgagt ggtgtcagtt                                              20

<210> SEQ ID NO 283
<211> LENGTH: 18
<212> TYPE: DNA
<213> ORGANISM: Artificial Sequence
<220> FEATURE:
<223> OTHER INFORMATION: Synthetic Construct

<400> SEQUENCE: 283
cagttgagtg gtgtcagt                                                18

<210> SEQ ID NO 284
<211> LENGTH: 19
<212> TYPE: DNA
<213> ORGANISM: Artificial Sequence
<220> FEATURE:
<223> OTHER INFORMATION: Synthetic Construct

<400> SEQUENCE: 284
gcagttgagt ggtgtcagt                                               19

<210> SEQ ID NO 285
<211> LENGTH: 20
<212> TYPE: DNA
<213> ORGANISM: Artificial Sequence
<220> FEATURE:
<223> OTHER INFORMATION: Synthetic Construct

<400> SEQUENCE: 285
ggcagttgag tggtgtcagt                                              20

<210> SEQ ID NO 286
<211> LENGTH: 18
```

```
<212> TYPE: DNA
<213> ORGANISM: Artificial Sequence
<220> FEATURE:
<223> OTHER INFORMATION: Synthetic Construct

<400> SEQUENCE: 286
gcagttgagt ggtgtcag                                                   18

<210> SEQ ID NO 287
<211> LENGTH: 19
<212> TYPE: DNA
<213> ORGANISM: Artificial Sequence
<220> FEATURE:
<223> OTHER INFORMATION: Synthetic Construct

<400> SEQUENCE: 287
ggcagttgag tggtgtcag                                                  19

<210> SEQ ID NO 288
<211> LENGTH: 20
<212> TYPE: DNA
<213> ORGANISM: Artificial Sequence
<220> FEATURE:
<223> OTHER INFORMATION: Synthetic Construct

<400> SEQUENCE: 288
aggcagttga gtggtgtcag                                                 20

<210> SEQ ID NO 289
<211> LENGTH: 18
<212> TYPE: DNA
<213> ORGANISM: Artificial Sequence
<220> FEATURE:
<223> OTHER INFORMATION: Synthetic Construct

<400> SEQUENCE: 289
ggcagttgag tggtgtca                                                   18

<210> SEQ ID NO 290
<211> LENGTH: 19
<212> TYPE: DNA
<213> ORGANISM: Artificial Sequence
<220> FEATURE:
<223> OTHER INFORMATION: Synthetic Construct

<400> SEQUENCE: 290
aggcagttga gtggtgtca                                                  19

<210> SEQ ID NO 291
<211> LENGTH: 20
<212> TYPE: DNA
<213> ORGANISM: Artificial Sequence
<220> FEATURE:
<223> OTHER INFORMATION: Synthetic Construct

<400> SEQUENCE: 291
caggcagttg agtggtgtca                                                 20

<210> SEQ ID NO 292
<211> LENGTH: 18
<212> TYPE: DNA
<213> ORGANISM: Artificial Sequence
<220> FEATURE:
<223> OTHER INFORMATION: Synthetic Construct

<400> SEQUENCE: 292
```
aggcagttga gtggtgtc                                                     18

<210> SEQ ID NO 293
<211> LENGTH: 19
<212> TYPE: DNA
<213> ORGANISM: Artificial Sequence
<220> FEATURE:
<223> OTHER INFORMATION: Synthetic Construct

<400> SEQUENCE: 293
caggcagttg agtggtgtc                                                    19

<210> SEQ ID NO 294
<211> LENGTH: 20
<212> TYPE: DNA
<213> ORGANISM: Artificial Sequence
<220> FEATURE:
<223> OTHER INFORMATION: Synthetic Construct

<400> SEQUENCE: 294
ccaggcagtt gagtggtgtc                                                   20

<210> SEQ ID NO 295
<211> LENGTH: 18
<212> TYPE: DNA
<213> ORGANISM: Artificial Sequence
<220> FEATURE:
<223> OTHER INFORMATION: Synthetic Construct

<400> SEQUENCE: 295
caggcagttg agtggtgt                                                     18

<210> SEQ ID NO 296
<211> LENGTH: 19
<212> TYPE: DNA
<213> ORGANISM: Artificial Sequence
<220> FEATURE:
<223> OTHER INFORMATION: Synthetic Construct

<400> SEQUENCE: 296
ccaggcagtt gagtggtgt                                                    19

<210> SEQ ID NO 297
<211> LENGTH: 20
<212> TYPE: DNA
<213> ORGANISM: Artificial Sequence
<220> FEATURE:
<223> OTHER INFORMATION: Synthetic Construct

<400> SEQUENCE: 297
gccaggcagt tgagtggtgt                                                   20

<210> SEQ ID NO 298
<211> LENGTH: 20
<212> TYPE: DNA
<213> ORGANISM: Artificial Sequence
<220> FEATURE:
<223> OTHER INFORMATION: Synthetic Construct

<400> SEQUENCE: 298
tgccaggcag ttgagtggtg                                                   20

<210> SEQ ID NO 299
<211> LENGTH: 18
<212> TYPE: DNA
<213> ORGANISM: Artificial Sequence

```
<220> FEATURE:
<223> OTHER INFORMATION: Synthetic Construct

<400> SEQUENCE: 299
actggatgcc acattttc                                                       18

<210> SEQ ID NO 300
<211> LENGTH: 18
<212> TYPE: DNA
<213> ORGANISM: Artificial Sequence
<220> FEATURE:
<223> OTHER INFORMATION: Synthetic Construct

<400> SEQUENCE: 300
gactggatgc cacatttt                                                       18

<210> SEQ ID NO 301
<211> LENGTH: 20
<212> TYPE: DNA
<213> ORGANISM: Artificial Sequence
<220> FEATURE:
<223> OTHER INFORMATION: Synthetic Construct

<400> SEQUENCE: 301
tggtaaagtg gactggatgc                                                     20

<210> SEQ ID NO 302
<211> LENGTH: 18
<212> TYPE: DNA
<213> ORGANISM: Artificial Sequence
<220> FEATURE:
<223> OTHER INFORMATION: Synthetic Construct

<400> SEQUENCE: 302
ggtaaagtgg actggatg                                                       18

<210> SEQ ID NO 303
<211> LENGTH: 19
<212> TYPE: DNA
<213> ORGANISM: Artificial Sequence
<220> FEATURE:
<223> OTHER INFORMATION: Synthetic Construct

<400> SEQUENCE: 303
tggtaaagtg gactggatg                                                      19

<210> SEQ ID NO 304
<211> LENGTH: 20
<212> TYPE: DNA
<213> ORGANISM: Artificial Sequence
<220> FEATURE:
<223> OTHER INFORMATION: Synthetic Construct

<400> SEQUENCE: 304
atggtaaagt ggactggatg                                                     20

<210> SEQ ID NO 305
<211> LENGTH: 18
<212> TYPE: DNA
<213> ORGANISM: Artificial Sequence
<220> FEATURE:
<223> OTHER INFORMATION: Synthetic Construct

<400> SEQUENCE: 305
tggtaaagtg gactggat                                                       18
```

```
<210> SEQ ID NO 306
<211> LENGTH: 19
<212> TYPE: DNA
<213> ORGANISM: Artificial Sequence
<220> FEATURE:
<223> OTHER INFORMATION: Synthetic Construct

<400> SEQUENCE: 306
atggtaaagt ggactggat                                                   19

<210> SEQ ID NO 307
<211> LENGTH: 20
<212> TYPE: DNA
<213> ORGANISM: Artificial Sequence
<220> FEATURE:
<223> OTHER INFORMATION: Synthetic Construct

<400> SEQUENCE: 307
gatggtaaag tggactggat                                                  20

<210> SEQ ID NO 308
<211> LENGTH: 20
<212> TYPE: DNA
<213> ORGANISM: Artificial Sequence
<220> FEATURE:
<223> OTHER INFORMATION: Synthetic Construct

<400> SEQUENCE: 308
cagagatggt ttccttaaac                                                  20

<210> SEQ ID NO 309
<211> LENGTH: 20
<212> TYPE: DNA
<213> ORGANISM: Artificial Sequence
<220> FEATURE:
<223> OTHER INFORMATION: Synthetic Construct

<400> SEQUENCE: 309
ccagagatgg tttccttaaa                                                  20

<210> SEQ ID NO 310
<211> LENGTH: 19
<212> TYPE: DNA
<213> ORGANISM: Artificial Sequence
<220> FEATURE:
<223> OTHER INFORMATION: Synthetic Construct

<400> SEQUENCE: 310
ccagagatgg tttccttaa                                                   19

<210> SEQ ID NO 311
<211> LENGTH: 18
<212> TYPE: DNA
<213> ORGANISM: Artificial Sequence
<220> FEATURE:
<223> OTHER INFORMATION: Synthetic Construct

<400> SEQUENCE: 311
ccagagatgg tttccta                                                     18

<210> SEQ ID NO 312
<211> LENGTH: 19
<212> TYPE: RNA
<213> ORGANISM: Artificial Sequence
<220> FEATURE:
<223> OTHER INFORMATION: Synthetic Construct
```

```
<400> SEQUENCE: 312
auaaggauga cugaggaag                                                 19

<210> SEQ ID NO 313
<211> LENGTH: 20
<212> TYPE: RNA
<213> ORGANISM: Artificial Sequence
<220> FEATURE:
<223> OTHER INFORMATION: Synthetic Construct

<400> SEQUENCE: 313
auaaggauga cugaggaaga                                                20

<210> SEQ ID NO 314
<211> LENGTH: 18
<212> TYPE: RNA
<213> ORGANISM: Artificial Sequence
<220> FEATURE:
<223> OTHER INFORMATION: Synthetic Construct

<400> SEQUENCE: 314
uaaggaugac ugaggaag                                                  18

<210> SEQ ID NO 315
<211> LENGTH: 19
<212> TYPE: RNA
<213> ORGANISM: Artificial Sequence
<220> FEATURE:
<223> OTHER INFORMATION: Synthetic Construct

<400> SEQUENCE: 315
uaaggaugac ugaggaaga                                                 19

<210> SEQ ID NO 316
<211> LENGTH: 20
<212> TYPE: RNA
<213> ORGANISM: Artificial Sequence
<220> FEATURE:
<223> OTHER INFORMATION: Synthetic Construct

<400> SEQUENCE: 316
uaaggaugac ugaggaagag                                                20

<210> SEQ ID NO 317
<211> LENGTH: 18
<212> TYPE: RNA
<213> ORGANISM: Artificial Sequence
<220> FEATURE:
<223> OTHER INFORMATION: Synthetic Construct

<400> SEQUENCE: 317
aaggaugacu gaggaaga                                                  18

<210> SEQ ID NO 318
<211> LENGTH: 19
<212> TYPE: RNA
<213> ORGANISM: Artificial Sequence
<220> FEATURE:
<223> OTHER INFORMATION: Synthetic Construct

<400> SEQUENCE: 318
aaggaugacu gaggaagag                                                 19

<210> SEQ ID NO 319
```

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 319
aaggaugacu gaggaagagu                                                    20

<210> SEQ ID NO 320
<211> LENGTH: 18
<212> TYPE: RNA
<213> ORGANISM: Artificial Sequence
<220> FEATURE:
<223> OTHER INFORMATION: Synthetic Construct

<400> SEQUENCE: 320
aggaugacug aggaagag                                                      18

<210> SEQ ID NO 321
<211> LENGTH: 19
<212> TYPE: RNA
<213> ORGANISM: Artificial Sequence
<220> FEATURE:
<223> OTHER INFORMATION: Synthetic Construct

<400> SEQUENCE: 321
aggaugacug aggaagagu                                                     19

<210> SEQ ID NO 322
<211> LENGTH: 20
<212> TYPE: RNA
<213> ORGANISM: Artificial Sequence
<220> FEATURE:
<223> OTHER INFORMATION: Synthetic Construct

<400> SEQUENCE: 322
aggaugacug aggaagagua                                                    20

<210> SEQ ID NO 323
<211> LENGTH: 18
<212> TYPE: RNA
<213> ORGANISM: Artificial Sequence
<220> FEATURE:
<223> OTHER INFORMATION: Synthetic Construct

<400> SEQUENCE: 323
ggaugacuga ggaagagu                                                      18

<210> SEQ ID NO 324
<211> LENGTH: 19
<212> TYPE: RNA
<213> ORGANISM: Artificial Sequence
<220> FEATURE:
<223> OTHER INFORMATION: Synthetic Construct

<400> SEQUENCE: 324
ggaugacuga ggaagagua                                                     19

<210> SEQ ID NO 325
<211> LENGTH: 20
<212> TYPE: RNA
<213> ORGANISM: Artificial Sequence
<220> FEATURE:
<223> OTHER INFORMATION: Synthetic Construct

<400> SEQUENCE: 325
```
ggaugacuga ggaagaguac                                                    20

<210> SEQ ID NO 326
<211> LENGTH: 18
<212> TYPE: RNA
<213> ORGANISM: Artificial Sequence
<220> FEATURE:
<223> OTHER INFORMATION: Synthetic Construct

<400> SEQUENCE: 326
gaugacugag gaagagua                                                      18

<210> SEQ ID NO 327
<211> LENGTH: 19
<212> TYPE: RNA
<213> ORGANISM: Artificial Sequence
<220> FEATURE:
<223> OTHER INFORMATION: Synthetic Construct

<400> SEQUENCE: 327
gaugacugag gaagaguac                                                     19

<210> SEQ ID NO 328
<211> LENGTH: 20
<212> TYPE: RNA
<213> ORGANISM: Artificial Sequence
<220> FEATURE:
<223> OTHER INFORMATION: Synthetic Construct

<400> SEQUENCE: 328
gaugacugag gaagaguacu                                                    20

<210> SEQ ID NO 329
<211> LENGTH: 18
<212> TYPE: RNA
<213> ORGANISM: Artificial Sequence
<220> FEATURE:
<223> OTHER INFORMATION: Synthetic Construct

<400> SEQUENCE: 329
augacugagg aagaguac                                                      18

<210> SEQ ID NO 330
<211> LENGTH: 19
<212> TYPE: RNA
<213> ORGANISM: Artificial Sequence
<220> FEATURE:
<223> OTHER INFORMATION: Synthetic Construct

<400> SEQUENCE: 330
augacugagg aagaguacu                                                     19

<210> SEQ ID NO 331
<211> LENGTH: 20
<212> TYPE: RNA
<213> ORGANISM: Artificial Sequence
<220> FEATURE:
<223> OTHER INFORMATION: Synthetic Construct

<400> SEQUENCE: 331
augacugagg aagaguacuc                                                    20

<210> SEQ ID NO 332
<211> LENGTH: 18
<212> TYPE: RNA

```
<213> ORGANISM: Artificial Sequence
<220> FEATURE:
<223> OTHER INFORMATION: Synthetic Construct

<400> SEQUENCE: 332
ugacugagga agaguacu                                                 18

<210> SEQ ID NO 333
<211> LENGTH: 19
<212> TYPE: RNA
<213> ORGANISM: Artificial Sequence
<220> FEATURE:
<223> OTHER INFORMATION: Synthetic Construct

<400> SEQUENCE: 333
ugacugagga agaguacuc                                                19

<210> SEQ ID NO 334
<211> LENGTH: 20
<212> TYPE: RNA
<213> ORGANISM: Artificial Sequence
<220> FEATURE:
<223> OTHER INFORMATION: Synthetic Construct

<400> SEQUENCE: 334
ugacugagga agaguacucu                                               20

<210> SEQ ID NO 335
<211> LENGTH: 19
<212> TYPE: DNA
<213> ORGANISM: Artificial Sequence
<220> FEATURE:
<223> OTHER INFORMATION: Synthetic Construct

<400> SEQUENCE: 335
cttcctcagt catccttat                                                19

<210> SEQ ID NO 336
<211> LENGTH: 20
<212> TYPE: DNA
<213> ORGANISM: Artificial Sequence
<220> FEATURE:
<223> OTHER INFORMATION: Synthetic Construct

<400> SEQUENCE: 336
tcttcctcag tcatccttat                                               20

<210> SEQ ID NO 337
<211> LENGTH: 18
<212> TYPE: DNA
<213> ORGANISM: Artificial Sequence
<220> FEATURE:
<223> OTHER INFORMATION: Synthetic Construct

<400> SEQUENCE: 337
cttcctcagt catcctta                                                 18

<210> SEQ ID NO 338
<211> LENGTH: 19
<212> TYPE: DNA
<213> ORGANISM: Artificial Sequence
<220> FEATURE:
<223> OTHER INFORMATION: Synthetic Construct

<400> SEQUENCE: 338
tcttcctcag tcatcctta                                                19
```

<210> SEQ ID NO 339
<211> LENGTH: 20
<212> TYPE: DNA
<213> ORGANISM: Artificial Sequence
<220> FEATURE:
<223> OTHER INFORMATION: Synthetic Construct

<400> SEQUENCE: 339
ctcttcctca gtcatcctta                                          20

<210> SEQ ID NO 340
<211> LENGTH: 18
<212> TYPE: DNA
<213> ORGANISM: Artificial Sequence
<220> FEATURE:
<223> OTHER INFORMATION: Synthetic Construct

<400> SEQUENCE: 340
tcttcctcag tcatcctt                                            18

<210> SEQ ID NO 341
<211> LENGTH: 19
<212> TYPE: DNA
<213> ORGANISM: Artificial Sequence
<220> FEATURE:
<223> OTHER INFORMATION: Synthetic Construct

<400> SEQUENCE: 341
ctcttcctca gtcatcctt                                           19

<210> SEQ ID NO 342
<211> LENGTH: 20
<212> TYPE: DNA
<213> ORGANISM: Artificial Sequence
<220> FEATURE:
<223> OTHER INFORMATION: Synthetic Construct

<400> SEQUENCE: 342
actcttcctc agtcatcctt                                          20

<210> SEQ ID NO 343
<211> LENGTH: 18
<212> TYPE: DNA
<213> ORGANISM: Artificial Sequence
<220> FEATURE:
<223> OTHER INFORMATION: Synthetic Construct

<400> SEQUENCE: 343
ctcttcctca gtcatcct                                            18

<210> SEQ ID NO 344
<211> LENGTH: 19
<212> TYPE: DNA
<213> ORGANISM: Artificial Sequence
<220> FEATURE:
<223> OTHER INFORMATION: Synthetic Construct

<400> SEQUENCE: 344
actcttcctc agtcatcct                                           19

<210> SEQ ID NO 345
<211> LENGTH: 20
<212> TYPE: DNA
<213> ORGANISM: Artificial Sequence
<220> FEATURE:

<223> OTHER INFORMATION: Synthetic Construct

<400> SEQUENCE: 345
tactcttcct cagtcatcct                                          20

<210> SEQ ID NO 346
<211> LENGTH: 18
<212> TYPE: DNA
<213> ORGANISM: Artificial Sequence
<220> FEATURE:
<223> OTHER INFORMATION: Synthetic Construct

<400> SEQUENCE: 346
actcttcctc agtcatcc                                            18

<210> SEQ ID NO 347
<211> LENGTH: 19
<212> TYPE: DNA
<213> ORGANISM: Artificial Sequence
<220> FEATURE:
<223> OTHER INFORMATION: Synthetic Construct

<400> SEQUENCE: 347
tactcttcct cagtcatcc                                           19

<210> SEQ ID NO 348
<211> LENGTH: 20
<212> TYPE: DNA
<213> ORGANISM: Artificial Sequence
<220> FEATURE:
<223> OTHER INFORMATION: Synthetic Construct

<400> SEQUENCE: 348
gtactcttcc tcagtcatcc                                          20

<210> SEQ ID NO 349
<211> LENGTH: 18
<212> TYPE: DNA
<213> ORGANISM: Artificial Sequence
<220> FEATURE:
<223> OTHER INFORMATION: Synthetic Construct

<400> SEQUENCE: 349
tactcttcct cagtcatc                                            18

<210> SEQ ID NO 350
<211> LENGTH: 19
<212> TYPE: DNA
<213> ORGANISM: Artificial Sequence
<220> FEATURE:
<223> OTHER INFORMATION: Synthetic Construct

<400> SEQUENCE: 350
gtactcttcc tcagtcatc                                           19

<210> SEQ ID NO 351
<211> LENGTH: 20
<212> TYPE: DNA
<213> ORGANISM: Artificial Sequence
<220> FEATURE:
<223> OTHER INFORMATION: Synthetic Construct

<400> SEQUENCE: 351
agtactcttc ctcagtcatc                                          20

```
<210> SEQ ID NO 352
<211> LENGTH: 18
<212> TYPE: DNA
<213> ORGANISM: Artificial Sequence
<220> FEATURE:
<223> OTHER INFORMATION: Synthetic Construct

<400> SEQUENCE: 352
gtactcttcc tcagtcat                                                 18

<210> SEQ ID NO 353
<211> LENGTH: 19
<212> TYPE: DNA
<213> ORGANISM: Artificial Sequence
<220> FEATURE:
<223> OTHER INFORMATION: Synthetic Construct

<400> SEQUENCE: 353
agtactcttc ctcagtcat                                                19

<210> SEQ ID NO 354
<211> LENGTH: 20
<212> TYPE: DNA
<213> ORGANISM: Artificial Sequence
<220> FEATURE:
<223> OTHER INFORMATION: Synthetic Construct

<400> SEQUENCE: 354
gagtactctt cctcagtcat                                               20

<210> SEQ ID NO 355
<211> LENGTH: 18
<212> TYPE: DNA
<213> ORGANISM: Artificial Sequence
<220> FEATURE:
<223> OTHER INFORMATION: Synthetic Construct

<400> SEQUENCE: 355
agtactcttc ctcagtca                                                 18

<210> SEQ ID NO 356
<211> LENGTH: 19
<212> TYPE: DNA
<213> ORGANISM: Artificial Sequence
<220> FEATURE:
<223> OTHER INFORMATION: Synthetic Construct

<400> SEQUENCE: 356
gagtactctt cctcagtca                                                19

<210> SEQ ID NO 357
<211> LENGTH: 20
<212> TYPE: DNA
<213> ORGANISM: Artificial Sequence
<220> FEATURE:
<223> OTHER INFORMATION: Synthetic Construct

<400> SEQUENCE: 357
agagtactct tcctcagtca                                               20

<210> SEQ ID NO 358
<211> LENGTH: 20
<212> TYPE: DNA
<213> ORGANISM: Artificial Sequence
<220> FEATURE:
<223> OTHER INFORMATION: Synthetic Construct
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'-O-methylcytidine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methylguanosine
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylcytidine
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methyluridine

<400> SEQUENCE: 358
nnnnncttgt tggatnnnnn                                                    20

<210> SEQ ID NO 359
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'-O-methylcytidine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methylcytidine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
```

```
<222> LOCATION: (16)..(16)
<223> OTHER INFORMATION: 2'-O-methyluridine
<220> FEATURE:
<221> NAME/KEY: modified_base
<222> LOCATION: (17)..(18)
<223> OTHER INFORMATION: 2'-O-methylguanosine
<220> FEATURE:
<221> NAME/KEY: modified_base
<222> LOCATION: (19)..(20)
<223> OTHER INFORMATION: 2'-O-methyladenosine

<400> SEQUENCE: 359
nnnnntttcc tctcannnnn                                                    20

<210> SEQ ID NO 360
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(4)
<223> OTHER INFORMATION: 2'-O-methyluridine
<220> FEATURE:
<221> NAME/KEY: modified_base
<222> LOCATION: (5)..(5)
<223> OTHER INFORMATION: 2'-O-methylguanosine
<220> FEATURE:
<221> NAME/KEY: modified_base
<222> LOCATION: (16)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyluridine
<220> FEATURE:
<221> NAME/KEY: modified_base
<222> LOCATION: (19)..(19)
<223> OTHER INFORMATION: 2'-O-methylguanosine
<220> FEATURE:
<221> NAME/KEY: modified_base
<222> LOCATION: (20)..(20)
<223> OTHER INFORMATION: 2'-O-methyluridine

<400> SEQUENCE: 360
nnnnntttgc aaacnnnnn                                                     20

<210> SEQ ID NO 361
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
```

```
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methylguanosine
<220> FEATURE:
<221> NAME/KEY: modified_base
<222> LOCATION: (3)..(5)
<223> OTHER INFORMATION: 2'-O-methyluridine
<220> FEATURE:
<221> NAME/KEY: modified_base
<222> LOCATION: (16)..(16)
<223> OTHER INFORMATION: 2'-O-methyluridine
<220> FEATURE:
<221> NAME/KEY: modified_base
<222> LOCATION: (17)..(17)
<223> OTHER INFORMATION: 2'-O-methylcytidine
<220> FEATURE:
<221> NAME/KEY: modified_base
<222> LOCATION: (18)..(18)
<223> OTHER INFORMATION: 2'-O-methyluridine
<220> FEATURE:
<221> NAME/KEY: modified_base
<222> LOCATION: (19)..(19)
<223> OTHER INFORMATION: 2'-O-methylguanosine
<220> FEATURE:
<221> NAME/KEY: modified_base
<222> LOCATION: (20)..(20)
<223> OTHER INFORMATION: 2'-O-methylcytidine

<400> SEQUENCE: 361
nnnnnctttg gtgatnnnnn                                                  20

<210> SEQ ID NO 362
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methylguanosine
<220> FEATURE:
<221> NAME/KEY: modified_base
<222> LOCATION: (16)..(17)
```

<223> OTHER INFORMATION: 2'-O-methylguanosine
<220> FEATURE:
<221> NAME/KEY: modified_base
<222> LOCATION: (18)..(18)
<223> OTHER INFORMATION: 2'-O-methylcytidine
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methylcytidine

<400> SEQUENCE: 362
nnnnngtgaa ggccannnnn                                            20

<210> SEQ ID NO 363
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methylcytidine
<220> FEATURE:
<221> NAME/KEY: modified_base
<222> LOCATION: (5)..(5)
<223> OTHER INFORMATION: 2'-O-methyluridine
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(17)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyluridine
<220> FEATURE:
<221> NAME/KEY: modified_base
<222> LOCATION: (19)..(20)
<223> OTHER INFORMATION: 2'-O-methylcytidine

<400> SEQUENCE: 363
nnnnncttcc tcagtnnnnn                                            20

<210> SEQ ID NO 364
<211> LENGTH: 20
<212> TYPE: DNA
<213> ORGANISM: Artificial Sequence
<220> FEATURE:

<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methylguanosine
<220> FEATURE:
<221> NAME/KEY: modified_base
<222> LOCATION: (3)..(3)
<223> OTHER INFORMATION: 2'-O-methyluridine
<220> FEATURE:
<221> NAME/KEY: modified_base
<222> LOCATION: (4)..(4)
<223> OTHER INFORMATION: 2'-O-methylcytidine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methylguanosine
<220> FEATURE:
<221> NAME/KEY: modified_base
<222> LOCATION: (17)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: 2'-O-methylcytidine
<220> FEATURE:
<221> NAME/KEY: modified_base
<222> LOCATION: (20)..(20)
<223> OTHER INFORMATION: 2'-O-methyladenosine

<400> SEQUENCE: 364
nnnnngtttc tccctnnnnn                                                 20

<210> SEQ ID NO 365
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(5)
<223> OTHER INFORMATION: 2'-O-methyladenosine

```
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyluridine
<220> FEATURE:
<221> NAME/KEY: modified_base
<222> LOCATION: (19)..(20)
<223> OTHER INFORMATION: 2'-O-methylguanosine

<400> SEQUENCE: 365
nnnnntggca catctnnnnn                                           20

<210> SEQ ID NO 366
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(5)
<223> OTHER INFORMATION: 2'-O-methyluridine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O-methylguanosine
<220> FEATURE:
<221> NAME/KEY: modified_base
<222> LOCATION: (18)..(18)
<223> OTHER INFORMATION: 2'-O-methyluridine
<220> FEATURE:
<221> NAME/KEY: modified_base
<222> LOCATION: (19)..(19)
<223> OTHER INFORMATION: 2'-O-methylcytidine
<220> FEATURE:
<221> NAME/KEY: modified_base
<222> LOCATION: (20)..(20)
<223> OTHER INFORMATION: 2'-O-methyluridine

<400> SEQUENCE: 366
nnnnncttcc tccacnnnnn                                           20

<210> SEQ ID NO 367
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylcytidine
<220> FEATURE:
```

```
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(4)
<223> OTHER INFORMATION: 2'-O-methylguanosine
<220> FEATURE:
<221> NAME/KEY: modified_base
<222> LOCATION: (5)..(5)
<223> OTHER INFORMATION: 2'-O-methyluridine
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methylguanosine

<400> SEQUENCE: 367
nnnnngtcaa caagcnnnnn                                              20

<210> SEQ ID NO 368
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: misc_feature
<222> LOCATION: (1)..(19)
<223> OTHER INFORMATION: phosphorothioate backbone
<220> FEATURE:
<221> NAME/KEY: modified_base
<222> LOCATION: (2)..(3)
<223> OTHER INFORMATION: 2'-O-methyluridine
<220> FEATURE:
<221> NAME/KEY: modified_base
<222> LOCATION: (4)..(4)
<223> OTHER INFORMATION: 2'-O-methylguanosine
<220> FEATURE:
<221> NAME/KEY: modified_base
<222> LOCATION: (15)..(15)
<223> OTHER INFORMATION: 2'-O-methylguanosine
<220> FEATURE:
<221> NAME/KEY: modified_base
<222> LOCATION: (16)..(18)
<223> OTHER INFORMATION: 2'-O-methyluridine
<220> FEATURE:
<221> NAME/KEY: modified_base
<222> LOCATION: (19)..(19)
<223> OTHER INFORMATION: 2'-O-methylcytidine

<400> SEQUENCE: 368
nnnnagtggt gtcannnnn                                               19

<210> SEQ ID NO 369
<211> LENGTH: 18
<212> TYPE: DNA
```

```
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'-O-methyluridine
<220> FEATURE:
<221> NAME/KEY: misc_feature
<222> LOCATION: (1)..(18)
<223> OTHER INFORMATION: phosphorothioate backbone
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (15)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylcytidine

<400> SEQUENCE: 369
nnnngtggtg tcagnnnn                                                 18

<210> SEQ ID NO 370
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylcytidine
<220> FEATURE:
<221> NAME/KEY: modified_base
<222> LOCATION: (1)..(18)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(4)
<223> OTHER INFORMATION: 2'-O-methylguanosine
<220> FEATURE:
<221> NAME/KEY: modified_base
<222> LOCATION: (15)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyladenosine

<400> SEQUENCE: 370
nnnntgtcaa caagnnnn                                                 18

<210> SEQ ID NO 371
<211> LENGTH: 20
<212> TYPE: DNA
<213> ORGANISM: Artificial Sequence
```

```
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methylguanosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methyluridine
<220> FEATURE:
<221> NAME/KEY: modified_base
<222> LOCATION: (17)..(17)
<223> OTHER INFORMATION: 2'-O-methylcytidine
<220> FEATURE:
<221> NAME/KEY: modified_base
<222> LOCATION: (18)..(19)
<223> OTHER INFORMATION: 2'-O-methyluridine
<220> FEATURE:
<221> NAME/KEY: modified_base
<222> LOCATION: (20)..(20)
<223> OTHER INFORMATION: 2'-O-methylguanosine

<400> SEQUENCE: 371
nnnnnatggc acatcnnnnn                                                   20

<210> SEQ ID NO 372
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: misc_feature
<222> LOCATION: (1)..(19)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methylguanosine
<220> FEATURE:
<221> NAME/KEY: modified_base
<222> LOCATION: (3)..(4)
<223> OTHER INFORMATION: 2'-O-methyladenosine
<220> FEATURE:
<221> NAME/KEY: modified_base
<222> LOCATION: (15)..(15)
```

```
<223> OTHER INFORMATION: 2'-O-methylcytidine
<220> FEATURE:
<221> NAME/KEY: modified_base
<222> LOCATION: (16)..(17)
<223> OTHER INFORMATION: 2'-O-methyluridine
<220> FEATURE:
<221> NAME/KEY: modified_base
<222> LOCATION: (18)..(19)
<223> OTHER INFORMATION: 2'-O-methylguanosine

<400> SEQUENCE: 372
nnnntggcac atctnnnnn                                                    19

<210> SEQ ID NO 373
<211> LENGTH: 19
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(19)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O-methyluridine
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyluridine
<220> FEATURE:
<221> NAME/KEY: modified_base
<222> LOCATION: (19)..(19)
<223> OTHER INFORMATION: 2'-O-methylguanosine

<400> SEQUENCE: 373
nnnnatggca catcnnnnn                                                    19

<210> SEQ ID NO 374
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyladenosine
```

```
<220> FEATURE:
<221> NAME/KEY: misc_feature
<222> LOCATION: (1)..(18)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methylguanosine
<220> FEATURE:
<221> NAME/KEY: modified_base
<222> LOCATION: (3)..(4)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O-methylcytidine
<220> FEATURE:
<221> NAME/KEY: modified_base
<222> LOCATION: (16)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylguanosine

<400> SEQUENCE: 374
nnnntggcac atctnnnn                                                 18

<210> SEQ ID NO 375
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(5)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyluridine
<220> FEATURE:
<221> NAME/KEY: modified_base
<222> LOCATION: (19)..(20)
<223> OTHER INFORMATION: 2'-O-methylguanosine

<400> SEQUENCE: 375
nnnnntggca catctnnnnn                                               20

<210> SEQ ID NO 376
<211> LENGTH: 20
```

```
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(5)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(5)
<223> OTHER INFORMATION: 2'-O-methyladenosine
<220> FEATURE:
<221> NAME/KEY: misc_feature
<222> LOCATION: (5)..(6)
<223> OTHER INFORMATION: phosphodiester backbone
<220> FEATURE:
<221> NAME/KEY: misc_feature
<222> LOCATION: (6)..(15)
<223> OTHER INFORMATION: phosphorothioate backbone
<220> FEATURE:
<221> NAME/KEY: misc_feature
<222> LOCATION: (15)..(16)
<223> OTHER INFORMATION: phosphodiester backbone
<220> FEATURE:
<221> NAME/KEY: misc_feature
<222> LOCATION: (16)..(20)
<223> OTHER INFORMATION: phosphorothioate backbone
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyluridine
<220> FEATURE:
<221> NAME/KEY: modified_base
<222> LOCATION: (19)..(20)
<223> OTHER INFORMATION: 2'-O-methylguanosine

<400> SEQUENCE: 376
nnnnntggca catctnnnnn                                             20

<210> SEQ ID NO 377
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methyluridine
<220> FEATURE:
<221> NAME/KEY: misc_feature
<222> LOCATION: (1)..(2)
<223> OTHER INFORMATION: phosphorothioate backbone
<220> FEATURE:
```

```
<221> NAME/KEY: modified_base
<222> LOCATION: (2)..(2)
<223> OTHER INFORMATION: 2'-O-methyladenosine
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: modified_base
<222> LOCATION: (4)..(5)
<223> OTHER INFORMATION: 2'-O-methyladenosine
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(16)
<223> OTHER INFORMATION: phosphorothioate backbone
<220> FEATURE:
<221> NAME/KEY: modified_base
<222> LOCATION: (16)..(16)
<223> OTHER INFORMATION: 2'-O-methylcytidine
<220> FEATURE:
<221> NAME/KEY: misc_feature
<222> LOCATION: (17)..(18)
<223> OTHER INFORMATION: phosphorothioate backbone
<220> FEATURE:
<221> NAME/KEY: modified_base
<222> LOCATION: (17)..(18)
<223> OTHER INFORMATION: 2'-O-methyluridine
```

```
<220> FEATURE:
<221> NAME/KEY: misc_feature
<222> LOCATION: (18)..(19)
<223> OTHER INFORMATION: phosphodiester backbone
<220> FEATURE:
<221> NAME/KEY: misc_feature
<222> LOCATION: (19)..(20)
<223> OTHER INFORMATION: phosphorothioate backbone
<220> FEATURE:
<221> NAME/KEY: modified_base
<222> LOCATION: (19)..(20)
<223> OTHER INFORMATION: 2'-O-methylguanosine

<400> SEQUENCE: 377
nnnnntggca catctnnnnn                                                   20

<210> SEQ ID NO 378
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-(2-methoxyethyl)-modified thymidine
<220> FEATURE:
<221> NAME/KEY: misc_feature
<222> LOCATION: (1)..(20)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-(2-methoxyethyl)-modified adenosine
<220> FEATURE:
<221> NAME/KEY: modified_base
<222> LOCATION: (3)..(3)
<223> OTHER INFORMATION: 2'-O-(2-methoxyethyl)-modified guanosine
<220> FEATURE:
<221> NAME/KEY: modified_base
<222> LOCATION: (4)..(5)
<223> OTHER INFORMATION: 2'-O-(2-methoxyethyl)-modified adenosine
<220> FEATURE:
<221> NAME/KEY: modified_base
<222> LOCATION: (16)..(16)
<223> OTHER INFORMATION: 2'-O-(2-methoxyethyl)-modified 5-methylcytidine
<220> FEATURE:
<221> NAME/KEY: modified_base
<222> LOCATION: (17)..(18)
<223> OTHER INFORMATION: 2'-O-(2-methoxyethyl)-modified thymidine
<220> FEATURE:
<221> NAME/KEY: modified_base
<222> LOCATION: (19)..(20)
<223> OTHER INFORMATION: 2'-O-(2-methoxyethyl)-modified guanosine

<400> SEQUENCE: 378
nnnnntggca catctnnnnn                                                   20

<210> SEQ ID NO 379
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(5)
<223> OTHER INFORMATION: phosphorothioate backbone
<220> FEATURE:
```

```
<221> NAME/KEY: modified_base
<222> LOCATION: (1)..(1)
<223> OTHER INFORMATION: 2'-O-(2-methoxyethyl)-modified thymidine
<220> FEATURE:
<221> NAME/KEY: modified_base
<222> LOCATION: (2)..(2)
<223> OTHER INFORMATION: 2'-O-(2-methoxyethyl)-modified adenosine
<220> FEATURE:
<221> NAME/KEY: modified_base
<222> LOCATION: (3)..(3)
<223> OTHER INFORMATION: 2'-O-(2-methoxyethyl)-modified guanosine
<220> FEATURE:
<221> NAME/KEY: modified_base
<222> LOCATION: (4)..(5)
<223> OTHER INFORMATION: 2'-O-(2-methoxyethyl)-modified adenosine
<220> FEATURE:
<221> NAME/KEY: misc_feature
<222> LOCATION: (5)..(6)
<223> OTHER INFORMATION: phosphodiester backbone
<220> FEATURE:
<221> NAME/KEY: misc_feature
<222> LOCATION: (6)..(15)
<223> OTHER INFORMATION: phosphorothioate backbone
<220> FEATURE:
<221> NAME/KEY: misc_feature
<222> LOCATION: (15)..(16)
<223> OTHER INFORMATION: phosphodiester backbone
<220> FEATURE:
<221> NAME/KEY: modified_base
<222> LOCATION: (16)..(16)
<223> OTHER INFORMATION: 2'-O-(2-methoxyethyl)-modified 5-methylcytidine
<220> FEATURE:
<221> NAME/KEY: misc_feature
<222> LOCATION: (16)..(20)
<223> OTHER INFORMATION: phosphorothioate backbone
<220> FEATURE:
<221> NAME/KEY: modified_base
<222> LOCATION: (17)..(18)
<223> OTHER INFORMATION: 2'-O-(2-methoxyethyl)-modified thymidine
<220> FEATURE:
<221> NAME/KEY: modified_base
<222> LOCATION: (19)..(20)
<223> OTHER INFORMATION: 2'-O-(2-methoxyethyl)-modified guanosine

<400> SEQUENCE: 379
nnnnntggca catctnnnnn                                               20

<210> SEQ ID NO 380
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-(2-methoxyethyl)-modified thymidine
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (2)..(2)
<223> OTHER INFORMATION: 2'-O-(2-methoxyethyl)-modified adenosine
<220> FEATURE:
<221> NAME/KEY: misc_feature
<222> LOCATION: (3)..(4)
<223> OTHER INFORMATION: phosphorothioate backbone
<220> FEATURE:
```

```
<221> NAME/KEY: modified_base
<222> LOCATION: (3)..(3)
<223> OTHER INFORMATION: 2'-O-(2-methoxyethyl)-modified guanosine
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: modified_base
<222> LOCATION: (4)..(5)
<223> OTHER INFORMATION: 2'-O-(2-methoxyethyl)-modified adenosine
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(16)
<223> OTHER INFORMATION: phosphorothioate backbone
<220> FEATURE:
<221> NAME/KEY: misc_feature
<222> LOCATION: (16)..(17)
<223> OTHER INFORMATION: phosphodiester backbone
<220> FEATURE:
<221> NAME/KEY: modified_base
<222> LOCATION: (16)..(16)
<223> OTHER INFORMATION: 2'-O-(2-methoxyethyl)-modified 5-methylcytidine
<220> FEATURE:
<221> NAME/KEY: misc_feature
<222> LOCATION: (17)..(18)
<223> OTHER INFORMATION: phosphorothioate backbone
<220> FEATURE:
<221> NAME/KEY: modified_base
<222> LOCATION: (17)..(18)
<223> OTHER INFORMATION: 2'-O-(2-methoxyethyl)-modified thymidine
<220> FEATURE:
<221> NAME/KEY: misc_feature
<222> LOCATION: (18)..(19)
<223> OTHER INFORMATION: phosphodiester backbone
<220> FEATURE:
<221> NAME/KEY: misc_feature
<222> LOCATION: (19)..(20)
<223> OTHER INFORMATION: phosphorothioate backbone
```

```
<220> FEATURE:
<221> NAME/KEY: modified_base
<222> LOCATION: (19)..(20)
<223> OTHER INFORMATION: 2'-O-(2-methoxyethyl)-modified guanosine

<400> SEQUENCE: 380
nnnnntggca catctnnnnn                                                      20

<210> SEQ ID NO 381
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: locked nucleic acid adenosine
<220> FEATURE:
<221> NAME/KEY: misc_feature
<222> LOCATION: (1)..(18)
<223> OTHER INFORMATION: phosphorothioate backbone
<220> FEATURE:
<221> NAME/KEY: modified_base
<222> LOCATION: (2)..(2)
<223> OTHER INFORMATION: locked nucleic acid guanosine
<220> FEATURE:
<221> NAME/KEY: modified_base
<222> LOCATION: (3)..(3)
<223> OTHER INFORMATION: locked nucleic acid adenosine
<220> FEATURE:
<221> NAME/KEY: modified_base
<222> LOCATION: (15)..(15)
<223> OTHER INFORMATION: locked nucleic acid 5-methylcytidine
<220> FEATURE:
<221> NAME/KEY: modified_base
<222> LOCATION: (16)..(17)
<223> OTHER INFORMATION: locked nucleic acid thymidine
<220> FEATURE:
<221> NAME/KEY: modified_base
<222> LOCATION: (18)..(18)
<223> OTHER INFORMATION: locked nucleic acid guanosine

<400> SEQUENCE: 381
nnnatggcac atctnnnn                                                        18

<210> SEQ ID NO 382
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: locked nucleic acid adenosine
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (2)..(2)
<223> OTHER INFORMATION: locked nucleic acid guanosine
<220> FEATURE:
<221> NAME/KEY: misc_feature
<222> LOCATION: (3)..(4)
<223> OTHER INFORMATION: phosphodiester backbone
<220> FEATURE:
```

```
<221> NAME/KEY: modified_base
<222> LOCATION: (3)..(3)
<223> OTHER INFORMATION: locked nucleic acid adenosine
<220> FEATURE:
<221> NAME/KEY: misc_feature
<222> LOCATION: (4)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(18)
<223> OTHER INFORMATION: phosphorothioate backbone
<220> FEATURE:
<221> NAME/KEY: modified_base
<222> LOCATION: (15)..(15)
<223> OTHER INFORMATION: locked nucleic acid 5-methylcytidine
<220> FEATURE:
<221> NAME/KEY: modified_base
<222> LOCATION: (16)..(17)
<223> OTHER INFORMATION: locked nucleic acid thymidine
<220> FEATURE:
<221> NAME/KEY: modified_base
<222> LOCATION: (18)..(18)
<223> OTHER INFORMATION: locked nucleic acid guanosine

<400> SEQUENCE: 382
nnnatggcac atctnnnn                                                 18

<210> SEQ ID NO 383
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: locked nucleic acid adenosine
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (2)..(2)
<223> OTHER INFORMATION: locked nucleic acid guanosine
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: modified_base
<222> LOCATION: (3)..(3)
<223> OTHER INFORMATION: locked nucleic acid adenosine
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
```

```
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(16)
<223> OTHER INFORMATION: phosphorothioate backbone
<220> FEATURE:
<221> NAME/KEY: modified_base
<222> LOCATION: (15)..(15)
<223> OTHER INFORMATION: locked nucleic acid 5-methylcytidine
<220> FEATURE:
<221> NAME/KEY: misc_feature
<222> LOCATION: (16)..(17)
<223> OTHER INFORMATION: phosphodiester backbone
<220> FEATURE:
<221> NAME/KEY: modified_base
<222> LOCATION: (16)..(17)
<223> OTHER INFORMATION: locked nucleic acid thymidine
<220> FEATURE:
<221> NAME/KEY: misc_feature
<222> LOCATION: (17)..(18)
<223> OTHER INFORMATION: phosphorothioate backbone
<220> FEATURE:
<221> NAME/KEY: modified_base
<222> LOCATION: (18)..(18)
<223> OTHER INFORMATION: locked nucleic acid guanosine

<400> SEQUENCE: 383
nnnatggcac atctnnnn                                                 18

<210> SEQ ID NO 384
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylcytidine
<220> FEATURE:
<221> NAME/KEY: misc_feature
<222> LOCATION: (1)..(18)
<223> OTHER INFORMATION: phosphorothioate backbone
<220> FEATURE:
```

```
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(4)
<223> OTHER INFORMATION: 2'-O-methylguanosine
<220> FEATURE:
<221> NAME/KEY: modified_base
<222> LOCATION: (15)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyladenosine

<400> SEQUENCE: 384
nnnntgtcaa caagnnnn                                                 18

<210> SEQ ID NO 385
<211> LENGTH: 18
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylcytidine
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(4)
<223> OTHER INFORMATION: 2'-O-methylguanosine
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(18)
<223> OTHER INFORMATION: phosphorothioate backbone
<220> FEATURE:
<221> NAME/KEY: modified_base
<222> LOCATION: (15)..(16)
<223> OTHER INFORMATION: 2'-O-methylcytidine
<220> FEATURE:
<221> NAME/KEY: modified_base
<222> LOCATION: (17)..(18)
<223> OTHER INFORMATION: 2'-O-methyladenosine

<400> SEQUENCE: 385
nnnntgtcaa caagnnnn                                                 18

<210> SEQ ID NO 386
<211> LENGTH: 18
<212> TYPE: DNA
```

```
<213> ORGANISM: Artificial Sequence
<220> FEATURE:
<223> OTHER INFORMATION: Synthetic Construct
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O-methylcytidine
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: modified_base
<222> LOCATION: (3)..(4)
<223> OTHER INFORMATION: 2'-O-methylguanosine
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(16)
<223> OTHER INFORMATION: phosphorothioate backbone
<220> FEATURE:
```

```
<221> NAME/KEY: modified_base
<222> LOCATION: (15)..(16)
<223> OTHER INFORMATION: 2'-O-methylcytidine
<220> FEATURE:
<221> NAME/KEY: misc_feature
<222> LOCATION: (16)..(17)
<223> OTHER INFORMATION: phosphodiester backbone
<220> FEATURE:
<221> NAME/KEY: misc_feature
<222> LOCATION: (17)..(18)
<223> OTHER INFORMATION: phosphorothioate backbone
<220> FEATURE:
<221> NAME/KEY: modified_base
<222> LOCATION: (17)..(18)
<223> OTHER INFORMATION: 2'-O-methyladenosine

<400> SEQUENCE: 386
nnnntgtcaa caagnnnn                                              18

<210> SEQ ID NO 387
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: 2'-O-(2-methoxyethyl)-modified 5-methylcytidine
<220> FEATURE:
<221> NAME/KEY: misc_feature
<222> LOCATION: (1)..(18)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-(2-methoxyethyl)-modified thymidine
<220> FEATURE:
<221> NAME/KEY: modified_base
<222> LOCATION: (3)..(4)
<223> OTHER INFORMATION: 2'-O-(2-methoxyethyl)-modified guanosine
<220> FEATURE:
<221> NAME/KEY: modified_base
<222> LOCATION: (15)..(16)
<223> OTHER INFORMATION: 2'-O-(2-methoxyethyl)-modified 5-methylcytidine
<220> FEATURE:
<221> NAME/KEY: modified_base
<222> LOCATION: (17)..(18)
<223> OTHER INFORMATION: 2'-O-(2-methoxyethyl)-modified adenosine

<400> SEQUENCE: 387
nnnntgtcaa caagnnnn                                              18

<210> SEQ ID NO 388
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: 2'-O-(2-methoxyethyl)-modified 5-methylcytidine
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: modified_base
<222> LOCATION: (2)..(2)
<223> OTHER INFORMATION: 2'-O-(2-methoxyethyl)-modified thymidine
<220> FEATURE:
<221> NAME/KEY: modified_base
<222> LOCATION: (3)..(4)
<223> OTHER INFORMATION: 2'-O-(2-methoxyethyl)-modified guanosine
```

<220> FEATURE:
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(18)
<223> OTHER INFORMATION: phosphorothioate backbone
<220> FEATURE:
<221> NAME/KEY: modified_base
<222> LOCATION: (15)..(16)
<223> OTHER INFORMATION: 2'-O-(2-methoxyethyl)-modified 5-methylcytidine
<220> FEATURE:
<221> NAME/KEY: modified_base
<222> LOCATION: (17)..(18)
<223> OTHER INFORMATION: 2'-O-(2-methoxyethyl)-modified adenosine

<400> SEQUENCE: 388
nnnntgtcaa caagnnnn                                                  18

<210> SEQ ID NO 389
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: 2'-O-(2-methoxyethyl)-modified 5-methylcytidine
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (2)..(2)
<223> OTHER INFORMATION: 2'-O-(2-methoxyethyl)-modified thymidine
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: modified_base
<222> LOCATION: (3)..(4)
<223> OTHER INFORMATION: 2'-O-(2-methoxyethyl)-modified guanosine
<220> FEATURE:
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)

```
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(15)
<223> OTHER INFORMATION: phosphodiester backbone
<220> FEATURE:
<221> NAME/KEY: misc_feature
<222> LOCATION: (15)..(16)
<223> OTHER INFORMATION: phosphorothioate backbone
<220> FEATURE:
<221> NAME/KEY: modified_base
<222> LOCATION: (15)..(16)
<223> OTHER INFORMATION: 2'-O-(2-methoxyethyl)-modified 5-methylcytidine
<220> FEATURE:
<221> NAME/KEY: misc_feature
<222> LOCATION: (16)..(17)
<223> OTHER INFORMATION: phosphodiester backbone
<220> FEATURE:
<221> NAME/KEY: misc_feature
<222> LOCATION: (17)..(18)
<223> OTHER INFORMATION: phosphorothioate backbone
<220> FEATURE:
<221> NAME/KEY: modified_base
<222> LOCATION: (17)..(18)
<223> OTHER INFORMATION: 2'-O-(2-methoxyethyl)-modified adenosine

<400> SEQUENCE: 389
nnnntgtcaa caagnnnn                                                    18

<210> SEQ ID NO 390
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: locked nucleic acid thymidine
<220> FEATURE:
<221> NAME/KEY: misc_feature
<222> LOCATION: (1)..(17)
<223> OTHER INFORMATION: phosphorothioate backbone
<220> FEATURE:
<221> NAME/KEY: modified_base
<222> LOCATION: (2)..(3)
<223> OTHER INFORMATION: locked nucleic acid guanosine
<220> FEATURE:
<221> NAME/KEY: modified_base
<222> LOCATION: (14)..(15)
<223> OTHER INFORMATION: locked nucleic acid 5-methylcytidine
<220> FEATURE:
<221> NAME/KEY: modified_base
<222> LOCATION: (16)..(17)
<223> OTHER INFORMATION: locked nucleic acid adenosine

<400> SEQUENCE: 390
```
nnntgtcaac aagnnnn                                                17

<210> SEQ ID NO 391
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: locked nucleic acid thymidine
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (2)..(3)
<223> OTHER INFORMATION: locked nucleic acid guanosine
<220> FEATURE:
<221> NAME/KEY: misc_feature
<222> LOCATION: (3)..(4)
<223> OTHER INFORMATION: phosphodiester backbone
<220> FEATURE:
<221> NAME/KEY: misc_feature
<222> LOCATION: (4)..(13)
<223> OTHER INFORMATION: phosphorothioate backbone
<220> FEATURE:
<221> NAME/KEY: misc_feature
<222> LOCATION: (13)..(14)
<223> OTHER INFORMATION: phosphodiester backbone
<220> FEATURE:
<221> NAME/KEY: misc_feature
<222> LOCATION: (14)..(17)
<223> OTHER INFORMATION: phosphorothioate backbone
<220> FEATURE:
<221> NAME/KEY: modified_base
<222> LOCATION: (14)..(15)
<223> OTHER INFORMATION: locked nucleic acid 5-methylcytidine
<220> FEATURE:
<221> NAME/KEY: modified_base
<222> LOCATION: (16)..(17)
<223> OTHER INFORMATION: locked nucleic acid adenosine

<400> SEQUENCE: 391
nnntgtcaac aagnnnn                                                17

<210> SEQ ID NO 392
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: locked nucleic acid thymidine
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphodiester backbone
<220> FEATURE:
<221> NAME/KEY: modified_base
<222> LOCATION: (2)..(3)
<223> OTHER INFORMATION: locked nucleic acid guanosine
<220> FEATURE:
<221> NAME/KEY: misc_feature
<222> LOCATION: (3)..(4)
<223> OTHER INFORMATION: phosphorothioate backbone
<220> FEATURE:

```
<221> NAME/KEY: misc_feature
<222> LOCATION: (4)..(5)
<223> OTHER INFORMATION: phosphodiester backbone
<220> FEATURE:
<221> NAME/KEY: misc_feature
<222> LOCATION: (5)..(6)
<223> OTHER INFORMATION: phosphorothioate backbone
<220> FEATURE:
<221> NAME/KEY: misc_feature
<222> LOCATION: (6)..(7)
<223> OTHER INFORMATION: phosphodiester backbone
<220> FEATURE:
<221> NAME/KEY: misc_feature
<222> LOCATION: (7)..(8)
<223> OTHER INFORMATION: phosphorothioate backbone
<220> FEATURE:
<221> NAME/KEY: misc_feature
<222> LOCATION: (8)..(9)
<223> OTHER INFORMATION: phosphodiester backbone
<220> FEATURE:
<221> NAME/KEY: misc_feature
<222> LOCATION: (9)..(10)
<223> OTHER INFORMATION: phosphorothioate backbone
<220> FEATURE:
<221> NAME/KEY: misc_feature
<222> LOCATION: (10)..(11)
<223> OTHER INFORMATION: phosphodiester backbone
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(13)
<223> OTHER INFORMATION: phosphodiester backbone
<220> FEATURE:
<221> NAME/KEY: misc_feature
<222> LOCATION: (13)..(14)
<223> OTHER INFORMATION: phosphorothioate backbone
<220> FEATURE:
<221> NAME/KEY: misc_feature
<222> LOCATION: (14)..(16)
<223> OTHER INFORMATION: phosphodiester backbone
<220> FEATURE:
<221> NAME/KEY: modified_base
<222> LOCATION: (14)..(15)
<223> OTHER INFORMATION: locked nucleic acid 5-methylcytidine
<220> FEATURE:
<221> NAME/KEY: misc_feature
<222> LOCATION: (16)..(17)
<223> OTHER INFORMATION: phosphorothioate backbone
<220> FEATURE:
<221> NAME/KEY: modified_base
<222> LOCATION: (16)..(17)
<223> OTHER INFORMATION: locked nucleic acid adenosine

<400> SEQUENCE: 392
nnntgtcaac aagnnnn                                              17

<210> SEQ ID NO 393
<211> LENGTH: 20
<212> TYPE: RNA
<213> ORGANISM: Artificial Sequence
<220> FEATURE:
<223> OTHER INFORMATION: Synthetic Construct

<400> SEQUENCE: 393
gaaaccaucu cugggauaag                                           20

<210> SEQ ID NO 394
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 394
aaaccaucuc ugggauaagg                                              20

<210> SEQ ID NO 395
<211> LENGTH: 20
<212> TYPE: RNA
<213> ORGANISM: Artificial Sequence
<220> FEATURE:
<223> OTHER INFORMATION: Synthetic Construct

<400> SEQUENCE: 395
aaccaucucu gggauaagga                                              20

<210> SEQ ID NO 396
<211> LENGTH: 20
<212> TYPE: RNA
<213> ORGANISM: Artificial Sequence
<220> FEATURE:
<223> OTHER INFORMATION: Synthetic Construct

<400> SEQUENCE: 396
accaucucug ggauaaggau                                              20

<210> SEQ ID NO 397
<211> LENGTH: 20
<212> TYPE: RNA
<213> ORGANISM: Artificial Sequence
<220> FEATURE:
<223> OTHER INFORMATION: Synthetic Construct

<400> SEQUENCE: 397
ccaucucugg gauaaggaug                                              20

<210> SEQ ID NO 398
<211> LENGTH: 20
<212> TYPE: RNA
<213> ORGANISM: Artificial Sequence
<220> FEATURE:
<223> OTHER INFORMATION: Synthetic Construct

<400> SEQUENCE: 398
caucucuggg auaaggauga                                              20

<210> SEQ ID NO 399
<211> LENGTH: 20
<212> TYPE: RNA
<213> ORGANISM: Artificial Sequence
<220> FEATURE:
<223> OTHER INFORMATION: Synthetic Construct

<400> SEQUENCE: 399
aucucuggga uaaggaugac                                              20

<210> SEQ ID NO 400
<211> LENGTH: 20
<212> TYPE: RNA
<213> ORGANISM: Artificial Sequence
<220> FEATURE:
<223> OTHER INFORMATION: Synthetic Construct

<400> SEQUENCE: 400
ucucugggau aaggaugacu                                              20

<210> SEQ ID NO 401
```

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 401
cucugggaua aggaugacug                                        20

<210> SEQ ID NO 402
<211> LENGTH: 20
<212> TYPE: RNA
<213> ORGANISM: Artificial Sequence
<220> FEATURE:
<223> OTHER INFORMATION: Synthetic Construct

<400> SEQUENCE: 402
ucugggauaa ggaugacuga                                        20

<210> SEQ ID NO 403
<211> LENGTH: 20
<212> TYPE: RNA
<213> ORGANISM: Artificial Sequence
<220> FEATURE:
<223> OTHER INFORMATION: Synthetic Construct

<400> SEQUENCE: 403
cugggauaag gaugacugag                                        20

<210> SEQ ID NO 404
<211> LENGTH: 20
<212> TYPE: RNA
<213> ORGANISM: Artificial Sequence
<220> FEATURE:
<223> OTHER INFORMATION: Synthetic Construct

<400> SEQUENCE: 404
ugggauaagg augacugagg                                        20

<210> SEQ ID NO 405
<211> LENGTH: 20
<212> TYPE: RNA
<213> ORGANISM: Artificial Sequence
<220> FEATURE:
<223> OTHER INFORMATION: Synthetic Construct

<400> SEQUENCE: 405
gggauaagga ugacugagga                                        20

<210> SEQ ID NO 406
<211> LENGTH: 20
<212> TYPE: RNA
<213> ORGANISM: Artificial Sequence
<220> FEATURE:
<223> OTHER INFORMATION: Synthetic Construct

<400> SEQUENCE: 406
ggauaaggau gacugaggaa                                        20

<210> SEQ ID NO 407
<211> LENGTH: 20
<212> TYPE: RNA
<213> ORGANISM: Artificial Sequence
<220> FEATURE:
<223> OTHER INFORMATION: Synthetic Construct

<400> SEQUENCE: 407
```
gcugaaacaa cugaaacuuc                                              20

<210> SEQ ID NO 408
<211> LENGTH: 20
<212> TYPE: RNA
<213> ORGANISM: Artificial Sequence
<220> FEATURE:
<223> OTHER INFORMATION: Synthetic Construct

<400> SEQUENCE: 408
gaaacaacug aaacuucagg                                              20

<210> SEQ ID NO 409
<211> LENGTH: 20
<212> TYPE: RNA
<213> ORGANISM: Artificial Sequence
<220> FEATURE:
<223> OTHER INFORMATION: Synthetic Construct

<400> SEQUENCE: 409
aaacaacuga aacuucaggg                                              20

<210> SEQ ID NO 410
<211> LENGTH: 20
<212> TYPE: RNA
<213> ORGANISM: Artificial Sequence
<220> FEATURE:
<223> OTHER INFORMATION: Synthetic Construct

<400> SEQUENCE: 410
aacaacugaa acuucaggga                                              20

<210> SEQ ID NO 411
<211> LENGTH: 20
<212> TYPE: RNA
<213> ORGANISM: Artificial Sequence
<220> FEATURE:
<223> OTHER INFORMATION: Synthetic Construct

<400> SEQUENCE: 411
acaacugaaa cuucagggaa                                              20

<210> SEQ ID NO 412
<211> LENGTH: 20
<212> TYPE: RNA
<213> ORGANISM: Artificial Sequence
<220> FEATURE:
<223> OTHER INFORMATION: Synthetic Construct

<400> SEQUENCE: 412
caacugaaac uucagggaaa                                              20

<210> SEQ ID NO 413
<211> LENGTH: 20
<212> TYPE: RNA
<213> ORGANISM: Artificial Sequence
<220> FEATURE:
<223> OTHER INFORMATION: Synthetic Construct

<400> SEQUENCE: 413
acugaaacuu cagggaaaag                                              20

<210> SEQ ID NO 414
<211> LENGTH: 19
<212> TYPE: RNA

```
<213> ORGANISM: Artificial Sequence
<220> FEATURE:
<223> OTHER INFORMATION: Synthetic Construct

<400> SEQUENCE: 414
aaccaucucu gggauaagg                                                    19

<210> SEQ ID NO 415
<211> LENGTH: 19
<212> TYPE: RNA
<213> ORGANISM: Artificial Sequence
<220> FEATURE:
<223> OTHER INFORMATION: Synthetic Construct

<400> SEQUENCE: 415
accaucucug ggauaagga                                                    19

<210> SEQ ID NO 416
<211> LENGTH: 19
<212> TYPE: RNA
<213> ORGANISM: Artificial Sequence
<220> FEATURE:
<223> OTHER INFORMATION: Synthetic Construct

<400> SEQUENCE: 416
ccaucucugg gauaaggau                                                    19

<210> SEQ ID NO 417
<211> LENGTH: 19
<212> TYPE: RNA
<213> ORGANISM: Artificial Sequence
<220> FEATURE:
<223> OTHER INFORMATION: Synthetic Construct

<400> SEQUENCE: 417
caucucuggg auaaggaug                                                    19

<210> SEQ ID NO 418
<211> LENGTH: 19
<212> TYPE: RNA
<213> ORGANISM: Artificial Sequence
<220> FEATURE:
<223> OTHER INFORMATION: Synthetic Construct

<400> SEQUENCE: 418
aucucuggga uaaggauga                                                    19

<210> SEQ ID NO 419
<211> LENGTH: 19
<212> TYPE: RNA
<213> ORGANISM: Artificial Sequence
<220> FEATURE:
<223> OTHER INFORMATION: Synthetic Construct

<400> SEQUENCE: 419 ucucuggau aaggaugac                                                     19

<210> SEQ ID NO 420
<211> LENGTH: 19
<212> TYPE: RNA
<213> ORGANISM: Artificial Sequence
<220> FEATURE:
<223> OTHER INFORMATION: Synthetic Construct

<400> SEQUENCE: 420
cucugggaua aggaugacu                                                    19
```

```
<210> SEQ ID NO 421
<211> LENGTH: 19
<212> TYPE: RNA
<213> ORGANISM: Artificial Sequence
<220> FEATURE:
<223> OTHER INFORMATION: Synthetic Construct

<400> SEQUENCE: 421
ucugggauaa ggaugacug                                                   19

<210> SEQ ID NO 422
<211> LENGTH: 19
<212> TYPE: RNA
<213> ORGANISM: Artificial Sequence
<220> FEATURE:
<223> OTHER INFORMATION: Synthetic Construct

<400> SEQUENCE: 422
cugggauaag gaugacuga                                                   19

<210> SEQ ID NO 423
<211> LENGTH: 19
<212> TYPE: RNA
<213> ORGANISM: Artificial Sequence
<220> FEATURE:
<223> OTHER INFORMATION: Synthetic Construct

<400> SEQUENCE: 423
ugggauaagg augacugag                                                   19

<210> SEQ ID NO 424
<211> LENGTH: 19
<212> TYPE: RNA
<213> ORGANISM: Artificial Sequence
<220> FEATURE:
<223> OTHER INFORMATION: Synthetic Construct

<400> SEQUENCE: 424
gggauaagga ugacugagg                                                   19

<210> SEQ ID NO 425
<211> LENGTH: 19
<212> TYPE: RNA
<213> ORGANISM: Artificial Sequence
<220> FEATURE:
<223> OTHER INFORMATION: Synthetic Construct

<400> SEQUENCE: 425
ggauaaggau gacugagga                                                   19

<210> SEQ ID NO 426
<211> LENGTH: 19
<212> TYPE: RNA
<213> ORGANISM: Artificial Sequence
<220> FEATURE:
<223> OTHER INFORMATION: Synthetic Construct

<400> SEQUENCE: 426
aacaacugaa acuucaggg                                                   19

<210> SEQ ID NO 427
<211> LENGTH: 19
<212> TYPE: RNA
<213> ORGANISM: Artificial Sequence
<220> FEATURE:
```

<223> OTHER INFORMATION: Synthetic Construct

<400> SEQUENCE: 427
acaacugaaa cuucaggga                                                    19

<210> SEQ ID NO 428
<211> LENGTH: 19
<212> TYPE: RNA
<213> ORGANISM: Artificial Sequence
<220> FEATURE:
<223> OTHER INFORMATION: Synthetic Construct

<400> SEQUENCE: 428
caacugaaac uucagggaa                                                    19

<210> SEQ ID NO 429
<211> LENGTH: 19
<212> TYPE: RNA
<213> ORGANISM: Artificial Sequence
<220> FEATURE:
<223> OTHER INFORMATION: Synthetic Construct

<400> SEQUENCE: 429
caacugaaac uucagggaa                                                    19

<210> SEQ ID NO 430
<211> LENGTH: 18
<212> TYPE: RNA
<213> ORGANISM: Artificial Sequence
<220> FEATURE:
<223> OTHER INFORMATION: Synthetic Construct

<400> SEQUENCE: 430
ccaucucugg gauaagga                                                     18

<210> SEQ ID NO 431
<211> LENGTH: 18
<212> TYPE: RNA
<213> ORGANISM: Artificial Sequence
<220> FEATURE:
<223> OTHER INFORMATION: Synthetic Construct

<400> SEQUENCE: 431
caucucuggg auaaggau                                                     18

<210> SEQ ID NO 432
<211> LENGTH: 18
<212> TYPE: RNA
<213> ORGANISM: Artificial Sequence
<220> FEATURE:
<223> OTHER INFORMATION: Synthetic Construct

<400> SEQUENCE: 432
aucucuggga uaaggaug                                                     18

<210> SEQ ID NO 433
<211> LENGTH: 18
<212> TYPE: RNA
<213> ORGANISM: Artificial Sequence
<220> FEATURE:
<223> OTHER INFORMATION: Synthetic Construct

<400> SEQUENCE: 433
ucucugggau aaggauga                                                     18

```
<210> SEQ ID NO 434
<211> LENGTH: 18
<212> TYPE: RNA
<213> ORGANISM: Artificial Sequence
<220> FEATURE:
<223> OTHER INFORMATION: Synthetic Construct

<400> SEQUENCE: 434
cucugggaua aggaugac                                                    18

<210> SEQ ID NO 435
<211> LENGTH: 18
<212> TYPE: RNA
<213> ORGANISM: Artificial Sequence
<220> FEATURE:
<223> OTHER INFORMATION: Synthetic Construct

<400> SEQUENCE: 435
ucugggauaa ggaugacu                                                    18

<210> SEQ ID NO 436
<211> LENGTH: 18
<212> TYPE: RNA
<213> ORGANISM: Artificial Sequence
<220> FEATURE:
<223> OTHER INFORMATION: Synthetic Construct

<400> SEQUENCE: 436
cugggauaag gaugacug                                                    18

<210> SEQ ID NO 437
<211> LENGTH: 18
<212> TYPE: RNA
<213> ORGANISM: Artificial Sequence
<220> FEATURE:
<223> OTHER INFORMATION: Synthetic Construct

<400> SEQUENCE: 437
ugggauaagg augacuga                                                    18

<210> SEQ ID NO 438
<211> LENGTH: 18
<212> TYPE: RNA
<213> ORGANISM: Artificial Sequence
<220> FEATURE:
<223> OTHER INFORMATION: Synthetic Construct

<400> SEQUENCE: 438
gggauaagga ugacugag                                                    18

<210> SEQ ID NO 439
<211> LENGTH: 18
<212> TYPE: RNA
<213> ORGANISM: Artificial Sequence
<220> FEATURE:
<223> OTHER INFORMATION: Synthetic Construct

<400> SEQUENCE: 439
ggauaaggau gacugagg                                                    18

<210> SEQ ID NO 440
<211> LENGTH: 18
<212> TYPE: RNA
<213> ORGANISM: Artificial Sequence
<220> FEATURE:
<223> OTHER INFORMATION: Synthetic Construct
```

```
<400> SEQUENCE: 440
acaacugaaa cuucaggg                                                 18

<210> SEQ ID NO 441
<211> LENGTH: 20
<212> TYPE: DNA
<213> ORGANISM: Artificial Sequence
<220> FEATURE:
<223> OTHER INFORMATION: Synthetic Construct

<400> SEQUENCE: 441
cttatcccag agatggtttc                                               20

<210> SEQ ID NO 442
<211> LENGTH: 20
<212> TYPE: DNA
<213> ORGANISM: Artificial Sequence
<220> FEATURE:
<223> OTHER INFORMATION: Synthetic Construct

<400> SEQUENCE: 442
ccttatccca gagatggttt                                               20

<210> SEQ ID NO 443
<211> LENGTH: 20
<212> TYPE: DNA
<213> ORGANISM: Artificial Sequence
<220> FEATURE:
<223> OTHER INFORMATION: Synthetic Construct

<400> SEQUENCE: 443
tccttatccc agagatggtt                                               20

<210> SEQ ID NO 444
<211> LENGTH: 20
<212> TYPE: DNA
<213> ORGANISM: Artificial Sequence
<220> FEATURE:
<223> OTHER INFORMATION: Synthetic Construct

<400> SEQUENCE: 444
atccttatcc cagagatggt                                               20

<210> SEQ ID NO 445
<211> LENGTH: 20
<212> TYPE: DNA
<213> ORGANISM: Artificial Sequence
<220> FEATURE:
<223> OTHER INFORMATION: Synthetic Construct

<400> SEQUENCE: 445
catccttatc ccagagatgg                                               20

<210> SEQ ID NO 446
<211> LENGTH: 20
<212> TYPE: DNA
<213> ORGANISM: Artificial Sequence
<220> FEATURE:
<223> OTHER INFORMATION: Synthetic Construct

<400> SEQUENCE: 446
tcatccttat cccagagatg                                               20

<210> SEQ ID NO 447
<211> LENGTH: 20
```

```
<212> TYPE: DNA
<213> ORGANISM: Artificial Sequence
<220> FEATURE:
<223> OTHER INFORMATION: Synthetic Construct

<400> SEQUENCE: 447
gtcatcctta tcccagagat                                              20

<210> SEQ ID NO 448
<211> LENGTH: 20
<212> TYPE: DNA
<213> ORGANISM: Artificial Sequence
<220> FEATURE:
<223> OTHER INFORMATION: Synthetic Construct

<400> SEQUENCE: 448
agtcatcctt atcccagaga                                              20

<210> SEQ ID NO 449
<211> LENGTH: 20
<212> TYPE: DNA
<213> ORGANISM: Artificial Sequence
<220> FEATURE:
<223> OTHER INFORMATION: Synthetic Construct

<400> SEQUENCE: 449
cagtcatcct tatcccagag                                              20

<210> SEQ ID NO 450
<211> LENGTH: 20
<212> TYPE: DNA
<213> ORGANISM: Artificial Sequence
<220> FEATURE:
<223> OTHER INFORMATION: Synthetic Construct

<400> SEQUENCE: 450
tcagtcatcc ttatcccaga                                              20

<210> SEQ ID NO 451
<211> LENGTH: 20
<212> TYPE: DNA
<213> ORGANISM: Artificial Sequence
<220> FEATURE:
<223> OTHER INFORMATION: Synthetic Construct

<400> SEQUENCE: 451
ctcagtcatc cttatcccag                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic Construct

<400> SEQUENCE: 452
cctcagtcat ccttatccca                                              20

<210> SEQ ID NO 453
<211> LENGTH: 20
<212> TYPE: DNA
<213> ORGANISM: Artificial Sequence
<220> FEATURE:
<223> OTHER INFORMATION: Synthetic Construct

<400> SEQUENCE: 453
```
tcctcagtca tccttatccc 20

<210> SEQ ID NO 454
<211> LENGTH: 20
<212> TYPE: DNA
<213> ORGANISM: Artificial Sequence
<220> FEATURE:
<223> OTHER INFORMATION: Synthetic Construct

<400> SEQUENCE: 454
ttcctcagtc atccttatcc 20

<210> SEQ ID NO 455
<211> LENGTH: 20
<212> TYPE: DNA
<213> ORGANISM: Artificial Sequence
<220> FEATURE:
<223> OTHER INFORMATION: Synthetic Construct

<400> SEQUENCE: 455
gaagtttcag ttgtttcagc 20

<210> SEQ ID NO 456
<211> LENGTH: 20
<212> TYPE: DNA
<213> ORGANISM: Artificial Sequence
<220> FEATURE:
<223> OTHER INFORMATION: Synthetic Construct

<400> SEQUENCE: 456
cctgaagttt cagttgtttc 20

<210> SEQ ID NO 457
<211> LENGTH: 20
<212> TYPE: DNA
<213> ORGANISM: Artificial Sequence
<220> FEATURE:
<223> OTHER INFORMATION: Synthetic Construct

<400> SEQUENCE: 457
ccctgaagtt tcagttgttt 20

<210> SEQ ID NO 458
<211> LENGTH: 20
<212> TYPE: DNA
<213> ORGANISM: Artificial Sequence
<220> FEATURE:
<223> OTHER INFORMATION: Synthetic Construct

<400> SEQUENCE: 458
tccctgaagt ttcagttgtt 20

<210> SEQ ID NO 459
<211> LENGTH: 20
<212> TYPE: DNA
<213> ORGANISM: Artificial Sequence
<220> FEATURE:
<223> OTHER INFORMATION: Synthetic Construct

<400> SEQUENCE: 459
ttccctgaag tttcagttgt 20

<210> SEQ ID NO 460
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 460
tttccctgaa gtttcagttg                                          20

<210> SEQ ID NO 461
<211> LENGTH: 20
<212> TYPE: DNA
<213> ORGANISM: Artificial Sequence
<220> FEATURE:
<223> OTHER INFORMATION: Synthetic Construct

<400> SEQUENCE: 461
cttttccctg aagtttcagt                                          20

<210> SEQ ID NO 462
<211> LENGTH: 19
<212> TYPE: DNA
<213> ORGANISM: Artificial Sequence
<220> FEATURE:
<223> OTHER INFORMATION: Synthetic Construct

<400> SEQUENCE: 462
ccttatccca gagatggtt                                           19

<210> SEQ ID NO 463
<211> LENGTH: 19
<212> TYPE: DNA
<213> ORGANISM: Artificial Sequence
<220> FEATURE:
<223> OTHER INFORMATION: Synthetic Construct

<400> SEQUENCE: 463
tccttatccc agagatggt                                           19

<210> SEQ ID NO 464
<211> LENGTH: 19
<212> TYPE: DNA
<213> ORGANISM: Artificial Sequence
<220> FEATURE:
<223> OTHER INFORMATION: Synthetic Construct

<400> SEQUENCE: 464
atccttatcc cagagatgg                                           19

<210> SEQ ID NO 465
<211> LENGTH: 19
<212> TYPE: DNA
<213> ORGANISM: Artificial Sequence
<220> FEATURE:
<223> OTHER INFORMATION: Synthetic Construct

<400> SEQUENCE: 465
catccttatc ccagagatg                                           19

<210> SEQ ID NO 466
<211> LENGTH: 19
<212> TYPE: DNA
<213> ORGANISM: Artificial Sequence
<220> FEATURE:
<223> OTHER INFORMATION: Synthetic Construct

<400> SEQUENCE: 466
tcatccttat cccagagat                                           19
```

<210> SEQ ID NO 467
<211> LENGTH: 19
<212> TYPE: DNA
<213> ORGANISM: Artificial Sequence
<220> FEATURE:
<223> OTHER INFORMATION: Synthetic Construct

<400> SEQUENCE: 467
gtcatcctta tcccagaga                                                19

<210> SEQ ID NO 468
<211> LENGTH: 19
<212> TYPE: DNA
<213> ORGANISM: Artificial Sequence
<220> FEATURE:
<223> OTHER INFORMATION: Synthetic Construct

<400> SEQUENCE: 468
agtcatcctt atcccagag                                                19

<210> SEQ ID NO 469
<211> LENGTH: 19
<212> TYPE: DNA
<213> ORGANISM: Artificial Sequence
<220> FEATURE:
<223> OTHER INFORMATION: Synthetic Construct

<400> SEQUENCE: 469
cagtcatcct tatcccaga                                                19

<210> SEQ ID NO 470
<211> LENGTH: 19
<212> TYPE: DNA
<213> ORGANISM: Artificial Sequence
<220> FEATURE:
<223> OTHER INFORMATION: Synthetic Construct

<400> SEQUENCE: 470
tcagtcatcc ttatcccag                                                19

<210> SEQ ID NO 471
<211> LENGTH: 19
<212> TYPE: DNA
<213> ORGANISM: Artificial Sequence
<220> FEATURE:
<223> OTHER INFORMATION: Synthetic Construct

<400> SEQUENCE: 471
ctcagtcatc cttatccca                                                19

<210> SEQ ID NO 472
<211> LENGTH: 19
<212> TYPE: DNA
<213> ORGANISM: Artificial Sequence
<220> FEATURE:
<223> OTHER INFORMATION: Synthetic Construct

<400> SEQUENCE: 472
cctcagtcat ccttatccc                                                19

<210> SEQ ID NO 473
<211> LENGTH: 19
<212> TYPE: DNA
<213> ORGANISM: Artificial Sequence
<220> FEATURE:
<223> OTHER INFORMATION: Synthetic Construct

```
<400> SEQUENCE: 473
tcctcagtca tccttatcc                                                19

<210> SEQ ID NO 474
<211> LENGTH: 19
<212> TYPE: DNA
<213> ORGANISM: Artificial Sequence
<220> FEATURE:
<223> OTHER INFORMATION: Synthetic Construct

<400> SEQUENCE: 474
ccctgaagtt tcagttgtt                                                19

<210> SEQ ID NO 475
<211> LENGTH: 19
<212> TYPE: DNA
<213> ORGANISM: Artificial Sequence
<220> FEATURE:
<223> OTHER INFORMATION: Synthetic Construct

<400> SEQUENCE: 475
tccctgaagt ttcagttgt                                                19

<210> SEQ ID NO 476
<211> LENGTH: 19
<212> TYPE: DNA
<213> ORGANISM: Artificial Sequence
<220> FEATURE:
<223> OTHER INFORMATION: Synthetic Construct

<400> SEQUENCE: 476
ttccctgaag tttcagttg                                                19

<210> SEQ ID NO 477
<211> LENGTH: 19
<212> TYPE: DNA
<213> ORGANISM: Artificial Sequence
<220> FEATURE:
<223> OTHER INFORMATION: Synthetic Construct

<400> SEQUENCE: 477
ttccctgaag tttcagttg                                                19

<210> SEQ ID NO 478
<211> LENGTH: 18
<212> TYPE: DNA
<213> ORGANISM: Artificial Sequence
<220> FEATURE:
<223> OTHER INFORMATION: Synthetic Construct

<400> SEQUENCE: 478
tccttatccc agagatgg                                                 18

<210> SEQ ID NO 479
<211> LENGTH: 18
<212> TYPE: DNA
<213> ORGANISM: Artificial Sequence
<220> FEATURE:
<223> OTHER INFORMATION: Synthetic Construct

<400> SEQUENCE: 479
atccttatcc cagagatg                                                 18

<210> SEQ ID NO 480
```

```
<211> LENGTH: 18
<212> TYPE: DNA
<213> ORGANISM: Artificial Sequence
<220> FEATURE:
<223> OTHER INFORMATION: Synthetic Construct

<400> SEQUENCE: 480
catccttatc ccagagat                                                   18

<210> SEQ ID NO 481
<211> LENGTH: 18
<212> TYPE: DNA
<213> ORGANISM: Artificial Sequence
<220> FEATURE:
<223> OTHER INFORMATION: Synthetic Construct

<400> SEQUENCE: 481
tcatccttat cccagaga                                                   18

<210> SEQ ID NO 482
<211> LENGTH: 18
<212> TYPE: DNA
<213> ORGANISM: Artificial Sequence
<220> FEATURE:
<223> OTHER INFORMATION: Synthetic Construct

<400> SEQUENCE: 482
gtcatcctta tcccagag                                                   18

<210> SEQ ID NO 483
<211> LENGTH: 18
<212> TYPE: DNA
<213> ORGANISM: Artificial Sequence
<220> FEATURE:
<223> OTHER INFORMATION: Synthetic Construct

<400> SEQUENCE: 483
agtcatcctt atcccaga                                                   18

<210> SEQ ID NO 484
<211> LENGTH: 18
<212> TYPE: DNA
<213> ORGANISM: Artificial Sequence
<220> FEATURE:
<223> OTHER INFORMATION: Synthetic Construct

<400> SEQUENCE: 484
cagtcatcct tatcccag                                                   18

<210> SEQ ID NO 485
<211> LENGTH: 18
<212> TYPE: DNA
<213> ORGANISM: Artificial Sequence
<220> FEATURE:
<223> OTHER INFORMATION: Synthetic Construct

<400> SEQUENCE: 485
tcagtcatcc ttatccca                                                   18

<210> SEQ ID NO 486
<211> LENGTH: 18
<212> TYPE: DNA
<213> ORGANISM: Artificial Sequence
<220> FEATURE:
<223> OTHER INFORMATION: Synthetic Construct

<400> SEQUENCE: 486
```

```
ctcagtcatc cttatccc                                                     18

<210> SEQ ID NO 487
<211> LENGTH: 18
<212> TYPE: DNA
<213> ORGANISM: Artificial Sequence
<220> FEATURE:
<223> OTHER INFORMATION: Synthetic Construct

<400> SEQUENCE: 487
cctcagtcat ccttatcc                                                     18

<210> SEQ ID NO 488
<211> LENGTH: 18
<212> TYPE: DNA
<213> ORGANISM: Artificial Sequence
<220> FEATURE:
<223> OTHER INFORMATION: Synthetic Construct

<400> SEQUENCE: 488
ccctgaagtt tcagttgt                                                     18

<210> SEQ ID NO 489
<211> LENGTH: 228
<212> TYPE: DNA
<213> ORGANISM: Artificial Sequence
<220> FEATURE:
<223> OTHER INFORMATION: Synthetic Construct

<400> SEQUENCE: 489
aatgaaatct tctgatttgt aagacatgct gccaagagat tagttttaca ccttcaggat       60
aaagactgct gagaaggttt aaggatgcta ttctgaaaag actgtggagg aagattaagg      120
aaaccatctc tgggataagg atgactgagg aaatttaagg atgccactct ggttaaaagc      180
tgaaacaact gaaacttcag ggaaaagaga aggcctggaa tctgatcc                   228

<210> SEQ ID NO 490
<211> LENGTH: 79
<212> TYPE: DNA
<213> ORGANISM: Artificial Sequence
<220> FEATURE:
<223> OTHER INFORMATION: Synthetic Construct

<400> SEQUENCE: 490
gggtcaatga tgacaaccca atgtcatgaa gaaatgtgat gacataaaat ttatgctcaa       60
taggattacg ctgagtccc                                                    79

<210> SEQ ID NO 491
<211> LENGTH: 79
<212> TYPE: DNA
<213> ORGANISM: Artificial Sequence
<220> FEATURE:
<223> OTHER INFORMATION: Synthetic Construct

<400> SEQUENCE: 491
gggtcaataa tggcaatcca atgtcatgaa gaaggtgat gacataaaat tcatgctcaa        60
taggattact ctgaggccc                                                    79

<210> SEQ ID NO 492
<211> LENGTH: 88
<212> TYPE: DNA
<213> ORGANISM: Artificial Sequence
<220> FEATURE:
```

<223> OTHER INFORMATION: Synthetic Construct

<400> SEQUENCE: 492
gggttcacaa agtgcaatcc ctcgagccaa tgtcatgaag aaaggtgatg acataaaatt    60
catgctcaat aggattatgc tgaggccc    88

<210> SEQ ID NO 493
<211> LENGTH: 79
<212> TYPE: DNA
<213> ORGANISM: Artificial Sequence
<220> FEATURE:
<223> OTHER INFORMATION: Synthetic Construct

<400> SEQUENCE: 493
ttgtcaatga taacaaccca aaatcatgaa cagaggtgat gatataaaaa tcatgctcaa    60
taggattacg ctgaggcac    79

<210> SEQ ID NO 494
<211> LENGTH: 69
<212> TYPE: DNA
<213> ORGANISM: Artificial Sequence
<220> FEATURE:
<223> OTHER INFORMATION: Synthetic Construct

<400> SEQUENCE: 494
tggccatcat aggtcatgaa gagtggtgat gacattaaaa tcatgatcaa taggattaca    60
ctgaggccc    69

<210> SEQ ID NO 495
<211> LENGTH: 82
<212> TYPE: DNA
<213> ORGANISM: Artificial Sequence
<220> FEATURE:
<223> OTHER INFORMATION: Synthetic Construct

<400> SEQUENCE: 495
gggtcaatga tgagaacctt atattgtcct gaagagcggt gatgacttaa aaatcatgct    60
caataggatt acgctgaggc cc    82

<210> SEQ ID NO 496
<211> LENGTH: 76
<212> TYPE: DNA
<213> ORGANISM: Artificial Sequence
<220> FEATURE:
<223> OTHER INFORMATION: Synthetic Construct

<400> SEQUENCE: 496
gggtcaatga tgagatgtta ccttgaagag aaatgatgac gtaaaaatta agttcagttg    60
gattacgctg aggccc    76

<210> SEQ ID NO 497
<211> LENGTH: 53
<212> TYPE: DNA
<213> ORGANISM: Artificial Sequence
<220> FEATURE:
<223> OTHER INFORMATION: Synthetic Construct

<400> SEQUENCE: 497
ttatattgtc ttcgacaggg aagatgacat aaaaattatg ttcaatagga tta    53

<210> SEQ ID NO 498
<211> LENGTH: 71

```
<212> TYPE: DNA
<213> ORGANISM: Artificial Sequence
<220> FEATURE:
<223> OTHER INFORMATION: Synthetic Construct

<400> SEQUENCE: 498
tcaataatga aatcttctga tttggtgaga aataatgcct taaaattaca ctcaatagga      60
ttatgctgag g                                                          71

<210> SEQ ID NO 499
<211> LENGTH: 33
<212> TYPE: DNA
<213> ORGANISM: Artificial Sequence
<220> FEATURE:
<223> OTHER INFORMATION: Synthetic Construct

<400> SEQUENCE: 499
taaaaatcat gctcaataga attaagctga ggc                                  33

<210> SEQ ID NO 500
<211> LENGTH: 20
<212> TYPE: DNA
<213> ORGANISM: Artificial Sequence
<220> FEATURE:
<223> OTHER INFORMATION: Synthetic Construct

<400> SEQUENCE: 500
atatgtggaa gccggaatct                                                 20

<210> SEQ ID NO 501
<211> LENGTH: 21
<212> TYPE: DNA
<213> ORGANISM: Artificial Sequence
<220> FEATURE:
<223> OTHER INFORMATION: Synthetic Construct

<400> SEQUENCE: 501
cccagaactc cctaatcaga a                                               21

<210> SEQ ID NO 502
<211> LENGTH: 20
<212> TYPE: DNA
<213> ORGANISM: Artificial Sequence
<220> FEATURE:
<223> OTHER INFORMATION: Synthetic Construct

<400> SEQUENCE: 502
atgacggtgg ctataccagg                                                 20

<210> SEQ ID NO 503
<211> LENGTH: 20
<212> TYPE: DNA
<213> ORGANISM: Artificial Sequence
<220> FEATURE:
<223> OTHER INFORMATION: Synthetic Construct

<400> SEQUENCE: 503
gtctccttcg agctgtttgc                                                 20

<210> SEQ ID NO 504
<211> LENGTH: 21
<212> TYPE: DNA
<213> ORGANISM: Artificial Sequence
<220> FEATURE:
<223> OTHER INFORMATION: Synthetic Construct
```

```
<400> SEQUENCE: 504
cctttctctc cagtgctcag a                                              21

<210> SEQ ID NO 505
<211> LENGTH: 21
<212> TYPE: DNA
<213> ORGANISM: Artificial Sequence
<220> FEATURE:
<223> OTHER INFORMATION: Synthetic Construct

<400> SEQUENCE: 505
cctgtgaact ttcaaccagg a                                              21

<210> SEQ ID NO 506
<211> LENGTH: 20
<212> TYPE: DNA
<213> ORGANISM: Artificial Sequence
<220> FEATURE:
<223> OTHER INFORMATION: Synthetic Construct

<400> SEQUENCE: 506
ggatcagact ccaggccttc                                                20

<210> SEQ ID NO 507
<211> LENGTH: 20
<212> TYPE: RNA
<213> ORGANISM: Artificial Sequence
<220> FEATURE:
<223> OTHER INFORMATION: Synthetic Construct

<400> SEQUENCE: 507
cccagguguc cuuuaaugaa                                                20

<210> SEQ ID NO 508
<211> LENGTH: 20
<212> TYPE: RNA
<213> ORGANISM: Artificial Sequence
<220> FEATURE:
<223> OTHER INFORMATION: Synthetic Construct

<400> SEQUENCE: 508
ccaggugucc uuuaaugaaa                                                20

<210> SEQ ID NO 509
<211> LENGTH: 20
<212> TYPE: RNA
<213> ORGANISM: Artificial Sequence
<220> FEATURE:
<223> OTHER INFORMATION: Synthetic Construct

<400> SEQUENCE: 509
ugaaaaugcu cuugacacca                                                20

<210> SEQ ID NO 510
<211> LENGTH: 20
<212> TYPE: RNA
<213> ORGANISM: Artificial Sequence
<220> FEATURE:
<223> OTHER INFORMATION: Synthetic Construct

<400> SEQUENCE: 510
gaaaaugcuc uugacaccaa                                                20

<210> SEQ ID NO 511
<211> LENGTH: 20
```

```
<212> TYPE: RNA
<213> ORGANISM: Artificial Sequence
<220> FEATURE:
<223> OTHER INFORMATION: Synthetic Construct

<400> SEQUENCE: 511
aaaugcucuu gacaccaaug                                               20

<210> SEQ ID NO 512
<211> LENGTH: 20
<212> TYPE: RNA
<213> ORGANISM: Artificial Sequence
<220> FEATURE:
<223> OTHER INFORMATION: Synthetic Construct

<400> SEQUENCE: 512
agaucaguag cuuccuuuac                                               20

<210> SEQ ID NO 513
<211> LENGTH: 20
<212> TYPE: RNA
<213> ORGANISM: Artificial Sequence
<220> FEATURE:
<223> OTHER INFORMATION: Synthetic Construct

<400> SEQUENCE: 513
ucaguagcuu ccuuuaccga                                               20

<210> SEQ ID NO 514
<211> LENGTH: 20
<212> TYPE: RNA
<213> ORGANISM: Artificial Sequence
<220> FEATURE:
<223> OTHER INFORMATION: Synthetic Construct

<400> SEQUENCE: 514
ucuagaacau ugagcuaugg                                               20

<210> SEQ ID NO 515
<211> LENGTH: 20
<212> TYPE: RNA
<213> ORGANISM: Artificial Sequence
<220> FEATURE:
<223> OTHER INFORMATION: Synthetic Construct

<400> SEQUENCE: 515
cuagaacauu gagcuaugga                                               20

<210> SEQ ID NO 516
<211> LENGTH: 20
<212> TYPE: RNA
<213> ORGANISM: Artificial Sequence
<220> FEATURE:
<223> OTHER INFORMATION: Synthetic Construct

<400> SEQUENCE: 516
aacauugagc uauggaagac                                               20

<210> SEQ ID NO 517
<211> LENGTH: 20
<212> TYPE: RNA
<213> ORGANISM: Artificial Sequence
<220> FEATURE:
<223> OTHER INFORMATION: Synthetic Construct

<400> SEQUENCE: 517
```
acauugagcu auggaagacu                                          20

<210> SEQ ID NO 518
<211> LENGTH: 20
<212> TYPE: RNA
<213> ORGANISM: Artificial Sequence
<220> FEATURE:
<223> OTHER INFORMATION: Synthetic Construct

<400> SEQUENCE: 518
cuauggaaga cucccaccua                                          20

<210> SEQ ID NO 519
<211> LENGTH: 20
<212> TYPE: RNA
<213> ORGANISM: Artificial Sequence
<220> FEATURE:
<223> OTHER INFORMATION: Synthetic Construct

<400> SEQUENCE: 519
uauggaagac ucccaccuaa                                          20

<210> SEQ ID NO 520
<211> LENGTH: 20
<212> TYPE: RNA
<213> ORGANISM: Artificial Sequence
<220> FEATURE:
<223> OTHER INFORMATION: Synthetic Construct

<400> SEQUENCE: 520
caagugcuac cgcacaggca                                          20

<210> SEQ ID NO 521
<211> LENGTH: 20
<212> TYPE: RNA
<213> ORGANISM: Artificial Sequence
<220> FEATURE:
<223> OTHER INFORMATION: Synthetic Construct

<400> SEQUENCE: 521
aagugcuacc gcacaggcau                                          20

<210> SEQ ID NO 522
<211> LENGTH: 20
<212> TYPE: RNA
<213> ORGANISM: Artificial Sequence
<220> FEATURE:
<223> OTHER INFORMATION: Synthetic Construct

<400> SEQUENCE: 522
uaccgcacag gcaugcugca                                          20

<210> SEQ ID NO 523
<211> LENGTH: 20
<212> TYPE: RNA
<213> ORGANISM: Artificial Sequence
<220> FEATURE:
<223> OTHER INFORMATION: Synthetic Construct

<400> SEQUENCE: 523
caggcaugcu gcagugaauu                                          20

<210> SEQ ID NO 524
<211> LENGTH: 20
<212> TYPE: RNA
<213> ORGANISM: Artificial Sequence

```
<220> FEATURE:
<223> OTHER INFORMATION: Synthetic Construct

<400> SEQUENCE: 524
aggcaugcug cagugaauuu                                               20

<210> SEQ ID NO 525
<211> LENGTH: 20
<212> TYPE: RNA
<213> ORGANISM: Artificial Sequence
<220> FEATURE:
<223> OTHER INFORMATION: Synthetic Construct

<400> SEQUENCE: 525
accguuguuu aaggaugcua                                               20

<210> SEQ ID NO 526
<211> LENGTH: 20
<212> TYPE: RNA
<213> ORGANISM: Artificial Sequence
<220> FEATURE:
<223> OTHER INFORMATION: Synthetic Construct

<400> SEQUENCE: 526
ccguuguuua aggaugcuau                                               20

<210> SEQ ID NO 527
<211> LENGTH: 20
<212> TYPE: RNA
<213> ORGANISM: Artificial Sequence
<220> FEATURE:
<223> OTHER INFORMATION: Synthetic Construct

<400> SEQUENCE: 527
cuguggagga agaaaacccu                                               20

<210> SEQ ID NO 528
<211> LENGTH: 20
<212> TYPE: RNA
<213> ORGANISM: Artificial Sequence
<220> FEATURE:
<223> OTHER INFORMATION: Synthetic Construct

<400> SEQUENCE: 528
aagaaaaccc uuuacccugu                                               20

<210> SEQ ID NO 529
<211> LENGTH: 20
<212> TYPE: RNA
<213> ORGANISM: Artificial Sequence
<220> FEATURE:
<223> OTHER INFORMATION: Synthetic Construct

<400> SEQUENCE: 529
agaaaacccu uuacccuguu                                               20

<210> SEQ ID NO 530
<211> LENGTH: 20
<212> TYPE: RNA
<213> ORGANISM: Artificial Sequence
<220> FEATURE:
<223> OTHER INFORMATION: Synthetic Construct

<400> SEQUENCE: 530
cucaacugcc uggcacugaa                                               20
```

```
<210> SEQ ID NO 531
<211> LENGTH: 20
<212> TYPE: RNA
<213> ORGANISM: Artificial Sequence
<220> FEATURE:
<223> OTHER INFORMATION: Synthetic Construct

<400> SEQUENCE: 531
aacugccugg cacugaaaau                                               20

<210> SEQ ID NO 532
<211> LENGTH: 20
<212> TYPE: RNA
<213> ORGANISM: Artificial Sequence
<220> FEATURE:
<223> OTHER INFORMATION: Synthetic Construct

<400> SEQUENCE: 532
acugccuggc acugaaaaug                                               20

<210> SEQ ID NO 533
<211> LENGTH: 20
<212> TYPE: RNA
<213> ORGANISM: Artificial Sequence
<220> FEATURE:
<223> OTHER INFORMATION: Synthetic Construct

<400> SEQUENCE: 533
guguuuaagg aaaccaucuc                                               20

<210> SEQ ID NO 534
<211> LENGTH: 20
<212> TYPE: RNA
<213> ORGANISM: Artificial Sequence
<220> FEATURE:
<223> OTHER INFORMATION: Synthetic Construct

<400> SEQUENCE: 534
guuuaaggaa accaucucug                                               20

<210> SEQ ID NO 535
<211> LENGTH: 20
<212> TYPE: RNA
<213> ORGANISM: Artificial Sequence
<220> FEATURE:
<223> OTHER INFORMATION: Synthetic Construct

<400> SEQUENCE: 535
aggaaaccau cucugauaag                                               20

<210> SEQ ID NO 536
<211> LENGTH: 20
<212> TYPE: RNA
<213> ORGANISM: Artificial Sequence
<220> FEATURE:
<223> OTHER INFORMATION: Synthetic Construct

<400> SEQUENCE: 536
ucuuuggcuu guugacacca                                               20

<210> SEQ ID NO 537
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 537
cuuuggcuug uugacaccag                                          20

<210> SEQ ID NO 538
<211> LENGTH: 20
<212> TYPE: DNA
<213> ORGANISM: Artificial Sequence
<220> FEATURE:
<223> OTHER INFORMATION: Synthetic Construct

<400> SEQUENCE: 538
ttcattaaag gacacctggg                                          20

<210> SEQ ID NO 539
<211> LENGTH: 20
<212> TYPE: DNA
<213> ORGANISM: Artificial Sequence
<220> FEATURE:
<223> OTHER INFORMATION: Synthetic Construct

<400> SEQUENCE: 539
tttcattaaa ggacacctgg                                          20

<210> SEQ ID NO 540
<211> LENGTH: 20
<212> TYPE: DNA
<213> ORGANISM: Artificial Sequence
<220> FEATURE:
<223> OTHER INFORMATION: Synthetic Construct

<400> SEQUENCE: 540
tggtgtcaag agcattttca                                          20

<210> SEQ ID NO 541
<211> LENGTH: 20
<212> TYPE: DNA
<213> ORGANISM: Artificial Sequence
<220> FEATURE:
<223> OTHER INFORMATION: Synthetic Construct

<400> SEQUENCE: 541
ttggtgtcaa gagcattttc                                          20

<210> SEQ ID NO 542
<211> LENGTH: 20
<212> TYPE: DNA
<213> ORGANISM: Artificial Sequence
<220> FEATURE:
<223> OTHER INFORMATION: Synthetic Construct

<400> SEQUENCE: 542
cattggtgtc aagagcattt                                          20

<210> SEQ ID NO 543
<211> LENGTH: 20
<212> TYPE: DNA
<213> ORGANISM: Artificial Sequence
<220> FEATURE:
<223> OTHER INFORMATION: Synthetic Construct

<400> SEQUENCE: 543
gtaaaggaag ctactgatct                                          20

<210> SEQ ID NO 544
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 544
tcggtaaagg aagctactga                                              20

<210> SEQ ID NO 545
<211> LENGTH: 20
<212> TYPE: DNA
<213> ORGANISM: Artificial Sequence
<220> FEATURE:
<223> OTHER INFORMATION: Synthetic Construct

<400> SEQUENCE: 545
ccatagctca atgttctaga                                              20

<210> SEQ ID NO 546
<211> LENGTH: 20
<212> TYPE: DNA
<213> ORGANISM: Artificial Sequence
<220> FEATURE:
<223> OTHER INFORMATION: Synthetic Construct

<400> SEQUENCE: 546
tccatagctc aatgttctag                                              20

<210> SEQ ID NO 547
<211> LENGTH: 20
<212> TYPE: DNA
<213> ORGANISM: Artificial Sequence
<220> FEATURE:
<223> OTHER INFORMATION: Synthetic Construct

<400> SEQUENCE: 547
gtcttccata gctcaatgtt                                              20

<210> SEQ ID NO 548
<211> LENGTH: 20
<212> TYPE: DNA
<213> ORGANISM: Artificial Sequence
<220> FEATURE:
<223> OTHER INFORMATION: Synthetic Construct

<400> SEQUENCE: 548
agtcttccat agctcaatgt                                              20

<210> SEQ ID NO 549
<211> LENGTH: 20
<212> TYPE: DNA
<213> ORGANISM: Artificial Sequence
<220> FEATURE:
<223> OTHER INFORMATION: Synthetic Construct

<400> SEQUENCE: 549
taggtgggag tcttccatag                                              20

<210> SEQ ID NO 550
<211> LENGTH: 20
<212> TYPE: DNA
<213> ORGANISM: Artificial Sequence
<220> FEATURE:
<223> OTHER INFORMATION: Synthetic Construct

<400> SEQUENCE: 550
```
ttaggtggga gtcttccata                                              20

<210> SEQ ID NO 551
<211> LENGTH: 20
<212> TYPE: DNA
<213> ORGANISM: Artificial Sequence
<220> FEATURE:
<223> OTHER INFORMATION: Synthetic Construct

<400> SEQUENCE: 551
tgcctgtgcg gtagcacttg                                              20

<210> SEQ ID NO 552
<211> LENGTH: 20
<212> TYPE: DNA
<213> ORGANISM: Artificial Sequence
<220> FEATURE:
<223> OTHER INFORMATION: Synthetic Construct

<400> SEQUENCE: 552
atgcctgtgc ggtagcactt                                              20

<210> SEQ ID NO 553
<211> LENGTH: 20
<212> TYPE: DNA
<213> ORGANISM: Artificial Sequence
<220> FEATURE:
<223> OTHER INFORMATION: Synthetic Construct

<400> SEQUENCE: 553
tgcagcatgc ctgtgcggta                                              20

<210> SEQ ID NO 554
<211> LENGTH: 20
<212> TYPE: DNA
<213> ORGANISM: Artificial Sequence
<220> FEATURE:
<223> OTHER INFORMATION: Synthetic Construct

<400> SEQUENCE: 554
aattcactgc agcatgcctg                                              20

<210> SEQ ID NO 555
<211> LENGTH: 20
<212> TYPE: DNA
<213> ORGANISM: Artificial Sequence
<220> FEATURE:
<223> OTHER INFORMATION: Synthetic Construct

<400> SEQUENCE: 555
aaattcactg cagcatgcct                                              20

<210> SEQ ID NO 556
<211> LENGTH: 20
<212> TYPE: DNA
<213> ORGANISM: Artificial Sequence
<220> FEATURE:
<223> OTHER INFORMATION: Synthetic Construct

<400> SEQUENCE: 556
tagcatcctt aaacaacggt                                              20

<210> SEQ ID NO 557
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 557
atagcatcct taaacaacgg                                                 20

<210> SEQ ID NO 558
<211> LENGTH: 20
<212> TYPE: DNA
<213> ORGANISM: Artificial Sequence
<220> FEATURE:
<223> OTHER INFORMATION: Synthetic Construct

<400> SEQUENCE: 558
agggttttct tcctccacag                                                 20

<210> SEQ ID NO 559
<211> LENGTH: 20
<212> TYPE: DNA
<213> ORGANISM: Artificial Sequence
<220> FEATURE:
<223> OTHER INFORMATION: Synthetic Construct

<400> SEQUENCE: 559
acagggtaaa gggttttctt                                                 20

<210> SEQ ID NO 560
<211> LENGTH: 20
<212> TYPE: DNA
<213> ORGANISM: Artificial Sequence
<220> FEATURE:
<223> OTHER INFORMATION: Synthetic Construct

<400> SEQUENCE: 560
aacagggtaa agggttttct                                                 20

<210> SEQ ID NO 561
<211> LENGTH: 20
<212> TYPE: DNA
<213> ORGANISM: Artificial Sequence
<220> FEATURE:
<223> OTHER INFORMATION: Synthetic Construct

<400> SEQUENCE: 561
ttcagtgcca ggcagttgag                                                 20

<210> SEQ ID NO 562
<211> LENGTH: 20
<212> TYPE: DNA
<213> ORGANISM: Artificial Sequence
<220> FEATURE:
<223> OTHER INFORMATION: Synthetic Construct

<400> SEQUENCE: 562
attttcagtg ccaggcagtt                                                 20

<210> SEQ ID NO 563
<211> LENGTH: 20
<212> TYPE: DNA
<213> ORGANISM: Artificial Sequence
<220> FEATURE:
<223> OTHER INFORMATION: Synthetic Construct

<400> SEQUENCE: 563
cattttcagt gccaggcagt                                                 20
```

<210> SEQ ID NO 564
<211> LENGTH: 20
<212> TYPE: DNA
<213> ORGANISM: Artificial Sequence
<220> FEATURE:
<223> OTHER INFORMATION: Synthetic Construct

<400> SEQUENCE: 564
gagatggttt ccttaaacac                                               20

<210> SEQ ID NO 565
<211> LENGTH: 20
<212> TYPE: DNA
<213> ORGANISM: Artificial Sequence
<220> FEATURE:
<223> OTHER INFORMATION: Synthetic Construct

<400> SEQUENCE: 565
cagagatggt ttccttaaac                                               20

<210> SEQ ID NO 566
<211> LENGTH: 20
<212> TYPE: DNA
<213> ORGANISM: Artificial Sequence
<220> FEATURE:
<223> OTHER INFORMATION: Synthetic Construct

<400> SEQUENCE: 566
cttatcagag atggtttcct                                               20

<210> SEQ ID NO 567
<211> LENGTH: 20
<212> TYPE: DNA
<213> ORGANISM: Artificial Sequence
<220> FEATURE:
<223> OTHER INFORMATION: Synthetic Construct

<400> SEQUENCE: 567
tggtgtcaac aagccaaaga                                               20

<210> SEQ ID NO 568
<211> LENGTH: 20
<212> TYPE: DNA
<213> ORGANISM: Artificial Sequence
<220> FEATURE:
<223> OTHER INFORMATION: Synthetic Construct

<400> SEQUENCE: 568
ctggtgtcaa caagccaaag                                               20

<210> SEQ ID NO 569
<211> LENGTH: 58
<212> TYPE: DNA
<213> ORGANISM: Artificial Sequence
<220> FEATURE:
<223> OTHER INFORMATION: Synthetic Construct

<400> SEQUENCE: 569
ggtgccattc tattataaat aacctgaccc attatttata atagaatggc accttttt     58

<210> SEQ ID NO 570
<211> LENGTH: 58
<212> TYPE: DNA
<213> ORGANISM: Artificial Sequence
<220> FEATURE:

<223> OTHER INFORMATION: Synthetic Construct

<400> SEQUENCE: 570
gctttcatca ataatgaaat aacctgaccc attatttcat tattgatgaa agcttttt    58

<210> SEQ ID NO 571
<211> LENGTH: 58
<212> TYPE: DNA
<213> ORGANISM: Artificial Sequence
<220> FEATURE:
<223> OTHER INFORMATION: Synthetic Construct

<400> SEQUENCE: 571
ggtctttcat caataatgat aacctgaccc attatcatta ttgatgaaag accttttt    58

<210> SEQ ID NO 572
<211> LENGTH: 58
<212> TYPE: DNA
<213> ORGANISM: Artificial Sequence
<220> FEATURE:
<223> OTHER INFORMATION: Synthetic Construct

<400> SEQUENCE: 572
gaaatcttct gatttgtaat aacctgaccc attattacaa atcagaagat ttctttt    58

<210> SEQ ID NO 573
<211> LENGTH: 58
<212> TYPE: DNA
<213> ORGANISM: Artificial Sequence
<220> FEATURE:
<223> OTHER INFORMATION: Synthetic Construct

<400> SEQUENCE: 573
gcacctaagg gaattagtat aacctgaccc attatactaa ttcccttagg tgctttt    58

<210> SEQ ID NO 574
<211> LENGTH: 58
<212> TYPE: DNA
<213> ORGANISM: Artificial Sequence
<220> FEATURE:
<223> OTHER INFORMATION: Synthetic Construct

<400> SEQUENCE: 574
gtttcaacca ggatttaaat aacctgaccc attatttaaa tcctggttga aactttt    58

<210> SEQ ID NO 575
<211> LENGTH: 58
<212> TYPE: DNA
<213> ORGANISM: Artificial Sequence
<220> FEATURE:
<223> OTHER INFORMATION: Synthetic Construct

<400> SEQUENCE: 575
gctttcaacc aggatttaat aacctgaccc attattaaat cctggttgaa gctttt    58

<210> SEQ ID NO 576
<211> LENGTH: 58
<212> TYPE: DNA
<213> ORGANISM: Artificial Sequence
<220> FEATURE:
<223> OTHER INFORMATION: Synthetic Construct

<400> SEQUENCE: 576
ggagatgtgc cattctatat aacctgaccc attatataga atggcacatc tcctttt    58

```
<210> SEQ ID NO 577
<211> LENGTH: 58
<212> TYPE: DNA
<213> ORGANISM: Artificial Sequence
<220> FEATURE:
<223> OTHER INFORMATION: Synthetic Construct

<400> SEQUENCE: 577
gtctttcatc aataatgaat aacctgaccc attattcatt attgatgaaa gactttt          58

<210> SEQ ID NO 578
<211> LENGTH: 58
<212> TYPE: DNA
<213> ORGANISM: Artificial Sequence
<220> FEATURE:
<223> OTHER INFORMATION: Synthetic Construct

<400> SEQUENCE: 578
gatcaataat gaaatcttat aacctgaccc attataagat ttcattattg atctttt          58

<210> SEQ ID NO 579
<211> LENGTH: 58
<212> TYPE: DNA
<213> ORGANISM: Artificial Sequence
<220> FEATURE:
<223> OTHER INFORMATION: Synthetic Construct

<400> SEQUENCE: 579
gtgtctttca tcaataatat aacctgaccc attatattat tgatgaaaga cactttt          58

<210> SEQ ID NO 580
<211> LENGTH: 58
<212> TYPE: DNA
<213> ORGANISM: Artificial Sequence
<220> FEATURE:
<223> OTHER INFORMATION: Synthetic Construct

<400> SEQUENCE: 580
gcaataatga aatcttctat aacctgaccc attatagaag atttcattat tgctttt          58

<210> SEQ ID NO 581
<211> LENGTH: 58
<212> TYPE: DNA
<213> ORGANISM: Artificial Sequence
<220> FEATURE:
<223> OTHER INFORMATION: Synthetic Construct

<400> SEQUENCE: 581
gcatgctgca gtgaatttat aacctgaccc attataaatt cactgcagca tgctttt          58

<210> SEQ ID NO 582
<211> LENGTH: 58
<212> TYPE: DNA
<213> ORGANISM: Artificial Sequence
<220> FEATURE:
<223> OTHER INFORMATION: Synthetic Construct

<400> SEQUENCE: 582
ggaaatcttc tgatttgtat aacctgaccc attatacaaa tcagaagatt tcctttt          58

<210> SEQ ID NO 583
<211> LENGTH: 58
<212> TYPE: DNA
<213> ORGANISM: Artificial Sequence
<220> FEATURE:
<223> OTHER INFORMATION: Synthetic Construct
```

<400> SEQUENCE: 583
ggtatattct atctagaaat aacctgaccc attatttcta gatagaatat accttttt        58

<210> SEQ ID NO 584
<211> LENGTH: 58
<212> TYPE: DNA
<213> ORGANISM: Artificial Sequence
<220> FEATURE:
<223> OTHER INFORMATION: Synthetic Construct

<400> SEQUENCE: 584
gtgctgcagt gaatttaaat aacctgaccc attatttaaa ttcactgcag cactttt        58

<210> SEQ ID NO 585
<211> LENGTH: 58
<212> TYPE: DNA
<213> ORGANISM: Artificial Sequence
<220> FEATURE:
<223> OTHER INFORMATION: Synthetic Construct

<400> SEQUENCE: 585
gtgtgccatt ctattataat aacctgaccc attattataa tagaatggca cactttt        58

<210> SEQ ID NO 586
<211> LENGTH: 58
<212> TYPE: DNA
<213> ORGANISM: Artificial Sequence
<220> FEATURE:
<223> OTHER INFORMATION: Synthetic Construct

<400> SEQUENCE: 586
gttaccatca gtgtttaaat aacctgaccc attatttaaa cactgatggt aacttttt       58

<210> SEQ ID NO 587
<211> LENGTH: 58
<212> TYPE: DNA
<213> ORGANISM: Artificial Sequence
<220> FEATURE:
<223> OTHER INFORMATION: Synthetic Construct

<400> SEQUENCE: 587
gcctgcaacc gttgtttaat aacctgaccc attattaaac aacggttgca ggctttt        58

<210> SEQ ID NO 588
<211> LENGTH: 58
<212> TYPE: DNA
<213> ORGANISM: Artificial Sequence
<220> FEATURE:
<223> OTHER INFORMATION: Synthetic Construct

<400> SEQUENCE: 588
gtatgtcttt catcaataat aacctgaccc attattattg atgaaagaca tactttt        58

<210> SEQ ID NO 589
<211> LENGTH: 20
<212> TYPE: DNA
<213> ORGANISM: Artificial Sequence
<220> FEATURE:
<223> OTHER INFORMATION: Synthetic Construct

<400> SEQUENCE: 589
acactgatgg taaagtggac        20

<210> SEQ ID NO 590
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 590
tagaatatac acgtcggtaa                                              20

<210> SEQ ID NO 591
<211> LENGTH: 20
<212> TYPE: DNA
<213> ORGANISM: Artificial Sequence
<220> FEATURE:
<223> OTHER INFORMATION: Synthetic Construct

<400> SEQUENCE: 591
tcaactgtcc cagtcacaac                                              20

<210> SEQ ID NO 592
<211> LENGTH: 20
<212> TYPE: DNA
<213> ORGANISM: Artificial Sequence
<220> FEATURE:
<223> OTHER INFORMATION: Synthetic Construct

<400> SEQUENCE: 592
tctagataga atatacacgt                                              20

<210> SEQ ID NO 593
<211> LENGTH: 20
<212> TYPE: DNA
<213> ORGANISM: Artificial Sequence
<220> FEATURE:
<223> OTHER INFORMATION: Synthetic Construct

<400> SEQUENCE: 593
tctagataga atatacacgt                                              20

<210> SEQ ID NO 594
<211> LENGTH: 20
<212> TYPE: DNA
<213> ORGANISM: Artificial Sequence
<220> FEATURE:
<223> OTHER INFORMATION: Synthetic Construct

<400> SEQUENCE: 594
ctccccatgc acacttgaga                                              20

<210> SEQ ID NO 595
<211> LENGTH: 20
<212> TYPE: DNA
<213> ORGANISM: Artificial Sequence
<220> FEATURE:
<223> OTHER INFORMATION: Synthetic Construct

<400> SEQUENCE: 595
catccttaaa caacggttgc                                              20

<210> SEQ ID NO 596
<211> LENGTH: 20
<212> TYPE: DNA
<213> ORGANISM: Artificial Sequence
<220> FEATURE:
<223> OTHER INFORMATION: Synthetic Construct

<400> SEQUENCE: 596
```
ggtgtaaaac taattccctt                                          20

<210> SEQ ID NO 597
<211> LENGTH: 20
<212> TYPE: DNA
<213> ORGANISM: Artificial Sequence
<220> FEATURE:
<223> OTHER INFORMATION: Synthetic Construct

<400> SEQUENCE: 597
aacaacggtt gcagggacag                                          20

<210> SEQ ID NO 598
<211> LENGTH: 20
<212> TYPE: DNA
<213> ORGANISM: Artificial Sequence
<220> FEATURE:
<223> OTHER INFORMATION: Synthetic Construct

<400> SEQUENCE: 598
tatggaagac tcccacctaa                                          20

<210> SEQ ID NO 599
<211> LENGTH: 20
<212> TYPE: DNA
<213> ORGANISM: Artificial Sequence
<220> FEATURE:
<223> OTHER INFORMATION: Synthetic Construct

<400> SEQUENCE: 599
ctatggaaga ctcccaccta                                          20

<210> SEQ ID NO 600
<211> LENGTH: 20
<212> TYPE: DNA
<213> ORGANISM: Artificial Sequence
<220> FEATURE:
<223> OTHER INFORMATION: Synthetic Construct

<400> SEQUENCE: 600
aagccttctc aagtgtgcat                                          20

<210> SEQ ID NO 601
<211> LENGTH: 20
<212> TYPE: DNA
<213> ORGANISM: Artificial Sequence
<220> FEATURE:
<223> OTHER INFORMATION: Synthetic Construct

<400> SEQUENCE: 601
ctatctagaa cattgagcta                                          20

<210> SEQ ID NO 602
<211> LENGTH: 20
<212> TYPE: DNA
<213> ORGANISM: Artificial Sequence
<220> FEATURE:
<223> OTHER INFORMATION: Synthetic Construct

<400> SEQUENCE: 602
accctctggt gttgtcacag                                          20

<210> SEQ ID NO 603
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 603
aaccctttac cctgttgttc                                                    20

<210> SEQ ID NO 604
<211> LENGTH: 79
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 604
gggtcaataa tgncaancca atgtcatgaa gaaaggtgat gacataaaat tcatgctcaa        60
taggattacg ctgaggccc                                                    79

<210> SEQ ID NO 605
<211> LENGTH: 78
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (44)..(44)
<223> OTHER INFORMATION: a, c, t, g, unknown or other

<400> SEQUENCE: 605
ggtcaatgat gagacttatn ttgtcttgaa gagagatgat gacntaaaaa ttatgctcaa        60
taggattacg ctgaggcc                                                     78
```

ANGELMAN SYNDROME ANTISENSE TREATMENT

CROSS-REFERENCE TO RELATED APPLICATIONS

This application is a continuation of copending application Ser. No. 16/767,916, filed May 28, 2020, which claims benefit of U.S. Provisional Application No. 62/593,431, filed Dec. 1, 2017, and Application Ser. No. 62/676,034, filed May 24, 2018, which are hereby incorporated herein by reference in their entirety.

SEQUENCE LISTING

This application contains a sequence listing filed in electronic form as an ASCII.txt file entitled "922001-1021_SL" created on Feb. 20, 2023 and having 149,028 bytes. The content of the sequence listing is incorporated herein in its entirety.

BACKGROUND

Angelman syndrome (AS) is a neurodevelopmental disorder that is associated with severe cognitive and motor deficits, epilepsy, sleep-disorder, and an atypical 'happy' disposition. Individuals with AS are often diagnosed at 2-3 years of age and have a normal life-span. They require assisted living and medical care throughout their lives. There are currently few treatment options for individuals with AS, most of which involve anti-epileptic medications to treat seizures.

Angelman syndrome is caused by mutations that affect the expression or function of the maternally inherited ubiquitin-protein ligase E3A (UBE3A) gene. Unlike most genes, UBE3A is subject to genomic imprinting, which is a rare, naturally occurring phenomenon that turns-off one allele of a gene while leaving the other allele on. In neurons of the central nervous system (CNS), the paternal UBE3A allele is off, whereas in all other cell types of the body, both alleles of UBE3A are on. Because of this, AS is always caused by mutations that affect the maternally inherited UBE3A allele.

The paternal UBE3A allele is turned-off by the UBE3A antisense transcript (UBE3A-AS), which is a component of a long RNA transcript that expresses several protein coding and noncoding transcripts. UBE3A-AS is expressed from the paternal allele and only in neurons of the CNS and is both sufficient and necessary to turn-off expression of the paternal UBE3A allele. It's unclear why UBE3A is imprinted in neurons, but it creates a unique opportunity to treat individuals with AS, because there is a functional, albeit inactive, copy of UBE3A on the paternal chromosome. Studies to date indicate that turning on the paternal UBE3A allele is a viable therapy to treat AS.

SUMMARY

Disclosed herein is a region in the 5'-end of UBE3A-AS transcript that is important for its stability. Based on these findings, antisense oligonucleotides (ASOs) were designed to target this region in order to terminate transcription of UBE3A-AS and reactivate expression of the paternal UBE3A allele. These ASOs targeting the 5'-end of UBE3A-AS are capable of stopping transcription of UBE3A-AS and turning on the paternal UBE3A allele. SNHG14 is a polycistronic transcript that encodes several different RNAs, including UBE3A-AS.

Accordingly, disclosed herein are ASOs containing a contiguous nucleotide sequence of 10 to 30 nucleotides (i.e., 10, 11, 12, 13, 14, 15, 16, 17, 18, 19, 20, 21, 22, 23, 24, 25, 26, 27, 28, 29, or 30) in length with at least 98% (i.e. 98%, 99%, or 100%) complementarity to target exons between the 3'-end of the SNORD115 and the 5'-end of SNORD109B, which is thought to represent the 5'-end of the UBE3A antisense transcript (UBE3A-AS). In particular the target exons can be in the 5'-end of UBE3A-AS, corresponding to position 25,511,577 to 25,516,681 on human chromosome 15 human genome assembly hg19. In some embodiments, the target nucleic acid is one of five exons located in the 5'-end of UBE3A-AS, which can correspond to positions 25,511,577 to 25,511,761 (exon 1), 25,512,059 to 25,512,191 (exon 2), 25,513,476 to 25,513,600 (exon 3), 25,514,752 to 25,514,880 (exon 4), and 25,516,565 to 25,516,681 (exon 5). Therefore, the target nucleic acid can be a contiguous nucleic acid sequence of 10 to 30 nucleotides within SEQ ID NO:1, 2, 3, 4, or 5.

In some embodiments, the target sequence is an exonic boundary involving UBE3A-AS exons 1-5, UBE3A-AS exon 5 and SNORD109B exon 1, and/or SNORD109B exons 1-2.

Methods and strategies for designing ASOs are known in the art. In some embodiments, the ASO is designed to target sequences that are conserved among human subjects. In some embodiments, the ASO is designed to target sequences that are conserved among primate subjects.

The oligonucleotide can be an antisense oligonucleotide (i.e., as will be understood by those of ordinary skill in the art—antisense to its target nucleic acid), e.g., with a gapmer design. The disclosed oligonucleotide is capable of inducing paternal UBE3A expression in a neuron by degradation, reduction, or removal of the UBE3A-AS transcript. It does this by targeting the 5'-end of UBE3A-AS at a site upstream of SNORD109B snoRNA. Examples of ASO designed to target exons 1-5 are provided in Tables 1, 2, 3, 4, or 5. For example, in some embodiments, the ASO comprises the nucleic acid sequence SEQ ID NO: 6, 7, 8, 9, 10, or 11.

The disclosed ASOs can also have one or more modifications to improve stability, solubility, activity, cellular distribution, and/or cellular uptake. For example, the disclosed ASO can contain one or more sugar-modified nucleosides and/or modified internucleoside linkages. For example, in some embodiments, the oligonucleotide comprises one or more internucleoside linkages modified from the natural phosphodiester to a linkage that is for example more resistant to nuclease attack. In some embodiments, the ASO contains one or more modified nucleobases that differ from naturally occurring nucleobases, but are functional during nucleic acid hybridization.

In some embodiments, the ASO is a DNA oligonucleotide. In some embodiments, the ASO is an RNA oligonucleotide. In still other embodiments, the ASO contains both deoxynucleotides and ribonucleotides. For example, the ASO can be a gapmer, headmer, or tailmer oligonucleotide. In some embodiments, the central block of a gapmer is flanked by blocks of modified ribonucleotides that protect the internal block from nuclease degradation. For example, the ASO can contain a stretch of 7, 8, 9, 10, or more natural DNA monomers to activate RNase H cleavage of the target RNA, along with 3, 4, or 5 modified ribonucleotide monomers at the 3'- and 5'-ends for protection against exonucleases. In some cases, the modified ribonucleotides are 2'-O-Methyl (OMe) RNA nucleotides, 2'-O-methoxyethyl (MOE)-modified nucleotides, or 2'-Locked Nucleic Acids (LNAs). Examples of gapmer ASOs are provided Tables 7, 11, and 17. Therefore, in some embodiments, the disclosed ASO has a nucleic acid sequence selected from SEQ ID NOs:362 to 392.

Also disclosed are pharmaceutical compositions comprising one or more of the ASOs disclosed herein and pharmaceutically acceptable diluents, carriers, salts and/or adjuvants.

Also disclosed are methods for in vivo or in vitro induction of UBE3A expression in a target cell where expression of paternal UBE3A is suppressed, by administering one or more of the disclosed ASOs or composition disclosed herein in an effective amount to said cell.

Also disclosed are methods for treating or preventing a disease, disorder or dysfunction associated with in vivo activity of UBE3A comprising administering a therapeutically or prophylactically effective amount of one or more of the disclosed ASOs to a subject suffering from or susceptible to the disease, disorder or dysfunction, such as Angelman syndrome.

The details of one or more embodiments of the invention are set forth in the accompanying drawings and the description below. Other features, objects, and advantages of the invention will be apparent from the description and drawings, and from the claims. For example, those skilled in the art, reading the specification will appreciate that the present disclosure demonstrates usefulness of certain sequences as described herein to impact expression of UBE3A, and furthermore teaches usefulness of oligonucleotide formats that are, or target (e.g., are complementary to), such sequences. Those skilled in the art will appreciate that the present disclosure is not limited to any particular mechanism of action—provided oligonucleotides may be useful regardless of whether they act via an antisense mechanism, for example, involving RNase H activity, and other therapeutic formats (e.g., siRNA, shRNA, nuclease gRNA, etc.) of oligonucleotides that are or target such sequences are also provided. Analogously, those skilled in the art will appreciate that the present disclosure, by defining useful sequences as described herein, also describes a variety of formats for such sequences (e.g., as part of a nucleic acid vector such as a vector from which they may be expressed (e.g., in vivo, in vitro, or both, etc.). Thus, those skilled in the art, reading the present disclosure, will appreciate that reference to "ASOs" herein is exemplary, and appropriate nucleic acids (e.g., oligonucleotides) may be utilized regardless of mechanism of action; those skilled in the art are aware of extensive literature regarding appropriate format and structure of nucleic acids (e.g., oligonucleotides) that operate via any of a variety of mechanisms (e.g., siRNA, shRNA, nuclease gRNA, etc.). In some embodiments, provided nucleic acids incorporate format and/or structural features known in the art to be useful in one or more mechanistic contexts (e.g., involving RNase H, RISC, a nucleic-acid-directed nuclease such as a Cas, etc.).

DESCRIPTION OF DRAWINGS

FIG. 1A shows RefSeq annotation of human PWS/AS imprinted region. FIG. 1B shows RefSeq annotation of PWS/AS imprinted orthologous region in mouse. FIG. 1C shows UBE3A-AS and 3'-end of UBE3A. FIG. 1D shows chain alignment showing orthologous regions between human, macaque (Cynomolgus macaque), pig, elephant, mouse, and rat. The target region is conserved among non-human primates but not rodents. FIG. 1D also shows genomic evolutionary rate profiling (GERP) plot of region. Positive values represent evolutionary constraint at specific DNA bases.

FIGS. 2A to 2E show an analysis of ASOs targeting mouse Ube3a-AS. FIG. 2A is a schematic of mouse Ube3a-AS transcript and approximate location of mouse-specific ASOs. Boxes and lines represent exons and introns, respectively. Arrow represents direction of transcription. FIG. 2B is a schematic of Ube3aYFP reporter allele used to measure paternal Ube3a protein levels. The Ube3aYFP mouse model was generated by targeting the yellow fluorescent protein (YFP) to the 3'-end of the endogenous Ube3a locus. Expression of Ube3a-AS inhibits transcription of the paternal Ube3aYFP allele, and loss of Ube3a-AS reactivates paternal Ube3aYFP expression, which can be detected by immunofluorescence imaging using an anti-YFP antibody. FIG. 2C is a schematic of experimental timeline to examine ASOs in mouse primary hippocampal neurons. Mouse primary hippocampal neurons were generated from newborn mice with a paternally inherited Ube3aYFP allele (0 DIV) and treated after 7 days in vitro (7 DIV). Three days post-treatment (10 DIV), Ube3aYFP protein levels were measured in individual cells. FIG. 2D contains immunofluorescent images showing paternal Ube3aYFP protein in primary neurons treated with vehicle (veh), a negative control ASO (ASO-C), Topotecan (Topo), ASO-B, and ASO 1.1. FIG. 2E shows mean paternal Ube3aYFP intensity levels in individual neuronal cells treated with vehicle (veh, 1% DMSO; n=3), control ASO (ASO-C, 15 µM; n=3), Topotecan (Topo, 0.3 µM; n=3), ASO-B (1, 5, 15 µM; n=3), ASO-1.1 (1, 5, 15 µM), ASO-1.2 (1, 5, 15 µM), and ASO 3.1 (1, 5, 15 µM). Abbreviations: YFP, yellow fluorescent protein; Tx, treatment; DIV, days in vitro; n.s., not significant. Error bars represent standard error of mean.

FIGS. 3A to 3D show analysis of ASOs targeting human UBE3A-AS. FIG. 3A is a schematic showing of human UBE3A-AS and approximate location of human-specific ASOs (ASOs 1-6). ASO-7 is located in an intron of UBE3A-AS. Boxes and lines represent exons and introns, respectively. FIG. 3B is a schematic of experimental timeline to examine ASOs in human GABAergic induced pluripotent stem cell (iPSC) derived neurons from a karyotypically normal individual. Human iPSC-derived neurons were treated after 14 DIV and then processed for RNA isolation at 20 DIV. FIGS. 3C and 3D show relative steady state RNA levels (normalized to ASO-C) of UBE3A-AS (FIG. 3C) and UBE3A (FIG. 3D) in iPSC-derived neurons treated with control ASO (ASO-C, 10 µM), and ASOs 1-7 (10 µM), and Topotecan (Topo, 1 µM). Abbreviations: Tx, treatment; DIV, days in vitro. Error bars represent standard error of mean.

FIGS. 4A to 4I show analysis of human ASO-4 and Topotecan in GABAergic iPSC-derived neurons. FIGS. 4A to 4F show relative expression (normalized to 1 nM) of UBE3A-AS (FIG. 4A), SNORD116 (FIG. 4B), IPW (FIG. 4C), SNORD115 (FIG. 4D), SNORD109A/B (FIG. 4E), and UBE3A (FIG. 4F) steady state RNA levels in iPSC-derived neurons treated with a 10-point ½ log dose curve of ASO-4 and Topotecan (1 nM, 3 nM, 10 nM, 30 nM, 100 nM, 300 nM, 1 µM, 3 µM, 10 µM, and 30 µM). FIG. 4G is a schematic of experimental timeline to examine ASO-4 in GABAergic iPSC-derived neurons treated at 59 DIV. FIG. 4H to 4I shows relative expression (normalized to ASO-C) of UBE3A-AS (FIG. 4H) and UBE3A (FIG. 4I) steady state RNA levels in iPSC-derived neurons treated with ASO-C(10 µM) and ASO-4 (1, 5, and 10 µM). Abbreviations: Tx, treatment. Error bars represent standard error of mean.

FIG. 5A is a schematic of experimental timeline to examine optimized ASOs in GABAergic iPSC-derived neurons. FIG. 5B shows relative expression of (normalized to water control) of UBE3A-AS steady state RNA levels in iPSC-derived neurons treated with a 5-point ½ log dose curve (30 nM, 100 nM, 300 nM, 1 µM, 3 µM; n=6) of ASO-3.1, ASO-3.2, ASO-4.1, ASO-4.2, ASO-4.3, ASO-4.4, ASO-6.1, ASO-4.1, and ASO-4.S. ASO-4.1 and ASO-4.S represent ASO-4 manufactured by two companies (ASO-4.1, Integrated DNA Technologies; ASO-4.S, Sigma-Aldrich). FIG. 5C is a schematic of experimental timeline to examine ASO-4 and ASO-6.1 in GABAergic iPSC-derived neurons. FIG. 5D shows relative expression of (normalized to 1 nM) of UBE3A-AS and UBE3A steady state RNA levels in iPSC-derived neurons treated with a 10-point ½ log dose curve (1 nM, 3 nM, 10 nM, 30 nM, 100 nM, 300 nM, 1 µM, 3 µM, 10 µM, and 30 µM; n=3) of ASO-4 (ASO-4.1 and ASO-4.S) and ASO-6.1. FIG. 5E is a schematic of experimental timeline to examine ASO-4 and ASO-6.1 in glutamatergic iPSC-derived neurons. FIG. 5F shows relative expression of (normalized to water control) of UBE3A-AS and UBE3A steady state RNA levels in iPSC-derived neurons treated with a 10-point ½ log dose curve (1 nM, 3 nM, 10 nM, 30 nM, 100 nM, 300 nM, 1 µM, 3 µM, 10 µM, and 30 uM; n=3) of ASO-4 (ASO-4.1 and ASO-4.S) and ASO-6.1. Error bars represent standard error of mean.

FIG. 6A to 6D show identification of ASO target region in mouse PWS/AS imprinted region. FIG. 6A shows RefSeq annotation of the orthologous PWS/AS imprinted region on mouse chromosome 7C. FIG. 6B illustrates a transcript assembly generated from RNA-sequencing (RNA-seq) data from mouse brain. FIG. 6C shows ASO target region showing Snord115 snoRNAs retained in exons of the Snord115 host-gene transcript/5'-end of Ube3a-AS. Aligned RNA-seq reads are depicted below assembled transcripts. Exons and introns are depicted by boxes and lines, respectively. FIG. 6D is a sequence alignment of snoRNAs in retained exons Snord115_ENSMUST00000101836 (SEQ ID NO:490), Snord115_ENSMUST00000101936 (SEQ ID NO:491), Snord115_ENSMUST00000104493 (SEQ ID NO:492), Snord115_ENSMUST00000082443 (SEQ ID NO:493), andSnord115_ENSMUST00000104427 (SEQ ID NO:494), showing retained snoRNAs have a degenerate C Box, which is required for functional snoRNA formation. FIG. 6D also discloses the consensus sequence as SEQ ID NO: 604.

FIGS. 7A to 7G show identification of ASO target region in human PWS/AS imprinted region. FIG. 7A shows RefSeq annotation of Prader-Willi/Angelman syndrome (PWS/AS) imprinted region. FIG. 7B shows RNA-seq assembly of the human PWS polycistronic transcript. FIG. 7C shows SNORD115-45 is retained in an exon at the 3'-end of the SNORD115 host-gene transcript/5'-end of UBE3A-AS. Aligned RNA-seq reads generated from adult human brain showing L1 LINE is transcribed. FIG. 7D shows RefSeq annotation of 3'-end of SNORD115 cluster (SNORD115-39-48 and SNORD109B). FIG. 7E shows location of L1 LINE element between SNORD115-44 and SNORD115-45. FIG. 7F shows chain alignment of placental mammals representing major clades showing conservation at SNORD115-45-48 region, albeit reduced in rodents. FIG. 7G shows sequence alignment of snoRNAs in target region to SNORD115-44 (functional snoRNA) (SEQ ID NO:495), SNORD115-48 (SEQ ID NO:496), SNORD115-45 (SEQ ID NO:497), SNORD115-46 (SEQ ID NO:498), and SNORD115-47 (SEQ ID NO:499), showing SNORD115-45 (retained), SNORD115-46 (partially retained), and SNORD116-47 have degenerate C Box, which is required for functional snoRNA formation. FIG. 7G also discloses the consensus sequence as SEQ ID NO: 605.

FIG. 8A shows fitted dose response curves of normalized UBE3A-AS steady state RNA levels in GABAergic iPSC-derived neurons treated with a 10-point ½ log dose curve (1 nM, 3 nM, 10 nM, 30 nM, 100 nM, 300 nM, 1 µM, 3 µM, 10 µM, and 30 µM; n=2) of ASO-4 and ASO-6.1 with different backbone and RNA modification designs. Dose response curves fitted using a 4-parameter logistic regression model (Hill). Graphs represent fitted models and standard error. The Y axis represents relative UBE3A-AS RNA levels and X axis represents log molar (M) concentrations of ASO. FIGS. 8B and 8C are hierarchical clustering dendrogram and constellation plots of fitted dose response curves showing relationship between candidate ASOs and grouping into 3 clusters.

DETAILED DESCRIPTION

Figure 1A:
FIGS. 1A to 1D illustrate the Prader-Willi/Angelman syndrome (PWS/AS) imprinted region in human and mouse.
Figure 1B:
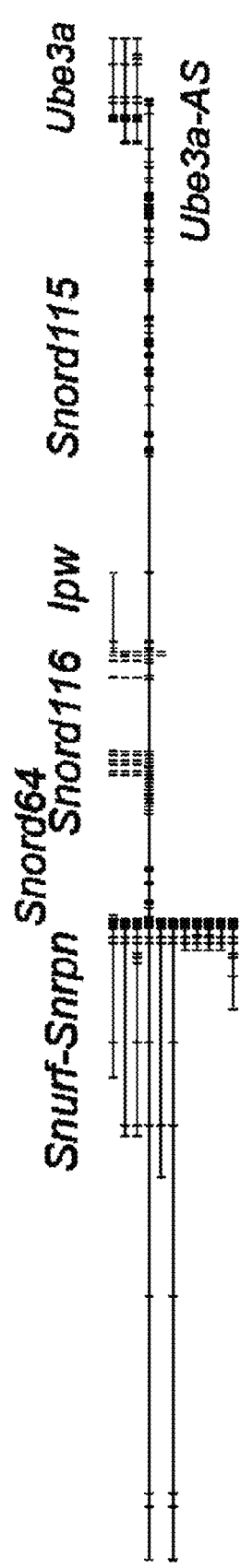
Figure 1C:
Figure 1D:
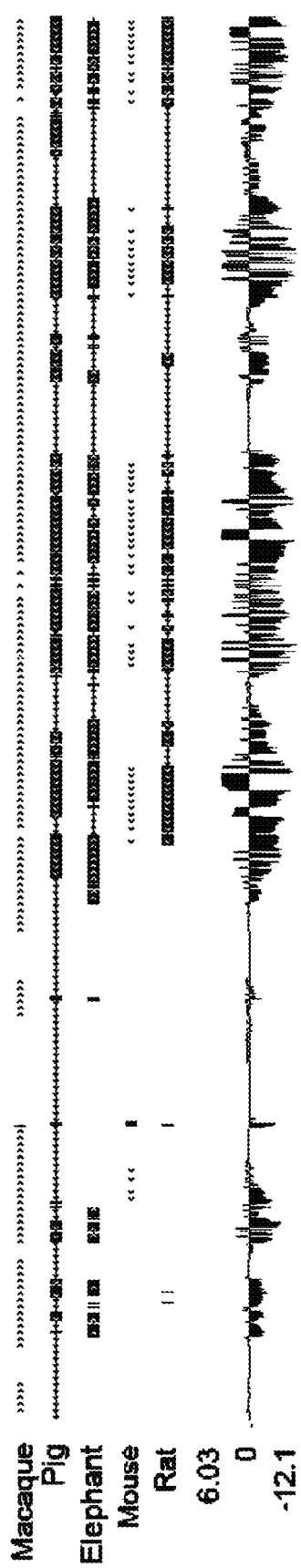

The UBE3A-AS/Ube3a-AS transcript, otherwise known as ubiquitin-protein ligase E3A antisense transcript and UBE3A-AS/Ube3a-AS, is the name for the transcript generated by transcription of the UBE3A-AS transcript, which is on the antisense DNA strand relative to the UBE3A gene. Note that gene names with all caps indicate human genes (e.g. UBE3A) and gene names with only the first letter capped indicate mouse genes (e.g. Ube3a). The UBE3A-AS transcript is transcribed as part of a large polycistronic transcription unit that encodes SNURF-SNRPN, a cluster of orphan C/D box small nucleolar RNAs (SNORDs), and several uncharacterized long noncoding RNAs. In both mouse and human, the UBE3A/Ube3a gene is imprinted in neurons of the central nervous system, where it is expressed only from the maternal allele. The UBE3A-AS/Ube3a-AS transcript is both necessary and sufficient to silence transcription of the paternal UBE3A/Ube3a allele, and inhibition of UBE3A-AS/Ube3a-AS reactivates transcription of the paternal UBE3A/Ube3a allele. Mutations affecting the function or expression of the maternally inherited UBE3A allele cause Angelman syndrome (AS). In AS, the paternal allele is functional but epigenetically silenced. If unsilenced in AS patients, the paternal UBE3A allele could be a source of functional UBE3A in neurons.

The polycistronic transcription unit (hereafter referred to as the PTU) encoding UBE3A-AS is about 450,000 basepairs long. Transcription of the PTU starts at upstream exons (U-exons) in the SNURF-SNRPN locus and stops towards the 5'-end of UBE3A. The PTU is organized (5'-3') as follows: SNURF-SNRPN, SNORD107, SNORD64, SNORD109A, SNORD116 (29 copies), IPW, SNORD115 (48 copies), SNORD109B, and UBE3A, which is orientated in the opposite direction of the upstream transcripts. The polycistronic transcript is alternatively spliced and subject to alternative 3'-processing. SNURF-SNRPN encodes two polypeptides. The SNORDs are in the introns of a host-gene transcript (SNHG14) and are generated by exonucleolytic debranching of the spliced introns. UBE3A-AS represents the 3'-end of the transcript that overlaps the UBE3A gene. Most C/D box snoRNAs play a role in ribosome biogenesis where they direct 2'-O-methylation of ribosomal RNAs (rRNA); however, the snoRNAs located in the PWS/AS region lack any sequence complementarity to known rRNAs; however, the SNORD115 snoRNA has been found to change the alternative splicing of the serotonin receptor 2C pre-mRNA.

Disclosed herein is evidence that the 5'-end of UBE3A-AS transcript is important for its stability. As disclosed herein, ASOs targeting the 5'-end of UBE3A-AS are capable of reducing UBE3A-AS levels, presumably by stopping transcription of UBE3A-AS, and turning-on the paternal UBE3A allele.

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide disclosed herein is man-made, e.g., chemically synthesized. The oligonucleotide disclosed herein may also comprise one or more modified nucleosides or nucleotides.

The term "antisense oligonucleotide" as used herein is defined as oligonucleotides capable of modulating expression of a target gene by hybridizing to a target nucleic acid, in particular to a contiguous sequence on a target nucleic acid. In some embodiments, the antisense oligonucleotides disclosed herein are single stranded.

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide are present in the contiguous nucleotide sequence. In some embodiments the oligonucleotide comprises the contiguous nucleotide sequence and may, optionally comprise further nucleotide(s), for example a nucleotide linker region which may be used to attach a functional group to the contiguous nucleotide sequence. The nucleotide linker region may or may not be complementary to the target nucleic acid.

Nucleotides are the building blocks of oligonucleotides and polynucleotides, and can include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In some embodiments, the modified nucleoside comprises a modified sugar moiety. The term modified nucleoside may also be used herein interchangeably with the term "nucleoside analogue" or modified "units" or modified "monomers".

The term "modified internucleoside linkage" is defined as generally understood by the skilled person as linkages other than phosphodiester (PO) linkages or natural phosphate linkages that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide disclosed herein, for example, within the gap region of a gapmer oligonucleotide, as well as in regions of modified nucleosides.

In some embodiments, the oligonucleotide comprises one or more internucleoside linkages modified from the natural phosphodiester to a linkage that is, for example, more resistant to nuclease attack. Nuclease resistance may be determined by incubating the oligonucleotide in blood serum or by using a nuclease resistance assay[e.g., snake venom phosphodiesterase (SVPD)], both are well known in the art. Internucleoside linkages which are capable of enhancing the nuclease resistance of an oligonucleotide are referred to as nuclease resistant internucleoside linkages.

In some embodiments at least 50% of the internucleoside linkages in the oligonucleotide, or contiguous nucleotide sequence thereof, are modified, such as at least 60%, such as at least 70%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified.

It will be recognized that, in some embodiments, the internucleoside linkages which link the oligonucleotide to a non-nucleotide functional group, such as a conjugate, may be phosphodiester. In some embodiments, the internucleoside linkages which link the oligonucleotide to a non-nucleotide functional group are modified.

In some embodiments all of the internucleoside linkages of the oligonucleotide, or contiguous nucleotide sequence thereof, are nuclease resistant internucleoside linkages.

Modified internucleoside linkages may, for example, be selected from the group comprising phosphorothioate, diphosphorothioate, and boranophosphate. In some embodiments, the modified internucleoside linkages are compatible with the RNase H recruitment of the oligonucleotide disclosed herein, for example, phosphorothioate, diphosphorothioate, or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmacokinetics and ease of manufacture. In preferred embodiments at least 50% of the internucleoside linkages in the oligonucleotide, or contiguous nucleotide sequence thereof, are phosphorothioate, such as at least 60%, such as at least 70%, such as at least 80%, or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal. Further internucleoside linkages are disclosed in WO2009/124238 (incorporated herein by reference). In an embodiment the internucleoside linkage is selected from linkers disclosed in WO2007/031091 (incorporated herein by reference).

Nuclease resistant linkages, such as phosphorothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide. WO2008/113832 is incorporated herein by reference for the teaching of oligonucleotides having phosphodiester linkages.

In some embodiments, all the internucleoside linkages in the oligonucleotide are phosphorothioate and/or boranophosphate linkages. In some embodiments, all the internucleoside linkages in the oligonucleotide are phosphorothioate linkages.

The term nucleobase includes the purine (e.g., adenine and guanine) and pyrimidine (e.g., uracil, thymine, and cytosine) moiety present in nucleosides and nucleotides which form hydrogen bonds in nucleic acid hybridization. The term nucleobase also encompasses modified nucleobases which may differ from naturally occurring nucleobases but are functional during nucleic acid hybridization. In this context "nucleobase" refers to both naturally occurring nucleobases, such as adenine, guanine, cytosine, thymidine, uracil, xanthine, and hypoxanthine, as well as non-naturally occurring variants.

In some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl-cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine, and 2-chloro-6-aminopurine.

The nucleobase moieties may be indicated by the letter code for each corresponding nucleobase, e.g., A, T, G, C, or U, wherein each letter may optionally include modified nucleobases of equivalent function. For example, in the exemplified oligonucleotides, the nucleobase moieties are selected from A, T, G, C, and 5-methyl cytosine (5mC). Combinations of these modifications may also be used. For example, 5mC LNA nucleosides may be used. Likewise, 2'-hydroxymethyl (2'-OMe) 5mC may be used.

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example, 5-methyl cytosine is often used in place of cytosine, and as such the term complementarity encompasses Watson Crick base-paring between non-modified and modified nucleobases.

The term "% complementary" as used herein, refers to the number of nucleotides in percent of a contiguous nucleotide sequence in a nucleic acid molecule (e.g., oligonucleotide) which, at a given position, are complementary to (i.e., form Watson Crick base pairs with) a contiguous nucleotide sequence, at a given position of a separate nucleic acid molecule (e.g., the target nucleic acid). The percentage is calculated by counting the number of aligned bases that form pairs between the two sequences, dividing by the total number of nucleotides in the oligonucleotide and multiplying by 100. In such a comparison a nucleobase/nucleotide which does not align (form a base pair) is termed a mismatch.

The term "hybridizing" or "hybridizes" as used herein is to be understood as two nucleic acid strands (e.g., an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature (Tm) defined as the temperature at which half of the oligonucleotides are duplexed with the target nucleic acid. At physiological conditions, Tm is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant (Kd) of the reaction by $\Delta G°=-RTln(Kd)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides disclosed herein hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal or −16 to −27 kcal such as −18 to −25 kcal.

In some embodiments, the disclosed oligonucleotide comprises a contiguous nucleotide sequence of at least 8 nucleotides which is complementary to or hybridizes to a target sequence present in the target nucleic acid molecule. The contiguous nucleotide sequence (and therefore the target sequence) comprises of at least 8 contiguous nucleotides, such as 9, 10, 11, 12, 13, 14, 15, 16, 17, 18, 19, 20, 21, 22, 23, 24, 25, 26, 27, 28, 29 or 30 contiguous nucleotides, such as from 12-25, such as from 14-18 contiguous nucleotides.

In some embodiments, the disclosed oligonucleotide is a functional nucleic acid, such as a siRNA, shRNA, or nuclease gRNA, that inhibits, mutates, or deletes the target nucleic acid sequence.

The term "modulation of expression" as used herein is to be understood as an overall term for an oligonucleotide's ability to alter the amount of UBE3A RNA/protein when compared to the amount of UBE3A before administration of the oligonucleotide. Alternatively modulation of expression may be determined by reference to a control experiment where the disclosed oligonucleotide is not administered. The modulation effected by the oligonucleotide is related to its ability to reduce, remove, prevent, lessen, lower or terminate the suppression of the paternal UBE3A-AS transcript, i.e., by targeting the 5'-end of UBE3A-AS, which is downstream of SNORD115-45 snoRNA. The modulation can also be viewed as the oligonucleotide's ability to restore, increase or enhance expression of paternal UBE3A, e.g., by removal or blockage of inhibitory mechanisms affected by UBE3A-AS.

The disclosed oligonucleotide may comprise one or more nucleosides which have a modified sugar moiety, i.e., a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance. Such modifications include those where the ribose ring structure is modified, e.g., by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g., UNA). Other sugar modified nucleosides include, for example, bicyclohexose nucleosides (WO2011/017521) or tricyclic nucleosides (WO2013/154798). Modified nucleosides also include nucleosides where the sugar moiety is replaced with a non-sugar moiety, for example, in the case of peptide nucleic acids (PNA) or morpholino nucleic acids.

Sugar modifications also include modifications made via altering the substituent groups on the ribose ring to groups other than hydrogen, or the 2'—OH group naturally found in DNA and RNA nucleosides. Substituents may, for example, be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

A 2' sugar modified nucleoside is a nucleoside which has a substituent other than H or —OH at the 2' position (2' substituted nucleoside) or comprises a 2' linked biradical, and includes 2' substituted nucleosides and LNA (2'-4' biradical bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA (O-Me), 2'-alkoxy-RNA, 2'-O-methoxyethyl-RNA (MOE), 2'-amino-DNA, 2'-Fluoro-RNA, and 2'-fluoro-ANA (F-ANA). For further examples, please see Freier & Altmann; Nucl. Acid Res., 1997, 25, 4429-4443 and Uhlmann; Curr. Opinion in Drug Development, 2000, 3(2), 293-213; and Deleavey and Damha, Chemistry and Biology 2012, 19, 937.

Locked Nucleic Acid (LNA) nucleosides are modified nucleosides which comprise a linker group (referred to as a biradical or a bridge) between C2' and C4' of the ribose sugar ring of a nucleotide. These nucleosides are also termed bridged nucleic acid or bicyclic nucleic acid (BNA) in the literature.

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the disclosed oligonucleotides are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example, gapmers, headmers, and tailmers.

The term "gapmer" as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks is missing, i.e., only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides).

Conjugation of the disclosed oligonucleotide to one or more non-nucleotide moieties may improve the pharmacology of the oligonucleotide, e.g., by affecting the activity, cellular distribution, cellular uptake, or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue, or cell type and thereby enhance the effectiveness of the oligonucleotide in that organ, tissue, or cell type. At the same time the conjugate may serve to reduce activity of the oligonucleotide in non-target cell types, tissues or organs, e.g., off target activity or activity in non-target cell types, tissues or organs. WO 93/07883 and WO 2013/033230 provides suitable conjugate moieties, which are hereby incorporated by reference. WO 2012/143379 provides a method of delivering a drug across the blood-brain-barrier by conjugation to an antibody fragment with affinity to the transferrin receptor, which are hereby incorporated by reference.

In some embodiments, the non-nucleotide moiety (conjugate moiety) is selected from the group consisting of carbohydrates, cell surface receptor ligands, drug substances, hormones, lipophilic substances, polymers, proteins, peptides, toxins (e.g., bacterial toxins), vitamins, viral proteins (e.g., capsids) or combinations thereof. In some embodiments the non-nucleotide moiety an antibody or antibody fragment, such as an antibody or antibody fragment that facilitates delivery across the blood-brain-barrier, in particular an antibody or antibody fragment targeting the transferrin receptor.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms, which are within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter, which those skilled in the art will appreciate may be assessed at a particular point in time, such that in some embodiments, inhibition may be or comprise a delay in onset or reduction in frequency. In some embodiments, inhibition can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

Antisense oligonucleotides (ASOs) were designed to target exons at the 5'-end of the SNORD115 host-gene transcript (AF400500), which encompasses SNORD115-46, SNORD115-47, SNORD115-48, and SNORD109B snoRNAs and is thought to represent the 5'-end of the UBE3A antisense transcript (UBE3A-AS). In particular the target nucleic acid can be the 5'-end of UBE3A-AS, corresponding to position 25,511,577 to 25,516,681 on human chromosome 15 human genome assembly hg19. In some embodiments, the target nucleic acid is one of five exons located in the 5'-end of UBE3A-AS, which can correspond to positions 25,511,577 to 25,511,761 (exon 1), 25,512,059 to 25,512,191 (exon 2), 25,513,476 to 25,513,600 (exon 3), 25,514,752 to 25,514,880 (exon 4), and 25,516,565 to 25,516,681 (exon 5).

Therefore, in some embodiments, the target nucleic acid is

```
                                      (Exon 1, SEQ ID NO: 1)
ATGATGATATGGAAGAAAAGCACTCTTTGGCCTGTTGTGACTGGGACAGTT

GACAGCACCCAGGTGTCCTTTAATGAAAATGCTCTTGACACCAATGCATCC

TAGCATCACAGCTTCAGGAAGCCTTCTCAAGTGTGCATGGGAGTACTATG

TCTTTCATCAATAATGAAATCTTCTGATTTG.
```

In some embodiments, the target nucleic acid is

```
                                      (Exon 2, SEQ ID NO: 2)
TAAGACATGCTGCCAAGAGATGTGCCATTCTATTATAAAAGATCAGTAGCT

TCCTTTACCGACGTGTATATTCTATCTAGAACATTGAGCTATGGAAGACTC

CCACCTAAGGGAATTAGTTTTACACCTTCAG.
```

In some embodiments, the target nucleic acid is

```
                                      (Exon 3, SEQ ID NO: 3)
ATAAAGACTGCTGAGAAGAGCACCCTCTGGTGTTGTCACAGAGGCAAGTGC

TACCGCACAGGCATGCTGCAGTGAATTTAACTGATCCTCTGTCCCTGCAAC

CGTTGTTTAAGGATGCTATTCTG.
```

In some embodiments, the target nucleic acid is

```
                                      (Exon 4, SEQ ID NO: 4)
AAAAGACTGTGGAGGAAGAAAACCCTTTACCCTGTTGTTCAGGGAGAAACT

GACACCACTCAACTGCCTGGCACTGAAAATGTGGCATCCAGTCCACTTTAC

CATCAGTGTTTAAGGAAACCATCTCTG.
```

In some embodiments, the target nucleic acid is (Exon 5, SEQ ID NO: 5)
ATAAGGATGACTGAGGAAGAGTACTCTTTGGCTTGTTGACACCAGCACAGC
TGACACACCCAGATATCTGTTTGGTCTCCTGTGAACTTTCAACCAGGATTT
AAGGATGCCACTCTG.

In some embodiments, the disclosed ASO has the nucleic acid sequence (ASO-1, SEQ ID NO: 6)
TAGAGGTGAAGGCCAGGCAC.

In some embodiments, the ASO has the nucleic acid sequence (ASO-2, SEQ ID NO: 7)
GTACTCTTCCTCAGTCATCC.

In some embodiments, the disclosed ASO has the nucleic acid sequence (ASO-3, SEQ ID NO: 8)
TGTCAGTTTCTCCCTGAACA.

In some embodiments, the disclosed ASO has the nucleic acid sequence (ASO-4, SEQ ID NO: 9)
TAGAATGGCACATCTCTTGG.

In some embodiments, the disclosed ASO has the nucleic acid sequence (ASO-6, SEQ ID NO: 10)
GTTTTCTTCCTCCACAGTCT.

In some embodiments, the disclosed ASO has the nucleic acid sequence (ASO-7, SEQ ID NO: 11)
CTGGTGTCAACAAGCCAAAG.

Additional ASOs that can target exon 1 of the 3'-end of the SNORD115 region are provided below in Table 1. Example ASOs that can target exon 2 of the 3'-end of the SNORD115 are provided below in Table 2. Example ASOs that can target exon 3 of the 3'-end of the SNORD115 are provided below in Table 3. Example ASOs that can target exon 4 of the 3'-end of the SNORD115 are provided below in Table 4. Example ASOs that can target exon 5 of the 3'-end of the SNORD115 are provided below in Table 5.

TABLE 1

Exon 1 ASOs

| Target Sequence (5'→3') | ASO (5'→3') |
|---|---|
| GAAAAUGCUCUUGACACC (SEQ ID NO: 12) | GGTGTCAAGAGCATTTTC (SEQ ID NO: 15) |
| GAAAAUGCUCUUGACACCA (SEQ ID NO: 13) | TGGTGTCAAGAGCATTTTC (SEQ ID NO: 16) |
| GAAAAUGCUCUUGACACCAA (SEQ ID NO: 14) | TTGGTGTCAAGAGCATTTTC (SEQ ID NO: 17) |

TABLE 2

Exon 2 ASOs

| Target Sequence (5'→3') | ASO (5'→3') |
|---|---|
| CAUGCUGCCAAGAGAUGU (SEQ ID NO: 18) | ACATCTCTTGGCAGCATG (SEQ ID NO: 67) |
| CAUGCUGCCAAGAGAUGUG (SEQ ID NO: 19) | CACATCTCTTGGCAGCATG (SEQ ID NO: 68) |
| CAUGCUGCCAAGAGAUGUGC (SEQ ID NO: 20) | GCACATCTCTTGGCAGCATG (SEQ ID NO: 69) |
| AUGCUGCCAAGAGAUGUG (SEQ ID NO: 21) | CACATCTCTTGGCAGCAT (SEQ ID NO: 70) |
| AUGCUGCCAAGAGAUGUGC (SEQ ID NO: 22) | GCACATCTCTTGGCAGCAT (SEQ ID NO: 71) |
| AUGCUGCCAAGAGAUGUGCC (SEQ ID NO: 23) | GGCACATCTCTTGGCAGCAT (SEQ ID NO: 72) |
| UGCUGCCAAGAGAUGUGCC (SEQ ID NO: 24) | GGCACATCTCTTGGCAGCA (SEQ ID NO: 73) |
| UGCUGCCAAGAGAUGUGCCA (SEQ ID NO: 25) | TGGCACATCTCTTGGCAGCA (SEQ ID NO: 74) |
| GCUGCCAAGAGAUGUGCCA (SEQ ID NO: 26) | TGGCACATCTCTTGGCAGC (SEQ ID NO: 75) |
| GCUGCCAAGAGAUGUGCCAU (SEQ ID NO: 27) | ATGGCACATCTCTTGGCAGC (SEQ ID NO: 76) |
| CUGCCAAGAGAUGUGCCA (SEQ ID NO: 28) | TGGCACATCTCTTGGCAG (SEQ ID NO: 77) |
| CUGCCAAGAGAUGUGCCAU (SEQ ID NO: 29) | ATGGCACATCTCTTGGCAG (SEQ ID NO: 78) |
| CUGCCAAGAGAUGUGCCAUU (SEQ ID NO: 30) | AATGGCACATCTCTTGGCAG (SEQ ID NO: 79) |

TABLE 2-continued

Exon 2 ASOs

| Target Sequence (5'→3') | ASO (5'→3') |
|---|---|
| UGCCAAGAGAUGUGCCAU (SEQ ID NO: 31) | ATGGCACATCTCTTGGCA (SEQ ID NO: 80) |
| UGCCAAGAGAUGUGCCAUU (SEQ ID NO: 32) | AATGGCACATCTCTTGGCA (SEQ ID NO: 81) |
| UGCCAAGAGAUGUGCCAUUC (SEQ ID NO: 33) | GAATGGCACATCTCTTGGCA (SEQ ID NO: 82) |
| GCCAAGAGAUGUGCCAUU (SEQ ID NO: 34) | AATGGCACATCTCTTGGC (SEQ ID NO: 83) |
| GCCAAGAGAUGUGCCAUUC (SEQ ID NO: 35) | GAATGGCACATCTCTTGGC (SEQ ID NO: 84) |
| GCCAAGAGAUGUGCCAUUCU (SEQ ID NO: 36) | AGAATGGCACATCTCTTGGC (SEQ ID NO: 85) |
| CCAAGAGAUGUGCCAUUC (SEQ ID NO: 37) | GAATGGCACATCTCTTGG (SEQ ID NO: 86) |
| CCAAGAGAUGUGCCAUUCU (SEQ ID NO: 38) | AGAATGGCACATCTCTTGG (SEQ ID NO: 87) |
| CCAAGAGAUGUGCCAUUCUA (SEQ ID NO: 39) | TAGAATGGCACATCTCTTGG (SEQ ID NO: 88) |
| CAAGAGAUGUGCCAUUCU (SEQ ID NO: 40) | AGAATGGCACATCTCTTG (SEQ ID NO: 89) |
| CAAGAGAUGUGCCAUUCUA (SEQ ID NO: 41) | TAGAATGGCACATCTCTTG (SEQ ID NO: 90) |
| CAAGAGAUGUGCCAUUCUAU (SEQ ID NO: 42) | ATAGAATGGCACATCTCTTG (SEQ ID NO: 91) |
| UCCUUUACCGACGUGUAU (SEQ ID NO: 43) | ATACACGTCGGTAAAGGA (SEQ ID NO: 92) |
| UCCUUUACCGACGUGUAUA (SEQ ID NO: 44) | TATACACGTCGGTAAAGGA (SEQ ID NO: 93) |
| UCCUUUACCGACGUGUAUAU (SEQ ID NO: 45) | ATATACACGTCGGTAAAGGA (SEQ ID NO: 94) |
| CCUUUACCGACGUGUAUA (SEQ ID NO: 46) | TATACACGTCGGTAAAGG (SEQ ID NO: 95) |
| CCUUUACCGACGUGUAUAU (SEQ ID NO: 47) | ATATACACGTCGGTAAAGG (SEQ ID NO: 96) |
| CCUUUACCGACGUGUAUAUU (SEQ ID NO: 48) | AATATACACGTCGGTAAAGG (SEQ ID NO: 97) |
| ACCGACGUGUAUAUUCUAUC (SEQ ID NO: 49) | GATAGAATATACACGTCGGT (SEQ ID NO: 98) |
| CCGACGUGUAUAUUCUAUC (SEQ ID NO: 50) | GATAGAATATACACGTCGG (SEQ ID NO: 99) |
| CCGACGUGUAUAUUCUAUCU (SEQ ID NO: 51) | AGATAGAATATACACGTCGG (SEQ ID NO: 100) |
| UCUAGAACAUUGAGCUAUGG (SEQ ID NO: 52) | CCATAGCTCAATGTTCTAGA (SEQ ID NO: 101) |
| CAUUGAGCUAUGGAAGAC (SEQ ID NO: 53) | GTCTTCCATAGCTCAATG (SEQ ID NO: 102) |
| CUAUGGAAGACUCCCACCUA (SEQ ID NO: 54) | TAGGTGGGAGTCTTCCATAG (SEQ ID NO: 103) |
| UAUGGAAGACUCCCACCUA (SEQ ID NO: 55) | TAGGTGGGAGTCTTCCATA (SEQ ID NO: 104) |
| UAUGGAAGACUCCCACCUAA (SEQ ID NO: 56) | TTAGGTGGGAGTCTTCCATA (SEQ ID NO: 105) |
| AUGGAAGACUCCCACCUA (SEQ ID NO: 57) | TAGGTGGGAGTCTTCCAT (SEQ ID NO: 106) |
| AUGGAAGACUCCCACCUAA (SEQ ID NO: 58) | TTAGGTGGGAGTCTTCCAT (SEQ ID NO: 107) |
| UGGAAGACUCCCACCUAA (SEQ ID NO: 59) | TTAGGTGGGAGTCTTCCA (SEQ ID NO: 108) |
| GACUCCCACCUAAGGGAAUU (SEQ ID NO: 60) | AATTCCCTTAGGTGGGAGTC (SEQ ID NO: 109) |
| ACUCCCACCUAAGGGAAU (SEQ ID NO: 61) | ATTCCCTTAGGTGGGAGT (SEQ ID NO: 110) |
| ACUCCCACCUAAGGGAAUU (SEQ ID NO: 62) | AATTCCCTTAGGTGGGAGT (SEQ ID NO: 111) |
| ACUCCCACCUAAGGGAAUUA (SEQ ID NO: 63) | TAATTCCCTTAGGTGGGAGT (SEQ ID NO: 112) |
| CUCCCACCUAAGGGAAUU (SEQ ID NO: 64) | AATTCCCTTAGGTGGGAG (SEQ ID NO: 113) |
| CUCCCACCUAAGGGAAUUA (SEQ ID NO: 65) | TAATTCCCTTAGGTGGGAG (SEQ ID NO: 114) |
| UCCCACCUAAGGGAAUUA (SEQ ID NO: 66) | TAATTCCCTTAGGTGGGA (SEQ ID NO: 115) |

TABLE 3

Exon 3 ASOs

| Target Sequence (5'→3') | ASO (5'→3') |
|---|---|
| GAUAAAGACUGCUGAGAAGA (SEQ ID NO: 116) | TCTTCTCAGCAGTCTTTATC (SEQ ID NO: 139) |
| AUAAAGACUGCUGAGAAGAG (SEQ ID NO: 117) | CTCTTCTCAGCAGTCTTTAT (SEQ ID NO: 140) |
| UAAAGACUGCUGAGAAGAGC (SEQ ID NO: 118) | GCTCTTCTCAGCAGTCTTTA (SEQ ID NO: 141) |
| AAAGACUGCUGAGAAGAGCA (SEQ ID NO: 119) | TGCTCTTCTCAGCAGTCTTT (SEQ ID NO: 142) |
| AAGACUGCUGAGAAGAGCAC (SEQ ID NO: 120) | GTGCTCTTCTCAGCAGTCTT (SEQ ID NO: 143) |
| AGACUGCUGAGAAGAGCACC (SEQ ID NO: 121) | GGTGCTCTTCTCAGCAGTCT (SEQ ID NO: 144) |
| GACUGCUGAGAAGAGCACCC (SEQ ID NO: 122) | GGGTGCTCTTCTCAGCAGTC (SEQ ID NO: 145) |
| CAAGUGCUACCGCACAGGCA (SEQ ID NO: 123) | TGCCTGTGCGGTAGCACTTG (SEQ ID NO: 146) |
| AAGUGCUACCGCACAGGCAU (SEQ ID NO: 124) | ATGCCTGTGCGGTAGCACTT (SEQ ID NO: 147) |
| AGUGCUACCGCACAGGCAUG (SEQ ID NO: 125) | CATGCCTGTGCGGTAGCACT (SEQ ID NO: 148) |
| UGCUACCGCACAGGCAUGCU (SEQ ID NO: 126) | AGCATGCCTGTGCGGTAGCA (SEQ ID NO: 149) |
| UACCGCACAGGCAUGCUGCA (SEQ ID NO: 127) | TGCAGCATGCCTGTGCGGTA (SEQ ID NO: 150) |
| GCACAGGCAUGCUGCAGUGA (SEQ ID NO: 128) | TCACTGCAGCATGCCTGTGC (SEQ ID NO: 151) |
| CACAGGCAUGCUGCAGUGAA (SEQ ID NO: 129) | TTCACTGCAGCATGCCTGTG (SEQ ID NO: 152) |
| ACAGGCAUGCUGCAGUGAAU (SEQ ID NO: 130) | ATTCACTGCAGCATGCCTGT (SEQ ID NO: 153) |
| CAGGCAUGCUGCAGUGAAUU (SEQ ID NO: 131) | AATTCACTGCAGCATGCCTG (SEQ ID NO: 154) |
| AGGCAUGCUGCAGUGAAUUU (SEQ ID NO: 132) | AAATTCACTGCAGCATGCCT (SEQ ID NO: 155) |
| GGCAUGCUGCAGUGAAUUUA (SEQ ID NO: 133) | TAAATTCACTGCAGCATGCC (SEQ ID NO: 156) |
| GCAUGCUGCAGUGAAUUUAA (SEQ ID NO: 134) | TTAAATTCACTGCAGCATGC (SEQ ID NO: 157) |
| CAUGCUGCAGUGAAUUUAAC (SEQ ID NO: 135) | GTTAAATTCACTGCAGCATG (SEQ ID NO: 158) |
| GCAGUGAAUUUAACUGAUCC (SEQ ID NO: 136) | GGATCAGTTAAATTCACTGC (SEQ ID NO: 159) |
| UCCCUGCAACCGUUGUUUAA (SEQ ID NO: 137) | TTAAACAACGGTTGCAGGGA (SEQ ID NO: 160) |
| CCCUGCAACCGUUGUUUAAG (SEQ ID NO: 138) | CTTAAACAACGGTTGCAGGG (SEQ ID NO: 161) |

TABLE 4

Exon 4 ASOs

| Target Sequence (5'→3') | ASO (5'→3') |
|---|---|
| AAAAGACUGUGGAGGAAGA (SEQ ID NO: 162) | TCTTCCTCCACAGTCTTTT (SEQ ID NO: 237) |
| AAAAGACUGUGGAGGAAGAA (SEQ ID NO: 163) | TTCTTCCTCCACAGTCTTTT (SEQ ID NO: 238) |
| AAAGACUGUGGAGGAAGAA (SEQ ID NO: 164) | TTCTTCCTCCACAGTCTTT (SEQ ID NO: 239) |
| AAAGACUGUGGAGGAAGAAA (SEQ ID NO: 165) | TTTCTTCCTCCACAGTCTTT (SEQ ID NO: 240) |
| AAGACUGUGGAGGAAGAAAA (SEQ ID NO: 166) | TTTTCTTCCTCCACAGTCTT (SEQ ID NO: 241) |
| AGACUGUGGAGGAAGAAAAC (SEQ ID NO: 167) | GTTTTCTTCCTCCACAGTCT (SEQ ID NO: 242) |
| ACUGUGGAGGAAGAAAAC (SEQ ID NO: 168) | GTTTTCTTCCTCCACAGT (SEQ ID NO: 243) |
| ACUGUGGAGGAAGAAAACC (SEQ ID NO: 169) | GGTTTTCTTCCTCCACAGT (SEQ ID NO: 244) |
| ACUGUGGAGGAAGAAAACCC (SEQ ID NO: 170) | GGGTTTTCTTCCTCCACAGT (SEQ ID NO: 245) |
| CUGUGGAGGAAGAAAACC (SEQ ID NO: 171) | GGTTTTCTTCCTCCACAG (SEQ ID NO: 246) |
| CUGUGGAGGAAGAAAACCC (SEQ ID NO: 172) | GGGTTTTCTTCCTCCACAG (SEQ ID NO: 247) |

TABLE 4-continued

| Exon 4 ASOs | |
|---|---|
| Target Sequence (5'→3') | ASO (5'→3') |
| AAAACCCUUUACCCUGUUG (SEQ ID NO: 173) | CAACAGGGTAAAGGGTTTT (SEQ ID NO: 248) |
| AAAACCCUUUACCCUGUUGU (SEQ ID NO: 174) | ACAACAGGGTAAAGGGTTTT (SEQ ID NO: 249) |
| AAACCCUUUACCCUGUUGUU (SEQ ID NO: 175) | AACAACAGGGTAAAGGGTTT (SEQ ID NO: 250) |
| UUGUUCAGGGAGAAACUG (SEQ ID NO: 176) | CAGTTTCTCCCTGAACAA (SEQ ID NO: 251) |
| UUGUUCAGGGAGAAACUGAC (SEQ ID NO: 177) | GTCAGTTTCTCCCTGAACAA (SEQ ID NO: 252) |
| UGUUCAGGGAGAAACUGA (SEQ ID NO: 178) | TCAGTTTCTCCCTGAACA (SEQ ID NO: 253) |
| UGUUCAGGGAGAAACUGAC (SEQ ID NO: 179) | GTCAGTTTCTCCCTGAACA (SEQ ID NO: 254) |
| UGUUCAGGGAGAAACUGACA (SEQ ID NO: 180) | TGTCAGTTTCTCCCTGAACA (SEQ ID NO: 255) |
| GUUCAGGGAGAAACUGACA (SEQ ID NO: 181) | TGTCAGTTTCTCCCTGAAC (SEQ ID NO: 256) |
| UCAGGGAGAAACUGACACCA (SEQ ID NO: 182) | TGGTGTCAGTTTCTCCCTGA (SEQ ID NO: 257) |
| CAGGGAGAAACUGACACCA (SEQ ID NO: 183) | TGGTGTCAGTTTCTCCCTG (SEQ ID NO: 258) |
| AGGGAGAAACUGACACCA (SEQ ID NO: 184) | TGGTGTCAGTTTCTCCCT (SEQ ID NO: 259) |
| AGGGAGAAACUGACACCAC (SEQ ID NO: 185) | GTGGTGTCAGTTTCTCCCT (SEQ ID NO: 260) |
| AGGGAGAAACUGACACCACU (SEQ ID NO: 186) | AGTGGTGTCAGTTTCTCCCT (SEQ ID NO: 261) |
| GGGAGAAACUGACACCAC (SEQ ID NO: 187) | GTGGTGTCAGTTTCTCCC (SEQ ID NO: 262) |
| GGGAGAAACUGACACCACU (SEQ ID NO: 188) | AGTGGTGTCAGTTTCTCCC (SEQ ID NO: 263) |
| GGGAGAAACUGACACCACUC (SEQ ID NO: 189) | GAGTGGTGTCAGTTTCTCCC (SEQ ID NO: 264) |
| GGAGAAACUGACACCACU (SEQ ID NO: 190) | AGTGGTGTCAGTTTCTCC (SEQ ID NO: 265) |
| GGAGAAACUGACACCACUC (SEQ ID NO: 191) | GAGTGGTGTCAGTTTCTCC (SEQ ID NO: 266) |
| GGAGAAACUGACACCACUCA (SEQ ID NO: 192) | TGAGTGGTGTCAGTTTCTCC (SEQ ID NO: 267) |
| GAGAAACUGACACCACUC (SEQ ID NO: 193) | GAGTGGTGTCAGTTTCTC (SEQ ID NO: 268) |
| GAGAAACUGACACCACUCA (SEQ ID NO: 194) | TGAGTGGTGTCAGTTTCTC (SEQ ID NO: 269) |
| GAGAAACUGACACCACUCAA (SEQ ID NO: 195) | TTGAGTGGTGTCAGTTTCTC (SEQ ID NO: 270) |
| AGAAACUGACACCACUCA (SEQ ID NO: 196) | TGAGTGGTGTCAGTTTCT (SEQ ID NO: 271) |
| AGAAACUGACACCACUCAA (SEQ ID NO: 197) | TTGAGTGGTGTCAGTTTCT (SEQ ID NO: 272) |
| AGAAACUGACACCACUCAAC (SEQ ID NO: 198) | GTTGAGTGGTGTCAGTTTCT (SEQ ID NO: 273) |
| GAAACUGACACCACUCAA (SEQ ID NO: 199) | TTGAGTGGTGTCAGTTC (SEQ ID NO: 274) |
| GAAACUGACACCACUCAAC (SEQ ID NO: 200) | GTTGAGTGGTGTCAGTTTC (SEQ ID NO: 275) |
| GAAACUGACACCACUCAACU (SEQ ID NO: 201) | AGTTGAGTGGTGTCAGTTTC (SEQ ID NO: 276) |
| AAACUGACACCACUCAAC (SEQ ID NO: 202) | GTTGAGTGGTGTCAGTTT (SEQ ID NO: 277) |
| AAACUGACACCACUCAACU (SEQ ID NO: 203) | AGTTGAGTGGTGTCAGTTT (SEQ ID NO: 278) |
| AAACUGACACCACUCAACUG (SEQ ID NO: 204) | CAGTTGAGTGGTGTCAGTTT (SEQ ID NO: 279) |
| AACUGACACCACUCAACU (SEQ ID NO: 205) | AGTTGAGTGGTGTCAGTT (SEQ ID NO: 280) |
| AACUGACACCACUCAACUG (SEQ ID NO: 206) | CAGTTGAGTGGTGTCAGTT (SEQ ID NO: 281) |
| AACUGACACCACUCAACUGC (SEQ ID NO: 207) | GCAGTTGAGTGGTGTCAGTT (SEQ ID NO: 282) |
| ACUGACACCACUCAACUG (SEQ ID NO: 208) | CAGTTGAGTGGTGTCAGT (SEQ ID NO: 283) |
| ACUGACACCACUCAACUGC (SEQ ID NO: 209) | GCAGTTGAGTGGTGTCAGT (SEQ ID NO: 284) |
| ACUGACACCACUCAACUGCC (SEQ ID NO: 210) | GGCAGTTGAGTGGTGTCAGT (SEQ ID NO: 285) |

TABLE 4-continued

Exon 4 ASOs

| Target Sequence (5'→3') | ASO (5'→3') |
|---|---|
| CUGACACCACUCAACUGC (SEQ ID NO: 211) | GCAGTTGAGTGGTGTCAG (SEQ ID NO: 286) |
| CUGACACCACUCAACUGCC (SEQ ID NO: 212) | GGCAGTTGAGTGGTGTCAG (SEQ ID NO: 287) |
| CUGACACCACUCAACUGCCU (SEQ ID NO: 213) | AGGCAGTTGAGTGGTGTCAG (SEQ ID NO: 288) |
| UGACACCACUCAACUGCC (SEQ ID NO: 214) | GGCAGTTGAGTGGTGTCA (SEQ ID NO: 289) |
| UGACACCACUCAACUGCCU (SEQ ID NO: 215) | AGGCAGTTGAGTGGTGTCA (SEQ ID NO: 290) |
| UGACACCACUCAACUGCCUG (SEQ ID NO: 216) | CAGGCAGTTGAGTGGTGTCA (SEQ ID NO: 291) |
| GACACCACUCAACUGCCU (SEQ ID NO: 217) | AGGCAGTTGAGTGGTGTC (SEQ ID NO: 292) |
| GACACCACUCAACUGCCUG (SEQ ID NO: 218) | CAGGCAGTTGAGTGGTGTC (SEQ ID NO: 293) |
| GACACCACUCAACUGCCUGG (SEQ ID NO: 219) | CCAGGCAGTTGAGTGGTGTC (SEQ ID NO: 294) |
| ACACCACUCAACUGCCUG (SEQ ID NO: 220) | CAGGCAGTTGAGTGGTGT (SEQ ID NO: 295) |
| ACACCACUCAACUGCCUGG (SEQ ID NO: 221) | CCAGGCAGTTGAGTGGTGT (SEQ ID NO: 296) |
| ACACCACUCAACUGCCUGGC (SEQ ID NO: 222) | GCCAGGCAGTTGAGTGGTGT (SEQ ID NO: 297) |
| CACCACUCAACUGCCUGGCA (SEQ ID NO: 223) | TGCCAGGCAGTTGAGTGGTG (SEQ ID NO: 298) |
| GAAAAUGUGGCAUCCAGU (SEQ ID NO: 224) | ACTGGATGCCACATTTTC (SEQ ID NO: 299) |
| AAAAUGUGGCAUCCAGUC (SEQ ID NO: 225) | GACTGGATGCCACATTTT (SEQ ID NO: 300) |
| GCAUCCAGUCCACUUUACCA (SEQ ID NO: 226) | TGGTAAAGTGGACTGGATGC (SEQ ID NO: 301) |
| CAUCCAGUCCACUUUACC (SEQ ID NO: 227) | GGTAAAGTGGACTGGATG (SEQ ID NO: 302) |
| CAUCCAGUCCACUUUACCA (SEQ ID NO: 228) | TGGTAAAGTGGACTGGATG (SEQ ID NO: 303) |
| CAUCCAGUCCACUUUACCAU (SEQ ID NO: 229) | ATGGTAAAGTGGACTGGATG (SEQ ID NO: 304) |
| AUCCAGUCCACUUUACCA (SEQ ID NO: 230) | TGGTAAAGTGGACTGGAT (SEQ ID NO: 305) |
| AUCCAGUCCACUUUACCAU (SEQ ID NO: 231) | ATGGTAAAGTGGACTGGAT (SEQ ID NO: 306) |
| AUCCAGUCCACUUUACCAUC (SEQ ID NO: 232) | GATGGTAAAGTGGACTGGAT (SEQ ID NO: 307) |
| GUUUAAGGAAACCAUCUCUG (SEQ ID NO: 233) | CAGAGATGGTTTCCTTAAAC (SEQ ID NO: 308) |
| UUUAAGGAAACCAUCUCUGG (SEQ ID NO: 234) | CCAGAGATGGTTTCCTTAAA (SEQ ID NO: 309) |
| UUAAGGAAACCAUCUCUGG (SEQ ID NO: 235) | CCAGAGATGGTTTCCTTAA (SEQ ID NO: 310) |
| UAAGGAAACCAUCUCUGG (SEQ ID NO: 236) | CCAGAGATGGTTTCCTTA (SEQ ID NO: 311) |

TABLE 5

Exon 5 ASOs

| Target Sequence (5'→3') | ASO (5'→3') |
|---|---|
| AUAAGGAUGACUGAGGAAG (SEQ ID NO: 312) | CTTCCTCAGTCATCCTTAT (SEQ ID NO: 335) |
| AUAAGGAUGACUGAGGAAGA (SEQ ID NO: 313) | TCTTCCTCAGTCATCCTTAT (SEQ ID NO: 336) |
| UAAGGAUGACUGAGGAAG (SEQ ID NO: 314) | CTTCCTCAGTCATCCTTA (SEQ ID NO: 337) |
| UAAGGAUGACUGAGGAAGA (SEQ ID NO: 315) | TCTTCCTCAGTCATCCTTA (SEQ ID NO: 338) |
| UAAGGAUGACUGAGGAAGAG (SEQ ID NO: 316) | CTCTTCCTCAGTCATCCTTA (SEQ ID NO: 339) |
| AAGGAUGACUGAGGAAGA (SEQ ID NO: 317) | TCTTCCTCAGTCATCCTT (SEQ ID NO: 340) |
| AAGGAUGACUGAGGAAGAG (SEQ ID NO: 318) | CTCTTCCTCAGTCATCCTT (SEQ ID NO: 341) |

TABLE 5-continued

Exon 5 ASOs

| Target Sequence (5'→3') | ASO (5'→3') |
|---|---|
| AAGGAUGACUGAGGAAGAGU (SEQ ID NO: 319) | ACTCTTCCTCAGTCATCCTT (SEQ ID NO: 342) |
| AGGAUGACUGAGGAAGAG (SEQ ID NO: 320) | CTCTTCCTCAGTCATCCT (SEQ ID NO: 343) |
| AGGAUGACUGAGGAAGAGU (SEQ ID NO: 321) | ACTCTTCCTCAGTCATCCT (SEQ ID NO: 344) |
| AGGAUGACUGAGGAAGAGUA (SEQ ID NO: 322) | TACTCTTCCTCAGTCATCCT (SEQ ID NO: 345) |
| GGAUGACUGAGGAAGAGU (SEQ ID NO: 323) | ACTCTTCCTCAGTCATCC (SEQ ID NO: 346) |
| GGAUGACUGAGGAAGAGUA (SEQ ID NO: 324) | TACTCTTCCTCAGTCATCC (SEQ ID NO: 347) |
| GGAUGACUGAGGAAGAGUAC (SEQ ID NO: 325) | GTACTCTTCCTCAGTCATCC (SEQ ID NO: 348) |
| GAUGACUGAGGAAGAGUA (SEQ ID NO: 326) | TACTCTTCCTCAGTCATC (SEQ ID NO: 349) |
| GAUGACUGAGGAAGAGUAC (SEQ ID NO: 327) | GTACTCTTCCTCAGTCATC (SEQ ID NO: 350) |
| GAUGACUGAGGAAGAGUACU (SEQ ID NO: 328) | AGTACTCTTCCTCAGTCATC (SEQ ID NO: 351) |
| AUGACUGAGGAAGAGUAC (SEQ ID NO: 329) | GTACTCTTCCTCAGTCAT (SEQ ID NO: 352) |
| AUGACUGAGGAAGAGUACU (SEQ ID NO: 330) | AGTACTCTTCCTCAGTCAT (SEQ ID NO: 353) |
| AUGACUGAGGAAGAGUACUC (SEQ ID NO: 331) | GAGTACTCTTCCTCAGTCAT (SEQ ID NO: 354) |
| UGACUGAGGAAGAGUACU (SEQ ID NO: 332) | AGTACTCTTCCTCAGTCA (SEQ ID NO: 355) |
| UGACUGAGGAAGAGUACUC (SEQ ID NO: 333) | GAGTACTCTTCCTCAGTCA (SEQ ID NO: 356) |
| UGACUGAGGAAGAGUACUCU (SEQ ID NO: 334) | AGAGTACTCTTCCTCAGTCA (SEQ ID NO: 357) |

The disclosed oligonucleotide is capable of modulating expression of paternal UBE3A, in particular induction or up-regulation of paternally expressed UBE3A in neuronal cells. The modulation is achieved by hybridizing to the 5'-end of UBE3A-AS. In certain embodiments the oligonucleotide disclosed herein hybridizes to a sub-sequence of the target nucleic acid of SEQ ID NO:1 with a $\Delta G°$ below $-10$ kcal, such as with a $\Delta G°$ between $-10$ to $-60$ kcal, such as $-12$ to $-40$, such as from $-15$ to $-30$ kcal or $-16$ to $-27$ kcal such as $-18$ to $-25$ kcal.

In some embodiments the disclosed oligonucleotides are capable of increasing the expression of UBE3A by least 20% compared to the expression level of UBE3A in a neuronal cell treated with saline or a non-targeting oligonucleotide, more preferably by at least 30%, 35%, 40%, 45%, 50%, 55%, 60%, 80%, 100%, 120%, 150%, 160%, 170%, 180%, 190%, 200%, 210%, 220%, 230%, 240% or 250% compared to the expression level of UBE3A in a neuronal cell treated with saline or a non-targeting oligonucleotide. In some embodiments, the disclosed oligonucleotides are capable of decreasing the level of the SNHG14 transcript downstream of SNORD115-45 by at least 20% compared to the level of the SNHG14 transcript downstream of SNORD1115-45 in a neuronal cell treated with saline or a non-targeting oligonucleotide, more preferably by at least 30%, 40%, 50%, 60%, 70%, 80%, 90% or 95% compared to the level of the SNHG14 transcript downstream of SNORD115-45 in a neuronal cell treated with saline or a non-targeting oligonucleotide.

Target modulation by the disclosed oligonucleotide is triggered by hybridization between a contiguous nucleotide sequence of the oligonucleotide and the target nucleic acid. In some embodiments the disclosed oligonucleotide comprises mismatches between the oligonucleotide and the target nucleic acid. Despite mismatches hybridization to the target nucleic acid may still be sufficient to show a desired modulation of UBE3A expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

The disclosed antisense oligonucleotide can have a contiguous nucleotide sequence of 10 to 30 nucleotides in length with at least 90% complementary, such as at least 91%, such as at least 92%, such as at least 93%, such as at least 94%, such as at least 95%, such as at least 96%, such as at least 97%, such as at least 98%, or 100% complementarity to one of five exons located in the 5'-end of UBE3A-AS disclosed herein.

Oligonucleotide design refers to the pattern of nucleoside sugar modifications in the oligonucleotide sequence. The disclosed antisense oligonucleotide comprises sugar-modified nucleosides and may also comprise DNA, RNA, or arabino nucleic acid (ANA) nucleosides. In some embodiments, the oligonucleotide comprises sugar-modified nucleosides and DNA nucleosides. In some embodiments, the oligonucleotide comprises sugar-modified nucleosides and RNA nucleosides. In some embodiments, the oligonucleotide comprises sugar-modified nucleosides and ANA nucleosides.

In some embodiments, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides.

In some embodiments, the oligonucleotide comprises at least one modified internucleoside linkage. In some embodiments, the internucleoside linkages within the contiguous nucleotide sequence are phosphorothioate or boranophosphate internucleoside linkages.

In some embodiments, the disclosed antisense oligonucleotide comprises one or more sugar modified nucleosides, such as 2' sugar modified nucleosides.

Preferably the disclosed antisense oligonucleotides comprise one or more LNA nucleosides or 2' sugar modified nucleoside wherein the 2' position is replaced by a substituent independently selected from the group consisting of, —F; —CF$_3$, —CN, —N$_3$, —NO, —NO$_2$, —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$—Cao alkenyl)$_2$; —O—(C$_2$-C$_{10}$ alkynyl), —S—(C$_2$-C$_{10}$ alkynyl), —NH—(C$_2$-C$_{10}$ alkynyl), —N(C$_2$-C$_{10}$ alkynyl)$_2$, —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl), —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), and —N(C$_1$-C$_{10}$ alkyl)-(C$_1$-C$_{10}$ alkylene)-O—(C$_1$-C$_{10}$ alkyl).

In some embodiments, the disclosed oligonucleotides comprises at least one LNA unit, such as 1, 2, 3, 4, 5, 6, 7, or 8 LNA units, such as from 2 to 6 LNA units, such as from 3 to 7 LNA units, 4 to 8 LNA units or 3, 4, 5, 6 or 7 LNA units. In some embodiments, all the modified nucleosides are LNA nucleosides. In some embodiments, LNA comprises a 2'-4' biradical bridge of -L-, wherein -L- is —OCH$_2$—, wherein —CH$_2$— is optionally substituted. In some embodiments, LNA comprises a 2'-4' biradical bridge of -L-, wherein -L- is —O—CH$_2$—. In some embodiments, LNA comprises a 2'-4' biradical bridge of -L-, wherein -L- is —O—CH(Et)-. In a further embodiment, the oligonucleotide may comprise both beta-D-oxy-LNA, and one or more of the following LNA units: thio-LNA, amino-LNA, oxy-LNA, and/or ENA in either the beta-D or alpha-L configurations or combinations thereof. In a further embodiment, all LNA cytosine units are 5-methyl-cytosine. In some embodiments, the oligonucleotide or contiguous nucleotide sequence has at least 1 LNA unit at the 5' end and at least 2 LNA units at the 3' end of the nucleotide sequence.

In some embodiments, the disclosed oligonucleotide is capable of recruiting RNase H. In some embodiments, the oligonucleotide has a gapmer design or structure also referred herein merely as "Gapmer". In a gapmer structure the oligonucleotide comprises at least three distinct structural regions a 5'-flank, a gap and a 3'-flank, F-G-F' in'5->3' orientation. In this design, flanking regions F and F' (also termed wing regions) comprise a contiguous stretch of modified nucleosides, which are complementary to the UBE3A-AS target nucleic acid, while the gap region, G, comprises a contiguous stretch of nucleotides which are capable of recruiting a nuclease, preferably an endonuclease such as RNase, for example, RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Flouro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides. In oligonucleotides with mixed flanks where the flanks comprise DNA the 5' and 3' nucleosides are modified nucleosides.

Methods for manufacturing the disclosed oligonucleotides are known. In some cases, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand).

In some embodiments, oligonucleotide synthesis methodologies are utilized that provide control of stereochemistry at one or more modified internucleoside linkages that include(s) a chiral atom. See, for example, WO2010/064146, WO2014/012081, WO2015/107425, WO2016/079183, WO2016/079181, WO2016/096938, WO2017/194498, and WO2018/177825, which are incorporated by reference for these methodologies.

Those skilled in the art will appreciate that useful nucleic acids provided by the present disclosure include those that store and/or express sequences of oligonucleotides described herein. In some embodiments, such nucleic acids may be or comprise vectors appropriate for delivery into and/or replication and/or expression in a cell (e.g., a microbial cell, for example for production and/or a mammalian cell, for example for treatment). Those skilled in the art are aware of a variety of technologies (e.g., recombinant nucleic acid technologies such as, for instance, that utilize one or more of amplification such as by polymerase chain reaction, cleavage such as by restriction digestion, linkage such as by ligation—whether in vitro or in vivo e.g., by gap repair, etc.).

Also disclosed are pharmaceutical compositions comprising any of the aforementioned oligonucleotides and/or oligonucleotide conjugates and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments, the diluent is artificial cerebrospinal fluid (aCSF).

The disclosed oligonucleotides may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Those skilled in the art are aware of a variety of formulation strategies useful for storage and/or administration of nucleic acid therapeutics such as oligonucleotide therapeutics. See, for example, Pushpendra et al "Nucleic Acids as Therapeutics" in *From Nucleic Acid Sequences to Molecular Medicines*, ed. Erdmann and Barciszewski, Springer-Verlag, 2012; Juliano "The Delivery of Therapeutic Oligonucleotides" *Nuc. Acids. Res.* 44:6518, 2016; etc.

In some embodiments, the oligonucleotide is formulated as a prodrug. In particular with respect to oligonucleotide conjugates, the conjugate moiety can be cleaved off the oligonucleotide once the prodrug is delivered to the site of action, e.g., the target cell.

Also disclosed are methods for treating or preventing a disease, comprising administering a therapeutically or prophylactically effective amount of an oligonucleotide, an oligonucleotide conjugate or a pharmaceutical composition disclosed herein to a subject suffering from or susceptible to the disease.

Also disclosed is use of the disclosed oligonucleotides for the manufacture of a medicament for the treatment of a disorder as referred to herein, or for a method of the treatment of as a disorder as referred to herein.

The disclosed pharmaceutical compositions may be administered by topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal) administration. In some embodiments, the disclosed pharmaceutical compositions are administered by a parenteral route including intravenous, intraarterial, subcutaneous, intraperitoneal or intramuscular injection or infusion, intrathecal or intracranial, e.g., intracerebral or intraventricular, administration. In some embodiments, the oligonucleotide is administered by intracerebral or intracerebroventricular injection. In another embodiment the active oligonucleotide or oligonucleotide conjugate is administered intrathecally. In some embodiments, the pharmaceutical composition is administered by intracisternae *magna* injection.

In some embodiments, AS therapy with pharmaceutical compositions described herein is administered to subject(s) suffering from or susceptible to AS. In some embodiments, a subject has been determined to have genetic characteristic associated with a defect in a maternal UBE3A gene. In some embodiments, an AS-associated genetic characteristic is or comprises a maternal deletion. In some embodiments, an AS-associated genetic characteristic is or comprises uniparental disomy. In some embodiments, an AS-associated genetic characteristic is or comprises a UBE3A mutation. In some embodiments, an AS-associated genetic characteristic is or comprises an imprinting defect.

In some embodiments, a subject has been determined to have one or more developmental history and/or laboratory finding characteristics that have been associated with AS such as, for example, one or more of:
(i) normal prenatal and birth history with normal head circumference and absence of major birth defects;
(ii) feeding difficulties as a neonate and/or as an infant;
(iii) developmental delay evident by 6-12 months of age, sometimes associated with truncal hypotonus;
(iv) unsteady limb movements and/or increased smiling;
(v) delayed but forward progression of development (no loss of skills);
(vi) normal metabolic, hematologic and chemical laboratory profiles;
(vii) structurally normal brain when assessed using MRI or CT (may have mild cortical atrophy or dysmyelination).

Alternatively or additionally, in some embodiments, a subject has been determined to display one or more clinical features that are consistently associated with AS such as, for example, one or more of:
(i) developmental delay, functionally severe
(ii) movement or balance disorder, usually ataxia of gait and/or tremulous movement of limbs. In some embodiments, such movement disorder can be mild. In some embodiments, such movement disorder may not appear as frank ataxia but can be or involve, for example, forward lurching, unsteadiness, clumsiness, or quick, jerky motion;
(iii) behavioral uniqueness: any combination of frequent laughter/smiling; apparent happy demeanor; easily excitable personality, often with uplifted hand-flapping or waving movements; hypermotoric behavior
(iv) speech impairment, such as for example absent or minimal use of words; alternatively or additionally, receptive and non-verbal communication skills higher than verbal ones.

Alternatively or additionally, in some embodiments, a subject has been determined to display one or more clinical features that are frequently (e.g., about 80% of the time) associated with AS such as, for example, one or more of:
(i) delayed, disproportionate growth in head circumference, usually resulting in microcephaly (≤2 S.D. of normal OFC) by age 2 years. In some embodiments, microcephaly is more pronounced in those with 15q11.2-q13 deletions;
(ii) seizures, onset usually <3 yrs. of age. In some embodiments, seizure severity may decrease with age but regardless, in some embodiments, the seizure disorder lasts throughout adulthood.
(iv) abnormal EEG, with a characteristic pattern, as is known in the art. In some embodiments, EEG abnormalities can occur in the first 2 years of life and can precede clinical features, and may not be correlated to clinical seizure events.

Alternatively or additionally, in some embodiments, a subject has been determined to display one or more clinical features that are sometimes (e.g., about 20-80% of the time) associated with AS such as, for example, one or more of:
(i) flat occiput
(ii) occipital groove
(iii) protruding tongue
(iv) tongue thrusting; suck/swallowing disorders
(v) feeding problems and/or truncal hypotonia during infancy
(vi) prognathia
(vii) wide mouth, wide-spaced teeth
(viii) frequent drooling
(ix) excessive chewing/mouthing behaviors
(x) strabismus
(xi) hypopigmented skin, light hair and eye color, in some embodiments determined as compared to family, and typically seen only in deletion cases
(xii) hyperactive lower extremity deep tendon reflexes
(xiii) uplifted, flexed arm position especially during ambulation
(xiv) wide-based gait with pronated or valgus-positioned ankles
(xv) increased sensitivity to heat
(xvi) abnormal sleep wake cycles and diminished need for sleep
(xvii) attraction to/fascination with water; fascination with crinkly items such as certain papers and plastics
(xviii) abnormal food related behaviors
(xix) obesity (in the older child)
(xx) scoliosis
(xxi) constipation In some embodiments, a therapeutic regimen for the treatment of AS with a nucleic acid therapeutic (e.g., an oligonucleotide therapeutic such as an ASO) as described herein is or comprises administration of one or more doses of a pharmaceutical composition that comprises and/or delivers an oligonucleotide as described herein.

In some embodiments, a subject to whom a provided therapeutic regimen is administered is receiving or has received one or more other AS therapeutics including, for example, one or more other nucleic acid therapeutics (e.g., one or more other oligonucleotides that target UBE3A-AS). See, for example, WO2014004572A3, U.S. Pat. No. 9,617, 539B2, US20170362592A1, and EP2864479B1.

In some embodiments, a subject to whom a provided therapeutic regimen is administered has suffered or is suffering from one or more seizures and/or is receiving or has received anti-seizure therapy. For example. In some embodiments, a subject may have received or be receiving one or more of valproic acid, clonazepam, phenobarbital, topiramate, carbamazepine, lamotrigine, leveltiracetam, phenytoin, zonisamide, ethosuxaminde, gabapentin, felbatame, oxcarbazepine, tranxene, ACTS, nitrazapam, pregabalin, mysoline, vigabatrin, etc. In some particular embodiments, a subject may have received or be receiving one or more of valproic acid, clonazepam, phenobarbital, topiramate, carbamazepine, lamotrigine, and/or levetiracetam.

Alternatively or additionally, in some embodiments, a subject may have received or be receiving dietary therapy such as, for example, a ketogenic diet, low glycemic index therapy, etc.

Still further alternatively or additionally, in some embodiments, a subject may have received or be receiving treatment with a vagal nerve stimulator.

As will be apparent to those skilled in the art reading the present disclosure, provided methods of treatment involve administering one or both of an oligonucleotide as described herein and an additional therapy (e.g., an alternative oligonucleotide and/or anti-epileptic therapy and/or one or more other therapeutic interventions), so that the subject receives combination therapy (e.g., is simultaneously exposed thereto, for example via overlapping dosing etc.). Also disclosed is the use of an oligonucleotide disclosed herein for the manufacture of a medicament wherein the medicament is in a dosage form for intrathecal administration.

Also disclosed is the use of an oligonucleotide disclosed herein for the manufacture of a medicament wherein the medicament is in a dosage form for intracerebral or intraventricular administration.

Also disclosed is the use of an oligonucleotide disclosed herein for the manufacture of a medicament wherein the medicament is in a dosage form for intracerebroventricular administration.

In some embodiments the oligonucleotide disclosed herein is for use in a combination treatment with another therapeutic agent. The therapeutic agent can for example be anticonvulsant medication.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Results

RNA-sequencing analysis of mouse and human CNS identified a region believed to be important for the stability and/or transcription of UBE3A-AS. Further analysis of the region showed low levels of sequence conservation between mouse and human (FIGS. 1A-1D).

Figure 2A:
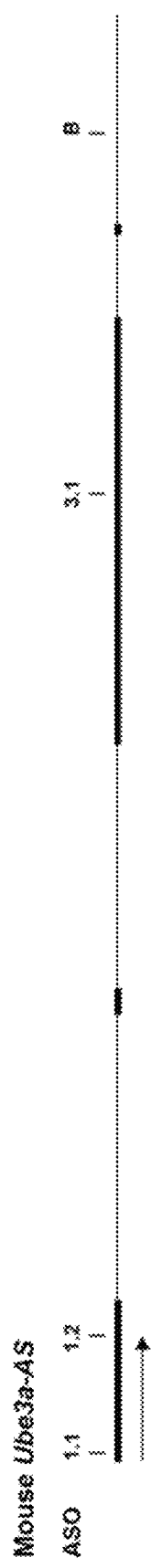
Figure 2C:
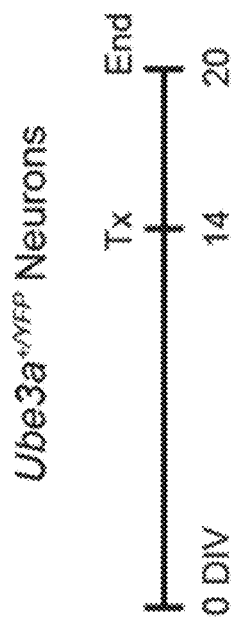
Figure 2B:
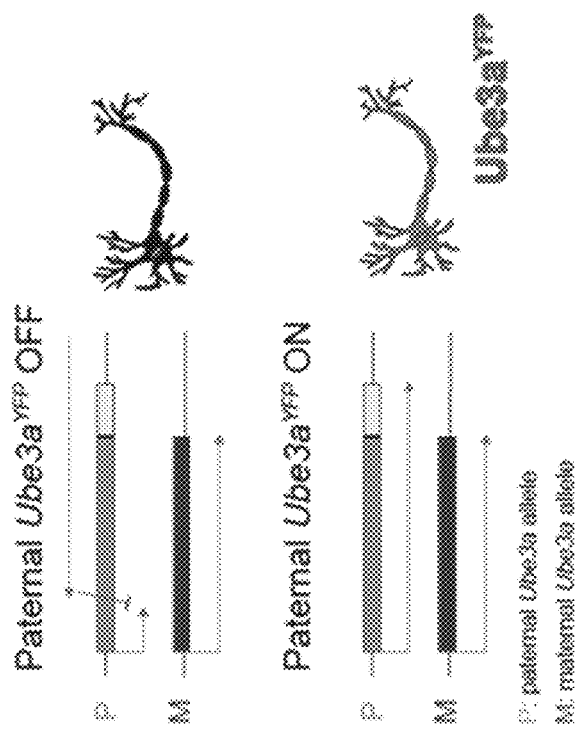
Figure 2D:
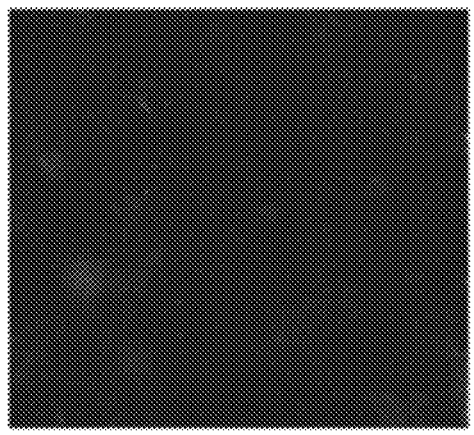
Figure 2D:
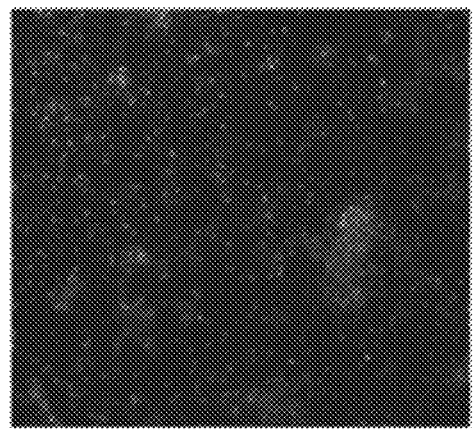
Figure 2D:
Figure 2D:
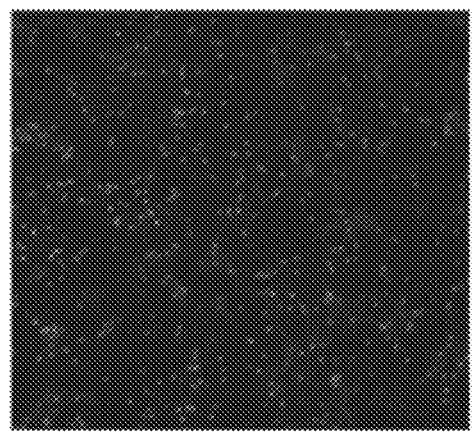
Figure 2E:
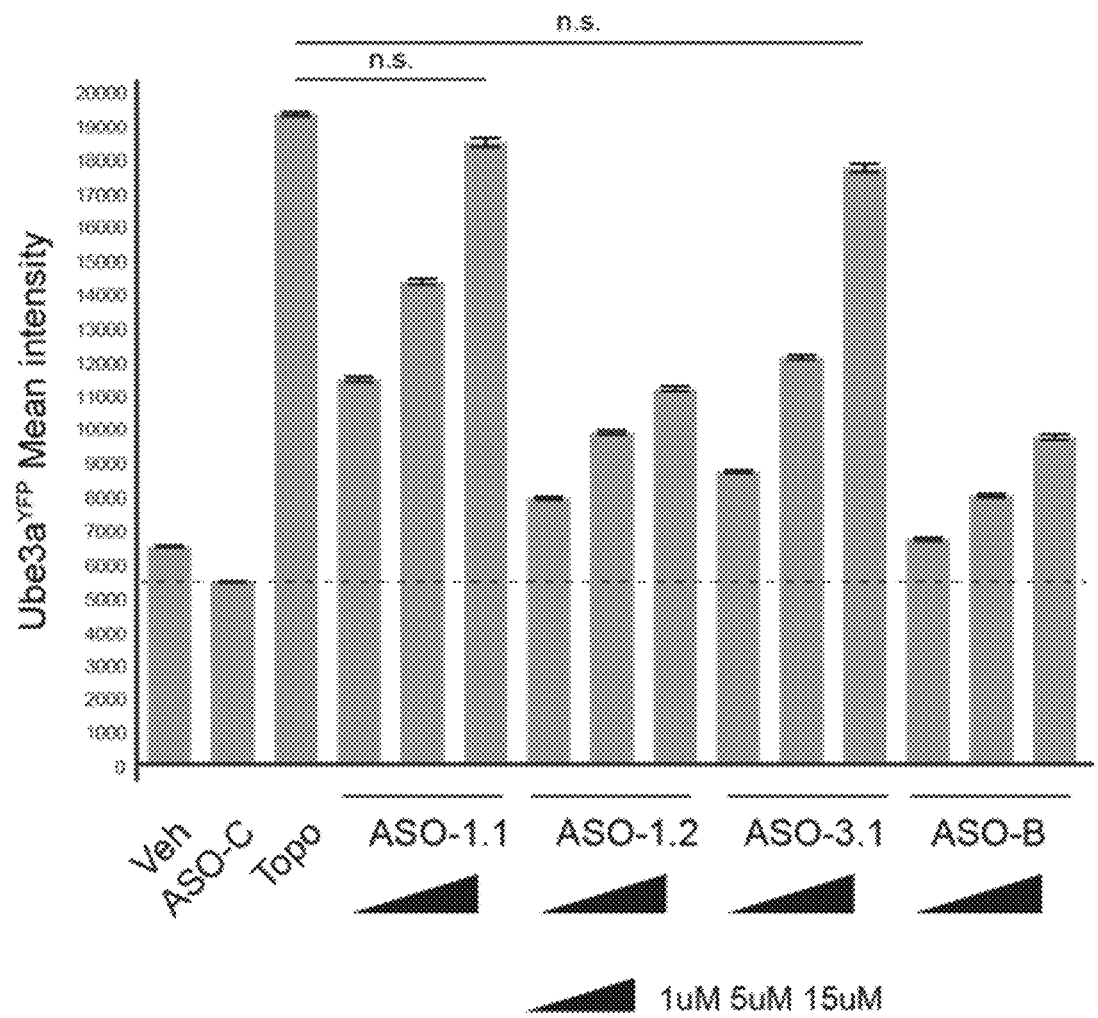

Based on these findings, mouse-specific ASOs were designed to target a specific region in the Ube3a-AS transcript (Table 6 and FIG. 2A). To test whether ASOs targeting this region reactivate expression of the paternal Ube3a allele, primary hippocampal neuronal cultures were generated from the Ube3aYFP reporter mouse model (Ube3a+/YFP; FIG. 2B) and treated at 7 days in vitro (DIV) with a control ASO [ASO-C(10 uM, n=3)], three ASOs targeting Ube3a-AS [ASO-1.1, ASO-1.2, ASO-3.1 (1 μM, 5 μM, and 15 μM, n=3)], and ASO-B (1 μM, 5 μM, and 15 μM, n=3)]. As a positive control, neurons were also treated with Topotecan[Topo (300 nM, n=3)] and a negative vehicle control [Veh (1%, n=3); FIG. 2 C]. Three days post-treatment (10 DIV), immunofluorescent imaging was used to quantify paternal Ube3aYFP protein levels in individual cells. Compared to controls (ASO-C and Veh), each treatment substantially increased paternal Ube3aYFP protein levels, with similar levels achieved in ASO-1.1 (15 μM), ASO-3.1 (15 μM), and Topotecan treatments (FIGS. 2D and 2E).

Figure 3C:
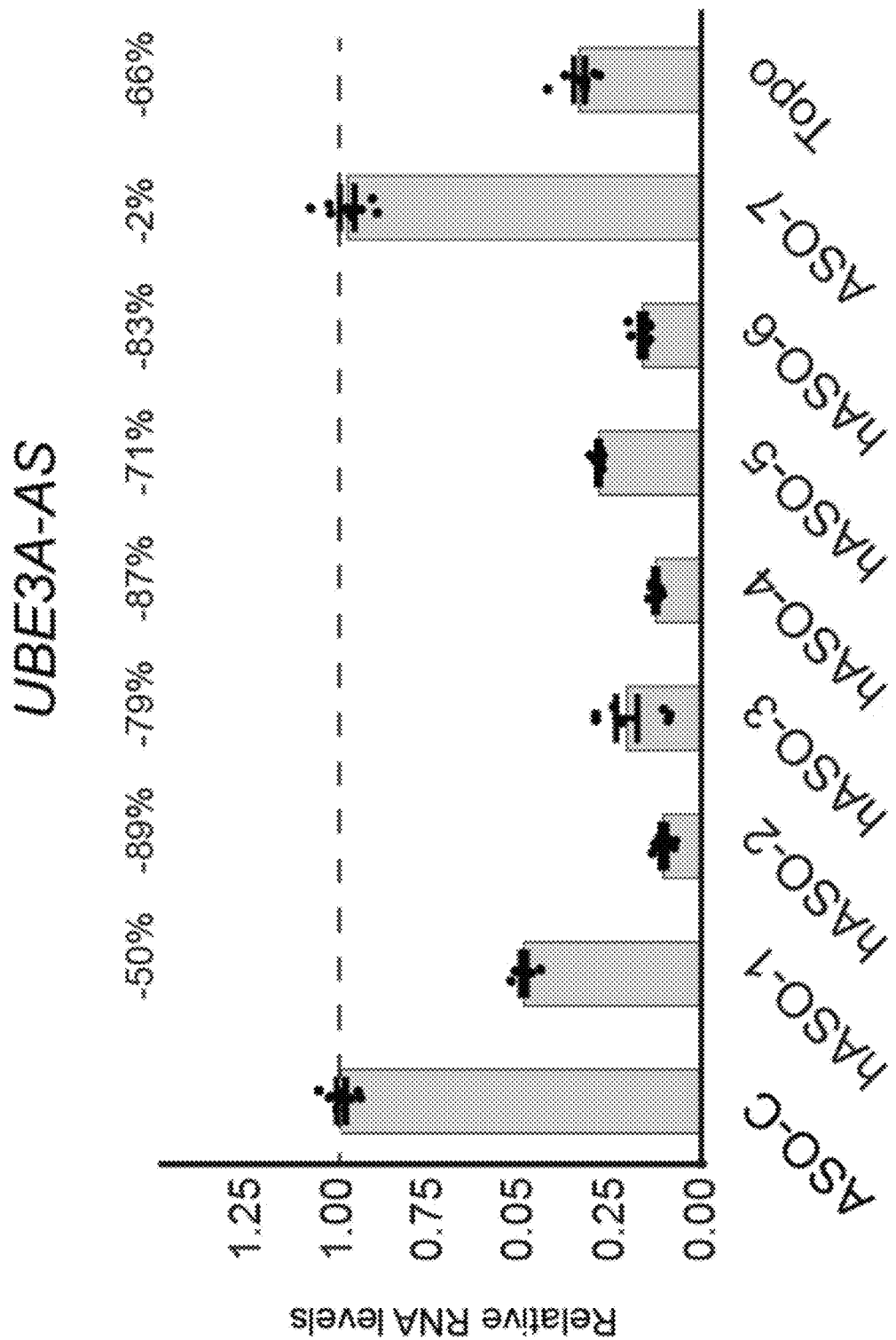
Figure 3D:
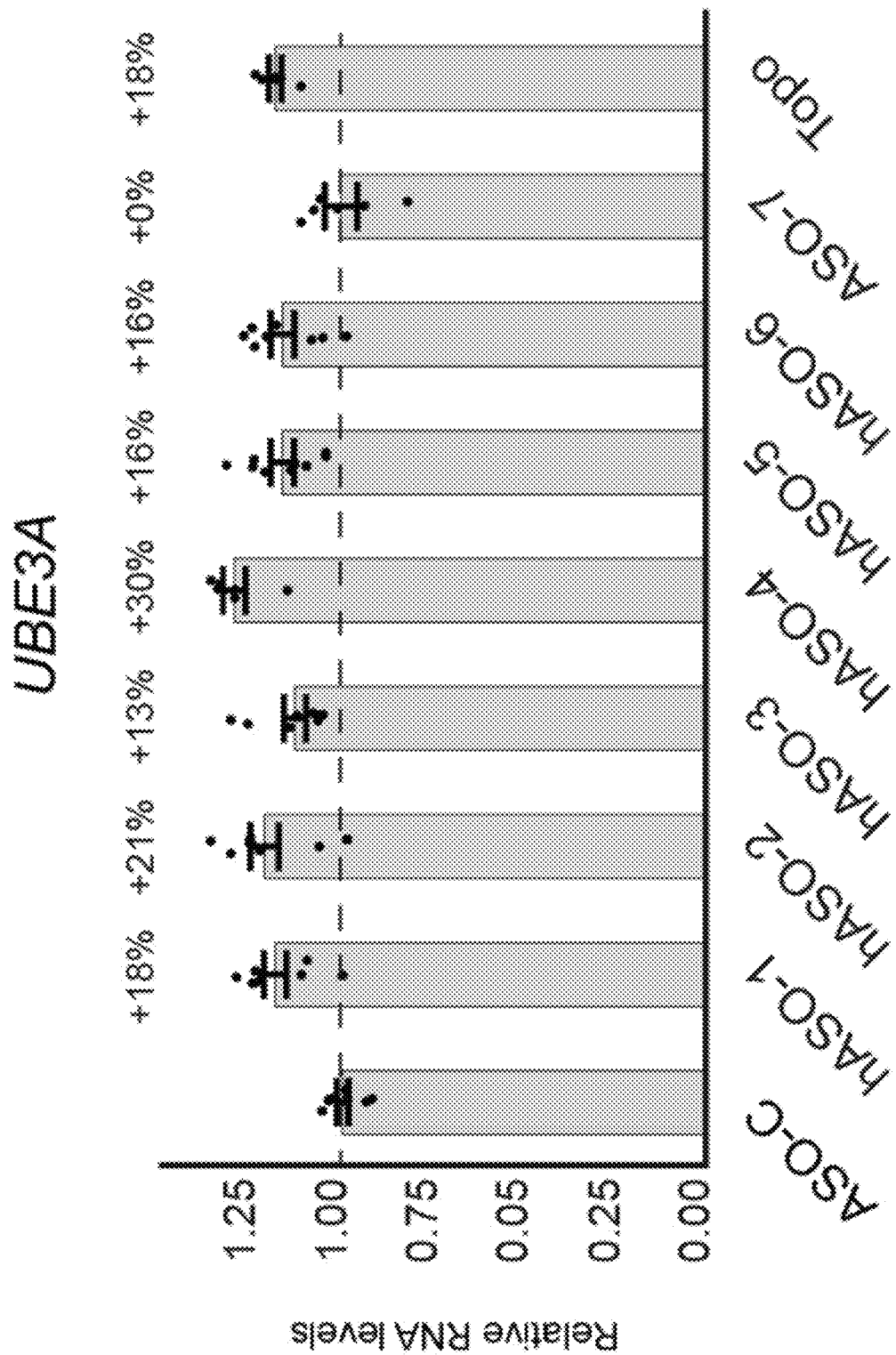

Human-specific ASOs were then designed to target this region, which included four ASOs targeting non-polymorphic regions in human and regions conserved (100%) with macaque (Rhesus and Cynomolgus) (Table 7 and FIG. 3A). Human induced pluripotent stem cell (iPSC) neural precursor cells were differentiated into GABAergic neurons for 14 DIV and then treated with a control ASO [ASO-C(10 μM, n=3)], Topotecan[Topo (1 μM, n=2)], and six ASOs targeting UBE3A-AS [ASO-1, ASO-2, ASO-3, ASO-4, ASO-5, and ASO-6 (10 μM, n=3)]. Additionally, an ASO targeting an intronic region downstream of SNORD109B was included (ASO-7). Six days post-treatment (20 DIV), RNA was isolated from the neurons and the steady state RNA levels of UBE3A-AS and UBE3A were estimated relative to the control treatment (FIG. 3B). With the exception of ASO-7, each ASO significantly decreased UBE3A-AS RNA levels, with ASO-2 and ASO-4 having the largest effect (Table 8 and FIG. 3C). UBE3A RNA levels also increased after treatment with each ASO (FIG. 3D).

The potency of ASO-4 was further examined given its effect on UBE3A-AS RNA levels. GABAergic iPSC-derived neurons were treated at 14 DIV with a 10-point % log dose response curve of ASO-4 and Topotecan, as a positive control and for comparisons between treatment[1 nM, 3 nM, 10 nM, 30 nM, 100 nM, 300 nM, 1 μM, 3 μM, 10 μM, and 30 μM (ASO-4, n=6; Topotecan, n=2)]. At 20 DIV, the steady state RNA levels of UBE3A-AS were measured and dose response curves fitted to estimate the $IC_{50}$ and $E_{max}$ (i.e., maximum UBE3A-AS inhibition) (Table 9 and FIG. 4A). The dose response curves of ASO-4 and Topotecan were significantly different (Parallelism test: $F_{(3,145)}=11.2$, p<0.0001), thus the relative potencies were not estimated. An equivalence test indicated that the $IC_{50}$ and $E_{max}$ of ASO-4 and Topotecan were not equivalent[ASO-4/Topotecan $IC_{50}$ ratio: =1.2 (Lower confidence limit=1.1; Upper confidence limit=1.3); $E_{max}$ ratio=−4.1 (Lower confidence limit=−12.9; Upper confidence limit=4.8)].

Figures 4D, 4E, 4F:
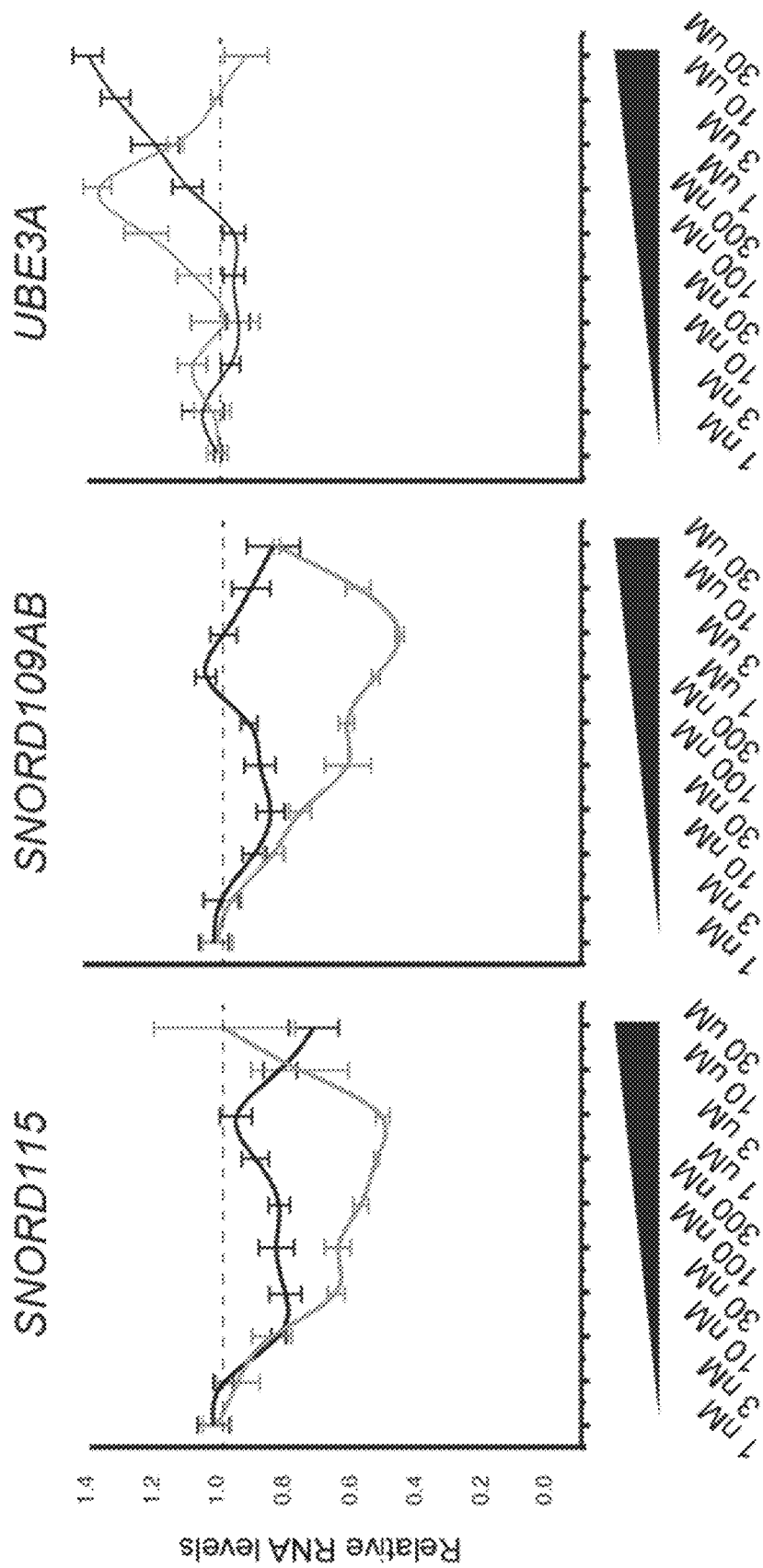

The effects of ASO-4 and Topotecan were then examined on the SNORD116, IPW, SNORD115, and SNORD109A RNAs, which are located upstream of the ASO-4 target region (see FIG. 1A). With the exception of SNORD116, ASO-4 had a significant effect on the RNA levels of IPW, SNORD115, and SNORD109A/B but not in a dose dependent manner. In contrast, Topotecan had a significant effect on SNORD116, IPW, SNORD115, and SNORD109A/B RNA levels that was dose dependent (Table 10 and FIGS. 4B-4E). Both ASO-4 and Topotecan increased total UBE3A RNA levels in a dose-dependent manner, except for Topotecan at higher concentrations (3 μM, 10 μM, and 30 μM; FIG. 4F).

Figures 4G, 4H, 4I:
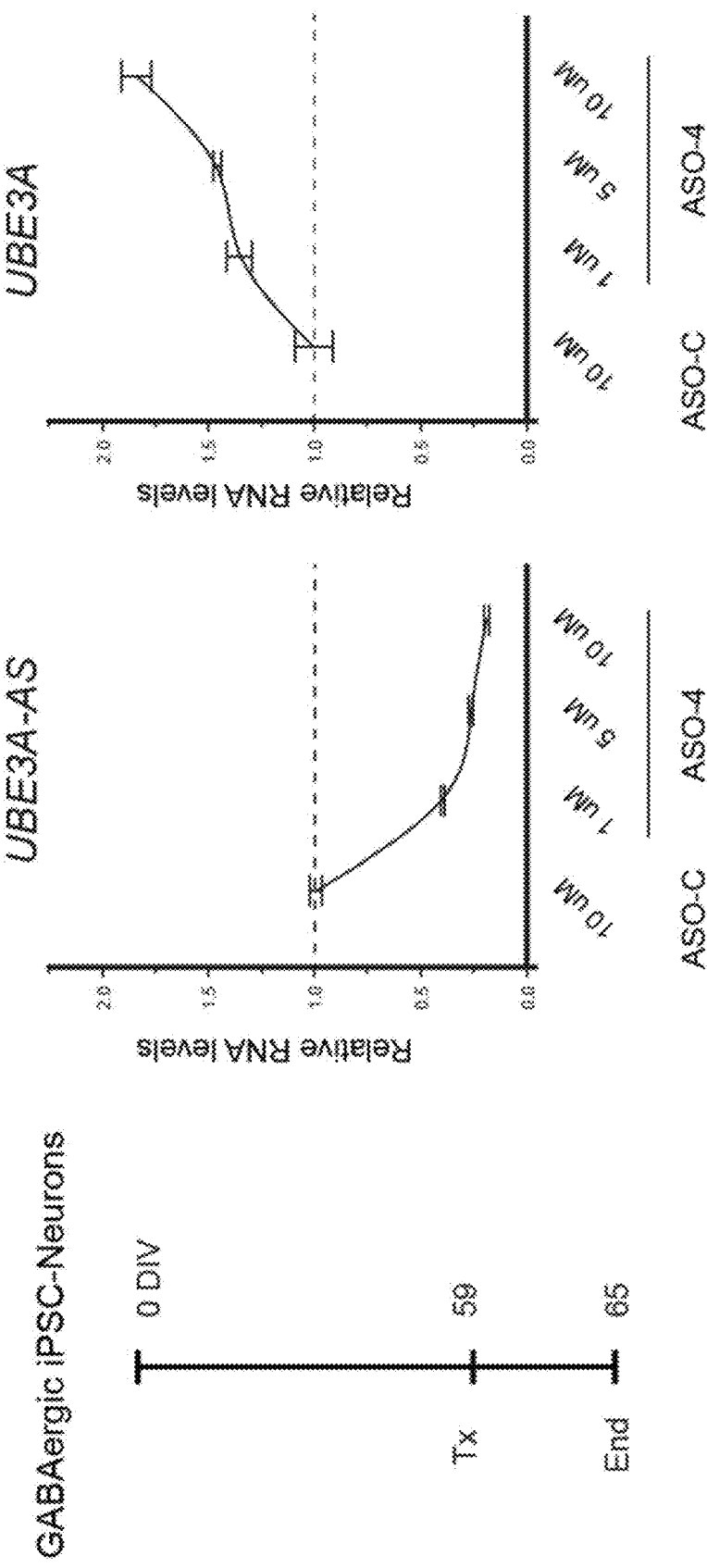

The potency of ASO-4 was further examined in iPSC-derived neurons at a later time point in differentiation. GABAergic iPSC-derived neurons were treated at 59 DIV with a control ASO [ASO-C, 10 μM (n=3)] and ASO-4 [1 uM, 5 μM, and 10 μM (n=3)], and the steady state RNA levels of UBE3A-AS and UBE3A were measured as described above (FIG. 4G). Unlike neurons treated with ASO-4 at an earlier time point, the RNA levels of UBE3A and UBE3A-AS were highly inversely correlated (FIGS. 4H and 4I). For example, the effect of ASO-4 (10 μM) on UBE3A-AS RNA levels was similar between neurons treated at 14 and 59 DIV [20 DIV: UBE3A-AS: ↓87% (95% confidence intervals (CI): 80 to 95%); 65 DIV: ↑81% (95% CI: 74 to 88%)], whereas the effect of ASO-4 on UBE3A RNA levels was substantially larger in neurons treated at 59 DIV [20 DIV: ↑30% (95% CI: 16 to 44%); 65 DIV: ↑86% (95% CI: 59% to 113%)].

Figure 5A:
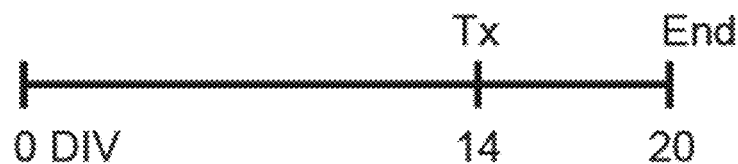
FIGS. 5A to 5F shows analysis of optimized ASOs in human GABAergic and glutamatergic iPSC-derived neurons.
Figure 5B:
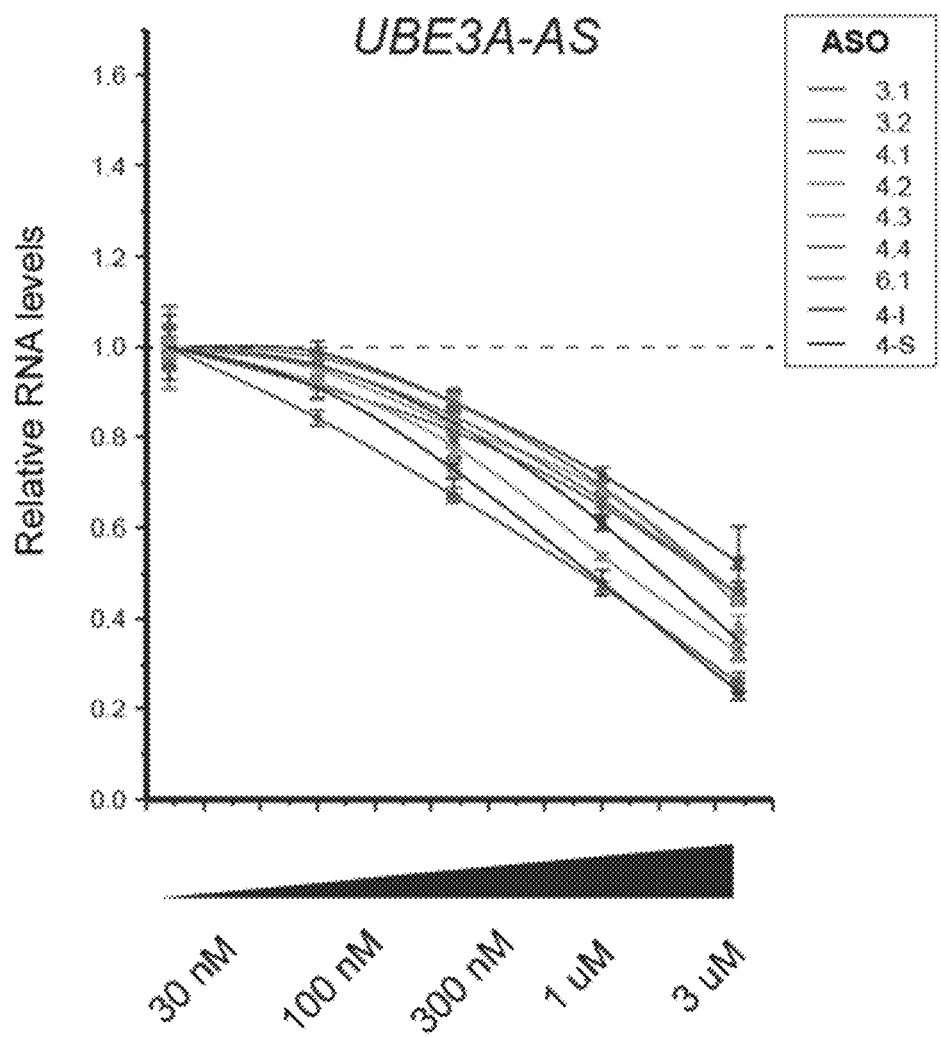
Figure 5C:

Additional ASOs targeting the 5'-end of UBE3A-AS were then designed to optimize the target sequences of ASO-4 (ASO-4.1, ASO-4.2, ASO-4.3, and ASO-4.4) as well as two other target regions, ASO-3 (ASO-3.1 and ASO-3.2) and ASO-6 (ASO-6.1) (Table 11). Additionally, ASO-4 was manufactured at two different vendors for comparative purposes (ASO-4.S, Sigma; ASO-4.1, Integrated DNA Technologies). Human iPSC-derived neurons (GABAergic) were treated at 14 DIV with a 5-point ½ log dose curve of ASO-3.1, ASO-3.2, ASO-4.S, ASO-4.1, ASO-4.1, ASO-4.2, ASO-4.3, ASO-4.4, and ASO-6.1 [30 nM, 100 nM, 300 nM, 1 μM (n=6)]. At 20 DIV, the IC$_{50}$ and E$_{max}$ of each ASO was estimated as described above (FIG. 5A-B and Table 12). The dose response curves were similar among ASOs (Parallelism test: $F_{(16,513)}$=1.6, p=0.06), with ASO-4 and ASO-6.1 having the highest relative potency (Table 13). No significant difference was observed between ASO-4.S and ASO-4.1.

Figure 5D:
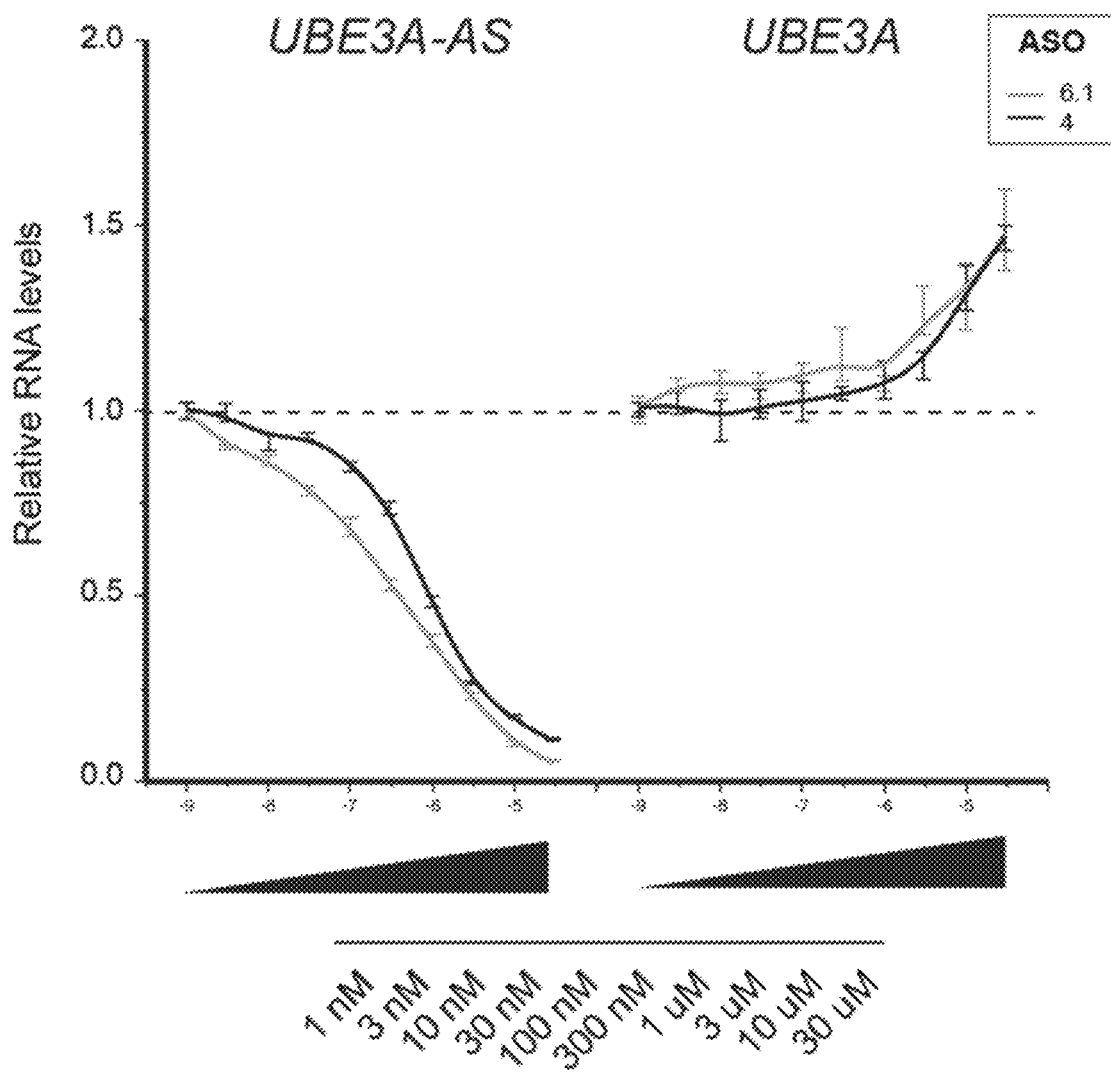
Figure 5E:
Figure 5F:
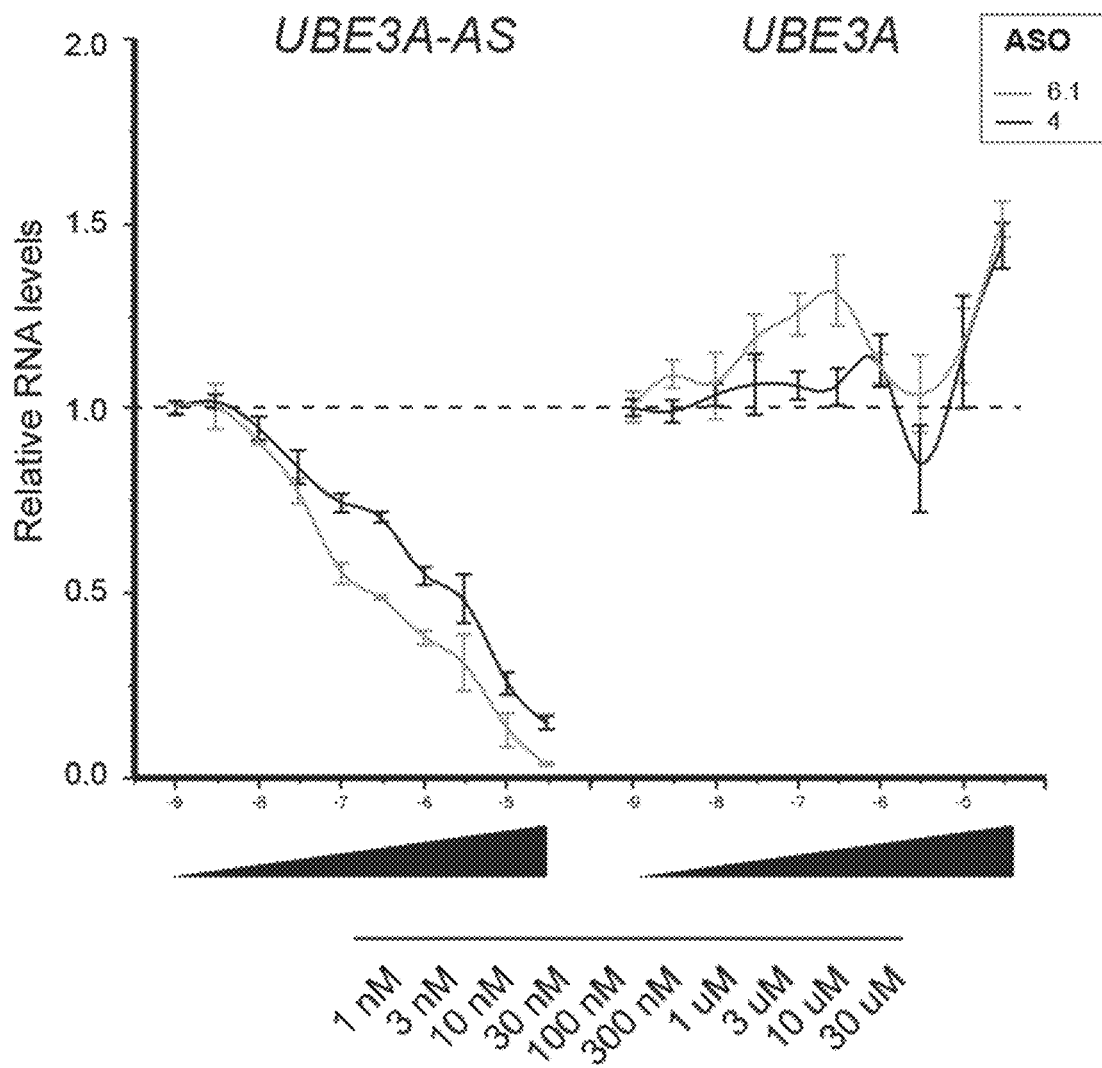
Figure 6A:
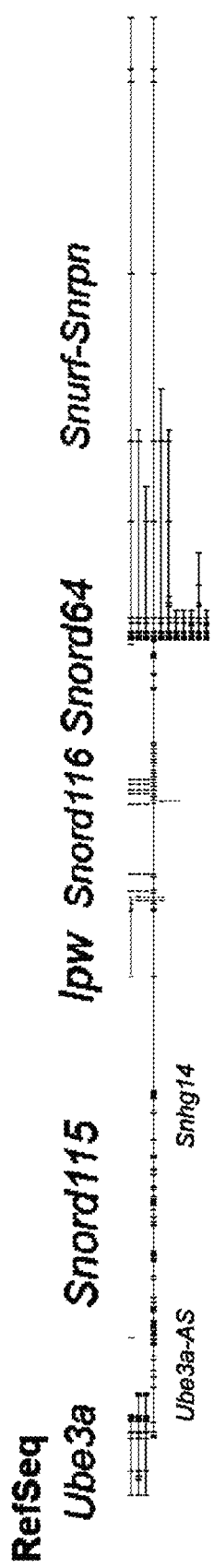
Figure 6D:
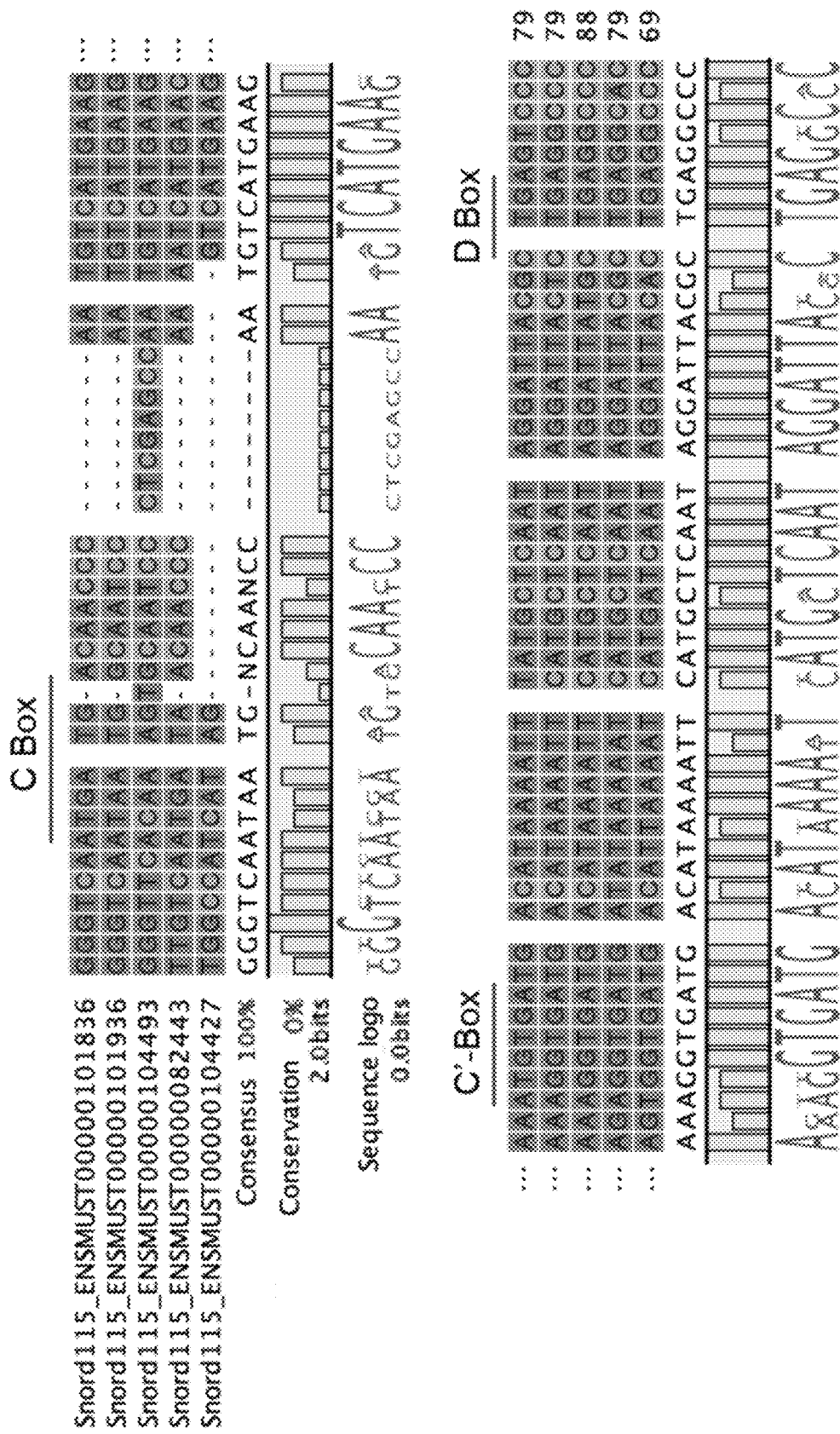
Figure 7A:
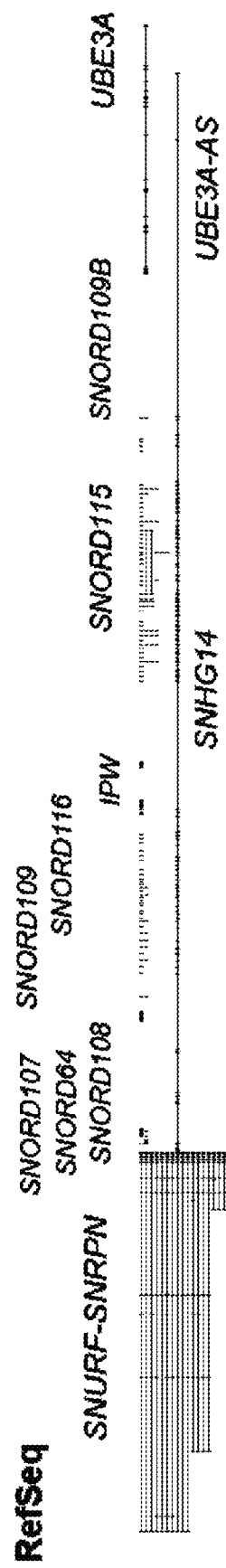
Figure 7B:
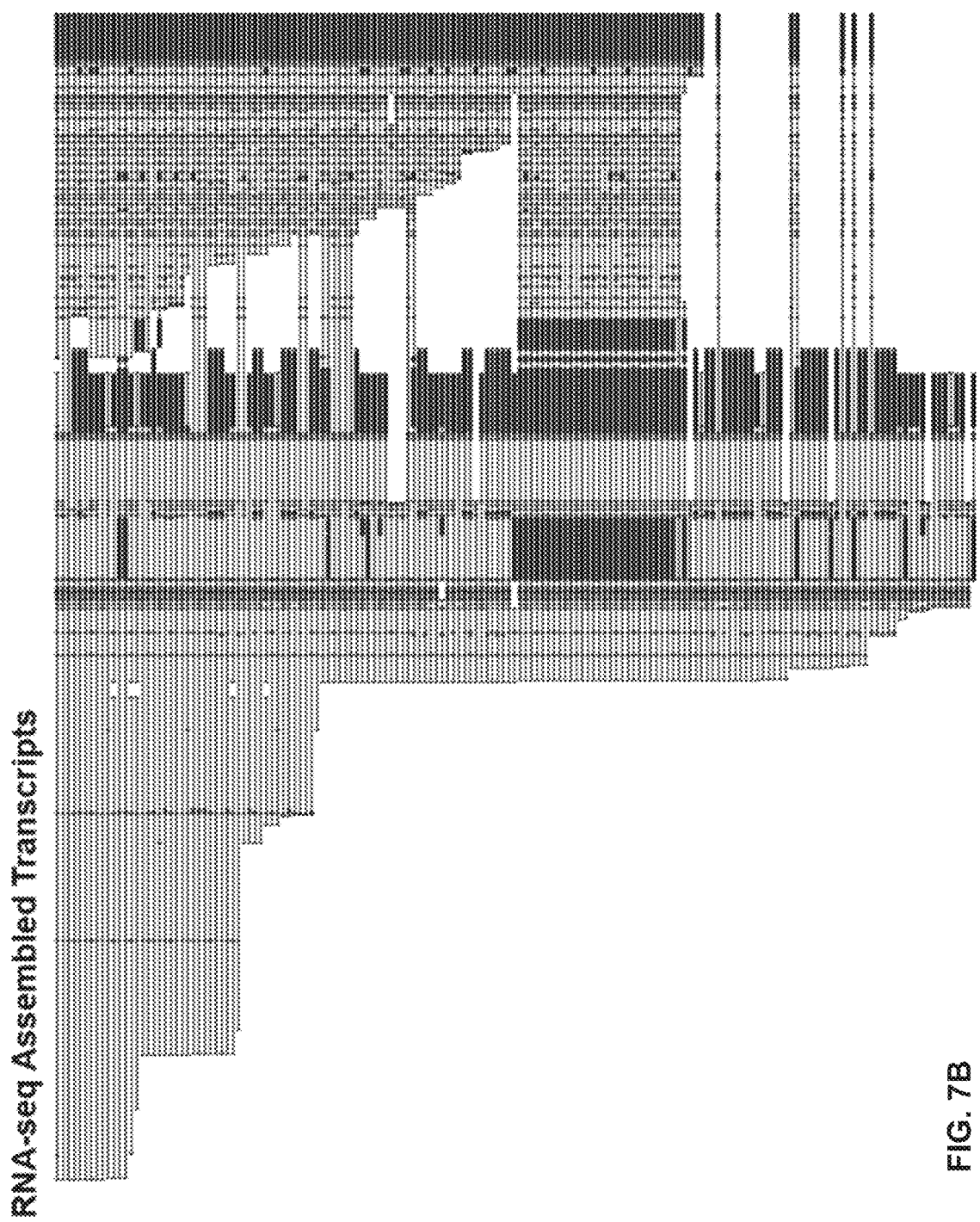
Figure 7C:
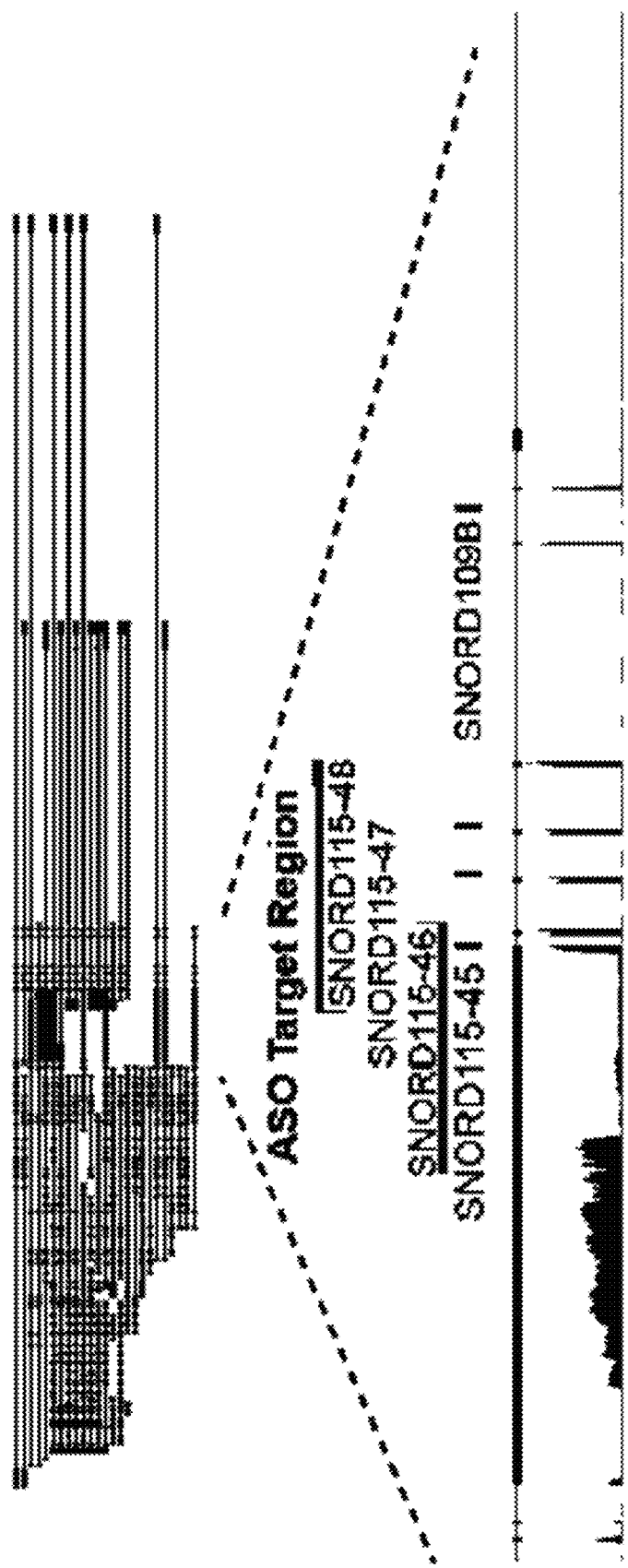
Figure 7G:
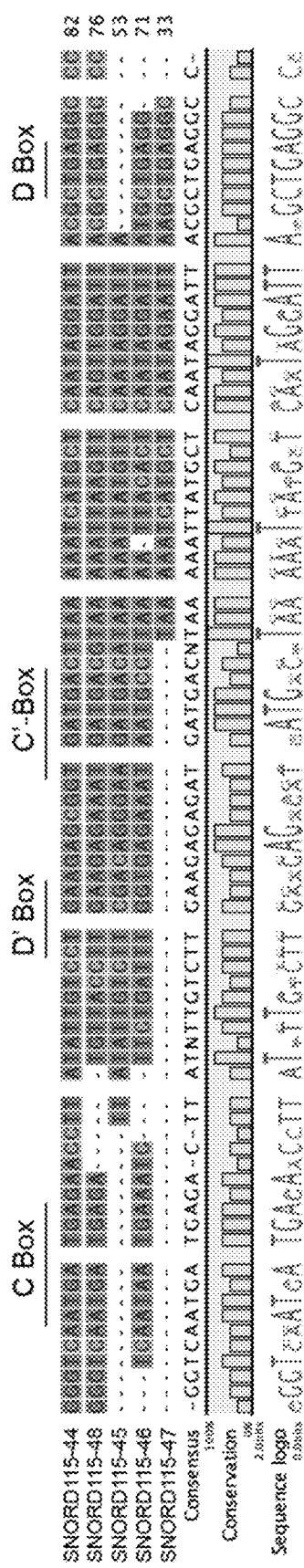

The potency of ASO-4 and ASO-6.1 was further examined in iPSC-derived neurons at a later time point in differentiation. GABAergic iPSC-derived neurons were treated at 29 DIV with a 10-point ½ log dose response curve of ASO-4 and ASO-6.1 [1 nM, 3 nM, 10 nM, 30 nM, 100 nM, 300 nM, 1 μM, 3 μM, 10 μM, and 30 μM (n=3)]. At 35 DIV, the IC$_{50}$ and E$_{max}$ of each ASO was estimated as described above (FIG. 5 C-D and Table 14). The dose response curves of ASO-4 and ASO-6.1 were not similar (Parallelism test: $F_{(3,172)}$=22.7, p<0.0001). An equivalence test indicated that ASO-4 and ASO-6.1 had equivalent potencies but different E$_{max}$ values [ASO-6.1/ASO-4 ratio: IC$_{50}$=1.03 (Lower confidence limit=1.0; Upper confidence limit=1.1); E$_{max}$=-1.3 (Lower confidence limit=-2.6; Upper confidence limit=-0.08)], with ASO-6.1 having the largest inhibition of UBE3A-AS levels. The effect of ASO-4 and ASO-6.1 on UBE3A RNA levels was similar, with each treatment increasing RNA levels in dose dependent manner (FIG. 5D).

ASO-4 and ASO-6.1 were also examined in glutamatergic iPSC-derived neurons. Glutamatergic iPSC-derived neurons were treated at 14 DIV with a 10-point % log dose response curve of ASO-4 and ASO-6.1 [1 nM, 3 nM, 10 nM, 30 nM, 100 nM, 300 nM, 1 μM, 3 μM, 10 μM, and 30 μM (n=3)]. At 20 DIV, the IC$_{50}$ and E$_{max}$ of each ASO was estimated as described above (FIG. 5E-F and Table 15). The dose response curves of ASO-4 and ASO-6.1 were similar and not significantly different (Parallelism test: $F_{(3,165)}$=1.9, p=0.1), with ASO-6.1 having the highest relative potency (Table 16). As expected, ASO-4 and ASO-6.1 increased UBE3A RNA levels in a dose dependent manner (FIG. 5F); however, there was a high degree of variation for each concentration that was not attributable to treatment ($R^2$=0.17).

CONCLUSIONS

Towards developing a therapy for AS, experiments were conducted to determine whether ASOs targeting a specific region inhibit Ube3a-AS/UBE3A-AS and reactivate expression of the paternal Ube3a/UBE3A allele in mouse and human neurons. Altogether, findings show that ASOs targeting this region in mouse and human neurons have potent antisense activity and reverse imprinting of Ube3a/UBE3A.

Two of the three ASOs (ASO-1.1 and ASO-3.1) targeting Ube3a-AS reactivated expression of the paternal Ube3a allele in mouse neurons to a level similar to that achieved by the optimal concentration of Topotecan (300 nM).

Likewise, each of the human-specific ASOs significantly reduced the steady state RNA levels of UBE3A-AS in human iPSC-derived neurons, with higher concentrations of ASO-4 and ASO-6.1 almost completely abolishing expression of UBE3A-AS. Given that ASO-4 and ASO-6.1 target regions that are 100% conserved between human and macaque, the efficacy of these ASOs can be examined in vivo in either Cynomolgus or Rhesus macaque. Unlike Topotecan, ASO-4 has a small, if any, effect on the upstream SNORD116, IPW, SNORD115, or SNORD109A/B RNAs, consistent with the notion that the ASO terminates transcription at or downstream of the target region.

Low concentrations (3 nM) of ASO-4 and ASO-6.1 significantly reduced UBE3A-AS RNA levels; however, higher concentrations (>100 nM) of ASO were necessary to increase UBE3A RNA levels. This may reflect a certain threshold required for UBE3A-AS to inhibit transcription of UBE3A, or a lag between the time that inactivation of UBE3A-AS leads to reactivation of paternal UBE3A, or the sensitivity of the assay used to quantify UBE3A RNA levels.

Collectively, findings suggest that ASOs targeting a candidate region in UBE3A-AS almost completely abolishes imprinting of UBE3A in neurons and reveals at least two ASOs for future clinical development.

Derivatives of ASO-4 and ASO-6.1 that are comprised of different RNA modifications [2'-hydroxymethyl (2'-OMe), 2'-methoxy-ethyl 2'-MOE, and locked nucleic acid (LNA)] and backbones [phosphorothioate (PS) and phosphodiester (PO)] have also been designed (Table 17).

TABLE 6

Mouse Ube3a-AS Oligonucleotides

| ASO | RNA Modification | RNA Backbone | DNA Backbone | Design (5'-3') | Sequence | SEQ ID |
|---|---|---|---|---|---|---|
| ASO-B | 2'-OMe | PS | PS | 5-10-5 | $C^O*C^O*A^O*G^O*C^O*c*t*t*g*t*t*g*g*a*t*A^O*U^O*C^O*A^O*U^O$ | SEQ ID NO: 358 |
| ASO-1.1 | 2'-OMe | PS | PS | 5-10-5 | $C^O*C^O*A^O*C^O*A^O*t*t*t*c*c*t*c*t*c*a*U^O*G^O*G^O*A^O*A^O$ | SEQ ID NO: 359 |
| ASO-1.2 | 2'-OMe | PS | PS | 5-10-5 | $G^O*A^O*G^O*U^O*G^O*t*t*t*g*c*a*a*a*c*c*A^O*A^O*U^O*G^O*U^O$ | SEQ ID NO: 360 |
| ASO-3.1 | 2'-OMe | PS | PS | 5-10-5 | $U^O*G^O*U^O*U^O*U^O*c*t*t*t*g*t*g*a*t*U^O*C^O*U^O*G^O*C^O$ | SEQ ID NO: 361 |

Capital letter, RNA;
lower-case letter, DNA;
$^O$, 2'-OMe;
PS & *, phosphorothioate

TABLE 7

Human UBE3A-AS Oligonucleotides

| ASO | RNA Modification | RNA Backbone | DNA Backbone | Design (5'-3') | Sequence | SEQ ID |
|---|---|---|---|---|---|---|
| ASO-1 | 2'-OMe | PS | PS | 5-10-5 | $U^O*A^O*G^O*A^O*G^O*g*t*g*a*a*g*g*c*c*a*G^O*G^O*C^O*A^O*C^O$ | SEQ ID NO: 362 |
| ASO-2 | 2'-OMe | PS | PS | 5-10-5 | $G^O*U^O*A^O*C^O*U^O*c*t*t*t*c*c*t*c*a*g*t*C^O*A^O*U^O*C^O*C^O$ | SEQ ID NO: 363 |
| ASO-3$^C$ | 2'-OMe | PS | PS | 5-10-5 | $U^O*G^O*U^O*C^O*A^O*g*t*t*t*c*t*c*c*t*G^O*A^O*A^O*C^O*A^O$ | SEQ ID NO: 364 |
| ASO-4$^C$ | 2'-OMe | PS | PS | 5-10-5 | $U^O*A^O*G^O*A^O*A^O*t*g*g*c*a*c*a*t*c*t*C^O*U^O*U^O*G^O*G^O$ | SEQ ID NO: 365 |
| ASO-5$^C$ | 2'-OMe | PS | PS | 5-10-5 | $G^O*U^O*U^O*U^O*U^O*c*t*t*c*c*t*c*c*a*c*A^O*G^O*U^O*C^O*U^O$ | SEQ ID NO: 366 |
| ASO-6$^C$ | 2'-OMe | PS | PS | 5-10-5 | $C^O*U^O*G^O*G^O*U^O*g*t*c*a*a*c*a*a*g*c*C^O*A^O*A^O*A^O*G^O$ | SEQ ID NO: 367 |

Abbreviations:
$^C$, conserved with macaque & non-polymorphic;
capital letter, RNA nucleotide;
lower-case letter, DNA nucleotide;
$^O$, 2'-OMe;
PS & *, phosphorothioate

TABLE 8

Analysis of Human ASOs on UBE3A-AS and UBE3A RNA levels

| ASO 1 | ASO 2 | Difference | Lower CI | Upper CI | Adj. P |
|---|---|---|---|---|---|
| UBE3A-AS | | | | | |
| ASO-C | ASO-2 | 0.89 | 0.82 | 0.97 | <.0001 |
| ASO-R | ASO-2 | 0.87 | 0.80 | 0.95 | <.0001 |
| ASO-C | ASO-4 | 0.87 | 0.80 | 0.95 | <.0001 |
| ASO-R | ASO-4 | 0.85 | 0.78 | 0.93 | <.0001 |
| ASO-C | ASO-6 | 0.83 | 0.75 | 0.90 | <.0001 |
| ASO-R | ASO-6 | 0.81 | 0.74 | 0.89 | <.0001 |
| ASO-C | ASO-3 | 0.79 | 0.71 | 0.86 | <.0001 |
| ASO-R | ASO-3 | 0.77 | 0.70 | 0.85 | <.0001 |
| ASO-C | ASO-5 | 0.71 | 0.63 | 0.78 | <.0001 |
| ASO-R | ASO-5 | 0.69 | 0.62 | 0.77 | <.0001 |
| ASO-C | Topo | 0.66 | 0.59 | 0.73 | <.0001 |
| ASO-R | Topo | 0.64 | 0.57 | 0.72 | <.0001 |
| ASO-C | ASO-1 | 0.51 | 0.43 | 0.58 | <.0001 |
| ASO-R | ASO-1 | 0.49 | 0.41 | 0.56 | <.0001 |
| ASO-1 | ASO-2 | 0.38 | 0.31 | 0.46 | <.0001 |
| ASO-1 | ASO-4 | 0.36 | 0.29 | 0.44 | <.0001 |
| ASO-1 | ASO-6 | 0.32 | 0.25 | 0.40 | <.0001 |
| ASO-1 | ASO-3 | 0.28 | 0.21 | 0.36 | <.0001 |
| Topo | ASO-2 | 0.23 | 0.16 | 0.31 | <.0001 |
| Topo | ASO-4 | 0.21 | 0.14 | 0.29 | <.0001 |
| ASO-1 | ASO-5 | 0.20 | 0.13 | 0.28 | <.0001 |
| ASO-5 | ASO-2 | 0.18 | 0.11 | 0.26 | <.0001 |
| Topo | ASO-6 | 0.17 | 0.10 | 0.24 | 0.0002 |
| ASO-5 | ASO-4 | 0.16 | 0.09 | 0.24 | 0.0003 |

TABLE 8-continued

Analysis of Human ASOs on UBE3A-AS and UBE3A RNA levels

| ASO 1 | ASO 2 | Difference | Lower CI | Upper CI | Adj. P |
|---|---|---|---|---|---|
| ASO-1 | Topo | 0.15 | 0.08 | 0.23 | 0.0004 |
| Topo | ASO-3 | 0.13 | 0.06 | 0.20 | 0.0018 |
| ASO-5 | ASO-6 | 0.12 | 0.04 | 0.20 | 0.0035 |
| ASO-3 | ASO-2 | 0.10 | 0.03 | 0.18 | 0.0111 |
| ASO-3 | ASO-4 | 0.08 | 0.01 | 0.16 | 0.0360 |
| ASO-5 | ASO-3 | 0.08 | 0.00 | 0.15 | 0.0381 |
| ASO-6 | ASO-2 | 0.06 | −0.01 | 0.14 | 0.11 |
| Topo | ASO-5 | 0.05 | −0.02 | 0.13 | 0.18 |
| ASO-6 | ASO-4 | 0.04 | −0.03 | 0.12 | 0.27 |
| ASO-3 | ASO-6 | 0.04 | −0.03 | 0.12 | 0.28 |
| ASO-4 | ASO-2 | 0.02 | −0.06 | 0.09 | 0.58 |
| ASO-C | ASO-R | 0.02 | −0.06 | 0.09 | 0.64 |
| UBE3A | | | | | |
| ASO-4 | ASO-C | 0.30 | 0.16 | 0.44 | 0.0004 |
| ASO-4 | ASO-R | 0.29 | 0.14 | 0.45 | 0.001 |
| ASO-2 | ASO-C | 0.21 | 0.09 | 0.34 | 0.002 |
| ASO-2 | ASO-R | 0.21 | 0.07 | 0.35 | 0.006 |
| ASO-1 | ASO-C | 0.18 | 0.06 | 0.31 | 0.007 |
| Topo | ASO-C | 0.18 | 0.04 | 0.32 | 0.01 |
| ASO-1 | ASO-R | 0.18 | 0.04 | 0.32 | 0.02 |
| Topo | ASO-R | 0.18 | 0.03 | 0.33 | 0.02 |
| ASO-4 | ASO-3 | 0.17 | 0.03 | 0.31 | 0.02 |
| ASO-5 | ASO-C | 0.16 | 0.04 | 0.29 | 0.01 |
| ASO-6 | ASO-C | 0.16 | 0.04 | 0.29 | 0.01 |
| ASO-5 | ASO-R | 0.16 | 0.02 | 0.30 | 0.03 |
| ASO-6 | ASO-R | 0.16 | 0.02 | 0.30 | 0.03 |
| ASO-4 | ASO-6 | 0.13 | −0.007 | 0.27 | 0.06 |
| ASO-4 | ASO-5 | 0.13 | −0.007 | 0.27 | 0.06 |
| ASO-3 | ASO-C | 0.13 | 0.00 | 0.26 | 0.04 |
| ASO-3 | ASO-R | 0.13 | −0.015 | 0.27 | 0.08 |
| ASO-4 | Topo | 0.11 | −0.04 | 0.27 | 0.1 |
| ASO-4 | ASO-1 | 0.11 | −0.03 | 0.25 | 0.1 |
| ASO-2 | ASO-3 | 0.08 | −0.04 | 0.21 | 0.2 |
| ASO-4 | ASO-2 | 0.08 | −0.06 | 0.22 | 0.2 |
| ASO-1 | ASO-3 | 0.05 | −0.07 | 0.18 | 0.4 |
| Topo | ASO-3 | 0.05 | −0.09 | 0.19 | 0.4 |
| ASO-2 | ASO-6 | 0.05 | −0.08 | 0.18 | 0.4 |
| ASO-2 | ASO-5 | 0.05 | −0.08 | 0.17 | 0.4 |
| ASO-5 | ASO-3 | 0.03 | −0.09 | 0.16 | 0.6 |
| ASO-6 | ASO-3 | 0.03 | −0.09 | 0.16 | 0.6 |
| ASO-2 | Topo | 0.03 | −0.1 | 0.17 | 0.7 |
| ASO-2 | ASO-1 | 0.03 | −0.01 | 0.16 | 0.6 |
| ASO-1 | ASO-6 | 0.02 | −0.1 | 0.15 | 0.7 |
| Topo | ASO-6 | 0.02 | −0.1 | 0.16 | 0.8 |
| ASO-1 | ASO-5 | 0.02 | −0.1 | 0.15 | 0.7 |
| Topo | ASO-5 | 0.02 | −0.1 | 0.16 | 0.8 |
| ASO-R | ASO-C | 0.00 | −0.1 | 0.14 | 0.9 |
| ASO-5 | ASO-6 | 0.00 | −0.1 | 0.13 | 0.9 |
| ASO-1 | Topo | 0.00 | −0.1 | 0.14 | 1.00 |

Abbreviations: ASO-C, ASO-control; Topo, Topotecan; Adj., Adjusted; CI, 95% confidence interval

TABLE 9

$IC_{50}$ and $E_{max}$ of ASO-4 and Topotecan

| Treatment | $IC_{50}$ Estimate (M) | $IC_{50}$ 95% CI (M) | $E_{max}$ Estimate | $E_{max}$ 95% CI | | 30 μM (Mean) |
|---|---|---|---|---|---|---|
| ASO-4 | 6.13E-07 | 3.47E-07  1.08E-06 | −0.06 | −0.23 | 0.10 | 0.09 |
| Topo | 3.37E-08 | 1.85E-08  6.14E-08 | 0.26 | 0.20 | 0.32 | 0.21 |

Full model parameter estimates from 4-parameter logistic regression model (Hill). $IC_{50}$ and confidence intervals represent molar concentration. $E_{max}$ and 30 uM values represent normalized UBE3A-AS RNA levels relative to vehicle.

TABLE 10

Analysis of ASO-4 and Topotecan on UBE3A, SNORD116, SNORD115, SNORD109A/B, and IPW RNA Levels

| Treatment | RNA | DF | DFDen | F Ratio | FDR |
|---|---|---|---|---|---|
| ASO-4 | UBE3A | 9 | 108 | 16.5 | <0.0001 |
| | SNORD109A/B | 9 | 104.9 | 2.6 | 0.01 |
| | SNORD115 | 9 | 108 | 4.0 | 0.0002 |
| | SNORD116 | 9 | 108 | 1.74 | 0.09 |
| | IPW | 9 | 108 | 4.1 | 0.0002 |
| Topotecan | UBE3A | 9 | 29 | 5.6 | 0.0002 |
| | SNORD109A/B | 9 | 29 | 28.2 | <0.0001 |
| | SNORD115 | 9 | 29 | 4.60 | 0.001 |
| | SNORD116 | 9 | 29 | 7.12 | <0.0001 |
| | IPW | 9 | 29 | 49.8 | <0.0001 |

Least squares linear regression.
Abbreviations: DF, degrees of freedom; DFDen, degrees of freedom density

TABLE 11

Optimized Human UBE3A-AS Antisense Oligonucleotides

| ASO | RNA Modification | RNA Backbone | DNA Backbone | Design (5'-3') | Sequence | SEQ ID |
|---|---|---|---|---|---|---|
| ASO-3.1$^C$ | 2'-OMe | PS | PS | 4-10-5 | G$^O$*U$^O$*U$^O$*G$^O$*a*g*t*g*g*t*g*t*c*a*G$^O$*U$^O$*U$^O$*U$^O$*C$^O$ | SEQ ID NO: 368 |
| ASO-3.2$^C$ | 2'-OMe | PS | PS | 4-10-4 | U$^O$*U$^O$*G$^O$*A$^O$*g*t*g*g*t*g*t*c*a*g*U$^O$*U$^O$*U$^O$*C$^O$ | SEQ ID NO: 369 |

TABLE 11-continued

Optimized Human UBE3A-AS Antisense Oligonucleotides

| ASO | RNA Modification | RNA Back-bone | DNA Back-bone | Design (5'-3') | Sequence | SEQ ID |
|---|---|---|---|---|---|---|
| ASO-6.1[C] | 2'-OMe | PS | PS | 4-10-4 | $C^O$*$U^O$*$G^O$*$G^O$*t*g*t*c*a*a*c*a*a*g*$C^O$*$C^O$*$A^O$*$A^O$ | SEQ ID NO: 370 |
| ASO-4.1[C] | 2'-OMe | PS | PS | 5-10-5 | $A^O$*$U^O$*$A^O$*$G^O$*$A^O$*a*t*g*g*c*a*c*a*t*c*$U^O$*$C^O$*$U^O$*$U^O$*$G^O$ | SEQ ID NO: 371 |
| ASO-4.2[C] | 2'-OMe | PS | PS | 4-10-5 | $A^O$*$G^O$*$A^O$*$A^O$*t*g*g*c*a*c*a*t*c*t*$C^O$*$U^O$*$U^O$*$G^O$*$G^O$ | SEQ ID NO: 372 |
| ASO-4.3[C] | 2'-OMe | PS | PS | 4-10-5 | $U^O$*$A^O$*$G^O$*$A^O$*a*t*g*g*c*a*c*a*t*c*$U^O$*$C^O$*$U^O$*$U^O$*$G^O$ | SEQ ID NO: 373 |
| ASO-4.4[C] | 2'-OMe | PS | PS | 4-10-4 | $A^O$*$G^O$*$A^O$*$A^O$*t*g*g*c*a*c*a*t*c*t*$C^O$*$U^O$*$U^O$*$G^O$ | SEQ ID NO: 374 |

[C], conserved with macaque & non-polymorphic;
capital letter, RNA nucleotide;
lower-case letter, DNA nucleotide;
[O], 2'-OMe;
PS & *, phosphorothioate

TABLE 12

$IC_{50}$ and $E_{max}$ of Optimized ASO Target Sequences

| Group | $IC_{50}$ Estimate | $IC_{50}$ 95% CI (M) | | 3 μM (Mean) |
|---|---|---|---|---|
| 6.1 | 5.20E-07 | 3.33E-07 | 8.11E-07 | 0.23 |
| 4.0 | 1.06E-06 | 9.31E-07 | 1.21E-06 | 0.29 |
| 4.2 | 1.08E-06 | 8.62E-07 | 1.35E-06 | 0.31 |
| 3.2 | 1.88E-06 | 1.39E-06 | 2.56E-06 | 0.44 |
| 4.3 | 2.03E-06 | 1.67E-06 | 2.47E-06 | 0.40 |
| 4.4 | 2.11E-06 | 1.73E-06 | 2.59E-06 | 0.44 |
| 4.1 | 2.27E-06 | 1.92E-06 | 2.68E-06 | 0.42 |
| 3.1 | 2.98E-06 | 2.45E-06 | 3.62E-06 | 0.51 |

Full model parameter estimates from 3-parameter logistic regression model. $IC_{50}$ and confidence intervals represent molar concentration. $E_{max}$ (3 uM) values represent normalized UBE3A-AS RNA levels relative to vehicle.

TABLE 13

Relative Potency of Optimized ASOs

| ASO | $IC_{50}$ (M) | Relative Potency | Std. Error |
|---|---|---|---|
| ASO 3.1 | 2.81E-06 | 0.53 | 0.059 |
| ASO 3.2 | 1.85E-06 | 0.81 | 0.086 |
| ASO 4.1 | 2.25E-06 | 0.66 | 0.072 |
| ASO 4.2 | 1.24E-06 | 1.21 | 0.13 |
| ASO 4.3 | 1.96E-06 | 0.76 | 0.081 |
| ASO 4.4 | 2.04E-06 | 0.73 | 0.079 |
| ASO 6.1 | 7.20E-07 | 2.07 | 0.21 |
| ASO 4.1 | 8.28E-07 | 1.80 | 0.19 |
| ASO 4.S | 1.49E-06 | 1 | 0 |

Parallel model parameter estimates from 3-parameter logistic regression model. Potency represents molar concentration.
Abbreviations: M, molar; Std. Error, standard error of mean.

TABLE 14

$IC_{50}$ and $E_{max}$ of ASO-4 and ASO-6.1 in GABAergic iPSC Neurons

| ASO | $IC_{50}$ Estimate | $IC_{50}$ 95% CI (M) | | $E_{max}$ Estimate | $E_{max}$ 95% CI | | 30 μM (Mean) |
|---|---|---|---|---|---|---|---|
| ASO-4 | 7.77E-07 | 6.86E-07 | 8.79E-07 | 0.08 | 0.05 | 0.11 | 0.11 |
| ASO-6.1 | 5.17E-07 | 3.41E-07 | 7.82E-07 | -0.11 | -0.22 | 0.01 | 0.06 |

Full model parameter estimates from 4-parameter logistic regression model (Hill). $IC_{50}$ and confidence intervals represent molar concentration. $E_{max}$ and 30 uM values represent normalized UBE3A-AS RNA levels relative to vehicle.

TABLE 15

$IC_{50}$ and $E_{max}$ of ASO-4 and ASO-6.1 in Glutamatergic iPSC Neurons

| ASO | $IC_{50}$ Estimate | $IC_{50}$ 95% CI (M) | | $E_{max}$ Estimate | $E_{max}$ 95% CI | | 30 μM (Mean) |
|---|---|---|---|---|---|---|---|
| ASO-4 | 1.21E-04 | 1.12E-13 | 1.32E+05 | -1.45 | -9.01 | 6.12 | 0.17 |
| ASO-6.1 | 2.44E-07 | 2.39E-08 | 2.50E-06 | -0.27 | -1.24 | 0.70 | 0.04 |

Full model parameter estimates from 4-parameter logistic regression model (Hill). $IC_{50}$ and conf dence intervals represent molar concentration. $E_{max}$ and 30 uM values represent normalized UBE3A-AS RNA levels relative to vehicle.

TABLE 16

Relative Potency of ASO-4 and ASO-6.1 in Glutamatergic Neurons

| ASO | IC$_{50}$ (M) | Relative Potency | Std. Error |
|---|---|---|---|
| ASO-4 | 3.06E-06 | 1 | 0 |
| ASO-6.1 | 7.8E-07 | 3.89 | 0.72 |

Parallel model parameter estimates from 4 Parameter logistic regression model.
Abbreviations: M, molar

TABLE 17

Derivatives of ASO-4 and ASO-6.1

| ASO | RNA Mod. | Backbone linkages | PO | Design (5'-3') | Sequence (5'-3') | SEQ ID |
|---|---|---|---|---|---|---|
| ASO-4.0.PS.O | OMe | PS | 0 | 5-10-5 | U$^O$*A$^O$*G$^O$*A$^O$*A$^O$*t*g*g*c*a*c*a*t*c*t*C$^O$*U$^O$*U$^O$*G$^O$*G$^O$ | SEQ ID NO: 375 |
| ASO-4.0.PO-1.O | OMe | PS/PO | 2 | 5-10-5 | U$^O$*A$^O$*G$^O$*A$^O$*A$^O$-t*g*g*c*a*c*a*t*c*t-C$^O$*U$^O$*U$^O$*G$^O$*G$^O$ | SEQ ID NO: 376 |
| ASO-4.0.PO-2.O | OMe | PS/PO | 0 | 5-10-5 | U$^O$*A$^O$-G$^O$*A$^O$-A$^O$-g*g-c*a-c*a-t*c-t*C$^O$-U$^O$*U$^O$-G$^O$*G$^O$ | SEQ ID NO: 377 |
| ASO-4.0.PS.M | MOE | PS | 0 | 5-10-5 | T$^M$*A$^M$*G$^M$*A$^M$*A$^M$*t*g*g*c*a*c*a*t*c*t*5mC$^M$*T$^M$*T$^M$*G$^M$*G$^M$ | SEQ ID NO: 378 |
| ASO-4.0.PO-1.M | MOE | PS/PO | 2 | 5-10-5 | T$^M$*A$^M$*G$^M$*A$^M$*A$^M$-t*g*g*c*a*c*a*t*c*t-5mC$^M$*T$^M$*T$^M$*G$^M$*G$^M$ | SEQ ID NO: 379 |
| ASO-4.0.PO-2.M | MOE | PS/PO | 9 | 5-10-5 | T$^M$*A$^M$-G$^M$*A$^M$-A$^M$-t-g*g-c*a-c*a-t*c-t*5mC$^M$-T$^M$*T$^M$-G$^M$*G$^M$ | SEQ ID NO: 380 |
| ASO-4.4.PS.L | LNA | PS | 0 | 3-11-4 | A$^L$*G$^L$*A$^L$*a*t*g*g*c*a*c*a*t*c*t*5mC$^L$*T$^L$*T$^L$*G$^L$ | SEQ ID NO: 381 |
| ASO-4.4.PO-1.L | LNA | PS/PO | 2 | 3-11-4 | A$^L$*G$^L$*A$^L$a*t*g*g*c*a*c*a*t*c*t-5mC$^L$*T$^L$*T$^L$*G$^L$ | SEQ ID NO: 382 |
| ASO-4.4.PO-2.L | LNA | PS/PO | 8 | 3-11-4 | A$^L$*G$^L$-A$^L$*a-t*g-g*c-a*c-a*t-c*t-5mC$^L$*T$^L$-T$^L$*G$^L$ | SEQ ID NO: 383 |
| ASO-6.1.PS.O | OMe | PS | 0 | 4-10-4 | C$^O$*U$^O$*G$^O$*G$^O$*t*g*t*c*a*a*c*a*a*g*C$^O$*C$^O$*A$^O$*A$^O$ | SEQ ID NO: 384 |
| ASO-6.1.PO-1.O | OMe | PS/PO | 2 | 4-10-4 | C$^O$*U$^O$*G$^O$*G$^O$*t*g*t*c*a*a*c*a*a*g-C$^O$*C$^O$*A$^O$*A$^O$ | SEQ ID NO: 385 |
| ASO-6.1.PO-2.O | OMe | PS/PO | 8 | 4-10-4 | C$^O$*U$^O$-G$^O$*G$^O$-t*g-t*c-a*a-c*a-a*g-C$^O$*C$^O$-A$^O$*A$^O$ | SEQ ID NO: 386 |
| ASO-6.1.PS.M | MOE | PS | 0 | 4-10-4 | 5mC$^M$*T$^M$*G$^M$*G$^M$*t*g*t*c*a*a*c*a*a*g*5mC$^M$*5mC$^M$*A$^M$*A$^M$ | SEQ ID NO: 387 |
| ASO-6.1.PO-1.M | MOE | PS/PO | 2 | 4-10-4 | 5mC$^M$*T$^M$*G$^M$*G$^M$-t*g*t*c*a*a*c*a*a*g-5mC$^M$*5mC$^M$*A$^M$*A$^M$ | SEQ ID NO: 388 |
| ASO-6.1.PO-2.M | MOE | PS/PO | 8 | 4-10-4 | 5mC$^M$*T$^M$-G$^M$*G$^M$-t*g-t*c-a*a-c*a-a*g-5mC$^M$*5mC$^M$-A$^M$*A$^M$ | SEQ ID NO: 389 |
| ASO-6.1.PS.L | LNA | PS | 0 | 3-10-4 | T$^L$*G$^L$*G$^L$*t*g*t*c*a*a*c*a*a*g*5mC$^L$*5mC$^L$*A$^L$*A$^L$ | SEQ ID NO: 390 |
| ASO-6.1.PO-1.L | LNA | PS/PO | 2 | 3-10-4 | T$^L$*G$^L$*G$^L$-t*g*t*c*a*a*c*a*a*g-5mC$^L$*5mC$^L$*A$^L$*A$^L$ | SEQ ID NO: 391 |
| ASO-6.1.PO-2.L | LNA | PS/PO | 8 | 3-10-4 | T$^L$*G$^L$-G$^L$*t-g*t-c*a-a*c-a*a-g*5mC$^L$-5mC$^L$-A$^L$*A$^L$ | SEQ ID NO: 392 |

Capital letter, RNA;
lower-case letter, DNA.
5mC, 5-methylcytosine.
Superscript:
$^O$, 2'-OMe;
$^M$, 2'-MOE;
$^L$, LNA.
PS & *, phosphorothioate;
PO & -, phosphodiester?

Materials and Methods

Antisense Oligonucleotide Design

Antisense oligonucleotides (ASOs) were designed using Soligo (Software for Statistical Folding of Nucleic Acids and Studies of Regulatory RNAs). Briefly, candidate ASOs (20-18mer) with the lowest binding site disruption energy and free binding energy were identified for each target sequence and then inspected for motifs with increased effectiveness. ASOs were further filtered based on accessibility within predicted lowest free energy centroid secondary structure of target sequence generated by Soligo. In some instances, secondary structure models were compared using lowest free energy structures generated by RNAfold and Mfold.

Human ASOs were filtered using the following criteria: 1) target sequence was polymorphic[dbSNP138, dbSNP150, and 1000 Genomes Phase 3 Integrated Variant Calls (SNV, INDEL, and SV)]; 2) target sequence was not 100% conserved with Rhesus and Cynomolgus macaque; 3) target sequence was located upstream of retained Snord115/SNORD115 snoRNA (per exon). Remaining ASOs were then ranked by free energy (<=-8 kcal/mol), average unpaired probability for target site nucleotides, binding site disruption energy (low>high), location within secondary structure (Ensembl Centroid), and presence/absence of sequence motifs associated with high/low effectiveness.

Mouse primary hippocampal neurons Primary cultures of hippocampal neurons were generated from P0-P1 pups (Ube3a$^{m+/p+}$ and Ube3a$^{m+/pYFP}$) by crossing Ube3a$^{m+/pYFP}$ males with wild-type C57BL/6J females. Genotypes were determined using methods described previously. Briefly, hippocampal neurons were cultured in Neurobasal A medium (Invitrogen, San Diego, Calif.) supplemented with B27 (Invitrogen) and penicillin/streptomycin (Invitrogen) on 96-well optical bottom plates coated with poly-D-Lysine (152028, Thermo Fisher Scientific) and laminin (23017-01, Thermo Fisher Scientific). Cultures were maintained at 37° C. in 5% $CO_2$ until use.

Mouse Neuron Imaging

Mouse primary hippocampal neurons were fixed at 10 DIV (3 days post treatment) with 4% paraformaldehyde. The cultures were then washed twice with 1×PBS, fixed in 4% paraformaldehyde in PBS for 15 min, and then washed three times in 1×PBS. The cells were blocked in 0.3% Triton-X100 in PBS (T-PBS) plus 5% goat or donkey serum for 1-2 hr at room temperature with gentle agitation. Cells were incubated with anti-GFP [Novus Biologicals, NB 600-308 (rabbit)] and anti-NeuN (Millipore, 05-557 (mouse)] antibodies for 24 hr at 4° C. with gentle agitation. Cells were washed 3 times in 0.1% Tween 20 1×PBS for 15 min each and then incubated with anti-rabbit 488 (Jackson ImmunoResearch, 111-545-144) and anti-mouse Cy3 (Jackson ImmunoResearch, 115-165-166) secondary antibodies for 24 hr at 4° C. in the dark. Cells were then washed 4 times in 0.1% Tween 20 1×PBS for 15 min each. Nuclei were labeled using Hoechst stain (Thermo Fisher Scientific) at a dilution of 1:1000 in the third wash.

Plates were imaged using the Cytation 5 and Gen5 Image+software (BioTek, Winooski, Vt.). Briefly, a 4×inverted objective was used to generate montage images of each well by acquiring 5×4 autofocused images with overlapping tiles for automatic image stitching. The filters used were DAPI (377,477), GFP (469, 525), and RFP (531, 593). Exposure time and gain were adjusted for each plate using the negative and positive controls. Auto-focus was performed on nuclei (Hoechst stain, DAPI) for each well, with the same focal height used for the GFP and RFP filters. Images were stitched together by Gen5 Image+software.

Single cell image analysis was performed using IN Cell Developer 6.0 (GE Healthcare Life Sciences, Pittsburgh, Pa.). Briefly, individual track masks were generated for either nuclei (Hoechst stain, DAPI) or mature neurons (NeuN, RFP) by optimizing inclusion and exclusion parameters based on size and intensity of randomly selected cells in the acquired images. The mean and median intensity values of GFP were then acquired within the boundaries of the selected mask, generating intensity values for Ube3aYFP within each cell.

Human Induced Pluripotent Stem Cell Derived Neurons

GABAergic and glutamatergic induced pluripotent stem cell (iPSC) derived neural precursor cells (NRC-100-010-001 and GNC-301-030-001, Cellular Dynamics International, Madison Wis.) were differentiated into neurons according to the manufactures protocol. Briefly, neural precursor cells were thawed and resuspended in chemically defined medium and added to sterile-culture plates coated with poly-D-lysine and laminin. The medium was replaced 24 hr after plating and then one-half of the medium was replaced every 3-5 days afterwards.

RNA Isolation

For cultured iPSC-derived neurons, RNA isolation and cDNA synthesis were performed using the Cell-to-CT kit (Thermo Fisher Scientific) in a lysate volume of 55 µl.

Analysis of RNA levels

The steady state RNA levels of target transcripts were measured using TaqMan quantitative reverse-transcription PCR (qRT-PCR) assays. Total reaction volume was 10 uL, including 2 µl of cDNA, 1×Gene Expression Master mix (4369016, Thermo Fisher Scientific, Waltham, Mass.), and 1×TaqMan primer assay (Thermo Fisher Scientific). Cycling conditions were 2 minutes at 50° C., 10 minutes at 95° C., and 40 cycles of 15 seconds at 95° C. and 1 minute at 60° C., with readings taken at the 60° C. step of every cycle. Reactions were run on a BIO-RAD T1000 CFX96 thermocycler (Bio-Rad Laboratories, Hercules Calif.), with internal control (PP/A, Hs99999904_m1, Thermo Fisher Scientific) and target[UBE3A-AS, Hs01372957_m1; SNORD116-11, Hs04275268_gH; SNORD115, Hs04275288_gH; IPW, Hs03455409_s1; SNORD109A/B, AP47WVR (Thermo Fisher Scientific); UBE3A: forward ATATGTGGAAGCCG-GAATCT (SEQ ID NO:500); reverse: CCCAGAACTCCCTAATCAGAA (SEQ ID NO:501); and, probe: ATGACGGTGGCTATACCAGG (SEQ ID NO:502)] reactions performed together. Data was retrieved and analyzed with the BIORAD CFX Maestro software (Bio-Rad Laboratories). Samples with internal control Cq values≥30 were filtered. Quality of data was visually inspected to identify discrepancies between technical and/or plate replicates. Measurements for inferential statistics and descriptive statistics consist of ΔΔCq values ($2^{-\Delta\Delta Cq} = 2^{-(Cq[target]-Cq[internal\ control])-(Cq[target]-Cq[internal\ control])}$).

Example 2: Identification of ASO Target Region

Analysis of RNA-sequencing data generated from mouse tissues and cells revealed a region located between the 3'-end of the Snord115 cluster and 5'-end of the Ube3a antisense (Ube3a-AS) transcript containing genetic elements believed to be important for processing of the Snord115 host-gene transcript and transcription of Ube3a-AS (FIGS. 6A-6D). Analysis of RNA-sequencing data generated from human tissues revealed a region located between the 3'-end of the SNORD115 cluster and SNORD109B (FIGS. 7A-7G)

that contained elements similar to those observed in mouse; however, comparative analysis of this region indicated that there was little to no sequence conservation between human and rodents.

Materials and Methods

RNA-Sequencing

RNA was isolated using Qiagen RNAeasy Plus (74136, Qiagen, Hilden, Germany). RNA concentration was determined using Qubit Fluorometric Quantitation (Thermo Fisher Scientific) and RNA quality was assessed using a 4200 Agilent TapeStation (Agilent, Santa Clara, Calif.). RNA-sequencing libraries were generated using the Illumina TruSeq Stranded Total RNA kit (20020597, Illumina, Inc., San Diego, Calif.) according to the manufacturer's protocol. 75 base-pair paired-end sequencing was performed using a NextSeq 500 (Illumina, San Diego, Calif.) at the Texas A&M Institute for Genome Sciences and Society Genomics core. Raw sequencing reads were processed using CASAVA. The resulting FASTQ sequences were examined using FASTQC.

FASTQ sequences were aligned to the human reference assembly (hg19) using Hisat2 (version 2.1.0), with the following settings: —fr. Aligned SAM sequences were then converted to binary BAM sequences, indexed, and sorted using Samtools. BAM files from individual samples were merged and indexed using Samtools. Aligned sequences were filtered using the view command in Samtools to remove non-uniquely aligned reads (quality>1).

A transcript assembly was generated for merged samples using Stringtie (version 1.3.4.d), with the following options: (stranded)—rf -f 0 -j 2. Single exon transcripts were excluded from the assembled transcripts using gffread (GFF utilities, Johns Hopkins University, Center for Computational Biology).

Example 3: Identification of Lead ASOs

Figure 8A:
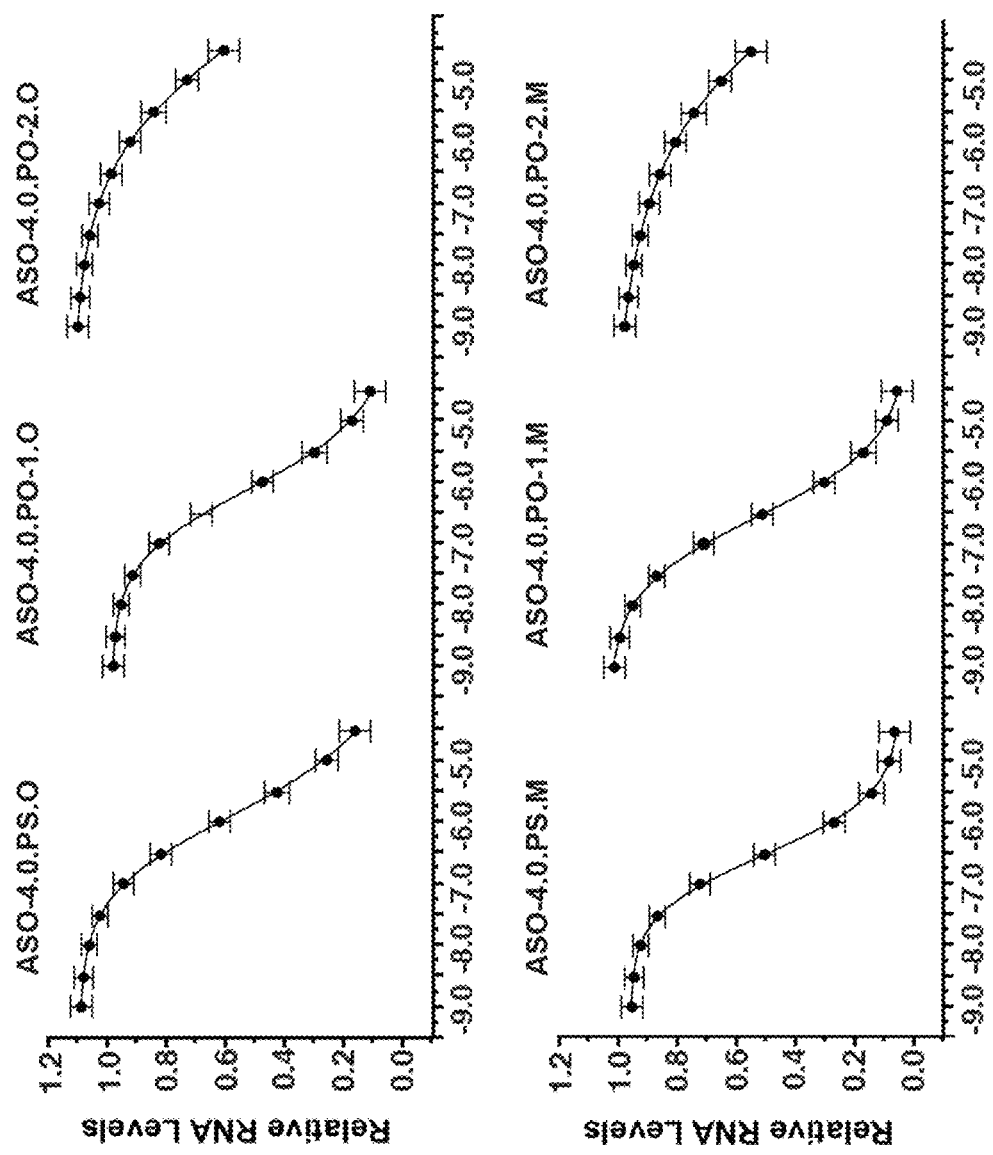
FIGS. 8A to 8C show pharmacodynamic analysis of candidate ASOs.
Figure 8B:
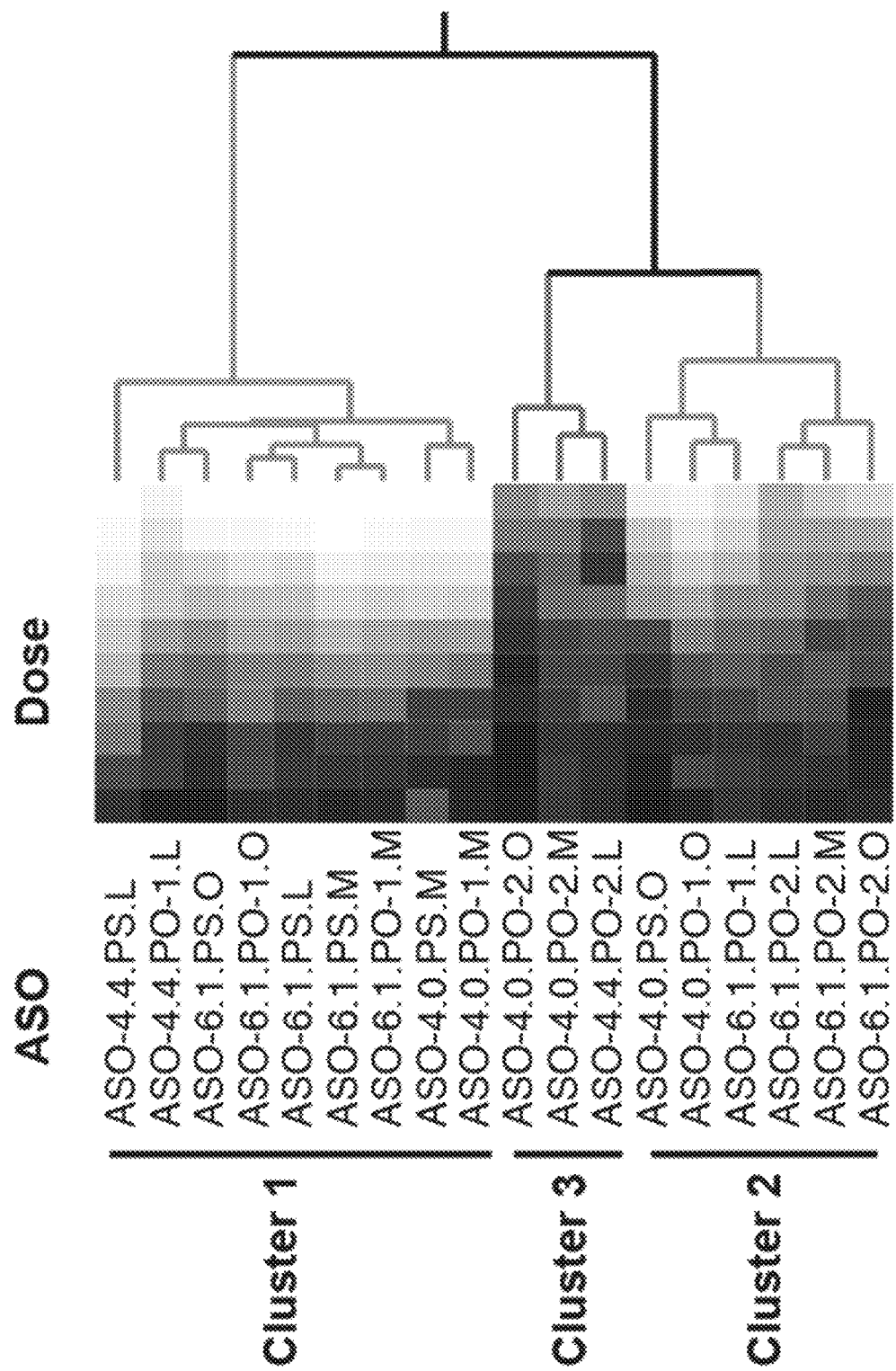
Figure 8C:
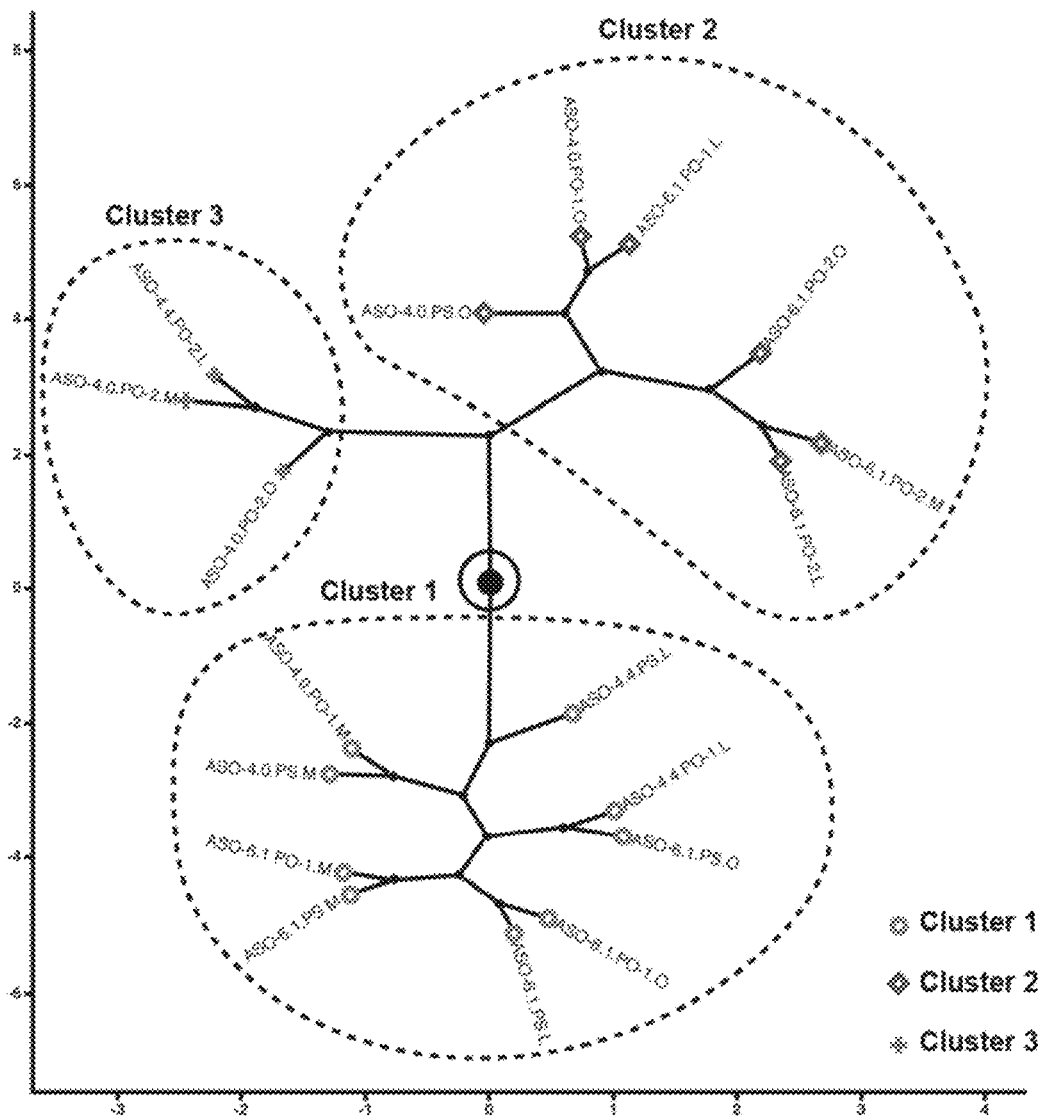

Eighteen ASOs targeting the ASO-4 and ASO-6.1 target sequences and consisting of different backbone designs and RNA modifications were designed to identify potential lead ASOs (Table 17). Normal iPSC derived-neurons (GABAergic) were treated with a 10-point ½ log dose response curve of each ASO to compare the $IC_{50}$ and $E_{max}$ values. Neural precursor cells were differentiated into neurons for at 18 DIV and then treated with a 10-point ½ log dose response ASOs[1 nM, 3 nM, 10 nM, 30 nM, 100 nM, 300 nM, 1 µM, 3 µM, 10 µM, and 30 µM (n=2)]. At 24 DIV, the steady state RNA levels of UBE3A-AS were measured and dose response curves fitted as described above (FIG. 8A and Table 18). The dose response curves were significantly different (Parallelism test: $F_{(51,606)}=7.86$; $p<0.0001$; $R^2=0.90$), thus relative potencies were not estimated. Hierarchical clustering of the fitted curves revealed 3 Clusters of ASOs, with Cluster 1 representing the 9 most potent ASOs (FIGS. 8B and 8C). Analysis of Cluster 1 indicated that the ASOs had similar curves (Parallelism test: $F_{(24,299)}=1.01$; $p=0.5$; $R^2=0.93$), and that ASO-4.4.PS.L was at least 3-times as potent as the other ASOs (Table 19). Further analysis, however, indicated that ASO-4.4.PS.L, ASO-6.1.PS.M, and ASO-6.1.PO-1.M had equivalent $IC_{50}$ values, whereas the other ASOs were slightly less potent (Table 20). Based on the relative potencies and internal selection criteria, ASO-4.4.PS.L and ASO-6.1.PO-1.0 were investigated further.

TABLE 18

$IC_{50}$ and $E_{max}$ of Candidate ASOs

| ASO | $IC_{50}$ (M) | $IC_{50}$ 95% CI (M) | | $E_{max}$ | $E_{max}$ 95% CI | | 30 µM (Mean) | Cluster |
|---|---|---|---|---|---|---|---|---|
| ASO-4.4.PS.L | 2.66E−08 | 3.66E−09 | 1.93E−07 | 0.0 | −0.23 | 0.23 | 0.05 | 1 |
| ASO-6.1.PS.M | 1.47E−07 | 6.80E−08 | 3.19E−07 | −0.05 | −0.21 | 0.12 | 0.02 | 1 |
| ASO-6.1.PO-1.M | 1.66E−07 | 7.15E−08 | 3.84E−07 | −0.02 | −0.20 | 0.16 | 0.04 | 1 |
| ASO-4.4.PO-1.L | 2.26E−07 | 8.95E−08 | 5.71E−07 | 0.04 | −0.17 | 0.25 | 0.1 | 1 |
| ASO-4.0.PO-1.M | 2.78E−07 | 1.52E−07 | 5.08E−07 | 0.02 | −0.11 | 0.15 | 0.05 | 1 |
| ASO-4.0.PS.M | 3.00E−07 | 1.80E−07 | 5.00E−07 | 0.05 | −0.06 | 0.15 | 0.05 | 1 |
| ASO-6.1.PO-1.O | 3.15E−07 | 7.98E−08 | 1.24E−06 | −0.1 | −0.50 | 0.26 | 0.04 | 1 |
| ASO-6.1.PS.L | 3.62E−07 | 1.37E−07 | 9.57E−07 | −0.07 | −0.32 | 0.18 | 0.04 | 1 |
| ASO-6.1.PS.O | 5.32E−07 | 1.20E−07 | 2.36E−06 | −0.2 | −0.67 | 0.29 | 0.05 | 1 |
| ASO-6.1.PO-2.L | 7.34E−07 | 5.35E−08 | 1.01E−05 | 0.3 | −0.11 | 0.76 | 0.4 | 2 |
| ASO-4.0.PO-1.O | 7.66E−07 | 3.70E−07 | 1.59E−06 | 0.05 | −0.12 | 0.23 | 0.1 | 2 |
| ASO-4.0.PS.O | 1.27E−06 | 5.13E−07 | 3.13E−06 | 0.06 | −0.20 | 0.31 | 0.1 | 2 |
| ASO-6.1.PO-1.L | 1.89E−06 | 4.42E−07 | 8.06E−06 | 0.03 | −0.34 | 0.39 | 0.2 | 2 |
| ASO-4.0.PO-2.O | 1.30E−04 | 1.65E−17 | 1.03E+09 | −0.3 | −9.51 | 8.94 | 0.6 | 2 |
| ASO-6.1.PO-2.M | 2.69E−04 | 9.85E−16 | 7.37E+07 | −1.2 | −13.16 | 10.77 | 0.3 | 2 |
| ASO-4.4.PO-2.L | 3.27E+01 | 0 | Inf | −2.7 | −577 | 571 | 0.6 | 3 |
| ASO-4.0.PO-2.M | 1.14E+05 | 0 | Inf | −76 | −74,958. | 74,805 | 0.5 | 3 |
| ASO-6.1.PO-2.O | 1.93E+10 | 0 | Inf | −5569 | −85,963,650 | 85,952,510 | 0.3 | 3 |

Full model parameter estimates from 4-parameter logistic regression model (Hill). IC50 and confidence intervals represent molar concentration. Emax and 30 uM values represent normalized UBE3A-AS RNA levels relative to vehicle.

Abbreviations:

Inf, infinity; 95% CI, 95% confidence intervals

TABLE 19

Relative potency of ASOs in Cluster 1

| ASO | IC$_{50}$ (M) | Relative Potency | Std Error |
|---|---|---|---|
| ASO-4.4.PS.L | 5.03E−08 | 1 | 0 |
| ASO-6.1.PS.M | 1.53E−07 | 0.3 | 0.08 |
| ASO-6.1.PO-1.M | 1.77E−07 | 0.3 | 0.07 |
| ASO-6.1.PO-1.O | 1.99E−07 | 0.3 | 0.06 |
| ASO-4.0.PS.M | 2.62E−07 | 0.2 | 0.05 |
| ASO-4.0.PO-1.M | 2.78E−07 | 0.2 | 0.04 |
| ASO-6.1.PS.L | 2.81E−07 | 0.2 | 0.04 |
| ASO-4.4.PO-1.L | 3.22E−07 | 0.2 | 0.04 |
| ASO-6.1.PS.O | 4.32E−07 | 0.1 | 0.03 |

Parallel model parameter estimates from 4 Parameter logistic regression model (Hill). Abbreviations: M, molar; Std, standard

TABLE 20

Equivalence of ASOs in Cluster 1 Relative to ASO-4.4.PS.L

| ASO | ASO | IC$_{50}$ Ratio | Lower and Upper Confidence Limits | | Limit Exceeded |
|---|---|---|---|---|---|
| ASO-4.4.PS.L | ASO-6.1.PO-1.M | 0.90 | 0.81 | 0.98 | Equivalent |
| | ASO-6.1.PS.M | 0.90 | 0.82 | 0.98 | Equivalent |
| | ASO-4.0.PO-1.M | 0.87 | 0.79 | 0.94 | Lower |
| | ASO-4.0.PS.M | 0.86 | 0.79 | 0.94 | Lower |
| | ASO-4.4.PO-1.L | 0.88 | 0.79 | 0.96 | Lower |
| | ASO-6.1.PO-1.O | 0.86 | 0.77 | 0.95 | Lower |
| | ASO-6.1.PS.L | 0.85 | 0.77 | 0.93 | Lower |
| | ASO-6.1.PS.O | 0.83 | 0.73 | 0.92 | Lower |

Two one-sided Tests

Materials and Methods

Methods were similar to those described in Example 2 unless noted otherwise.

Figure 9:
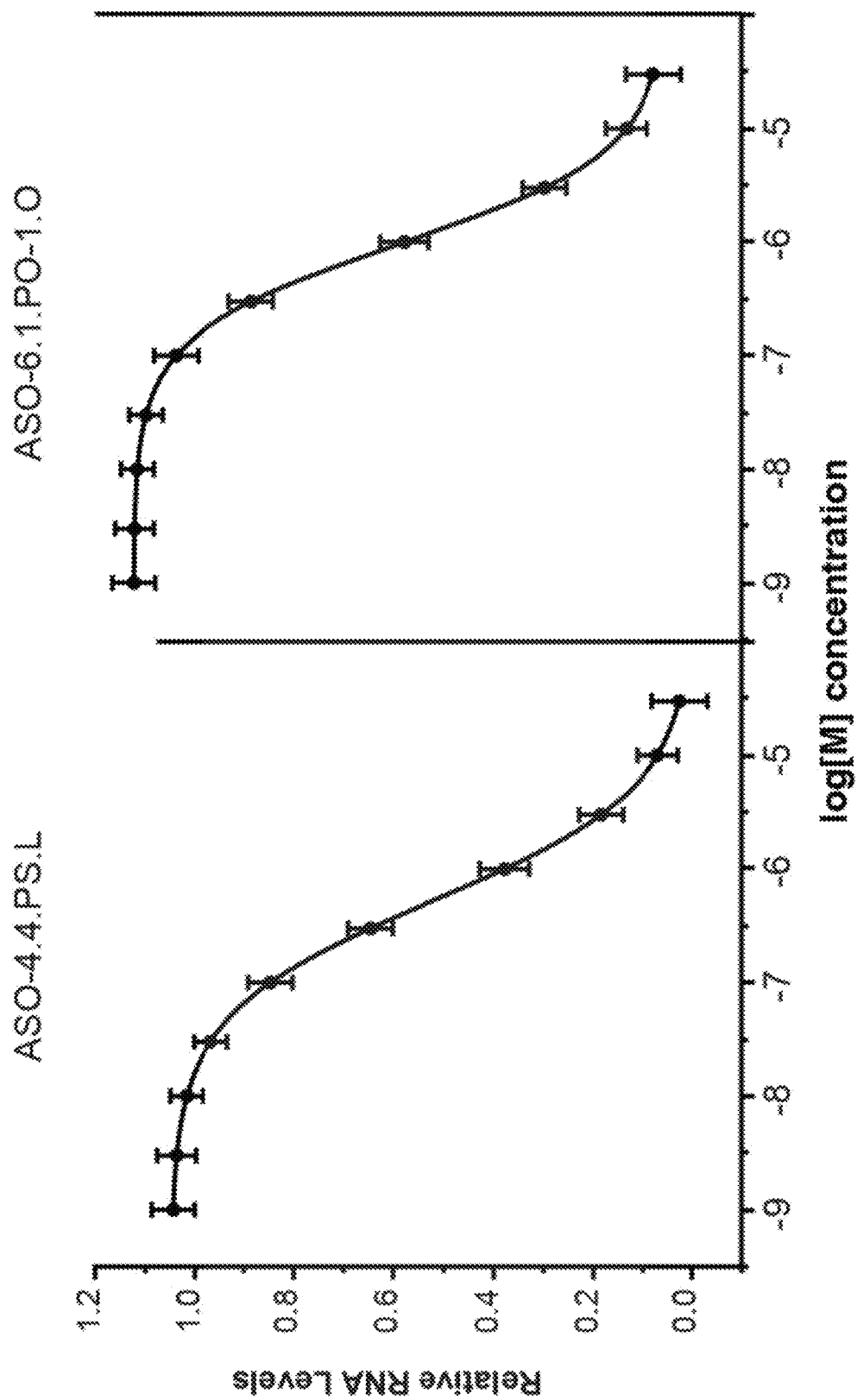
FIG. 9 shows pharmacodynamic analysis of ASO-6.1.PO-1.0 and ASO-4.4.PS.L in Angelman syndrome iPSC-derived neurons. 4-Parameter logistic regression model (Hill) of normalized UBE3A-AS steady state RNA levels in Angelman syndrome iPSC-derived neurons treated with a 10-point ½ log dose curve (1 nM, 3 nM, 10 nM, 30 nM, 100 nM, 300 nM, 1 µM, 3 µM, 10 µM, and 30 µM; n=3) of ASO-6.1.PO-1.0 and ASO-4.4.PS.L.

Example 4: Pharmacodynamic Analysis of ASO-6.1-PO-1.0 and ASO-4.4.PS.L in Angelman Syndrome iPSC Neurons The potencies of ASO-6.1.PS.O and ASO-4.4.PS.L were then examined in iPSC derived-neurons from an Angelman syndrome patient with a maternal derived deletion of the 15q11-q13 region. Induced pluripotent stem cells were differentiated into neurons and then treated with a 10-point ½ log dose response curve of ASO-6.1.PO-1.0 and ASO-4.4.PS.L [1 nM, 3 nM, 10 nM, 30 nM, 100 nM, 300 nM, 1 µM, 3 µM, 10 µM, and 30 µM (n=3)]. Six days following treatment, the steady state RNA levels of UBE3A-AS were measured and dose response curves were fitted as described above (FIG. 9A). The dose response curves were similar between ASOs (Parallelism test: $F_{(3,132)}=1.07$, p=0.4, $R^2=0.82$), with ASO-4.4.PS.L (437 nM) being approximately 2.7-fold more potent than ASO-6.1.PO-1.0 (1.22 uM). The IC$_{50}$ values were equivalent[ASO-6.1.PO-1.O/ASO-4.4.PS.L IC$_{50}$ ratio: =0.96 (Lower confidence limit=0.9; Upper confidence limit=1.0)]. The E$_{max}$ values were similar (30 µM: ASO-4.4.PS.L=0.01±0.0007; ASO-6.1.PO-1.O=0.05±0.004) but not considered equivalent due to the confidence intervals[ASO-6.1.PO-1.0/ASO-4.4.PS.L E$_{max}$ ratio: =−9.1 (Lower confidence limit=−224; Upper confidence limit=205)].

Materials and Methods

Methods were similar to those described in Example 2 unless noted otherwise.

Angelman syndrome induced pluripotent stem cells derived neurons Angelman syndrome iPS cells (AG1-0 iPSCs) (ECN001, Kerafast, Boston, Mass.) were co-cultured on irradiated murine embryonic fibroblasts in human embryonic stem cell medium [DMEM/F12 (11330-057, Gibco Biosciences, Dublin, Ireland), 20% Knockout Serum Replacement (10828-028, Thermo Fisher Scientific), 1×Non-essential amino acids, 2 mM L-glutamine, 7 µl/mL 2-Mercaptoethanol, and 4 µg/mL basic Fibroblast Growth Factor]. For the first passage, AG1-0 cells were passaged according to the product manual for PluriSTEM Human ES/iPS Medium (SCM130, Millipore Sigma, Burlington, Mass.), which is feeder-free and utilizes Dispase II (SCM133, Millipore Sigma) to dissociate cells. Matrigel™ hESC-qualified Matrix (354277, Corning BD Biosciences, Corning, N.Y.) was used as an extracellular matrix. At the second passage, the matrix was switched to vitronectin (CC130, Millipore Sigma). During subsequent passages, areas of differentiation were manually removed until differentiated cells represented approximately <5% of the colonies. After four subsequent passages, AG1-0 cells were differentiated using the Millipore ES/iPS Neurogenesis Kit (SCR603, SCM110, and SCM111) but lacking vitronectin as an extracellular matrix. The initial passage was performed with EZ-LiFT (SCM139, Millipore Sigma) to obtain high quality PS cells. Neural progenitor cells were frozen at stage zero (P$_0$) and subsequently thawed for differentiation. Differentiation was performed on sterile culture plates coated with poly-D-lysine (10 µg/mL) and laminin[10 µg/mL (23017-015, Gibco) in differentiation medium (SCM111) for 10 days of differentiation. In some instances, cells were differentiated in Cellular Dynamics Maintenance Medium (NRM-100-121-001, Cellular Dynamics International, Madison, Wis.).

Figure 10:
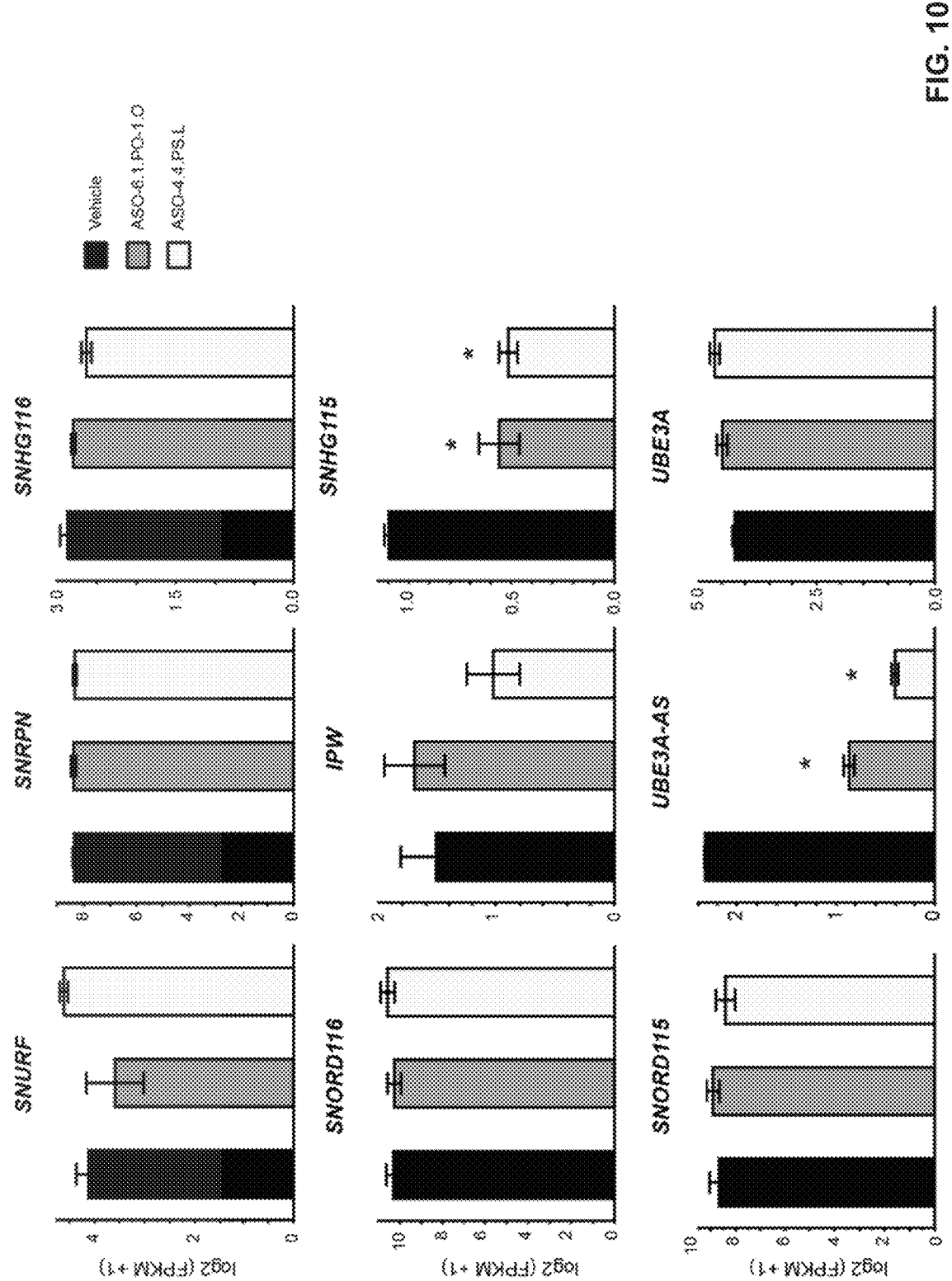
FIG. 10 shows expression analysis of RNAs encoded by the PWS polycistronic transcript in Angelman syndrome iPSC neurons treated with ASO-6.1-PO-1.0 and ASO-4.4.PS.L. Shown are normalized steady state RNA levels of SNURF, SNRPN, SNHG116, SNORD116 snoRNAs, IPW, SNHG115, SNORD115 snoRNAs, UBE3A-AS, and UBE3A in AS iPSC-derived neurons treated with vehicle (1% $H_2O$; n=3), ASO-6.1.PO-1.0 (30 µM; n=3), and ASO-4.4.PS.L (30 µM; n=3). Data represents mean percentage of RNA relative to vehicle. Error bars represent standard error of mean. Asterisk (*) denotes statistically significant differences ($p<0.05$) using one-way ANOVA with Dunnett's multiple comparison test relative to vehicle.

Example 5: Expression Analysis of the PWS Polycistronic Transcript in Angelman Syndrome iPSC Neurons Treated with ASO-6.1-PO-1.0 and ASO-4.4.PS.L To determine whether ASO-4.4.PS.L and ASO-6.1.PO-1.0 affect the levels of RNA transcripts encoded by the PWS polycistronic transcript, RNA-sequencing was performed on AS PS cells treated with each ASO and the steady state RNA levels of SNURF, SNRPN, the SNORD116 host-gene transcript (SNHG116), the SNORD116 snoRNAs, IPW, the SNORD115 host-gene transcript (SNHG115), the SNORD115 snoRNAs, and UBE3A-AS were quantified. UBE3A steady state RNA levels were also measured. Angelman syndrome PS cells were differentiated into neurons as described above and then treated with vehicle (1% H2O, n=3), ASO-4.4.PS.L (30 u µM, n=3) and ASO-6.1.PO-1.0 (30 µM, n=3). Six days post-treatment, RNA RNA-sequencing was performed on total RNA (rRNA depleted) isolated from the cultures. To generate annotations of the SNHG116, SNHG115, and UBE3A-AS transcripts, a transcriptome was assembled from the vehicle RNA-seq data and then incorporated into the reference gene annotation. Relative to vehicle, the steady state RNA levels of SNURF, SNRPN, SNHG116, the SNORD116 snoRNAs, and the SNORD115 snoRNAs were similar and not significantly different. ASO-4.4.PS.L, but not ASO-6.1.PO-1.0, reduced IPW levels (1.5-fold), but the effect was not significant. ASO-6.1.PO-1.0 and ASO-4.4.PS.L significantly reduced SNHG115 and UBE3A-AS RNA levels. ASO-6.1.PO-1.0 and ASO-4.4.PS.L had a similar effect on SNHG115 levels; however, ASO-4.4.PS.L had a much larger effect on UBE3A-AS RNA levels than ASO-6.1.PO-1.0 (ASO-4.4.PS.L: −6.1-fold change; ASO-6.1.PO-1.0: −2.8-fold change). ASO treatment increased UBE3A RNA levels by approximately 1.2-fold, but the effect was not significant (FIG. 10 and Table 21).

TABLE 21

Effect of ASO Treatment on RNA Levels of PWS Polycistronic Transcripts and UBE3A

| Gene | Treatment | Difference | Std Error | t Ratio | Adjusted P |
|---|---|---|---|---|---|
| SNURF | ASO-6.1.PO-1.O | −0.53 | 0.51 | −1.02 | 0.5 |
| | ASO-4.4.PS.L | 0.49 | 0.51 | 0.96 | 0.6 |
| SNRPN | ASO-6.1.PO-1.O | 0.03 | 0.11 | 0.30 | 0.9 |
| | ASO-4.4.PS.L | −0.02 | 0.11 | −0.16 | 1.0 |
| SNHG116 | ASO-6.1.PO-1.O | −0.07 | 0.10 | −0.75 | 0.7 |
| | ASO-4.4.PS.L | −0.24 | 0.10 | −2.49 | 0.08 |
| SNORD116 | ASO-6.1.PO-1.O | −0.04 | 0.46 | −0.08 | 1.0 |
| | ASO-4.4.PS.L | 0.27 | 0.45 | 0.60 | 0.8 |
| IPW | ASO-6.1.PO-1.O | 0.18 | 0.37 | 0.49 | 0.8 |
| | ASO-4.4.PS.L | −0.49 | 0.37 | −1.33 | 0.4 |
| SNH115G | ASO-6.1.PO-1.O | −0.55 | 0.09 | −5.92 | 0.002 |
| | ASO-4.4.PS.L | −0.58 | 0.09 | −6.33 | 0.001 |
| SNORD115 | ASO-6.1.PO-1.O | 0.24 | 0.52 | 0.45 | 0.8 |
| | ASO-4.4.PS.L | −0.26 | 0.49 | −0.54 | 0.8 |
| UBE3A-AS | ASO-6.1.PO-1.O | −1.48 | 0.06 | −24.17 | <0.0001 |
| | ASO-4.4.PS.L | −1.94 | 0.06 | −31.56 | <0.0001 |
| UBE3A | ASO-6.1.PO-1.O | 0.74 | 0.48 | 1.53 | 0.3 |
| | ASO-4.4.PS.L | 0.90 | 0.48 | 1.88 | 0.2 |

One way ANOVA with Dunnett's multiple comparison test relative to vehicle.

Materials and Methods

Methods were similar to those described in Example 4 unless noted otherwise.

Differential Expression Analysis of PWS RNAs

Normalized FPKM (fragments per thousand per million) values of the RefSeq gene annotation will be estimated using Cuffnorm with the default settings and the following option: −u. The FPKM values of each gene annotation was determined for each sample from the output file and used for descriptive and inferential statistics.

Figure 11:
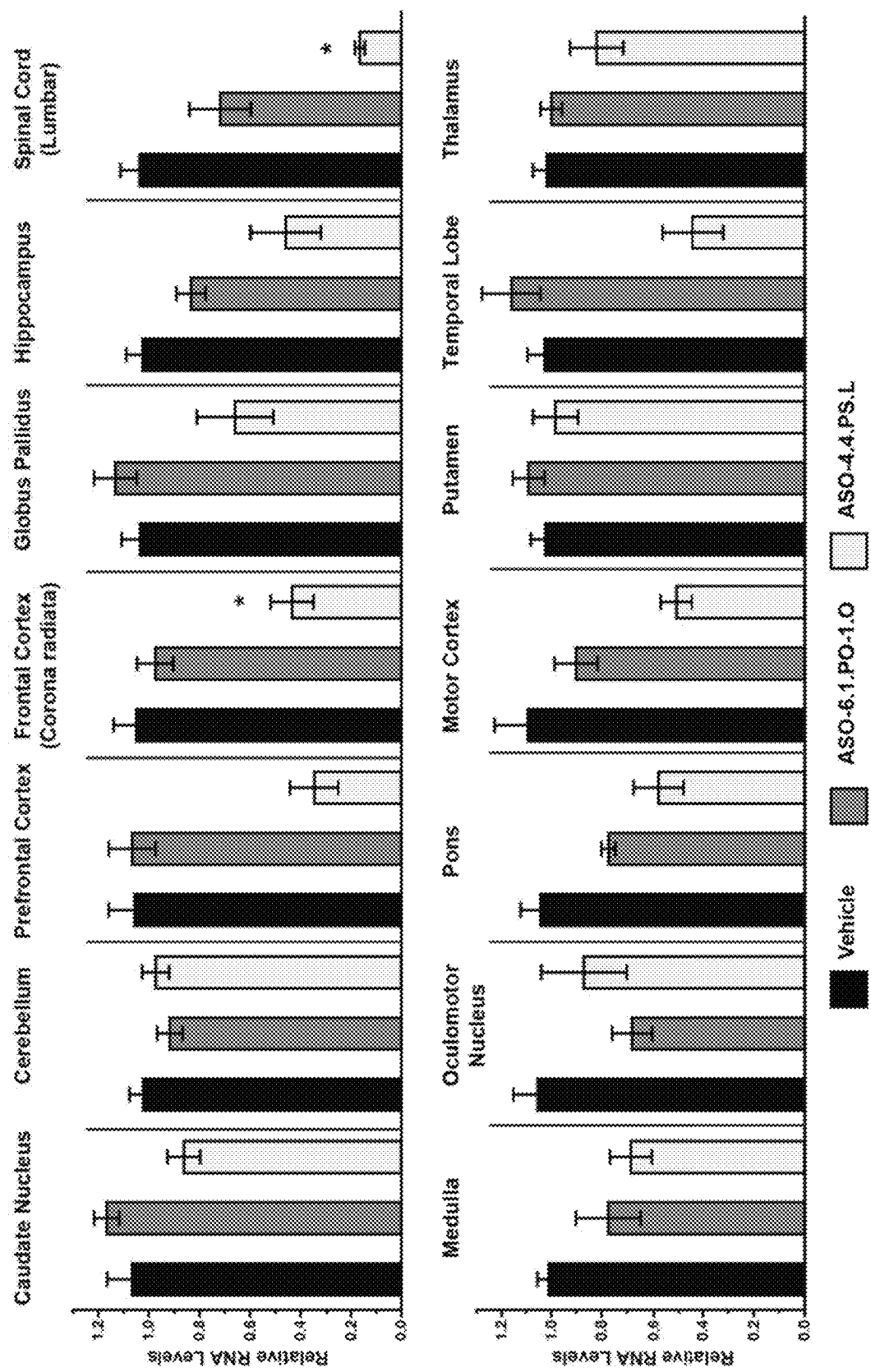
FIG. 11 shows pharmacodynamic analysis of ASO-6.1.PO-1.0 and ASO-4.4.PS.L in Cynomolgus macaque. Shown are steady state RNA levels of UBE3A-AS in macaque CNS regions treated with vehicle (0.9% saline; n=5), ASO-6.1.PO-1.0 (10 mg; n=3), and ASO-4.4.PS.L (10 mg; n=3). Data represents means percentage of UBE3A-AS RNA relative to vehicle. Error bars represent standard error of mean. Asterisk (*) denotes statistically significant differences ($p<0.05$) using one-way ANOVA with Dunnett's multiple comparison test relative to vehicle.

Example 6: Pharmacodynamic Analysis of ASO-6.1-PO-1.0 and ASO-4.4.PS.L in Cynomolgus Macaque The ASO-4 and ASO-6 target regions are conserved across several non-human primate (NHP) species, thus enabling both safety and efficacy studies in a large animal model. To examine the efficacy of ASO-4.4.PS.L and ASO-6.1.PO-1.0 in the central nervous system (CNS), ASOs were delivered to Cynomolgus macaques by intrathecal lumbar puncture. Animals were administered a single bolus injection of vehicle (0.9% saline, n=5), ASO-6.1.PO-1.0 (10 mg, n=3), and ASO.4.4.PS.L (10 mg, n=3). Twenty-eight days following treatment, central nervous (CNS) tissues were collected and the steady state RNA levels of UBE3A-AS were measured. Overall, ASO-4.4.PS.L had a larger effect on UBE3A-AS RNA levels than ASO-6.1.PO-1.0 (Table 22). ASO-4.4.PS.L reduced UBE3A-AS RNA in most CNS regions, with large effects in temporal lobe, primary motor cortex, pons, medulla, hippocampus, globus pallidus, frontal cortex (Corona radiata), prefrontal cortex, and lumbar spinal cord. Similarly, ASO-6.1.PO-1.0 reduced UBE3A-AS RNA levels in most CNS regions, with large effects observed in pons, oculomotor nucleus, and lumbar spinal cord (FIG. 11 and Table 23).

TABLE 22

Effect Size of ASO Treatment on UBE3A-AS RNA Levels in CNS

| Treatment | Treatment* | Cohen's d | 95% Confidence Intervals | | FDR |
|---|---|---|---|---|---|
| Vehicle | ASO-4.4.PS.L | 1.4 | 1.0 | 1.8 | 2.3E−10 |
| ASO-6.1.PO-1.O | ASO-4.4.PS.L | 1.0 | 0.6 | 1.5 | 6.4E−06 |
| Vehicle | ASO-6.1.PO-1.O | 0.3 | −0.06 | 0.7 | 0.09 |

Students t-test with FDR adjusted P values
Cohen's d effect sizes: 0.2, small; 0.5, medium; 0.8, large; 1.2, very large
Abbreviations: FDR, false discovery rate

TABLE 23

Effect of ASO Treatment on UBE3A-AS RNA Levels in CNS Regions

| CNS Region | ASO | Difference | Std Error | t Ratio | Adjusted P |
|---|---|---|---|---|---|
| Caudate Nucleus | ASO-6.1.PO-1.O | 0.10 | 0.22 | 0.46 | 0.9 |
| | ASO-4.4.PS.L | −0.21 | 0.22 | −0.94 | 0.6 |
| Cerebellum | ASO-6.1.PO-1.O | −0.11 | 0.09 | −1.15 | 0.5 |
| | ASO-4.4.PS.L | −0.05 | 0.09 | −0.53 | 0.8 |
| Frontal cortex | ASO-6.1.PO-1.O | 0.01 | 0.27 | 0.04 | 0.9 |
| | ASO-4.4.PS.L | −0.71 | 0.27 | −2.66 | 0.05 |
| Frontal Cortex (Corona radiata) | ASO-6.1.PO-1.O | −0.08 | 0.22 | −0.34 | 0.9 |
| | ASO-4.4.PS.L | −0.62 | 0.22 | −2.79 | 0.04 |
| Globus Pallidus | ASO-6.1.PO-1.O | 0.10 | 0.24 | 0.40 | 0.9 |
| | ASO-4.4.PS.L | −0.38 | 0.24 | −1.54 | 0.3 |
| Hippocampus | ASO-6.1.PO-1.O | −0.19 | 0.21 | −0.91 | 0.6 |
| | ASO-4.4.PS.L | −0.57 | 0.21 | −2.66 | 0.05 |
| Spinal Cord (Lumbar) | ASO-6.1.PO-1.O | −0.32 | 0.20 | −1.63 | 0.2 |
| | ASO-4.4.PS.L | −0.87 | 0.20 | −4.46 | 0.004 |
| Medulla | ASO-6.1.PO-1.O | −0.24 | 0.20 | −1.16 | 0.45 |
| | ASO-4.4.PS.L | −0.32 | 0.20 | −1.59 | 0.3 |
| Oculomotor Nucleus | ASO-6.1.PO-1.O | −0.37 | 0.29 | −1.27 | 0.4 |
| | ASO-4.4.PS.L | −0.18 | 0.29 | −0.62 | 0.8 |
| Pons | ASO-6.1.PO-1.O | −0.27 | 0.21 | −1.30 | 0.4 |
| | ASO-4.4.PS.L | −0.47 | 0.21 | −2.25 | 0.1 |
| Motor Cortex | ASO-6.1.PO-1.O | −0.19 | 0.30 | −0.65 | 0.8 |
| | ASO-4.4.PS.L | −0.59 | 0.30 | −1.99 | 0.1 |
| Putamen | ASO-6.1.PO-1.O | 0.07 | 0.15 | 0.44 | 0.9 |
| | ASO-4.4.PS.L | −0.04 | 0.15 | −0.25 | 0.9 |
| Temporal Lobe | ASO-6.1.PO-1.O | 0.13 | 0.25 | 0.54 | 0.8 |
| | ASO-4.4.PS.L | −0.59 | 0.25 | −2.39 | 0.08 |
| Thalamus | ASO-6.1.PO-1.O | −0.02 | 0.14 | −0.14 | 0.9 |
| | ASO-4.4.PS.L | −0.20 | 0.14 | −1.46 | 0.3 |

One way ANOVA with Dunnett's multiple comparison test relative to vehicle.

Materials and Methods

Administration of ASOs

NHP studies were performed at Northern Biomedical Research and Charles River Laboratories using protocols approved by the institutions respective Institutional Animal Care and Use Committees. Male and female Cynomolgus macaques (Macaca fascicularis) weighing 2-4 kg were anesthetized and single 1 mL dose of ASO or vehicle was administered via intrathecal lumbar puncture. The dosing solution was prepared by dissolution of lyophilized ASO in the vehicle control article (0.9% sodium chloride) and was filtered through a 0.2-μm filter. CNS and spinal cord samples were harvested, and the CNS was sectioned into 4-mm coronal slices. Tissue samples were flash frozen and stored at −80° C. until RNA isolation.

RNA Isolation

A 4 mm tissue punch was taken from each region of interest of which approximately half was used for RNA isolation. RNA isolation was performed using the Qiagen RNeasy Plus Mini kit (74136, Qiagen) with tissue disruption and lysis performed with 5 mm stainless steel beads in a TissueLyser II. The RNA was eluted in two volumes of 30 µl water, for a total elution volume of 60 µl. RNA was quantified using the Qubit with the RNA XR assay (Q33224, Thermo Fisher Scientific). cDNA was synthesized from 2 µg of input RNA using the High Capacity RNA-to-cDNA kit (4387406, Thermo Fisher Scientific) in a total reaction volume of 50 µl.

Analysis of UBE3A-AS RNA Levels in Tissues

Cynomolgus macaque UBE3A-AS RNA levels were estimated using SYBR Green quantitative reverse-transcription PCR (qRT-PCR). Total reaction volume was 10 µl, including 2 µl of cDNA, 1×PowerUp SYBR Green Master mix (A25741, Thermo Fisher Scientific), and 500 nM of each primer (forward and reverse). Cycling conditions were 2 minutes at 50° C., 2 minutes at 95° C., and 40 cycles of 15 seconds at 95° C. and 1 minute at 60° C., with readings taken at the 60° C. step of every cycle. Reactions were run on a BIO-RAD T1000 CFX96 thermocycler, with internal control (PPIA, forward: GTCTCCTTCGAGCTGTTTGC (SEQ ID NO:503); reverse: CCTTTCTCTCCAGTGCTCAGA (SEQ ID NO:504)) and target (UBE3A-AS, forward: CCTGTGAACTTTCAACCAGGA (SEQ ID NO:505); reverse: GGATCAGACTCCAGGCCTTC (SEQ ID NO:506)) reactions performed separately. Data was retrieved and initial analysis was done with the BIORAD CFX Maestro software, with in depth statistical analyses performed with Excel and JMP.

Example 7: ASOs Targeting Exonic Boundaries of Spliced UBE3A-AS Transcripts

In some embodiments, the target sequence is an exonic boundary involving UBE3A-AS exons 1-5 and SNORD109B exons 1-2. Target sequences consist of 38 nucleotides (19 nucleotides of each exon) centered on the exonic boundary of each exon (19 nucleotides representing the 5' and 3'-ends of adjacent exons). There were 12 segments of sequences, with exonic boundaries involving segments 1-2, 2-3, 3-4, 5-6, 7-8, 9-10, and 11-12. The chromosomal coordinates are provided in Table 24. A single merged junction sequence was created that shows the spliced exons (1, exonic junction) and intervening exonic sequences ([ ]). ASOs (20-, 19-, and 18-mer) targeting the exonic junctions are provided in Table 25.

Merged Junction-Sequence

```
                                                  (SEQ ID NO: 489)
AATGAAATCTTCTGATTTG|TAAGACATGCTGCCAAGAG[ ]ATTAGTT

TTACACCTTCAG|GATAAAGACTGCTGAGAAG[ ]GTTTAAGGATGCTA

TTCTG|AAAAGACTGTGGAGGAAGA[ ]TTAAGGAAACCATCTCTGG|G

ATAAGGATGACTGAGGAA[ ]ATTTAAGGATGCCACTCTG|GTTAAAAG

CTGAAACAACT[ ]GAAACTTCAGGGAAAAGAG|AAGGCCTGGAATCTG

ATCC.
| = 3'-5' exonic junction
[ ] = intervening exonic sequence
```

TABLE 24

Chromosome 15 coordinates of targeted exonic junctions

| Segment | Start | End | Exonic Region |
|---|---|---|---|
| 1 | 25,511,743 | 25,511,761 | 3' |
| 2 | 25,512,059 | 25,512,079 | 5' |
| 3 | 25,512,175 | 25,512,191 | 3' |
| 4 | 25,513,475 | 25,513,493 | 5' |
| 5 | 25,513,582 | 25,513,600 | 3' |
| 6 | 25,514,752 | 25,514,770 | 5' |
| 7 | 25,514,863 | 25,514,881 | 3' |
| 8 | 25,516,564 | 25,516,582 | 5' |
| 9 | 25,516,663 | 25,516,681 | 3' |
| 10 | 25,522,514 | 25,522,532 | 5' |
| 11 | 25,522,537 | 25,522,556 | 3' |
| 12 | 25,523,994 | 25,524,012 | 5' |

Human chromosome 15 coordinates (hg19 reference assembly)

TABLE 25

List of Junction ASOs and corresponding target regions

| ASO size | Target Sequence (5'-3') | | ASO sequence (5'-3') | |
|---|---|---|---|---|
| 20-mer | GAAACCAUCUCUGGGAUAAG | SEQ ID NO: 393 | CTTATCCCAGAGATGGTTTC | SEQ ID NO: 441 |
| | AAACCAUCUCUGGGAUAAGG | SEQ ID NO: 394 | CCTTATCCCAGAGATGGTTT | SEQ ID NO: 442 |
| | AACCAUCUCUGGGAUAAGGA | SEQ ID NO: 395 | TCCTTATCCCAGAGATGGTT | SEQ ID NO: 443 |
| | ACCAUCUCUGGGAUAAGGAU | SEQ ID NO: 396 | ATCCTTATCCCAGAGATGGT | SEQ ID NO: 444 |
| | CCAUCUCUGGGAUAAGGAUG | SEQ ID NO: 397 | CATCCTTATCCCAGAGATGG | SEQ ID NO: 445 |
| | CAUCUCUGGGAUAAGGAUGA | SEQ ID NO: 398 | TCATCCTTATCCCAGAGATG | SEQ ID NO: 446 |
| | AUCUCUGGGAUAAGGAUGAC | SEQ ID NO: 399 | GTCATCCTTATCCCAGAGAT | SEQ ID NO: 447 |
| | UCUCUGGGAUAAGGAUGACU | SEQ ID NO: 400 | AGTCATCCTTATCCCAGAGA | SEQ ID NO: 448 |
| | CUCUGGGAUAAGGAUGACUG | SEQ ID NO: 401 | CAGTCATCCTTATCCCAGAG | SEQ ID NO: 449 |
| | UCUGGGAUAAGGAUGACUGA | SEQ ID NO: 402 | TCAGTCATCCTTATCCCAGA | SEQ ID NO: 450 |
| | CUGGGAUAAGGAUGACUGAG | SEQ ID NO: 403 | CTCAGTCATCCTTATCCCAG | SEQ ID NO: 451 |
| | UGGGAUAAGGAUGACUGAGG | SEQ ID NO: 404 | CCTCAGTCATCCTTATCCCA | SEQ ID NO: 452 |
| | GGGAUAAGGAUGACUGAGGA | SEQ ID NO: 405 | TCCTCAGTCATCCTTATCCC | SEQ ID NO: 453 |
| | GGAUAAGGAUGACUGAGGAA | SEQ ID NO: 406 | TTCCTCAGTCATCCTTATCC | SEQ ID NO: 454 |
| | GCUGAAACAACUGAAACUUC | SEQ ID NO: 407 | GAAGTTTCAGTTGTTTCAGC | SEQ ID NO: 455 |
| | GAAACAACUGAAACUUCAGG | SEQ ID NO: 408 | CCTGAAGTTTCAGTTGTTTC | SEQ ID NO: 456 |
| | AAACAACUGAAACUUCAGGG | SEQ ID NO: 409 | CCCTGAAGTTTCAGTTGTTT | SEQ ID NO: 457 |
| | AACAACUGAAACUUCAGGGA | SEQ ID NO: 410 | TCCCTGAAGTTTCAGTTGTT | SEQ ID NO: 458 |
| | ACAACUGAAACUUCAGGGAA | SEQ ID NO: 411 | TTCCCTGAAGTTTCAGTTGT | SEQ ID NO: 459 |
| | CAACUGAAACUUCAGGGAAA | SEQ ID NO: 412 | TTTCCCTGAAGTTTCAGTTG | SEQ ID NO: 460 |
| | ACUGAAACUUCAGGGAAAAG | SEQ ID NO: 413 | CTTTTCCCTGAAGTTTCAGT | SEQ ID NO: 461 |

TABLE 25-continued

List of Junction ASOs and corresponding target regions

| ASO size | Target Sequence (5'-3') | | ASO sequence (5'-3') | |
|---|---|---|---|---|
| 19-mer | AACCAUCUCUGGGAUAAGG | SEQ ID NO: 414 | CCTTATCCCAGAGATGGTT | SEQ ID NO: 462 |
| | ACCAUCUCUGGGAUAAGGA | SEQ ID NO: 415 | TCCTTATCCCAGAGATGGT | SEQ ID NO: 463 |
| | CCAUCUCUGGGAUAAGGAU | SEQ ID NO: 416 | ATCCTTATCCCAGAGATGG | SEQ ID NO: 464 |
| | CAUCUCUGGGAUAAGGAUG | SEQ ID NO: 417 | CATCCTTATCCCAGAGATG | SEQ ID NO: 465 |
| | AUCUCUGGGAUAAGGAUGA | SEQ ID NO: 418 | TCATCCTTATCCCAGAGAT | SEQ ID NO: 466 |
| | UCUCUGGGAUAAGGAUGAC | SEQ ID NO: 419 | GTCATCCTTATCCCAGAGA | SEQ ID NO: 467 |
| | CUCUGGGAUAAGGAUGACU | SEQ ID NO: 420 | AGTCATCCTTATCCCAGAG | SEQ ID NO: 468 |
| | UCUGGGAUAAGGAUGACUG | SEQ ID NO: 421 | CAGTCATCCTTATCCCAGA | SEQ ID NO: 469 |
| | CUGGGAUAAGGAUGACUGA | SEQ ID NO: 422 | TCAGTCATCCTTATCCCAG | SEQ ID NO: 470 |
| | UGGGAUAAGGAUGACUGAG | SEQ ID NO: 423 | CTCAGTCATCCTTATCCCA | SEQ ID NO: 471 |
| | GGGAUAAGGAUGACUGAGG | SEQ ID NO: 424 | CCTCAGTCATCCTTATCCC | SEQ ID NO: 472 |
| | GGAUAAGGAUGACUGAGGA | SEQ ID NO: 425 | TCCTCAGTCATCCTTATCC | SEQ ID NO: 473 |
| | AACAACUGAAACUUCAGGG | SEQ ID NO: 426 | CCCTGAAGTTTCAGTTGTT | SEQ ID NO: 474 |
| | ACAACUGAAACUUCAGGGA | SEQ ID NO: 427 | TCCCTGAAGTTTCAGTTGT | SEQ ID NO: 475 |
| | CAACUGAAACUUCAGGGAA | SEQ ID NO: 428 | TTCCCTGAAGTTTCAGTTG | SEQ ID NO: 476 |
| | CAACUGAAACUUCAGGGAA | SEQ ID NO: 429 | TTCCCTGAAGTTTCAGTTG | SEQ ID NO: 477 |
| 18-mer | CCAUCUCUGGGAUAAGGA | SEQ ID NO: 430 | TCCTTATCCCAGAGATGG | SEQ ID NO: 478 |
| | CAUCUCUGGGAUAAGGAU | SEQ ID NO: 431 | ATCCTTATCCCAGAGATG | SEQ ID NO: 479 |
| | AUCUCUGGGAUAAGGAUG | SEQ ID NO: 432 | CATCCTTATCCCAGAGAT | SEQ ID NO: 480 |
| | UCUCUGGGAUAAGGAUGA | SEQ ID NO: 433 | TCATCCTTATCCCAGAGA | SEQ ID NO: 481 |
| | CUCUGGGAUAAGGAUGAC | SEQ ID NO: 434 | GTCATCCTTATCCCAGAG | SEQ ID NO: 482 |
| | UCUGGGAUAAGGAUGACU | SEQ ID NO: 435 | AGTCATCCTTATCCCAGA | SEQ ID NO: 483 |
| | CUGGGAUAAGGAUGACUG | SEQ ID NO: 436 | CAGTCATCCTTATCCCAG | SEQ ID NO: 484 |
| | UGGGAUAAGGAUGACUGA | SEQ ID NO: 437 | TCAGTCATCCTTATCCCA | SEQ ID NO: 485 |
| | GGGAUAAGGAUGACUGAG | SEQ ID NO: 438 | CTCAGTCATCCTTATCCC | SEQ ID NO: 486 |
| | GGAUAAGGAUGACUGAGG | SEQ ID NO: 439 | CCTCAGTCATCCTTATCC | SEQ ID NO: 487 |
| | ACAACUGAAACUUCAGGG | SEQ ID NO: 440 | CCCTGAAGTTTCAGTTGT | SEQ ID NO: 488 |

TABLE 26 siRNA targeting UBE3a-AS exons 1-5

| Target sequence | | siRNA | |
|---|---|---|---|
| CCCAGGUGUCCUUUAAUGAA | SEQ ID NO: 507 | TTCATTAAAGGACACCTGGG | SEQ ID NO: 538 |
| CCAGGUGUCCUUUAAUGAAA | SEQ ID NO: 508 | TTTCATTAAAGGACACCTGG | SEQ ID NO: 539 |
| UGAAAAUGCUCUUGACACCA | SEQ ID NO: 509 | TGGTGTCAAGAGCATTTTCA | SEQ ID NO: 540 |
| GAAAAUGCUCUUGACACCAA | SEQ ID NO: 510 | TTGGTGTCAAGAGCATTTTC | SEQ ID NO: 541 |
| AAAUGCUCUUGACACCAAUG | SEQ ID NO: 511 | CATTGGTGTCAAGAGCATTT | SEQ ID NO: 542 |
| AGAUCAGUAGCUUCCUUUAC | SEQ ID NO: 512 | GTAAAGGAAGCTACTGATCT | SEQ ID NO: 543 |
| UCAGUAGCUUCCUUUACCGA | SEQ ID NO: 513 | TCGGTAAAGGAAGCTACTGA | SEQ ID NO: 544 |
| UCUAGAACAUUGAGCUAUGG | SEQ ID NO: 514 | CCATAGCTCAATGTTCTAGA | SEQ ID NO: 545 |
| CUAGAACAUUGAGCUAUGGA | SEQ ID NO: 515 | TCCATAGCTCAATGTTCTAG | SEQ ID NO: 546 |
| AACAUUGAGCUAUGGAAGAC | SEQ ID NO: 516 | GTCTTCCATAGCTCAATGTT | SEQ ID NO: 547 |
| ACAUUGAGCUAUGGAAGACU | SEQ ID NO: 517 | AGTCTTCCATAGCTCAATGT | SEQ ID NO: 548 |
| CUAUGGAAGACUCCCACCUA | SEQ ID NO: 518 | TAGGTGGGAGTCTTCCATAG | SEQ ID NO: 549 |
| UAUGGAAGACUCCCACCUAA | SEQ ID NO: 519 | TTAGGTGGGAGTCTTCCATA | SEQ ID NO: 550 |
| CAAGUGCUACCGCACAGGCA | SEQ ID NO: 520 | TGCCTGTGCGGTAGCACTTG | SEQ ID NO: 551 |
| AAGUGCUACCGCACAGGCAU | SEQ ID NO: 521 | ATGCCTGTGCGGTAGCACTT | SEQ ID NO: 552 |
| UACCGCACAGGCAUGCUGCA | SEQ ID NO: 522 | TGCAGCATGCCTGTGCGGTA | SEQ ID NO: 553 |
| CAGGCAUGCUGCAGUGAAUU | SEQ ID NO: 523 | AATTCACTGCAGCATGCCTG | SEQ ID NO: 554 |
| AGGCAUGCUGCAGUGAAUUU | SEQ ID NO: 524 | AAATTCACTGCAGCATGCCT | SEQ ID NO: 555 |
| ACCGUUGUUUAAGGAUGCUA | SEQ ID NO: 525 | TAGCATCCTTAAACAACGGT | SEQ ID NO: 556 |

TABLE 26-continued siRNA targeting UBE3a-AS exons 1-5

| Target sequence | | siRNA | |
|---|---|---|---|
| CCGUUGUUUAAGGAUGCUAU | SEQ ID NO: 526 | ATAGCATCCTTAAACAACGG | SEQ ID NO: 557 |
| CUGUGGAGGAAGAAAACCCU | SEQ ID NO: 527 | AGGGTTTTCTTCCTCCACAG | SEQ ID NO: 558 |
| AAGAAAACCCUUUACCCUGU | SEQ ID NO: 528 | ACAGGGTAAAGGGTTTTCTT | SEQ ID NO: 559 |
| AGAAAACCCUUUACCCUGUU | SEQ ID NO: 529 | AACAGGGTAAAGGGTTTTCT | SEQ ID NO: 560 |
| CUCAACUGCCUGGCACUGAA | SEQ ID NO: 530 | TTCAGTGCCAGGCAGTTGAG | SEQ ID NO: 561 |
| AACUGCCUGGCACUGAAAAU | SEQ ID NO: 531 | ATTTTCAGTGCCAGGCAGTT | SEQ ID NO: 562 |
| ACUGCCUGGCACUGAAAAUG | SEQ ID NO: 532 | CATTTTCAGTGCCAGGCAGT | SEQ ID NO: 563 |
| GUGUUUAAGGAAACCAUCUC | SEQ ID NO: 533 | GAGATGGTTTCCTTAAACAC | SEQ ID NO: 564 |
| GUUUAAGGAAACCAUCUCUG | SEQ ID NO: 534 | CAGAGATGGTTTCCTTAAAC | SEQ ID NO: 565 |
| AGGAAACCAUCUCUGAUAAG | SEQ ID NO: 535 | CTTATCAGAGATGGTTTCCT | SEQ ID NO: 566 |
| UCUUUGGCUUGUUGACACCA | SEQ ID NO: 536 | TGGTGTCAACAAGCCAAAGA | SEQ ID NO: 567 |
| CUUUGGCUUGUUGACACCAG | SEQ ID NO: 537 | CTGGTGTCAACAAGCCAAAG | SEQ ID NO: 568 |

TABLE 27 shRNA targeting UBE3a-AS exons 1-5

| | |
|---|---|
| GGTGCCATTCTATTATAAAtaacctgacccattaTTTATAATAGAATGGCACCTTTTT | SEQ ID NO: 569 |
| GCTTTCATCAATAATGAAAtaacctgacccattaTTTCATTATTGATGAAAGCTTTTT | SEQ ID NO: 570 |
| GGTCTTTCATCAATAATGAtaacctgacccattaTCATTATTGATGAAAGACCTTTTT | SEQ ID NO: 571 |
| GAAATCTTCTGATTTGTAAtaacctgacccattaTTACAAATCAGAAGATTTCTTTTT | SEQ ID NO: 572 |
| GCACCTAAGGGAATTAGTAtaacctgacccattaTACTAATTCCCTTAGGTGCTTTTT | SEQ ID NO: 573 |
| GTTTCAACCAGGATTTAAAtaacctgacccattaTTTAAATCCTGGTTGAAACTTTTT | SEQ ID NO: 574 |
| GCTTTCAACCAGGATTTAAtaacctgacccattaTTAAATCCTGGTTGAAAGCTTTTT | SEQ ID NO: 575 |
| GGAGATGTGCCATTCTATAtaacctgacccattaTATAGAATGGCACATCTCCTTTTT | SEQ ID NO: 576 |
| GTCTTTCATCAATAATGAAtaacctgacccattaTTCATTATTGATGAAAGACTTTTT | SEQ ID NO: 577 |
| GATCAATAATGAAATCTTAtaacctgacccattaTAAGATTTCATTATTGATCTTTTT | SEQ ID NO: 578 |
| GTGTCTTTCATCAATAATAtaacctgacccattaTATTATTGATGAAAGACACTTTTT | SEQ ID NO: 579 |
| GCAATAATGAAATCTTCTAtaacctgacccattaTAGAAGATTTCATTATTGCTTTTT | SEQ ID NO: 580 |
| GCATGCTGCAGTGAATTTAtaacctgacccattaTAAATTCACTGCAGCATGCTTTTT | SEQ ID NO: 581 |
| GGAAATCTTCTGATTTGTAtaacctgacccattaTACAAATCAGAAGATTTCCTTTTT | SEQ ID NO: 582 |
| GGTATATTCTATCTAGAAAtaacctgacccattaTTTCTAGATAGAATATACCTTTTT | SEQ ID NO: 583 |
| GTGCTGCAGTGAATTTAAAtaacctgacccattaTTTAAATTCACTGCAGCACTTTTT | SEQ ID NO: 584 |
| GTGTGCCATTCTATTATAAtaacctgacccattaTTATAATAGAATGGCACACTTTTT | SEQ ID NO: 585 |
| GTTACCATCAGTGTTTAAAtaacctgacccattaTTTAAACACTGATGGTAACTTTTT | SEQ ID NO: 586 |
| GCCTGCAACCGTTGTTTAAtaacctgacccattaTTAAACAACGGTTGCAGGCTTTTT | SEQ ID NO: 587 |
| GTATGTCTTTCATCAATAAtaacctgacccattaTTATTGATGAAAGACATACTTTTT | SEQ ID NO: 588 |

TABLE 28

CRISPR Guide RNAs targeting UBE3a-AS exons 1-5

| Strand | Sequence | SEQ ID | PAM |
|---|---|---|---|
| − | ACACTGATGGTAAAGTGGAC | SEQ ID NO: 589 | TGG |
| − | TAGAATATACACGTCGGTAA | SEQ ID NO: 590 | AGG |
| − | TCAACTGTCCCAGTCACAAC | SEQ ID NO: 591 | AGG |
| − | TCTAGATAGAATATACACGT | SEQ ID NO: 592 | CGG |
| − | TCTAGATAGAATATACACGT | SEQ ID NO: 593 | CGG |
| − | CTCCCCATGCACACTTGAGA | SEQ ID NO: 594 | AGG |
| − | CATCCTTAAACAACGGTTGC | SEQ ID NO: 595 | AGG |
| − | GGTGTAAAACTAATTCCCTT | SEQ ID NO: 596 | AGG |
| − | AACAACGGTTGCAGGGACAG | SEQ ID NO: 597 | AGG |
| + | TATGGAAGACTCCCACCTAA | SEQ ID NO: 598 | GGG |
| + | CTATGGAAGACTCCCACCTA | SEQ ID NO: 599 | AGG |
| + | AAGCCTTCTCAAGTGTGCAT | SEQ ID NO: 600 | GGG |
| + | CTATCTAGAACATTGAGCTA | SEQ ID NO: 601 | TGG |
| + | ACCCTCTGGTGTTGTCACAG | SEQ ID NO: 602 | AGG |
| + | AACCCTTTACCCTGTTGTTC | SEQ ID NO: 603 | AGG |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An antisense oligonucleotide comprising the nucleotide sequence $A^L*G^L*A^L*a*t*g*g*c*a*c*a*t*c*t*5mC^L*T^L*T^L*G^L$ (SEQ ID NO: 381), wherein:
   capital letters denote RNA nucleosides;
   lower case letters denote DNA nucleosides;
   5mC denotes a 5-methylcytosine nucleoside;
   superscript L denotes a locked nucleic acid (LNA) nucleoside; and
   asterisks denote phosphorothioate internucleoside linkages.

* * * * *